(12) United States Patent
Kotake et al.

(10) Patent No.: US 7,256,178 B2
(45) Date of Patent: Aug. 14, 2007

(54) PHYSIOLOGICALLY ACTIVE SUBSTANCES

(75) Inventors: Yoshihiko Kotake, Tsuchiura (JP); Jun Niijima, Tsukuba (JP); Yoshio Fukuda, Tsukuba (JP); Mitsuo Nagai, Tsukuba (JP); Regina Mikie Kanada, Tsukuba (JP); Susumu Takeda, Iwata (JP); Takashi Nakashima, Iwata (JP); Masashi Yoshida, Iwata (JP); Toshio Tsuchida, Iwata (JP); Tomohiro Sameshima, Iwata (JP)

(73) Assignees: Eisai Co., Ltd., Tokyo (JP); Mercian Corporation, Tokyo (JP)

( * ) Notice: Subject to any disclaimer, the term of this patent is extended or adjusted under 35 U.S.C. 154(b) by 0 days.

(21) Appl. No.: 10/522,731

(22) PCT Filed: Jul. 31, 2003

(86) PCT No.: PCT/JP03/09753

§ 371 (c)(1),
(2), (4) Date: Jan. 28, 2005

(87) PCT Pub. No.: WO2004/011661

PCT Pub. Date: Feb. 5, 2004

(65) Prior Publication Data

US 2005/0245514 A1    Nov. 3, 2005

(30) Foreign Application Priority Data

Jul. 31, 2002    (JP)    ............... 2002-224105

(51) Int. Cl.
 A01N 43/04    (2006.01)
 A61K 31/70    (2006.01)
 A61K 39/00    (2006.01)
 A61K 39/38    (2006.01)
 A61K 39/40    (2006.01)

(52) U.S. Cl. ................... 514/28; 424/184.1; 424/168.1

(58) Field of Classification Search ................. 514/28; 424/184.1, 168.1
See application file for complete search history.

(56) References Cited

U.S. PATENT DOCUMENTS 6,712,617 B2 *    3/2004    Detmar et al. .............. 434/407

FOREIGN PATENT DOCUMENTS

| JP | 4352783 | * | 4/1992 |
|---|---|---|---|
| JP | 4-352783 A | | 12/1992 |
| JP | 4-352783 A | | 12/1992 |
| WO | WO 02/060890 A1 | | 8/2002 |
| WO | WO-02/060890 A1 | | 8/2002 |

OTHER PUBLICATIONS

Ruichi Morishita, "Recent Progress in Gene Therapy for Cardiovascular Disease", Circ Journal, vol. 66, pp. 1077-1086.*
Moon-Seok Cha, "Endogenous Production of Nitric Oxide by Vascular Endothelial Growth Factor Down-Regulates Proliferation of Choriocarcinoma Cells", Biochemical and Biophysical Research Communications, vol. 282, pp. 1061-1066.*
Proceedings for 2003 Annual Meeting of Japan Society for Bioscience, Biotechnology, and Agrochemistry, pp. 123-124, (2003).
Seki-Asano et al., Antibiotics, vol. 47, pp. 1395-1401, (1994).
Sakai et al., "Shinki ko-shuyo kassei busshitsu pladienolide ni kansuru kenkyu (1)-shinki 12-inkan macrolide pladienolide B no tanri to kozo", Japan Society for Bioscience, Biotechnology, and Agrochemistry, Taikai Koen Yoshishu, Mar. 2003, p. 123.
Akifumi et al., "Shinki ko-shuyo kassei busshitsu pladienolide ni kansuru kenkyu (2) VEGF sansei yokusei kassei o shihyo to shita pladienolide-rui no kozo kassei sokan", Japan Society for Bioscience, Biotechnology, and Agrochemistry, Taikai Koen Yoshishu, Mar. 2003, p. 124.
Keiji Muzui et al., "Shinki ko-shuyo kassei busshitsu pladienolide ni kansuru kenkyu (3)-pladienolide-rui no yakuri kassei (in vitro, in vivo)", Japan Society for Bioscience, Biotechnology, and Agrochemistry, Taikai Koen Yoshishu, Mar. 2003, p. 124.

* cited by examiner

*Primary Examiner*—Margaret D. Seaman
*Assistant Examiner*—Niloofar Rahmani
(74) *Attorney, Agent, or Firm*—Birch, Stewart, Kolasch & Birch, LLP

(57) ABSTRACT

Compounds represented by the following general formula (I), pharmacologically acceptable salts thereof or hydrates of the same: (I) wherein W represents

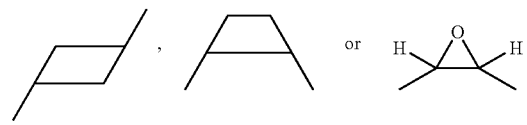

and $R^3$, $R^7$, $R^{16}$, $R^{17}$, $R^{20}$, $R^{21}$ and $R^{21'}$ are the same or different and each represents hydrogen, etc. Because of inhibiting angiogenesis and inhibiting the production of VEGF particularly in hypoxia, the compounds (I) are useful as remedies for solid cancer.

39 Claims, No Drawings

PHYSIOLOGICALLY ACTIVE SUBSTANCES

TECHNICAL FIELD

The present invention relates to a 12-membered ring macrolide compound useful as a pharmaceutical agent, a method for producing the same, and use of the same.

BACKGROUND ART

Conventionally, compounds having cytotoxicity have been used as antitumor agents, and a lot of screenings carrying out using cytotoxicity as an index. As a result, since most of the conventional antitumor agents affect cancer cells and, at the same time, normal tissues with active cell proliferation, for example, the bone marrow and intestine epithelium, QOL of patients is not sufficiently improved.

Further, under existing circumstances, antitumor agents have come to have a rather beneficial effect on treating leukemia, but are not necessarily effective for solid tumors. Therefore, antitumor agents that are effective for solid tumors and are highly safe have been strongly demanded.

Fermentation products of microorganisms have been screened mainly using cytotoxicity in vitro as an index, in order to use these products as antitumor agents. As a result, many cytotoxic compounds have been discovered. However, most of the compounds have been confirmed to show cytotoxic activities only in vitro, and few compounds have been found to have an antitumor activities in vivo. Furthermore, very few compounds exhibit efficacy against solid cancers.

DISCLOSURE OF THE INVENTION

An object of the present invention is to discover compounds that show antitumor activities not only in vitro but also in vivo, and have antitumor activities on solid cancers from fermentation products of microorganism, or their derivatives.

It is considered that tumorgenesis of normal cells mutations of a gene in the cell occurs so that an abnormal gene is expressed. In this situation, the present inventors have conducted extensive studies, based on the assumption that alteration of gene expression in tumor cells can cause inhibition of proliferation of tumor cells, namely, proliferation of tumor cells can be inhibited by, for example, changing the gene of ongocene or tumor suppressor gene, or changing the gene expression of a gene involved in cell cycle. The present inventors have screened fermentation products of various microorganisms and their derivatives using VEGF (Vascular Endothelial Growth Factor) production by U251 cells under hypoxic stimulation as an index, in the expectation that compounds which alter gene expression, in particular, compounds which inhibit VEGF production under low hypoxic condition, inhibit angiogenesis by tumors and, furthermore, exhibit antitumor activity against solid cancers. As a result, the present inventors have discovered novel physiologically active substances, a 12-membered ring macrolide compound, named 11107, and its analogues, which inhibit VEGF production under low hypoxic condition in vitro and, further, inhibit proliferation of solid cancer cells in vivo.

As a result of further extensive studies, the present inventors have found that, among the 11107 analogues, 6-deoxy 11107D, in which the hydroxyl group of 11107D at the 6-position is replaced by a hydrogen, and compounds obtained by chemical modification of the 6-deoxy 11107D (hereinafter the compounds are referred to as "6-deoxy 11107D derivatives") are stable in an aqueous solution, and that these derivatives not only inherit the characteristics of stability from of 11107D, but also inhibit proliferation of solid tumor cells more potently in vivo experiments. These findings have led to the accomplishment of the present invention.

Given as a related art, most structurally similar to the compound of the present invention is FD-895, which is a 12-membered ring macrolide compound (JP-A-04-352783) represented by the formula (XIV):

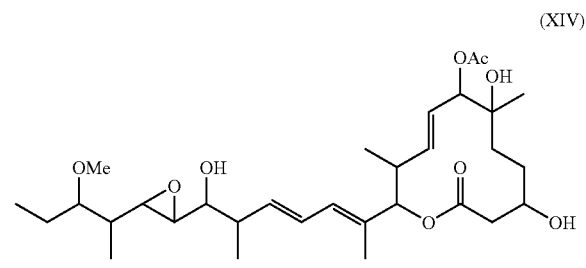

The above-described gazette discloses that FD-895 has cytotoxic activity in vitro against P388 mouse leukemia cells, L-1210 mouse leukemia cells, and HL-60 human leukemia cells in a RPM-1640 culture medium (Column No. 6, Table 2 of the gazette). However, it is reported that FD-895 did not show antitumor activity in an in vivo experiment using P388 mouse leukemia cells (Seki-Asano M. et al., Antibiotics, 47, 1395-1401, 1994).

Furthermore, as described later, since FD-895 is instable in an aqueous solution, it is expected to be inappropriate to mix the compound with an infusion solution upon administered. Therefore, FD-895 does not have sufficient qualities as an antitumor agent.

Therefore, the present invention relates to:

1. A compound represented by the formula (I):

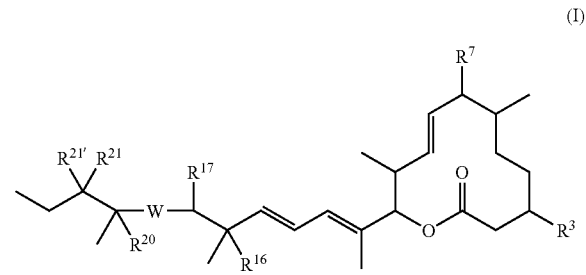

wherein W represents

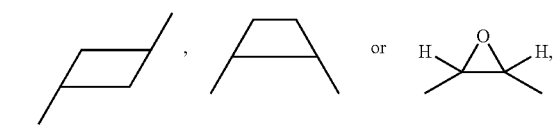

and $R^3$, $R^7$, $R^{16}$, $R^{17}$, $R^{20}$, $R^{21}$ and $R^{21'}$, the same or different, independently represent 1) a hydrogen atom,
2) a hydroxyl group or oxo group, provided that the oxo group is limited to an oxo group formed by $R^3$ or $R^7$ in combination with a carbon atom to which $R^3$ or $R^7$ is bonded, and an oxo group formed by $R^{21}$ and $R^{21'}$ together in combination with the carbon atom to which $R^{21}$ and $R^{21'}$ are bonded,
3) a $C_1$ to $C_{22}$ alkoxy group which may have a substituent,
4) an unsaturated $C_2$ to $C_{22}$ alkoxy group which may have a substituent,
5) a $C_7$ to $C_{22}$ aralkyloxy group which may have a substituent,
6) a 5-membered to 14-membered heteroaralkyloxy group which may have a substituent,
7) RC(=Y)—O—, wherein Y represents an oxygen atom or sulfur atom, and R represents
　a) a hydrogen atom,
　b) a $C_1$ to $C_{22}$ alkyl group which may have a substituent,
　c) an unsaturated $C_2$ to $C_{22}$ alkyl group which may have a substituent,
　d) a $C_6$ to $C_{14}$ aryl group which may have a substituent,
　e) a 5-membered to 14-membered heteroaryl group which may have a substituent,
　f) a $C_7$ to $C_{22}$ aralkyl group which may have a substituent,
　g) a 5-membered to 14-membered heteroaralkyl group which may have a substituent,
　h) a $C_1$ to $C_{22}$ alkoxy group which may have a substituent,
　i) an unsaturated $C_2$ to $C_{22}$ alkoxy group which may have a substituent,
　j) a $C_6$ to $C_{14}$ aryloxy group which may have a substituent,
　k) a $C_3$ to $C_{14}$ cycloalkyl group which may have a substituent,
　l) a 3-membered to 14-membered non-aromatic heterocyclic group which may have a substituent or
　m) a 5-membered to 14-membered heteroaryloxy group which may have a substituent,
8) $R^{S1}R^{S2}R^{S3}SiO$—, wherein $R^{S1}$, $R^{S2}$ and $R^{S3}$, the same or different, independently represent
　a) a $C_1$ to $C_6$ alkyl group or
　b) a $C_6$ to $C_{14}$ aryl group,
9) a halogen atom,
10) $R^{N1}R^{N2}N$—$R^M$—, wherein $R^M$ represents
　a) a single bond,
　b) —CO—O—,
　c) —$SO_2$—O—,
　d) —CS—O— or
　e) —CO—$NR^{N3}$—, wherein $R^{N3}$ represents a hydrogen atom or a $C_1$ to $C_6$ alkyl group which may have a substituent, provided that, the leftmost bond in b) to e) is bonded to the nitrogen atom,
$R^{N1}$ and $R^{N2}$, the same or different, independently represent
　a) a hydrogen atom,
　b) a $C_1$ to $C_{22}$ alkyl group which may have a substituent,
　c) an unsaturated $C_2$ to $C_{22}$ alkyl group which may have a substituent,
　d) an aliphatic $C_2$ to $C_{22}$ acyl group which may have a substituent,
　e) an aromatic $C_7$ to $C_{15}$ acyl group which may have a substituent,
　f) a $C_6$ to $C_{14}$ aryl group which may have a substituent,
　g) a 5-membered to 14-membered heteroaryl group which may have a substituent,
　h) a $C_7$ to $C_{22}$ aralkyl group which may have a substituent,
　i) a $C_1$ to $C_{22}$ alkylsulfonyl group which may have a substituent,
　j) a $C_6$ to $C_{14}$ arylsulfonyl group which may have a substituent,
　k) a 3-membered to 14-membered non-aromatic heterocyclic group formed by $R^{N1}$ and $R^{N2}$ together in combination with the nitrogen atom to which $R^{N1}$ and $R^{N2}$ are bonded, wherein the 3-membered to 14-membered non-aromatic heterocyclic group may have a substituent,
　l) a 5-membered to 14-membered heteroaralkyl group which may have a substituent,
　m) a $C_3$ to $C_{14}$ cycloalkyl group which may have a substituent or
　n) a 3-membered to 14-membered non-aromatic heterocyclic group which may have a substituent,
11) $R^{N4}SO_2$—O—, wherein $R^{N4}$ represents
　a) a $C_1$ to $C_{22}$ alkyl group which may have a substituent,
　b) a $C_6$ to $C_{14}$ aryl group which may have a substituent,
　c) a $C_1$ to $C_{22}$ alkoxy group which may have a substituent,
　d) an unsaturated $C_2$ to $C_{22}$ alkoxy group which may have a substituent,
　e) a $C_6$ to $C_{14}$ aryloxy group which may have a substituent,
　f) a 5-membered to 14-membered heteroaryloxy group which may have a substituent,
　g) a $C_7$ to $C_{22}$ aralkyloxy group which may have a substituent or
　h) a 5-membered to 14-membered heteroaralkyloxy group which may have a substituent,
12) $(R^{N5}O)_2PO$—O—, wherein $R^{N5}$ represents
　a) a $C_1$ to $C_{22}$ alkyl group which may have a substituent,
　b) an unsaturated $C_2$ to $C_{22}$ alkyl group which may have a substituent,
　c) a $C_6$ to $C_{14}$ aryl group which may have a substituent,
　d) a 5-membered to 14-membered heteroaryl group which may have a substituent,
　e) a $C_7$ to $C_{22}$ aralkyl group which may have a substituent or
　f) a 5-membered to 14-membered heteroaralkyl group which may have a substituent,
13) $(R^{N1}R^{N2}N)_2PO$—O—, wherein $R^{N1}$ and $R^{N2}$ are the same as defined above or
14) $(R^{N1}R^{N2}N)(R^{N5}O)PO$—O—, wherein $R^{N1}$, $R^{N2}$ and $R^{N5}$ are the same as defined above; a pharmacologically acceptable salt thereof, or a hydrate of those;

2. The compound according to 1 represented by the formula (I-a):

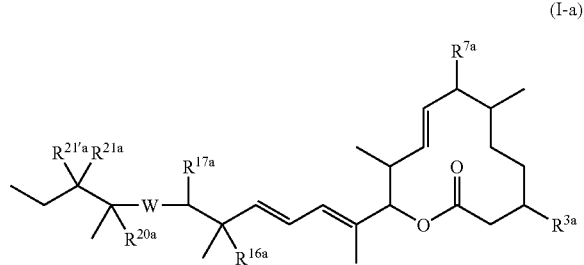

wherein W is the same as defined above, and $R^{3a}$, $R^{7a}$, $R^{16a}$, $R^{17a}$, $R^{20a}$, $R^{21a}$ and $R^{21a'}$, the same or different, independently represent
1) a hydrogen atom,
2) a hydroxyl group or oxo group, provided that the oxo group is limited to an oxo group formed by $R^{3a}$ or $R^{7a}$ in combination with the carbon atom to which $R^{3a}$ or $R^{7a}$ is bonded, and an oxo group formed by $R^{21a}$ and $R^{21a'}$ together in combination with a carbon atom to which $R^{21a}$ and $R^{21a'}$ are bonded, 3) a $C_1$ to $C_{22}$ alkoxy group which may have a substituent,
4) $R^a C(=Y^a)$—O—, wherein $Y^a$ represents an oxygen atom or sulfur atom, and $R^a$ represents
   a) a hydrogen atom,
   b) a $C_1$ to $C_{22}$ alkyl group which may have a substituent,
   c) an unsaturated $C_2$ to $C_{22}$ alkyl group which may have a substituent,
   d) a $C_6$ to $C_{14}$ aryl group which may have a substituent,
   e) a 5-membered to 14-membered heteroaryl group which may have a substituent,
   f) a $C_7$ to $C_{22}$ aralkyl group which may have a substituent,
   g) a 5-membered to 14-membered heteroaralkyl group which may have a substituent,
   h) a $C_1$ to $C_{22}$ alkoxy group which may have a substituent,
   i) an unsaturated $C_2$ to $C_{22}$ alkoxy group which may have a substituent,
   j) a $C_6$ to $C_{14}$ aryloxy group which may have a substituent,
   k) a $C_3$ to $C_{14}$ cycloalkyl group which may have a substituent,
   l) a 3-membered to 14-membered non-aromatic heterocyclic group which may have a substituent or
   m) a 5-membered to 14-membered heteroaryloxy group which may have a substituent,
5) $R^{aS1}R^{aS2}R^{aS3}SiO$—, wherein $R^{aS1}$, $R^{aS2}$ and $R^{aS3}$, the same or different, independently represent
   a) a $C_1$ to $C_6$ alkyl group or
   b) a $C_6$ to $C_{14}$ aryl group or
6) $R^{aN1}R^{aN2}N$—$R^{aM}$—, wherein $R^{aM}$ represents
   a) —CO—O— or
   b) —CS—O—, provided that, the leftmost bond in a) or b) is bonded to the nitrogen atom, and
   $R^{aN1}$ and $R^{aN2}$, the same or different, independently represent
   a) a hydrogen atom,
   b) a $C_1$ to $C_{22}$ alkyl group which may have a substituent,
   c) an unsaturated $C_2$ to $C_{22}$ alkyl group which may have a substituent,
   d) an aliphatic $C_2$ to $C_{22}$ acyl group which may have a substituent,
   e) an aromatic $C_7$ to $C_{15}$ acyl group which may have a substituent,
   f) a $C_6$ to $C_{14}$ aryl group which may have a substituent,
   g) a 5-membered to 14-membered heteroaryl group which may have a substituent,
   h) a $C_7$ to $C_{22}$ aralkyl group which may have a substituent,
   i) a $C_1$ to $C_{22}$ alkylsulfonyl group which may have a substituent,
   j) a $C_6$ to $C_{14}$ arylsulfonyl group which may have a substituent,
   k) a 3-membered to 14-membered non-aromatic heterocyclic group formed by $R^{aN1}$ and $R^{aN2}$ together in combination with the nitrogen atom to which $R^{aN1}$ and $R^{aN2}$ are bonded, wherein the 3-membered to 14-membered non-aromatic heterocyclic group may have a substituent,
   l) a 5-membered to 14-membered heteroaralkyl group which may have a substituent,
   m) a $C_3$ to $C_{14}$ cycloalkyl group which may have a substituent or
   n) a 3-membered to 14-membered non-aromatic heterocyclic group which may have a substituent; a pharmacologically acceptable salt thereof, or a hydrate of those;

3. The compound according to 1 represented by the formula (I-b):

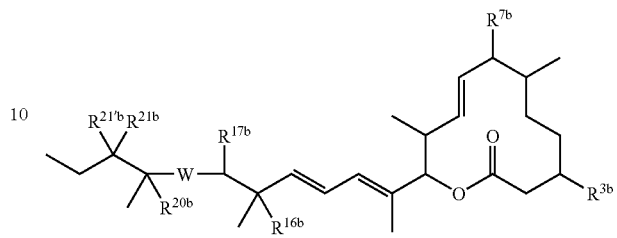

wherein W is the same as defined above, and $R^{3b}$, $R^{7b}$, $R^{16b}$, $R^{17b}$, $R^{20b}$, $R^{21b}$ and $R^{21'b}$, the same or different, independently represent 1) a hydrogen atom,
2) a hydroxyl group or oxo group, provided that the oxo group is limited to an oxo group formed by $R^{3b}$ or $R^{7b}$ in combination with the carbon atom to which $R^{3b}$ or $R^{7b}$ is bonded, and an oxo group formed by $R^{21b}$ and $R^{21b'}$ together in combination with the carbon atom to which $R^{21b}$ and $R^{21b'}$ are bonded,
3) a $C_1$ to $C_{22}$ alkoxy group which may have a substituent,
4) $R^b C(=O)$—O—, wherein $R^b$ represents
   a) a $C_1$ to $C_{22}$ alkyl group which may have a substituent,
   b) an unsaturated $C_2$ to $C_{22}$ alkyl group which may have a substituent,
   c) a $C_7$ to $C_{22}$ aralkyl group which may have a substituent,
   d) a 5-membered to 14-membered heteroaralkyl group which may have a substituent,
   e) a $C_6$ to $C_{14}$ aryloxy group which may have a substituent,
   f) a $C_3$ to $C_{14}$ cycloalkyl group which may have a substituent or
   g) a 3-membered to 14-membered non-aromatic heterocyclic group which may have a substituent,
5) $R^{bS1}R^{bS2}R^{bS3}SiO$—, wherein $R^{bS1}$, $R^{bS2}$ and $R^{bS3}$, the same or different, independently represent
   a) a $C_1$ to $C_6$ alkyl group or
   b) a $C_6$ to $C_{14}$ aryl group or
6) $R^{bN1}R^{bN2}N$—$R^{bM}$—, wherein $R^{bM}$ represents
   a) —CO—O— or
   b) —CS—O—, provided that, the leftmost bond in a) or b) is bonded to the nitrogen atom, and
   $R^{bN1}$ and $R^{bN2}$, the same or different, independently represent
   a) a hydrogen atom,
   b) a $C_1$ to $C_{22}$ alkyl group which may have a substituent,
   c) a 3-membered to 14-membered non-aromatic heterocyclic group formed by $R^{bN1}$ and $R^{bN2}$ together in combination with the nitrogen atom to which $R^{bN1}$ and $R^{bN2}$ are bonded, wherein the 3-membered to 14-membered non-aromatic heterocyclic group may have a substituent,
   d) a $C_3$ to $C_{14}$ cycloalkyl group which may have a substituent or
   e) a 3-membered to 14-membered non-aromatic heterocyclic group which may have a substituent; a pharmacologically acceptable salt thereof, or hydrate of those;

4. The compound according to 1 represented by the formula (I-c):

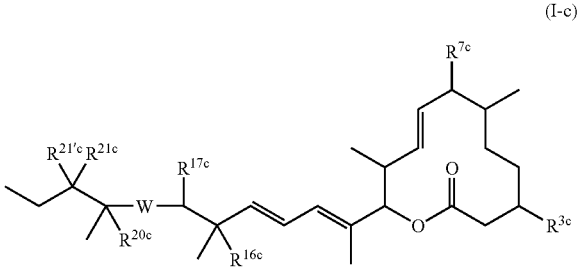

(I-c)

wherein W is the same as defined above, and $R^{3c}$, $R^{7c}$, $R^{16c}$, $R^{17c}$, $R^{20c}$, $R^{21c}$ and $R^{21'c}$, the same or different, independently represent
1) a hydrogen atom,
2) a hydroxyl group or oxo group, provided that the oxo group is limited to an oxo group formed by $R^{3c}$ or $R^{7c}$ in combination with the carbon atom to which $R^{3c}$ or $R^{7c}$ is bonded, and an oxo group formed by $R^{21c}$ and $R^{21c'}$ together in combination with the carbon atom to which $R^{21c}$ and $R^{21c'}$ are bonded,
3) $R^c C(=O)-O-$, wherein $R^c$ represents a $C_1$ to $C_{22}$ alkyl group which may have a substituent,
4) $R^{cS1}R^{cS2}R^{cS3}SiO-$, wherein $R^{cS1}$, $R^{cS2}$ and $R^{cS3}$, the same or different, independently represent
  a) a $C_1$ to $C_6$ alkyl group or
  b) a $C_6$ to $C_{14}$ aryl group or
5) $R^{cN1}R^{cN2}N-R^{cM}-$, wherein $R^{cM}$ represents $-CO-O-$, provided that the leftmost bond is bonded to the nitrogen atom, and
  $R^{cN1}$ and $R^{cN2}$, the same or different, independently represent
  a) a hydrogen atom,
  b) a $C_1$ to $C_{22}$ alkyl group which may have a substituent,
  c) a 3-membered to 14-membered non-aromatic heterocyclic group formed by $R^{cN1}$ and $R^{cN2}$ together in combination with the nitrogen atom to which $R^{cN1}$ and $R^{cN2}$ are bonded, wherein the 3-membered to 14-membered non-aromatic heterocyclic group may have a substituent,
  d) a $C_3$ to $C_{14}$ cycloalkyl group which may have a substituent or
  e) a 3-membered to 14-membered non-aromatic heterocyclic group which may have a substituent; a pharmacologically acceptable salt thereof, or a hydrate of those;

5. The compound according to 1 represented by the formula (I-d):

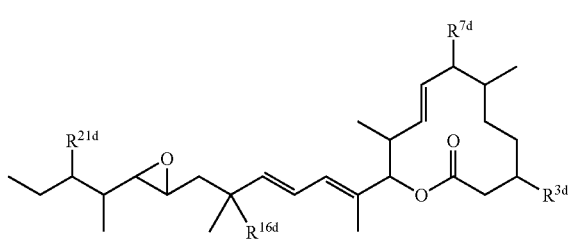

(I-d)

wherein $R^{3d}$ and $R^{16d}$, the same or different, independently represent
1) a hydroxyl group,
2) a $C_1$ to $C_{22}$ alkoxy group which may have a substituent,
3) an unsaturated $C_2$ to $C_{22}$ alkoxy group which may have a substituent,
4) a $C_7$ to $C_{22}$ aralkyloxy group which may have a substituent,
5) $R^d C(=O)-O-$, wherein $R^d$ represents
  a) a hydrogen atom,
  b) a $C_1$ to $C_{22}$ alkyl group which may have a substituent,
  c) an unsaturated $C_2$ to $C_{22}$ alkyl group which may have a substituent,
  d) a $C_6$ to $C_{14}$ aryl group which may have a substituent,
  e) a 5-membered to 14-membered heteroaryl group which may have a substituent,
  f) a $C_7$ to $C_{22}$ aralkyl group which may have a substituent,
  g) a 5-membered to 14-meinbered heteroaralkyl group which may have a substituent,
  h) a $C_1$ to $C_{22}$ alkoxy group which may have a substituent,
  i) an unsaturated $C_2$ to $C_{22}$ alkoxy group which may have a substituent,
  j) a $C_6$ to $C_{14}$ aryloxy group which may have a substituent or
  k) a 5-membered to 14-membered heteroaryloxy group which may have a substituent or
6) $R^{dN1}R^{dN2}N-CO-O-$, wherein $R^{dN1}$ and $R^{dN2}$, the same or different, independently represent
  a) a hydrogen atom,
  b) a $C_1$ to $C_{22}$ alkyl group which may have a substituent,
  c) an unsaturated $C_2$ to $C_{22}$ alkyl group which may have a substituent,
  d) a $C_6$ to $C_{14}$ aryl group which may have a substituent,
  e) a 5-meinbered to 14-membered heteroaryl group which may have a substituent,
  f) a $C_7$ to $C_{22}$ aralkyl group which may have a substituent,
  g) a 5-meinbered to 14-membered heteroaralkyl group which may have a substituent,
  h) a $C_3$ to $C_{14}$ cycloalkyl group which may have a substituent,
  i) a 3-membered to 14-membered non-aromatic heterocyclic group which may have a substituent or
  j) a 3-membered to 14-membered non-aromatic heterocyclic group formed by $R^{dN1}$ and $R^{dN2}$ together in combination with the nitrogen atom to which $R^{dN1}$ and $R^{dN2}$ are bonded, wherein the 3-membered to 14-membered non-aromatic heterocyclic group may have a substituent and $R^{7d}$ and $R^{21d}$, the same or different, independently represent
1) a hydroxyl group,
2) a $C_1$ to $C_{22}$ alkoxy group which may have a substituent,
3) an unsaturated $C_2$ to $C_{22}$ alkoxy group which may have a substituent,
4) a $C_7$ to $C_{22}$ aralkyloxy group which may have a substituent,
5) $R^d C(=O)-O-$, wherein $R^d$ is the same as defined above,
6) $R^{dN1}R^{dN2}N-CO-O-$, wherein $R^{dN1}$ and $R^{dN2}$ are the same as defined above,
7) $R^{dN1}R^{dN2}N-SO_2-O-$, wherein $R^{dN1}$ and $R^{dN2}$ are the same as defined above,
8) $R^{dN1}R^{dN2}N-CS-O-$, wherein $R^{dN1}$ and $R^{dN2}$ are the same as defined above,
9) $R^{dN4}-SO_2-O-$, wherein $R^{dN4}$ represents
  a) a $C_1$ to $C_{22}$ alkyl group which may have a substituent,
  b) a $C_6$ to $C_{14}$ aryl group which may have a substituent,
  c) a $C_1$ to $C_{22}$ alkoxy group which may have a substituent, d) an unsaturated $C_2$ to $C_{22}$ alkoxy group which may have a substituent,
e) a $C_6$ to $C_{14}$ aryloxy group which may have a substituent,
f) a 5-membered to 14-membered heteroaryloxy group which may have a substituent,
g) a $C_7$ to $C_{22}$ aralkyloxy group which may have a substituent or
h) a 5-membered to 14-membered heteroaralkyloxy group which may have a substituent,
10) $(R^{dN5}O)_2PO—O—$, wherein $R^{dN5}$ represents
   a) a $C_1$ to $C_{22}$ alkyl group which may have a substituent,
   b) an unsaturated $C_2$ to $C_{22}$ alkyl group which may have a substituent,
   c) a $C_6$ to $C_{14}$ aryl group which may have a substituent,
   d) a 5-membered to 14-membered heteroaryl group which may have a substituent,
   e) a $C_7$ to $C_{22}$ aralkyl group which may have a substituent or
   f) a 5-membered to 14-membered heteroaralkyl group which may have a substituent,
11) $(R^{dN1}R^{dN2}N)_2PO—O—$, wherein $R^{dN1}$ and $R^{dN2}$ are the same as defined above or
12) $(R^{dN1}R^{dN2}N)(R^{dN5}O)PO—O—$, wherein $R^{dN1}$, $R^{dN2}$ and $R^{dN5}$ are the same as defined above; a pharmacologically acceptable salt thereof, or a hydrate of those;
6. The compound according to 1, wherein $R^7$ and/or $R^{21}$ are independently represented by $RC(=Y)—O—$, wherein Y and R are the same as defined above, or $R^{N1}R^{N2}N—R^{M'}—$, wherein $R^{M'}$ represents
   a) —CO—O— or
   b) —CS—O—, provided that, the leftmost bond in a) or b) is bonded to the nitrogen atom, and
   $R^{N1}$ and $R^{N2}$ are the same as defined above; a pharmacologically acceptable salt thereof, or a hydrate of those;
7. The compound according to 5 represented by the formula (I-e):

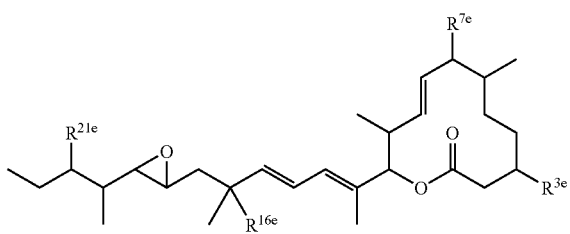

(I-e)

wherein $R^{3e}$, $R^{16e}$ and $R^{21e}$, the same or different, independently represent
1) a hydroxyl group,
2) a $C_1$ to $C_{22}$ alkoxy group which may have a substituent,
3) an unsaturated $C_2$ to $C_{22}$ alkoxy group which may have a substituent,
4) a $C_7$ to $C_{22}$ aralkyloxy group which may have a substituent,
5) an aliphatic $C_2$ to $C_6$ acyl group which may have a substituent or
6) $R^{eN1}R^{eN2}N—CO—O—$, wherein $R^{eN1}$ and $R^{eN2}$ independently represent
   a) a hydrogen atom or
   b) a $C_1$ to $C_6$ alkyl group which may have a substituent and $R^{7e}$ represents $R^e—C(=Y^e)—O—$, wherein $Y^e$ represents an oxygen atom or sulfur atom, and $R^e$ represents
   a) a hydrogen atom,
   b) a $C_1$ to $C_{22}$ alkyl group which may have a substituent,
   c) a $C_6$ to $C_{14}$ aryl group which may have a substituent,
   d) a 5-membered to 14-membered heteroaryl group which may have a substituent,
   e) a $C_7$ to $C_{10}$ aralkyl group which may have a substituent,
   f) a 5-membered to 14-meinbered heteroaralkyl group which may have a substituent,
   g) a 3-membered to 14-merobered non-aromatic heterocyclic group which may have a substituent,
   h) a group of the formula (III):

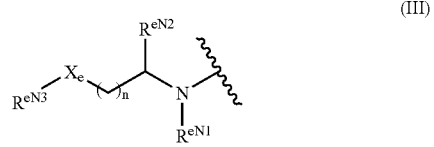

(III)

wherein A) n represents an integer of 0 to 4, $X_e$ represents
   i) —$CHR^{eN4}$—,
   ii) —$NR^{eN5}$—,
   iii) —O—,
   iv) —S—,
   v) —SO— or
   vi) —$SO_2$—,
$R^{eN1}$ represents
   i) a hydrogen atom or
   ii) a $C_1$ to $C_6$ alkyl group which may have a substituent,
$R^{eN2}$ represents
   i) a hydrogen atom or
   ii) a $C_1$ to $C_6$ alkyl group which may have a substituent,
$R^{eN3}$ and $R^{eN4}$, the same or different, independently represent
   i) a hydrogen atom,
   ii) a $C_1$ to $C_6$ alkyl group which may have a substituent,
   iii) an unsaturated $C_2$ to $C_{10}$ alkyl group which may have a substituent,
   iv) a $C_6$ to $C_{14}$ aryl group which may have a substituent,
   v) a 5-membered to 14-membered heteroaryl group which may have a substituent,
   vi) a $C_7$ to $C_{10}$ aralkyl group which may have a substituent,
   vii) a $C_3$ to $C_8$ cycloalkyl group which may have a substituent,
   viii) a $C_4$ to $C_9$ cycloalkylalkyl group which may have a substituent,
   ix) a 5-membered to 14-membered heteroaralkyl group which may have a substituent,
   x) a 5-membered to 14-membered non-aromatic heterocyclic group which may have a substituent,
   xi) —$NR^{eN6}R^{eN7}$, wherein $R^{eN6}$ and $R^{eN7}$, the same or different, independently represent a hydrogen atom or a $C_1$ to $C_6$ alkyl group which may have a substituent or
   xii) a 5-membered to 14-membered non-aromatic heterocyclic group formed by $R^{eN3}$ and $R^{eN4}$ together in combination with the carbon atom to which $R^{eN3}$ and $R^{eN4}$ are bonded, wherein the 5-membered to 14-membered non-aromatic heterocyclic group may have a substituent and
$R^{eN5}$ represents
   i) a hydrogen atom,
   ii) a $C_1$ to $C_6$ alkyl group which may have a substituent, iii) an unsaturated $C_2$ to $C_{10}$ alkyl group which may have a substituent,
iv) a $C_6$ to $C_{14}$ aryl group which may have a substituent,
v) a 5-membered to 14-membered heteroaryl group which may have a substituent,
vi) a $C_7$ to $C_{10}$ aralkyl group which may have a substituent,
vii) a $C_3$ to $C_8$ cycloalkyl group which may have a substituent,
viii) a $C_4$ to $C_9$ cycloalkylalkyl group which may have a substituent,
ix) a 5-membered to 14-membered heteroaralkyl group which may have a substituent,
x) a 5-membered to 14-membered non-aromatic heterocyclic group which may have a substituent or
xi) a 5-membered to 14-membered non-aromatic heterocyclic group formed by $R^{eN3}$ and $R^{eN5}$ together in combination with the nitrogen atom to which $R^{eN3}$ and $R^{eN5}$ are bonded, wherein the 5-membered to 14-membered non-aromatic heterocyclic group may have a substituent, B)

$X_e$, n, $R^{eN3}$, $R^{eN4}$ and $R^{eN5}$ independently represent the same group as defined above, and $R^{eN1}$ and $R^{eN2}$ independently represent a 5-membered to 14-membered non-aromatic heterocyclic group formed by $R^{eN1}$ and $R^{eN2}$ together, wherein the 5-membered to 14-membered non-aromatic heterocyclic group may have a substituent, C)
$X_e$, n, $R^{eN2}$, $R^{eN4}$ and $R^{eN5}$ independently represent the same group as defined above, and $R^{eN1}$ and $R^{eN2}$ independently represent a 5-membered to 14-membered non-aromatic heterocyclic group formed by $R^{eN1}$ and $R^{eN2}$ together, wherein the 5-membered to 14-membered non-aromatic heterocyclic group may have a substituent or D)
$X_e$, n, $R^{eN1}$, $R^{eN4}$ and $R^{eN5}$ independently represent the same group as defined above, and $R^{eN2}$ and $R^{eN3}$ independently represent a 5-membered to 14-membered non-aromatic heterocyclic group formed by $R^{eN2}$ and $R^{eN3}$ together, wherein the 5-membered to 14-membered non-aromatic heterocyclic group may have a substituent or i) a group of the formula (IV):

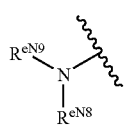

(IV)

wherein $R^{eN8}$ and $R^{eN9}$, the same or different, independently represent
i) a hydrogen atom,
ii) a $C_1$ to $C_6$ alkyl group which may have a substituent,
iii) a $C_6$ to $C_{14}$ aryl group which may have a substituent,
iv) a 5-membered to 14-membered heteroaryl group which may have a substituent,
v) a $C_7$ to $C_{10}$ aralkyl group which may have a substituent or
vi) a 5-membered to 14-membered heteroaralkyl group which may have a substituent; a pharmacologically acceptable salt thereof, or a hydrate of those;

8. The compound according to 5, wherein $R^{7e}$ and/or $R^{21e}$ are independently represented by $R^{e1}C(=Y^{e1})$—O—, wherein $Y^{e1}$ represents an oxygen atom or sulfur atom, and $R^{e1}$ represents
1) a hydrogen atom,
2) a $C_1$ to $C_6$ alkyl group which may have a substituent,
3) a $C_6$ to $C_{10}$ aryl group which may have a substituent,
4) a 5-membered to 14-membered heteroaryl group which may have a substituent,
5) a $C_7$ to $C_{10}$ aralkyl group which may have a substituent or
6) a 5-membered to 14-membered heteroaralkyl group which may have a substituent; a pharmacologically acceptable salt thereof, or a hydrate of those;

9. The compound according to 5, wherein $R^{7e}$ and/or $R^{21e}$ are independently represented by $R^{e2}C(=Y^{e2})$—O—, wherein $Y^{e2}$ represents an oxygen atom or sulfur atom, and $R^{e2}$ represents a group of the formula (III'):

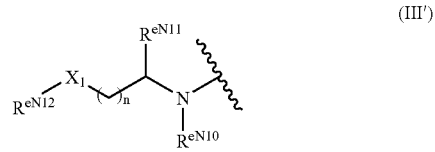

(III')

wherein A) n represents an integer of 0 to 4,
$X_1$ represents
1) —$CHR^{eN13}$—,
2) —$NR^{eN14}$—,
3) —O—,
4) —S—,
5) —SO— or
6) —$SO_2$—, $R^{eN10}$ and $R^{eN11}$, the same or different, independently represent
1) a hydrogen atom or
2) a $C_1$ to $C_6$ alkyl group which may have a substituent, $R^{eN12}$ and $R^{eN13}$, the same or different, independently represent
1) a hydrogen atom,
2) a $C_1$ to $C_6$ alkyl group which may have a substituent,
3) an unsaturated $C_2$ to $C_{10}$ alkyl group which may have a substituent,
4) a $C_6$ to $C_{14}$ aryl group which may have a substituent,
5) a 5-membered to 14-membered heteroaryl group which may have a substituent,
6) a $C_7$ to $C_{10}$ aralkyl group which may have a substituent,
7) a $C_3$ to $C_8$ cycloalkyl group which may have a substituent,
8) a $C_4$ to $C_9$ cycloalkylalkyl group which may have a substituent,
9) a 5-membered to 14-membered heteroaralkyl group which may have a substituent,
10) a 5-membered to 14-membered non-aromatic heterocyclic group which may have a substituent,
11) —$NR^{eN15}R^{eN16}$, wherein $R^{eN15}$ and $R^{eN16}$, the same or different, independently represent a hydrogen atom or a $C_1$ to $C_6$ alkyl group which may have a substituent or
12) a 5-membered to 14-membered non-aromatic heterocyclic group formed by $R^{eN12}$ and $R^{eN13}$ together, wherein the 5-membered to 14-membered non-aromatic heterocyclic group may have a substituent and $R^{eN14}$ represents 1) a hydrogen atom,
2) a $C_1$ to $C_6$ alkyl group which may have a substituent,
3) an unsaturated $C_2$ to $C_{10}$ alkyl group which may have a substituent,
4) a $C_6$ to $C_{14}$ aryl group which may have a substituent,
5) a 5-membered to 14-membered heteroaryl group which may have a substituent,
6) a $C_7$ to $C_{10}$ aralkyl group which may have a substituent,
7) a $C_3$ to $C_8$ cycloalkyl group which may have a substituent,
8) a $C_4$ to $C_9$ cycloalkylalkyl group which may have a substituent,
9) a 5-membered to 14-membered heteroaralkyl group which may have a substituent,
10) a 5-membered to 14-membered non-aromatic heterocyclic group which may have a substituent,
11) a 5-membered to 14-membered non-aromatic heterocyclic group formed together by the nitrogen atom to which $R^{eN14}$ is bonded, and one substituent selected from the group consisting of $R^{eN10}$, $R^{eN11}$ and $R^{eN12}$, wherein the 5-membered to 14-membered non-aromatic heterocyclic group may have a substituent or
12) a 5-membered to 14-membered non-aromatic heterocyclic group formed together by the nitrogen atom to which $R^{eN14}$ is bonded, and two substituents selected from the group consisting of $R^{eN10}$, $R^{eN11}$ and $R^{eN12}$, wherein the 5-membered to 14-membered non-aromatic heterocyclic group may have a substituent or B)
n, $X_1$, $R^{eN11}$, $R^{eN13}$ and $R^{eN14}$ are the same as defined above, and $R^{eN10}$ and $R^{eN12}$ together form a 5-membered to 14-membered non-aromatic heterocyclic group formed by $R^{eN10}$ and $R^{eN12}$, wherein the 5-membered to 14-membered non-aromatic heterocyclic group may have a substituent; a pharmacologically acceptable salt thereof, or a hydrate of those;

10. The compound according to 5, wherein $X_1$ represents —$NR^{eN14}$—, wherein $NR^{eN14}$ is the same as defined above; a pharmacologically acceptable salt thereof, or a hydrate of those;

11. The compound according to 5, wherein $R^{7e}$ and/or $R^{21e}$ independently represent $R^{e3}C(=Y^{e3})$—O—, wherein $Y^{e3}$ represents an oxygen atom or sulfur atom, and $R^{e3}$ represents a group of the formula (V):

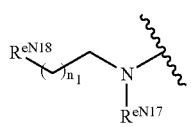

(V)

wherein $n_1$ represents an integer of 0 to 6,
$R^{eN17}$ represents
1) a hydrogen atom or
2) a $C_1$ to $C_6$ alkyl group which may have a substituent and
$R^{eN18}$ represents
1) a hydrogen atom,
2) an amino group which may have a substituent,
3) a pyridyl group which may have a substituent,
4) a pyrrolidin-1-yl group which may have a substituent,
5) a piperidin-1-yl group which may have a substituent,
6) a morpholin-4-yl group which may have a substituent or
7) a piperazin-1-yl group which may have a substituent; a pharmacologically acceptable salt thereof, or a hydrate of those;

12. The compound according to 5, wherein $R^{7e}$ and/or $R^{21e}$ independently represent $R^{e4}CO$—O—, wherein $R^{e4}$ represents a group of the formula (VI):

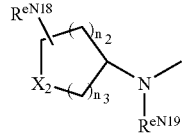

(VI)

wherein $n_2$ and $n_3$, the same or different, independently represent an integer of 0 to 4,
$X_2$ represents
1) —$CHR^{eN21}$—,
2) —$NR^{eN22}$—,
3) —O—,
4) —S—,
5) —SO— or
6) —$SO_2$—,
$R^{eN19}$ represents
1) a hydrogen atom or
2) a $C_1$ to $C_6$ alkyl group which may have a substituent,
$R^{eN20}$ represents
1) a hydrogen atom,
2) a $C_1$ to $C_6$ alkyl group which may have a substituent,
3) a $C_6$ to $C_{14}$ aryl group which may have a substituent or
4) a $C_7$ to $C_{10}$ aralkyl group which may have a substituent,
$R^{eN21}$ represents
1) a hydrogen atom,
2) a $C_1$ to $C_6$ alkyl group which may have a substituent,
3) an unsaturated $C_2$ to $C_{10}$ alkyl group which may have a substituent,
4) a $C_6$ to $C_{14}$ aryl group which may have a substituent,
5) a 5-membered to 14-membered heteroaryl group which may have a substituent,
6) a $C_7$ to $C_{10}$ aralkyl group which may have a substituent,
7) a $C_3$ to $C_8$ cycloalkyl group which may have a substituent,
8) a $C_4$ to $C_9$ cycloalkylalkyl group which may have a substituent,
9) a 5-membered to 14-membered heteroaralkyl group which may have a substituent,
10) —$NR^{eN23}R^{eN24}$, wherein $R^{eN23}$ and $R^{eN24}$, the same or different, independently represent a hydrogen atom or a $C_1$ to $C_6$ alkyl group which may have a substituent or
11) a 5-membered to 14-membered non-aromatic heterocyclic group which may have a substituent and
$R^{eN22}$ represents
1) a hydrogen atom,
2) a $C_1$ to $C_6$ alkyl group which may have a substituent,
3) an unsaturated $C_2$ to $C_{10}$ alkyl group which may have a substituent,
4) a $C_6$ to $C_{14}$ aryl group which may have a substituent,
5) a 5-membered to 14-membered heteroaryl group which may have a substituent,
6) a $C_7$ to $C_{10}$ aralkyl group which may have a substituent,
7) a $C_3$ to $C_8$ cycloalkyl group which may have a substituent,
8) a $C_4$ to $C_9$ cycloalkylalkyl group which may have a 9) a 5-membered to 14-membered heteroaralkyl group which may have a substituent or
10) a 5-membered to 14-membered non-aromatic heterocyclic group which may have a substituent; a pharmacologically acceptable salt thereof, or a hydrate of those;

13. The compound according to 5, wherein $R^{7e}$ and/or $R^{21e}$ independently represent $R^{e5}CO-O-$, wherein $R^{e5}$ represents a group of the formula (VII):

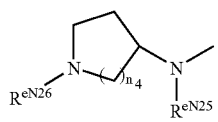

(VII)

wherein $n_4$ represents 1 or 2,
$R^{eN25}$ represents
  1) a hydrogen atom or
  2) a $C_1$ to $C_6$ alkyl group which may have a substituent and
$R^{eN26}$ represents
  1) a hydrogen atom or
  2) a $C_1$ to $C_6$ alkyl group which may have a substituent; a pharmacologically acceptable salt thereof, or a hydrate of those;

14. The compound according to 5, wherein $R^{7e}$ and/or $R^{21e}$ independently represent $R^{e6}CO-O-$, wherein $R^{e6}$ represents a group of the formula (VIII):

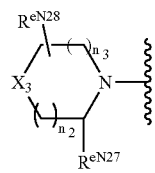

(VIII)

wherein $n_2$ and $n_3$, the same or different, independently represent an integer of 0 to 4,
$X_3$ represents
  1) $-CHR^{eN29}-$,
  2) $-NR^{eN30}-$,
  3) $-O-$,
  4) $-S-$,
  5) $-SO-$ or
  6) $-SO_2-$,
$R^{eN27}$ represents
  1) a hydrogen atom or
  2) a $C_1$ to $C_6$ alkyl group which may have a substituent,
$R^{eN28}$ represents
  1) a hydrogen atom,
  2) a $C_1$ to $C_6$ alkyl group which may have a substituent,
  3) a $C_6$ to $C_{14}$ aryl group which may have a substituent or
  4) a $C_7$ to $C_{10}$ aralkyl group which may have a substituent,
$R^{eN29}$ represents
  1) a hydrogen atom,
  2) a $C_1$ to $C_6$ alkyl group which may have a substituent,
  3) an unsaturated $C_2$ to $C_{10}$ alkyl group which may have a substituent,
  4) a $C_1$ to $C_6$ alkoxy group which may have a substituent,
  5) a $C_6$ to $C_{14}$ aryl group which may have a substituent,
  6) a 5-membered to 14-membered heteroaryl group which may have a substituent,
  7) a $C_7$ to $C_{10}$ aralkyl group which may have a substituent,
  8) a $C_3$ to $C_8$ cycloalkyl group which may have a substituent,
  9) a $C_4$ to $C_9$ cycloalkylalkyl group which may have a substituent,
  10) a 5-membered to 14-membered heteroaralkyl group which may have a substituent,
  11) $-NR^{eN31}R^{eN32}$, wherein $R^{eN31}$ and $R^{eN32}$, the same or different, independently represent a hydrogen atom or a $C_1$ to $C_6$ alkyl group which may have a substituent or form a 5-membered to 14-membered non-aromatic heterocyclic group together with the nitrogen atom to which $R^{eN31}$ and $R^{eN32}$ are bonded or
  12) a 5-membered to 14-membered non-aromatic heterocyclic group which may have a substituent and
$R^{eN30}$ represents
  1) a hydrogen atom,
  2) a $C_1$ to $C_6$ alkyl group which may have a substituent,
  3) an unsaturated $C_2$ to $C_{10}$ alkyl group which may have a substituent,
  4) a $C_6$ to $C_{14}$ aryl group which may have a. substituent,
  5) a 5-membered to 14-membered heteroaryl group which may have a substituent,
  6) a $C_7$ to $C_{10}$ aralkyl group which may have a substituent,
  7) a $C_3$ to $C_8$ cycloalkyl group which may have a substituent,
  8) a $C_4$ to $C_9$ cycloalkylalkyl group which may have a substituent,
  9) a 5-membered to 14-membered heteroaralkyl group which may have a substituent or
  10) a 5-membered to 14-membered non-aromatic heterocyclic group which may have a substituent; a pharmacologically acceptable salt thereof, or a hydrate of those;

15. The compound according to 5, wherein $R^{7e}$ and/or $R^{21e}$ independently represent $R^{e7}CO-O-$, wherein $R^{e7}$ represents a group of the formula (IX):

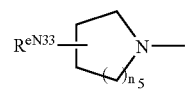

(IX)

wherein $n_5$ represents an integer of 1 to 3, and
$R^{eN33}$ represents
  1) an amino group,
  2) an amino group which may have a substituent,
  3) a pyrrolidin-1-yl group which may have a substituent,
  4) a piperidin-1-yl group which may have a substituent or
  5) a morpholin-4-yl group which may have a substituent; a pharmacologically acceptable salt thereof, or a hydrate of those;

16. The compound according to 5, wherein $R^{7e}$ and/or $R^{21e}$ independently represent $R^{e8}CO-O-$, wherein $R^{e8}$ represents a group of the formula (X):

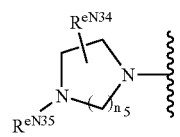

(X)

wherein $n_5$ represents an integer of 1 to 3, $R^{eN34}$ represents
1) a hydrogen atom,
2) a $C_1$ to $C_6$ alkyl group which may have a substituent,
3) a $C_6$ to $C_{14}$ aryl group which may have a substituent or
4) a $C_7$ to $C_{10}$ aralkyl group which may have a substituent and $R^{eN35}$ represents
1) a hydrogen atom,
2) a $C_1$ to $C_6$ alkyl group which may have a substituent,
3) a $C_3$ to $C_8$ cycloalkyl group which may have a substituent,
4) a 3-membered to 8-membered non-aromatic heterocyclic group which may have a substituent,
5) a $C_6$ to $C_{14}$ aryl group which may have a substituent,
6) a 5-membered to 14-membered heteroaryl group which may have a substituent,
7) a $C_7$ to $C_{10}$ aralkyl group which may have a substituent,
8) a 5-membered to 14-membered heteroaralkyl group which may have a substituent or
9) a $C_4$ to $C_9$ cycloalkylalkyl group which may have a substituent; a pharmacologically acceptable salt thereof, or a hydrate of those;

17. The compound according to 5, wherein $R^{7e}$ and/or $R^{21e}$ independently represent $R^{e9}CO$—O—, wherein $R^{e9}$ represents a group of the formula (XI):

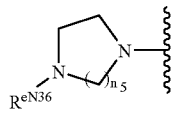

(XI)

wherein $n_5$ represents an integer of 1 to 3, and $R^{eN36}$ represents
1) a hydrogen atom,
2) a $C_1$ to $C_8$ alkyl group which may have a substituent,
3) a $C_3$ to $C_6$ cycloalkyl group which may have a substituent,
4) a $C_4$ to $C_9$ cycloalkylalkyl group which may have a substituent,
5) a $C_7$ to $C_{10}$ aralkyl group which may have a substituent,
6) a pyridyl group which may have a substituent or
7) a tetrahydropyranyl group which may have a substituent; a pharmacologically acceptable salt thereof, or a hydrate of those;

18. The compound according to 5, wherein $R^{7e}$ and/or $R^{21e}$ independently represent $R^{e10}CO$—O—, wherein $R^{e10}$ represents a group of the formula (XII):

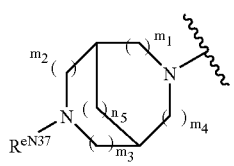

(XII)

wherein $m_1$, $m_2$, $m_3$ and $m_4$, the same or different, independently represent 0 or 1,
$n_5$ represents an integer of 1 to 3, and
$R^{eN37}$ represents
1) a hydrogen atom,
2) a $C_1$ to $C_6$ alkyl group which may have a substituent,
3) an unsaturated $C_2$ to $C_{10}$ alkyl group which may have a substituent,
4) a $C_6$ to $C_{14}$ aryl group which may have a substituent,
5) a 5-membered to 14-membered heteroaryl group which may have a substituent,
6) a $C_7$ to $C_{10}$ aralkyl group which may have a substituent,
7) a $C_3$ to $C_8$ cycloalkyl group which may have a substituent,
8) a $C_4$ to $C_9$ cycloalkylalkyl group which may have a substituent,
9) a 5-membered to 14-membered heteroaralkyl group which may have a substituent or
10) a 5-membered to 14-membered non-aromatic heterocyclic group which may have a substituent; a pharmacologically acceptable salt thereof, or a hydrate of those;

19. The compound according to 5, wherein $R^{7e}$ and/or $R^{21e}$ independently represent $R^{e11}CO$—O—, wherein $R^{e11}$ represents a group of the formula (XIII):

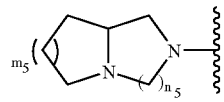

(XIII)

wherein $m_5$ represents an integer of 1 to 3, and $n_5$ represents 2 or 3; a pharmacologically acceptable salt thereof, or a hydrate of those;

20. The compound according to 5, wherein $R^{7e}$ and/or $R^{21e}$ independently represent $R^{e12}CO$—O—, wherein $R^{e12}$ represents a group selected from a group consisting of:

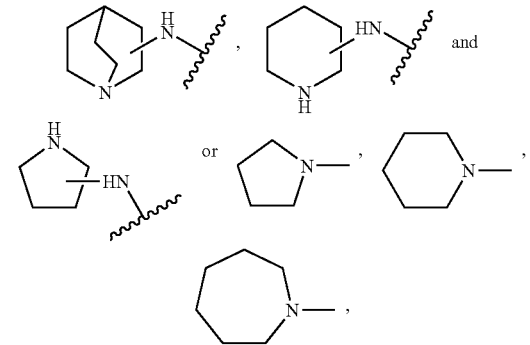

or a group selected from a group consisting of

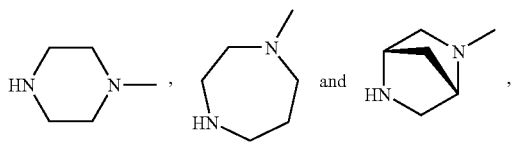

and both of which may have a substituent on the ring; a pharmacologically acceptable salt thereof, or a hydrate of those;

21. The compound according to 1, wherein $R^{16}$ is a hydroxyl group; a pharmacologically acceptable salt thereof, or a hydrate of those;

22. The compound according to 1, wherein

[1] W is

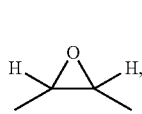

R$^3$ and R$^{21}$ are a hydroxyl group, R$^7$ is an acetoxy group, and R$^{16}$, R$^{17}$, R$^{20}$ and R$^{21'}$ are a hydrogen atom,

[2] W is

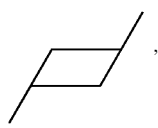

R$^3$ and R$^{21}$ are a hydroxyl group, R$^7$ is an acetoxy group, and R$^{16}$, R$^{17}$, R$^{20}$ and R$^{21'}$ are a hydrogen atom,

[3] W is

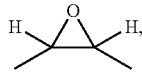

R$^3$, R$^{16}$ and R$^{21}$ are a hydroxyl group, R$^7$ is an acetoxy group, and R$^{17}$, R$^{20}$ and R$^{21'}$ are a hydrogen atom,

[4] W is

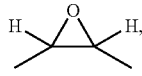

R$^{21}$ and R$^{21'}$ form an oxo group together with the carbon atom to which R$^{21}$ and R$^{21'}$ are bonded, R$^3$, R$^{16}$ and R$^{20}$ are a hydroxyl group, R$^7$ is an acetoxy group, and R$^{17}$ is a hydrogen atom,

[5] W is

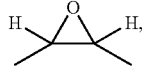

R$^3$, R$^{16}$, R$^{20}$ and R$^{21}$ are a hydroxyl group, R$^7$ is an acetoxy group, and R$^{17}$ and R$^{21'}$ are a hydrogen atom,

[6] W is

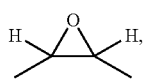

R$^3$, R$^7$, R$^{16}$ and R$^{21}$ are a hydroxyl group, and R$^{17}$, R$^{20}$ and R$^{21'}$ are a hydrogen atom,

[7] W is

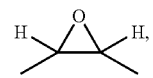

R$^3$, R$^{17}$, R$^{16}$ and R$^{21}$ are a hydroxyl group, R$^7$ is an acetoxy group, and R$^{20}$ and R$^{21'}$ are a hydrogen atom or

[8] W is

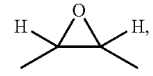

R$^{21}$ and R$^{21'}$ form an oxo group together with the carbon atom to which R$^{21}$ and R$^{21'}$ are bonded, R$^3$ and R$^{16}$ are a hydroxyl group, R$^7$ is an acetoxy group, and R$^{17}$ and R$^{20}$ are a hydrogen atom; a pharmacologically acceptable salt thereof, or a hydrate of those;

23. The compound according to 1, which is (8E,12E,14E)-3,16,21-trihydroxy-6,10,12,16,20-pentamethyl-7-((4-methylpiperazin-1-yl)carbonyl)oxy-18,19-epoxytricosa-8,12,14-trien-11-olide (compound 18),
    (8E,12E,14E)-3,16,21-trihydroxy-6,10,12,16,20-pentamethyl-7-((4-methylhomopiperazin-1-yl)carbonyl)oxy-18,19-epoxytricosa-8,12,14-trien-11-olide (compound 19),
    (8E,12E,14E)-3,16,21-trihydroxy-6,10,12,16,20-pentamethyl-7-((4-(piperidin-1-yl)piperidin-1-yl)carbonyl)oxy-18,19-epoxytricosa-8,12,14-trien-11-olide (compound 21),
    (8E,12E,14E)-7-((4-ethylpiperazin-1-yl)carbonyl)oxy-3,16,21-trihydroxy-6,10,12,16,20-pentamethyl-18,19-epoxytricosa-8,12,14-trien-11-olide (compound 24),
    (8E,12E,14E)-7-(N-(3-(N',N'-dimethylamino)propyl)-N-methylcarbamoyloxy)-3,16,21-trihydroxy-6,10,12,16,20-pentamethyl-18,19-epoxytricosa-8,12,14-trien-11-olide (compound 27),
    (8E,12E,14E)-3,16,21-trihydroxy-6,10,12,16,20-pentamethyl-7-((piperazin-1-yl)carbonyl)oxy-18,19-epoxytricosa-8,12,14-trien-11-olide (compound 28),
    (8E,12E,14E)-3,16,21-trihydroxy-6,10,12,16,20-pentamethyl-7-(N-methyl-N-(1-methylpiperidin-4-yl)carbamoyloxy)-18,19-epoxytricosa-8,12,14-trien-11-olide (compound 29),
    (8E,12E,14E)-3,16,21-trihydroxy-7-((4-isopropylhomopiperazin-1-yl)carbonyl)oxy-6,10,12,16,20-pentamethyl-18,19-epoxytricosa-8,12,14-trien-11-olide (compound 39), (8E,12E,14E)-3,16,21-trihydroxy-7-((4-(4-hydroxypiperidin-1-yl)piperidin-1-yl)carbonyl)oxy-6,10,12,16,20-pentamethyl-18,19-epoxytricosa-8,12,14-trien-11-olide (compound 40),
    (8E,12E,14E)-3,16,21-trihydroxy-6,10,12,16,20-pentamethyl-7-((4-(morpholin-4-yl)piperidin-1-yl)carbonyl)oxy-18,19-epoxytricosa-8,12,14-trien-11-olide (compound 42),
    (8E,12E,14E)-7-((4-ethylhomopiperazin-1-yl)carbonyl)oxy-3,16,21-trihydroxy-6,10,12,16,20-pentamethyl-18,19-epoxytricosa-8,12,14-trien-11-olide (compound 43), (8E,12E,14E)-3,16,21-trihydroxy-7-((4-isopropylpiperazin-1-yl)carbonyl)oxy-6,10,12,16,20-pentamethyl-18,19-epoxytricosa-8,12,14-trien-11-olide (compound 44), (8E,12E,14E)-3,16,21-trihydroxy-7-(((1S,4S)-5-isopropyl-2,5-diazabicyclo[2.2.1]heptan-2-yl)carbonyl)oxy-6,10,12,16,20-pentamethyl-18,19-epoxytricosa-8,12,14-trien-11-olide (compound 49), (8E,12E,14E)-7-(N-(2-(N',N'-dimethylamino)ethyl)-N-methylcarbamoyloxy)-3,16,21-trihydroxy-6,10,12,16,20-pentamethyl-18,19-epoxytricosa-8,12,14-trien-11-olide (compound 50), (8E,12E,14E)-7-(N-(2-(N',N'-dimethylamino)ethyl)carbamoyloxy)-3,16,21-trihydroxy-6,10,12,16,20-pentamethyl-18,19-epoxytricosa-8,12,14-trien-11-olide (compound 51) or (8E,12E,14E)-3,16,21-trihydroxy-6,10,12,16,20-pentamethyl-7-(((1S,4S)-5-methyl-2,5-diazabicyclo[2.2.1]heptan-2-yl)carbonyl)oxy-18,19-epoxytricosa-8,12,14-trien-11-olide (compound 55);

24. The compound according to 1, which is (8E,12E,14E)-3,16,21-trihydroxy-6,10,12,16,20-pentamethyl-7-(N-methyl-N-(1-methylpiperidin-4-yl)carbamoyloxy)-18,19-epoxytricosa-8,12,14-trien-11-olide (compound 29), (8E,12E,14E)-3,16,21-trihydroxy-7-((4-isopropylhomopiperazin-1-yl)carbonyl)oxy-6,10,12,16,20-pentamethyl-18,19-epoxytricosa-8,12,14-trien-11-olide (compound 39), (8E,12E,14E)-7-((4-ethylhomopiperazin-1-yl)carbonyl)oxy-3,16,21-trihydroxy-6,10,12,16,20-pentamethyl-18,19-epoxytricosa-8,12,14-trien-11-olide (compound 43), (8E,12E,14E)-3,16,21-trihydroxy-7-((4-isopropylpiperazin-1-yl)carbonyl)oxy-6,10,12,16,20-pentamethyl-18,19-epoxytricosa-8,12,14-trien-11-olide (compound 44) or (8E,12E,14E)-3,16,21-trihydroxy-6,10,12,16,20-pentamethyl-7-(((1S,4S)-5-methyl-2,5-diazabicyclo[2.2.1]heptan-2-yl)carbonyl)oxy-18,19-epoxytricosa-8,12,14-trien-11-olide (compound 55);

25. A medicine comprising the compound according to any one of 1 to 24, a pharmacologically acceptable salt thereof, or a hydrate of those as an active ingredient;

26. A pharmaceutical composition comprising the compound according to any one of 1 to 24, a pharmacologically acceptable salt thereof, or a hydrate of those as an active ingredient;

27. The medicine according to 25 as an agent for preventing or treating a disease for which gene expression control is effective;

28. The medicine according to 25 as an agent for preventing or treating a disease for which suppression of VEGF production is effective;

29. The medicine according to 25 as an agent for preventing or treating a disease for which an antiangiogenic effect is effective;

30. The medicine according to 25 as an angiogenesis inhibitor;

31. The medicine according to 25 as an antitumor agent;

32. The medicine according to 25 as a therapeutic agent for treating hemangioma;

33. The medicine according to 25 as a cancer metastasis inhibitor;

34. The medicine according to 25 as a therapeutic agent for treating retinal neovascularization or diabetic retinopathy;

35. The medicine according to 25 as a therapeutic agent for treating inflammatory disease;

36. The medicine according to 25 as a therapeutic agent for treating inflammatory diseases consisting of deforamant arthritis, rheumatoid arthritis, psoriasis, and delayed hypersensitive reaction;

37. The medicine according to 25 as a therapeutic agent for treating atherosclerosis;

38. The medicine according to 25 as a therapeutic agent for treating a solid cancer;

39. The medicine according to 38, wherein the solid tumor is lung cancer, brain tumor, breast cancer, prostate cancer, ovarian cancer, colon cancer or melanoma;

40. The medicine according to 25 as a therapeutic agent for treating leukemia;

41. The medicine according to 25 as an antitumor agent based on gene expression control;

42. The medicine according to 25 as an antitumor agent based on VEGF suppression of production;

43. The medicine according to 25 as an antitumor agent based on an effect of angiogenesis inhibition;

44. A method for preventing or treating a disease for which gene expression control is effective, comprising administering a pharmacologically effective dose of the medicine according to 25 to a patient.

45. A method for preventing or treating a disease for which suppression of VEGF production is effective, comprising administering a pharmacologically effective dose of the medicine according to 25 to a patient;

46. A method for preventing or treating a disease for which angiogenesis inhibition is effective, comprising administering a pharmacologically effective dose of the medicine according to 25 to a patient;

47. Use of the compound according to any one of 1 to 24, a pharmacologically acceptable salt thereof or a hydrate of those, for manufacturing an agent for preventing or treating a disease for which gene expression control is effective;

48. Use of the compound according to any one of 1 to 24, a pharmacologically acceptable salt thereof or a hydrate of those, for manufacturing an agent for preventing or treating a disease for which suppression of VEGF production is effective;

49. Use of the compound according to any of 1 to 24, a pharmacologically acceptable salt thereof or a hydrate of those, for manufacturing an agent for preventing or treating a disease for which angiogenesis inhibition is effective;

50. Use of the compound according to any one of 1 to 24, a pharmacologically acceptable salt thereof or a hydrate of those, for manufacuturing an agent for preventing or treating a solid cancer;

51. A method for producing a 6-deoxy 11107 compound, characterized in that the method comprises culturing a microorganism belonging to the genus *Streptomyces*, which is capable of producing a compound of the formula (I):

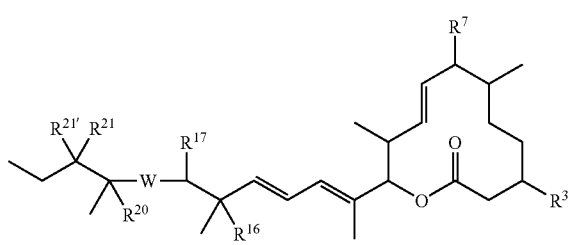

(I)

wherein [1] W is

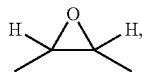

$R^3$ and $R^{21}$ are a hydroxyl group, $R^7$ is an acetoxy group, and $R^{16}$, $R^{17}$, $R^{20}$ and $R^{21'}$ are a hydrogen atom or

[2] W is

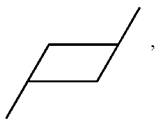

$R^3$ and $R^{21}$ are a hydroxyl group, $R^7$ is an acetoxy group, and $R^{16}$, $R^{17}$, $R^{20}$ and $R^{21'}$ are a hydrogen atom; and collecting the compound as defined in [1] or [2] (hereinafter referred to as "6-deoxy 11107 compound") from the culture;

52. *Streptomyces* sp. strain A-1543 (FERM BP-8442) that is capable of producing the 6-deoxy 11107 compound according to 51;

53. A method for producing a 6-deoxy compound by biologically converting for compound of the formula (I):

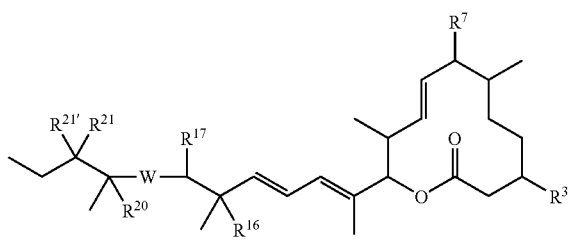

(I)

wherein [1] W is

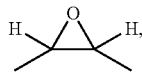

$R^3$ and $R^{21}$ are a hydroxyl group, $R^7$ is an acetoxy group, and $R^{16}$, $R^{17}$, $R^{20}$ and $R^{21'}$ are a hydrogen atom (hereinafter referred to as "6-deoxy 11107B") into a compound of the formula (I), wherein

[3] W is

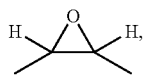

$R^3$, $R^{16}$ and $R^{21}$ are a hydroxyl group, $R^7$ is an acetoxy group, and $R^{17}$, $R^{20}$ and $R^{21'}$ are a hydrogen atom,

[4] W is

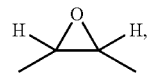

$R^{21}$ and $R^{21'}$ form an oxo group together with the carbon atom to which $R^{21}$ and $R^{21'}$ are bonded, $R^3$, $R^{16}$ and $R^{20}$ are a hydroxyl group, $R^7$ is an acetoxy group, and $R^{17}$ is a hydrogen atom,

[5] W is

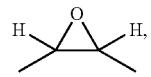

$R^3$, $R^{16}$, $R^{20}$ and $R^{21}$ are a hydroxyl group, $R^7$ is an acetoxy group, and $R^{17}$ and $R^{21'}$ are a hydrogen atom,

[6] W is

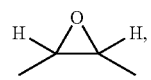

$R^3$, $R^7$, $R^{16}$ and $R^{21}$ are a hydroxyl group, and $R^{17}$, $R^{20}$ and $R^{21'}$ are a hydrogen atom,

[7] W is

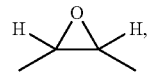

$R^3$, $R^{17}$, $R^{16}$ and $R^{21}$ are a hydroxyl group, $R^7$ is an acetoxy group, and $R^{20}$ and $R^{21'}$ are a hydrogen atom or

[8] W is

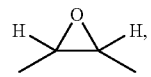

$R^{21}$ and $R^{21'}$ form an oxo group together with the carbon atom to which $R^{21}$ and $R^{21'}$ are bonded, $R^3$ and $R^{16}$ are a hydroxyl group, $R^7$ is an acetoxy group, and $R^{17}$ and $R^{20}$ are a hydrogen atom (these compounds are hereinafter referred to as "6-deoxy compounds"), comprising 1) a step that can conduct the biological conversion, the step of incubating 6-deoxy 11107B in the presence of a culture solution of a strain selected from microorganisms belonging to bacteria or a product prepared from culture cells of the strain, and 2) collecting a 6-deoxy compound from the incubated solution;

54. The method according to 53, wherein the microorganism belonging to bacteria is strain A-1544 (FERM BP-8446) or strain A-1545 (FERM BP-8447); and 55. Strain A-1544 (FERM BP-8446) or strain A-1545 (FERM BP-8447) which is capable of converting 6-deoxy 11107B into a 6-deoxy compound.

BEST MODE FOR CARRYING OUT THE INVENTION

Various terms, symbols, and the like used in the present specification will be described.

In the present specification, a chemical formula of the compound of the present invention is illustrated as a plan chemical formula for convenience. However, the present invention can include given isomers derived from the chemical formula. The present invention can include all isomers and mixtures of such as geometric isomers which are generated from the confirguration of the compound, optical isomers based on asymmetric carbon, rotamers, stereoisomers, and tautomers, and mixtures of these isomers. The present invention is not limited to the expediential description of a chemical formula, and can include any one of the above-described isomers or mixtures thereof. Accordingly, the compound of the present invention exist as an optically active substance or racemate when the compound has an asymmetric carbon atom in the molecule, and both the optically active substance and the racemate are included in the present invention. Although crystal polymorphs of the compound may be present, the compound is not limited to only one crystal form and may be present as a single crystal form or a mixture of multiple crystal forms. The compound of the formula (I) of the present invention or its salt may be an anhydrate or hydrate. Both an anhydrate and a hydrate are included in the present invention. A metabolite generated by decomposition of the compound of the formula (I) of the present invention in vivo, and a prodrug of the compound of the formula (I) of the present invention or its salt are included in the present invention.

The "halogen atom" used in the specification of the present application refers to a fluorine atom, chlorine atom, bromine atom and iodine atom. For example, a fluorine atom, chlorine atom and bromine atom are preferable. Of these, for example, a fluorine atom and chlorine atom are typically preferable.

The "$C_1$ to $C_{22}$ alkyl group" used in the specification of the present application refers to a linear or branched alkyl group having 1 to 22 carbon atoms. Examples include a methyl group, ethyl group, n-propyl group, iso-propyl group, n-butyl group, iso-butyl group, sec-butyl group, tert-butyl group, n-pentyl group, 1,1-dimethylpropyl group, 1,2-dimethylpropyl group, 2,2-dimethylpropyl group, 1-ethylpropyl group, n-hexyl group, 1-ethyl-2-methylpropyl group, 1,1,2-trimethylpropyl group, 1-propylpropyl group, 1-methylbutyl group, 2-methylbutyl group, 1,1-dimethylbutyl group, 1,2-dimethylbutyl group, 2,2-dimethylbutyl group, 1,3-dimethylbutyl group, 2,3-dimethylbutyl group, 2-ethylbutyl group, 2-methylpentyl group, 3-methylpentyl group, n-heptyl group, n-octyl group, n-nonyl group and n-decyl group.

The "$C_1$ to $C_{22}$ alkyl group" preferably refers to a linear or branched alkyl group having 1 to 6 carbon atoms. Examples include a methyl group, ethyl group, n-propyl group, iso-propyl group, n-butyl group, iso-butyl group, sec-butyl group, tert-butyl group and n-pentyl group. Of these, for example, a methyl group, ethyl group, propyl group, iso-propyl group, n-butyl group, iso-butyl group and tert-butyl group are preferable.

The "unsaturated $C_2$ to $C_{22}$ alkyl group" used in the specification of the present application refers to a linear or branched alkenyl group having 2 to 22 carbon atoms or a linear or branched alkynyl group having 2 to 22 carbon atoms. Examples include a vinyl group, allyl group, 1-propenyl group, iso-propenyl group, 2-methyl-1-propenyl group, 2-methyl-2-propenyl group, 1-butenyl group, 2-butenyl group, 3-butenyl group, 1-pentenyl group, 1-hexenyl group, 1,3-hexanedienyl group, 1,5-hexanedienyl group, ethynyl group, 1-propynyl group, 2-propynyl group, 1-butynyl group, 2-butynyl group, 3-butynyl group, 1-ethynyl-2-propynyl group, 2-methyl-3-butynyl group, 1-pentynyl group, 1-hexynyl group, 1,3-hexanediynyl group and 1,5-hexanediynyl group. The "unsaturated $C_2$ to $C_{22}$ alkyl group" preferably refers to a linear or branched alkenyl group having 2 to 10 carbon atoms or a linear or branched alkynyl group having 2 to 10 carbon atoms. Preferable examples include a vinyl group, allyl group, 1-propenyl group, isopropenyl group, 3-methyl-2-butenyl group, 3,7-dimethyl-2,6-octadienyl group, ethynyl group, 1-propynyl group, 2-propynyl group, 1-butynyl group, 2-butynyl group, 3-butynyl group and 3-methyl-1-propynyl group.

The "$C_6$ to $C_{14}$ aryl group" used in the specification of the present application refers to an aromatic hydrocarbon group composed of 6 to 14 carbon atoms and includes a monocyclic group and condensed ring such as a bicyclic group, or tricyclic group. Examples include a phenyl group, indenyl group, 1-naphthyl group, 2-naphthyl group, azulenyl group, heptalenyl group, indacenyl group, acenaphthyl group, fluorenyl group, phenalenyl group, phenanthrenyl group and anthracenyl group. For example, a phenyl group, 1-naphthyl group, and 2-naphthyl group are preferable.

The "5-membered to 14-membered heteroaryl group" in the specification of the present application refers to a monocyclic, bicyclic, or tricyclic 5-membered to 14-membered aromatic heterocyclic group containing one or more hetero atoms selected from the group consisting of a nitrogen atom, sulfur atom and oxygen atom. Preferable examples include nitrogen-containing aromatic heterocyclic group such as a pyrrolyl group, pyridinyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, quinolinyl group, isoquinolinyl group, quinolizinyl group, phthalazinyl group, naphthylidinyl group, quinoxalinyl group, quinazolinyl group, cinnolinyl group, pteridinyl group, imidazotriazinyl group, pyrazinopyridazinyl group, acridinyl group, phenanthridinyl group, carbazolyl group, carbazolinyl group, perimidinyl group, phenanthrolinyl group, phenazinyl group, imidazopyridinyl group, imidazopyrimidinyl group, pyrazolopyridinyl group and pyrazolopyridinyl group; sulfur-containing aromatic heterocyclic group such as a thienyl group and benzothienyl group; oxygen-containing aromatic heterocyclic group such as a furyl group, pyranyl group, cyclopentapyranyl group, benzofuryl group and isobenzofuryl group; and aromatic heterocyclic groups containing two or more different hetero atoms such as a thiazolyl group, isothiazolyl group, benzothiazolyl group, benzothiadiazolyl group, phenothiazinyl group, isoxazolyl group, furazanyl group, phenoxazinyl group, oxazolyl group, isoxazoyl group, benzoxazolyl group, oxadiazolyl group, pyrazolooxazolyl group, imidazothiazolyl group, thienofuranyl group, furopyrrolyl group and pyridoxazinyl group. For example, a thienyl group, furyl group, pyridinyl group, pyridazinyl group, pyrimidinyl-group and pyrazinyl group are preferable.

The "3-membered to 14-membered non-aromatic heterocyclic group" in the specification of the present application refers to a monocyclic, bicyclic, or tricyclic 3-membered to 14-membered non-aromatic heterocyclic group, which may contain one or more hetero atoms selected from the group consisting of a nitrogen atom, sulfur atom and oxygen atom.

Preferable examples include an aziridinyl group, azetidyl group, pyrrolidinyl group, pyrrolyl group, piperidinyl group, piperazinyl group, homopiperidinyl group, homopiperazinyl group, imidazolyl group, pyrazolidinyl group, imidazolidinyl group, morpholinyl group, thiomorpholinyl group, imidazolinyl group, oxazolinyl group, 2,5-diazabicyclo[2.2.1]heptyl group, 2,5-diazabicyclo[2.2.2]octyl group, 3,8-diazabicyclo[3.2.1]octyl group, 1,4-diazabicyclo[4.3.0]nonyl group, quinuclidinyl group, tetrahydrofuranyl group and tetrahydrothiophenyl group. The above-described non-aromatic heterocyclic groups include a group derived from a pyridone ring, and a non-aromatic condensed ring (for example, a group derived from a phthalimide ring, succinimide ring or the like).

The "$C_7$ to $C_{22}$ aralkyl group" used in the specification of the present application refers to a group of the above-defined "$C_1$ to $C_{22}$ alkyl group" on which the above-defined "$C_6$ to $C_{14}$ aryl group" is substituted as a substituent for replaceble moiety thereof. Specific examples include a benzyl group, phenethyl group, 3-phenylpropyl group, 4-phenylbutyl group, 1-naphthylmethyl group and 2-naphthylmethyl group. An aralkyl group having 7 to 10 carbon atoms, for example, a benzyl group or phenethyl group, is preferable.

The "5-membered to 14-membered heteroaralkyl group" used in the specification of the present application refers a group of the above-defined "$C_1$ to $C_{22}$ alkyl group" having the above-defined "5-membered to 14-membered heteroaryl group" as a substituent. Specific examples include a thienylmethyl group, furylmethyl group, pyridinylmethyl group, pyridazinylmethyl group, pyrimidinylmethyl group, and pyrazinyl methyl group. For example, a thienylmethyl group, furylmethyl group and pyridinylmethyl group are preferable.

The "$C_3$ to $C_{14}$ cycloalkyl group" used in the specification of the present application refers to a cycloalkyl group composed of 3 to 14 carbon atoms. Examples of the suitable group include a cyclopropyl group, cyclobutyl group, cyclopentyl group, cyclohexyl group, cycloheptyl group and cyclooctyl group. For example, a cyclopentyl group, a cyclohexyl group, cycloheptyl group and cyclooctyl group are preferable.

The "$C_4$ to $C_9$ cycloalkylalkyl group" used in the specification of the present application refers to a group of the above-defined "$C_1$ to $C_{22}$ alkyl group" having the above-defined "$C_3$ to $C_{14}$ cycloalkyl group" as a substituent. Specific examples include a cyclopropylmethyl group, cyclobutylmethyl group, cyclopentylmethyl group, cyclohexylmethyl group, cycloheptylmethyl group and cyclooctylmethyl group. For example, a cyclopropylmethyl group, cyclobutylmethyl group and cyclopentylmethyl group are preferable.

The "$C_1$ to $C_{22}$ alkoxy group" used in the specification of the present application refers to a group obtained by bonding an oxygen atom to a terminal of the above-defined "$C_1$ to $C_{22}$ alkyl group". Examples of the suitable group include a methoxy group, ethoxy group, n-propoxy group, iso-propoxy group, n-butoxy group, iso-butoxy group, sec-butoxy group, tert-butoxy group, n-pentyloxy group, iso-pentyloxy group, sec-pentyloxy group, n-hexyloxy group, iso-hexyloxy group, 1,1-dimethylpropyloxy group, 1,2-dimethylpropoxy group, 2,2-dimethylpropyloxy group, 1-ethyl-2-methylpropoxy group, 1,1,2-trimethylpropoxy group, 1,2,2-trimethylpropoxy group, 1,1-dimethylbutoxy group, 1,2-dimethylbutoxy group, 2,2-dimethylbutoxy group, 2,3-dimethylbutyloxy group, 1,3-dimethylbutoxy group, 2-ethylbutoxy group, 2-methylpentoxy group, 3-methylpentoxy group and hexyloxy group. For example, a methoxy group, ethoxy group, n-propoxy group, iso-propoxy group, iso-butoxy group and 2,2-dimethylpropyloxy group are preferable.

The "unsaturated $C_2$ to $C_{22}$ alkoxy group" used in the specification of the present application refers to a group obtained by bonding an oxygen atom to a terminal of the above-defined "unsaturated $C_2$ to $C_{22}$ alkyl group". Examples of the suitable group include a vinyloxy group, allyloxy group, 1-propenyloxy group, isopropenyloxy group, 2-methyl-1-propenyloxy group, 2-methyl-2-propenyloxy group, 1-butenyloxy group, 2-butenyloxy group, 3-butenyloxy group, 1-pentenyloxy group, 1-hexenyloxy group, 1,3-hexanedienyloxy group, 1,5-hexanedienyloxy group, propargyloxy group and 2-butynyloxy group. For example, an allyloxy group, propargyloxy group and 2-butynyloxy group are preferable.

The "$C_6$ to $C_{14}$ aryloxy group" used in the specification of the present application refers to a group obtained by bonding an oxygen atom to a terminal of the above-defined "$C_6$ to $C_{14}$ aryl group". Specific examples include a phenyloxy group, indenyloxy group, 1-naphthyloxy group, 2-naphthyloxy group, azulenyloxy group, heptalenyloxy group, indacenyloxy group, acenaphthyloxy group, fluorenyloxy group, phenalenyloxy group, phenanthrenyloxy group, and anthracenyloxy group. For example, a phenyloxy group, 1-naphthyloxy group and 2-naphthyloxy group are preferable.

The "$C_7$ to $C_{22}$ aralkyloxy group" used in the specification of the present application refers to a group obtained by bonding an oxygen atom to a terminal of the above-defined "$C_7$ to $C_{22}$ aralkyl group". Specific examples include a benzyloxy group, phenethyloxy group, 3-phenylpropyloxy group, 4-phenylbutyloxy group, 1-naphthylmethyloxy group and 2-naphthylmethyloxy group. For example, a benzyloxy group is preferable.

The "5-membered to 14-membered heteroaralkyloxy group" used in the specification of the present application refers to a group obtained by bonding an oxygen atom to a terminal of the above-defined "5-membered to 14-membered heteroaralkyl group". Specific examples include a thienylmethyloxy group, furylmethyloxy group, pyridinylmethyloxy group, pyridazinylmethyloxy group, pyrimidinylmethyloxy group and pyrazinylmethyloxy group. For example, a thienylmethyloxy group, furylmethyloxy group and pyridinylmethyloxy group are preferable.

The "5-membered to 14-membered heteroaryloxy group" used in the specification of the present application refers to a group obtained by bonding an oxygen atom to a terminal of the above-defined "5-membered to 14-membered heteroaryl group". Specific examples include a pyrrolyloxy group, pyridinyloxy group, pyridazinyloxy group, pyrimidinyloxy group, pyrazinyloxy group, triazolyloxy group, tetrazolyloxy group, benzotriazolyloxy group, pyrazolyloxy group, imidazolyloxy group, benzimidazolyloxy group, indolyloxy group, isoindolyloxy group, indolizinyloxy group, purinyloxy group, indazolyloxy group, quinolinyloxy group, isoquinolinyloxy group, quinolizinyloxy group, phthalazyloxy group, naphthyridinyloxy group, quinoxalinyloxy group, quinazolinyloxy group, cinnolinyloxy group, pteridinyloxy group, imidazotriazinyloxy group, pyrazinopyridazinyloxy group, acridinyloxy group, phenanthridinyloxy group, carbazolyloxy group, carbazolinyloxy group, perimidinyloxy group, phenanthrolinyloxy group, phenazinyloxy group, imidazopyridinyloxy group, imidazopyrimidinyloxy group, pyrazolopyridinyloxy group, pyrazolopyridinyloxy group, thienyloxy group, benzothienyloxy group, furyloxy group, pyranyloxy group, cyclopentapyranyloxy group, benzofuryloxy group, isobenzofuryloxy group, thiazolyloxy group, isothiazolyloxy group, benzothiazolyloxy group, benzothiadiazolyloxy group, phenothiazinyloxy group, isoxazolyloxy group, furazanyloxy group, phenoxazinyloxy group, oxazolyloxy group, isoxazolyloxy group, benzoxazolyloxy group, oxadiazolyloxy group, pyrazolooxazolyloxy group, imidazothiazolyloxy group, thienofuranyloxy group, furopyrrolyloxy group and pyridoxazinyloxy group. For example, a thienyloxy group, pyridinyloxy group, pyrimidinyloxy group and pyrazinyloxy group are preferable.

The "aliphatic $C_2$ to $C_{22}$ acyl group" used in the specification of the present application refers to a group obtained by bonding a carbonyl group to a terminal of the above-defined "$C_1$ to $C_{22}$ alkyl group" or "unsaturated $C_2$ to $C_{22}$ alkyl group". Examples include an acetyl group, propionyl group, butyryl group, iso-butyryl group, valeryl group, iso-valeryl group, pivaloyl group, caproyl group, decanoyl group, lauroyl group, myristoyl group, palmitoyl group, stearoyl group, arachidoyl group, acryloyl group, propioloyl group, crotonoyl group, iso-crotonoyl group, oleoyl group and linolenoyl group. An aliphatic acyl group having 2 to 6 carbon atoms, for example, an acetyl group, propionyl group, butyryl group, isobutyryl group and acryloyl group are preferable.

The "aromatic $C_7$ to $C_{15}$ acyl group" used in the specification of the present application refers to a group obtained by bonding a carbonyl group to a terminal of the above-defined "$C_6$ to $C_{14}$ aryl group" or "5-membered to 14-membered heteroaryl group". Examples include a benzoyl group, 1-naphthoyl group, 2-naphthoyl group, picolinoyl group, nicotinoyl group, isonicotinoyl group, furoyl group and thiophenecarbonyl group. For example, a benzoyl group, picolinoyl group, nicotinoyl group and isonicotinoyl group are preferable.

The "$C_1$ to $C_{22}$ alkylsulfonyl group" used in the specification of the present application refers to a sulfonyl group to which the above-defined "$C_1$ to $C_{22}$ alkyl group" is bonded. Specific examples include a methanesulfonyl group, ethanesulfonyl group, n-propanesulfonyl group and iso-propanesulfonyl group. For example, a methanesulfonyl group is preferable.

The "$C_6$ to $C_{14}$ arylsulfonyl group" used in the specification of the present application refers to a sulfonyl group to which the above-defined "$C_6$ to $C_{14}$ aryl group" is bonded. Specific examples include a benzenesulfonyl group, 1-naphthalenesulfonyl group and 2-naphthalenesulfonyl group. For example, a benzenesulfonyl group is preferable.

The "aliphatic $C_2$ to $C_{22}$ acyloxy group" used in the specification of the present application refers to a group obtained by bonding an oxygen atom to a terminal of the above-defined "aliphatic $C_2$ to $C_{22}$ acyl group". Examples include an acetoxy group, propionyloxy group and acryloxy group. For example, an acetoxy group and propionyloxy group are preferable.

The "$C_2$ to $C_{22}$ alkoxycarbonyl group" used in the specification of the present application refers to a group obtained by bonding a carbonyl group to a terminal of the above-defined "$C_1$ to $C_{22}$ alkoxy group". Examples include a methoxycarbonyl group, ethoxycarbonyl group, n-propoxycarbonyl group, iso-propoxycarbonyl group, n-butoxycarbonyl group, iso-butoxycarbonyl group, sec-butoxycarbonyl group, and tert-butoxycarbonyl group. For example, an ethoxycarbonyl group, iso-propoxycarbonyl group and tert-butoxycarbonyl group are preferable.

The "unsaturated $C_3$ to $C_{22}$ alkoxycarbonyl group" used in the specification of the present application refers to a group obtained by bonding a carbonyl group to a terminal of the above-defined "unsaturated $C_2$ to $C_{22}$ alkoxy group". Examples include a vinyloxycarbonyl group, allyloxycarbonyl group, 1-propenyloxycarbonyl group, iso-propenyloxycarbonyl group, propargyloxycarbonyl group and 2-butynyloxycarbonyl group. For example, an allyloxycarbonyl group is preferable.

The "$C_1$ to $C_{22}$ alkylthio group" used in the specification of the present application refers to a group obtained by bonding a sulfur atom to a terminal of the above-defined "$C_1$ to $C_{22}$ alkyl group". Examples include a methylthio group, ethylthio group, n-propylthio group and iso-propylthio group. For example, a methylthio group and ethylthio group are preferable.

The "$C_1$ to $C_{22}$ alkylsulfinyl group" used in the specification of the present application refers to a group obtained by bonding a sulfinyl group to a terminal of the above-defined "$C_1$ to $C_{22}$ alkyl group". Examples include a methylthio group, ethylthio group, n-propylthio group and iso-propylthio group. For example, a methylsulfinyl group and ethylsulfinyl group are preferable.

The "$C_1$ to $C_{22}$ alkylsulfonyloxy group" used in the specification of the present application refers to a group obtained by bonding an oxygen atom to a terminal of the above-defined "$C_1$ to $C_{22}$ alkylsulfonyl group". Examples include a methanesulfonyloxy group, ethanesulfonyloxy group, n-propanesulfonyloxy group and iso-propanesulfonyloxy group. For example, a methylsulfonyloxy group is preferable.

Given as the substituent in a group "which may have a substituent" used in the specification of the present application is one or more groups selected from:

(1) a halogen atom,
(2) a hydroxyl group,
(3) a thiol group,
(4) a nitro group,
(5) a nitroso group,
(6) a cyano group,
(7) a carboxyl group,
(8) a sulfonyloxy group,
(9) an amino group,
(10) a $C_1$ to $C_{22}$ alkyl group
(for example, a methyl group, ethyl group, n-propyl group, iso-propyl group, n-butyl group, iso-butyl group, sec-butyl group or tert-butyl group),
(11) an unsaturated $C_2$ to $C_{22}$ alkyl group
(for example, a vinyl group, allyl group, 1-propenyl group, isopropenyl group, ethynyl group, 1-propynyl group, 2-propynyl group, 1-butynyl group, 2-butynyl group or 3-butynyl group),
(12) a $C_6$ to $C_{14}$ aryl group
(for example, a phenyl group, 1-naphthyl group or 2-naphthyl group),
(13) a 5-membered to 14-membered heteroaryl group
(for example, a thienyl group, furyl group, pyridinyl group, pyridazinyl group, pyrimidinyl group or pyrazinyl group),
(14) a 3-membered to 14-membered non-aromatic heterocyclic group
(for example, an aziridinyl group, azetidyl group, pyrrolidinyl group, pyrrolyl group, piperidinyl group, piperazinyl group, homopiperidinyl group, homopiperazinyl group, imidazolyl group, pyrazolidinyl group, imidazolidyl group, morpholinyl group, thiomorpholinyl group, imidazolinyl group, oxazolinyl group or quinuclidinyl group),

(15) a $C_3$ to $C_{14}$ cycloalkyl group (for example, a cyclopropyl group, cyclobutyl group, cyclopentyl group, cyclohexyl group, cycloheptyl group or cyclooctyl group),

(16) a $C_1$ to $C_{22}$ alkoxy group
(for example, a methoxy group, ethoxy group, n-propoxy group, iso-propoxy group, sec-propoxy group, n-butoxy group, iso-butoxy group or tert-butoxy group),

(17) an unsaturated $C_2$ to $C_{22}$ alkoxy group
(for example, a vinyloxy group, allyloxy group, 1-propenyloxy group, isopropenyloxy group, ethynyloxy group, 1-propynyloxy group, 2-propynyloxy group, 1-butynyloxy group or 2-butynyloxy group),

(18) a $C_6$ to $C_{14}$ aryloxy group
(for example, a phenyloxy group, 1-naphthyloxy group or 2-naphthyloxy group),

(19) a $C_7$ to $C_{22}$ aralkyloxy group (for example, a benzyloxy group, phenethyloxy group, 3-phenylpropyloxy group, 4-phenylbutyloxy group, 1-naphthylmethyloxy group or 2-naphthylmethyloxy group),

(20) a 5-membered to 14-membered heteroaralkyloxy group
(for example, a thienylmethyloxy group, furylmethyloxy group, pyridinylmethyloxy group, pyridazinylmethyloxy group, pyrimidinylmethyloxy group or pyrazinylmethyloxy group),

(21) a 5-membered to 14-membered heteroaryloxy group
(for example, a thienyloxy group, furyloxy group, pyridinyloxy group, pyridazinyloxy group, pyrimidinyloxy group or pyrazinyloxy group),

(22) an aliphatic $C_2$ to $C_{22}$ acyl group
(for example, an acetyl group, propionyl group, butyryl group, iso-butyryl group, valeryl group, iso-valeryl group, pivaloyl group, caproyl group, decanoyl group, lauroyl group, myristoyl group, palmitoyl group, stearoyl group, arachidoyl group, acryloyl group, propioloyl group, crotonoyl group, iso-crotonoyl group, oleoyl group or linolenoyl group),

(23) an aromatic $C_7$ to $C_{15}$ acyl group
(for example, a benzoyl group, 1-naphthoyl group or 2-naphthoyl group),

(24) an aliphatic $C_2$ to $C_{22}$ acyloxy group
(for example, an acetoxy group, propionyloxy group or acryloxy group),

(25) a $C_2$ to $C_{22}$ alkoxycarbonyl group
(for example, a methoxycarbonyl group, ethoxycarbonyl group, n-propoxycarbonyl group, iso-propoxycarbonyl group, n-butoxycarbonyl group, iso-butoxycarbonyl group, sec-butoxycarbonyl group or tert-butoxycarbonyl group),

(26) an unsaturated $C_3$ to $C_{22}$ alkoxycarbonyl group
(for example, a vinyloxycarbonyl group, allyloxycarbonyl group, 1-propenyloxycarbonyl group, isopropenyloxycarbonyl group, propargyloxycarbonyl group or 2-butynyloxycarbonyl group),

(27) a $C_1$ to $C_{22}$ alkylthio group
(for example, a rnethylthio group, ethylthio group, n-propylthio group or iso-propylthio group),

(28) a $C_1$ to $C_{22}$ alkylsulfinyl group
(for example, a methylsulfinyl group, ethylsulfinyl group, n-propanesulfinyl group or iso-propanesulfinyl group),

(29) a $C_1$ to $C_{22}$ alkylsulfonyl group
(for example, a methanesulfonyl group, ethanesulfonyl group, n-propanesulfonyl group or iso-propanesulfonyl group),

(30) a $C_6$ to $C_{14}$ arylsulfonyl group
(for example, a benzenesulfonyl group, 1-naphthalenesulfonyl group or 2-naphthalenesulfonyl group),

(31) a $C_1$ to $C_{22}$ alkylsulfonyloxy group
(for example, a methanesulfonyloxy group, ethanesulfonyloxy group, n-propanesulfonyloxy group or iso-propanesulfonyloxy group),

(32) a carbamoyl group,

(33) a formyl group, and the like. For example, an amino group, a $C_1$ to $C_{22}$ alkyl group, an unsaturated $C_2$ to $C_{22}$ alkyl group, a $C_6$ to $C_{14}$ aryl group, a 5-membered to 14-membered heteroaryl group, a 3-membered to 14-membered non-aromatic heterocyclic group and a $C_3$ to $C_{14}$ cycloalkyl group are preferable. In particular, the substituent is preferably one or two substituents such as an amino group, a $C_1$ to $C_{22}$ alkyl group, a 3-membered to 14-membered non-aromatic heterocyclic group, and a $C_3$ to $C_{14}$ cycloalkyl group, for example. In addition, the above-described amino group (9) and carbamoyl group (31) given as the substituents in the above-described group "which may have a substituent" may be each further substituted with one or two $C_1$ to $C_{22}$ alkyl groups, unsaturated $C_2$ to $C_{22}$ alkyl groups or $C_6$ to $C_{14}$ aryl groups.

Next, the compound of the formula (I) of the present invention will be elucidated.

The compound of the formula (I) inhibits VEGF production under a hypoxic condition, possesses an activity of inhibiting proliferation of solid cancer cells in vivo, and shows in vivo activity at a dose not causing a significant reduction in the body weight. Among them, the above-described compound of the formula (I-a) is preferable, and the compound of the formula (I-b) is more preferable, and the compound of the formula (I-c) is particularly preferable. Further, the compound of the formula (I), wherein $R^{16}$ is a hydroxyl group, is a compound exhibiting particularly excellent stability in an aqueous solution.

Since the compound of the formula (I) is prepared by using a known conversion reaction for functional groups (for example, a hydroxyl group) present at the 3-position, 7-position, 16-position and 21-position, the same substituents can be introduced into the 3-position, 7-position, 16-position and 21-position. Since the structural feature is the side chain at the 7-position and/or the side chain at the 21-position, a group of more preferable compounds can be defined as the compounds of the formula (I-d). In addition, the compounds of the formula (I), wherein $R^{21}$ forms an oxo moiety together with a carbon atom to which $R^{21}$ is bonded, as well as the compounds of the formula (I-d), represent a group of compounds possessing good activity. As detailed aspects of more preferable compounds among the compounds of the formula (I-d), the compounds of the above-described items "7." to "20." of the present invention can be exemplified.

Preferable examples of the compound of the formula (I) will be described below. A group of preferable compounds, including compounds of later-described examples, is represented by, for example, (8E,12E,14E)-3,16,21-trihydroxy-6,10,12,16,20-pentamethyl-7-((4-methylpiperazin-1-yl)carbonyl)oxy-18,19-epoxytricosa-8,12,14-trien-11-olide (compound 18), (8E,12E,14E)-3,16,21-trihydroxy-6,10,12,16,20-pentamethyl-7-((4-methylhomopiperazin-1-yl)carbonyl)oxy-18,19-epoxytricosa-8,12,14-trien-11-olide (compound 19), (8E,12E,14E)-3,16,21-trihydroxy-6,10,12,16,20-pentamethyl-7-((4-(piperidin-1-yl)piperidin-1-yl(carbonyl)oxy-18,19-epoxytricosa-8,12,14-trien-11-olide (compound 21), (8E,12E,14E)-7-((4-ethylpiperazin-1-yl)carbonyl)oxy-3,16,21-trihydroxy-6,10,12,16,20-pentamethyl-18,19-epoxytricosa-8,12,14-trien-11-olide (compound 24), (8E,12E,14E)-3,16,21-trihydroxy-6,10,12,16,20- pentamethyl-7-(N-methyl-N-(3-(N',N'-dimethylamino)propyl)carbamoyloxy)-18,19-epoxytricosa-8,12,14-trien-11-olide (compound 27), (8E,12E,14E)-3,16,21-trihydroxy-6,10,12,16,20-pentamethyl-7-((piperazin-1-yl)carbonyl)oxy-18,19-epoxytricosa-8,12,14-trien-11-olide (compound 28), (8E,12E,14E)-3,16,21-trihydroxy-6,10,12,16,20-pentamethyl-7-(N-methyl-N-(1-methylpiperidin-4-yl)carbamoyloxy)-18,19-epoxytricosa-8,12,14-trien-11-olide (compound 29), (8E,12E,14E)-3,16,21-trihydroxy-7-((4-isopropylhomopiperazin-1-yl)carbonyl)oxy-6,10,12,16,20-pentamethyl-18,19-epoxytricosa-8,12,14-trien-11-olide (compound 39), (8E,12E,14E)-3,16,21-trihydroxy-7-((4-(4-hydroxypiperidin-1-yl)piperidin-1-yl)carbonyl)oxy-6,10,12,16,20-pentamethyl-18,19-epoxytricosa-8,12,14-trien-11-olide (compound 40), (8E,12E,14E)-3,16,21-trihydroxy-6,10,12,16,20-pentamethyl-7-((4-(morpholin-4-yl)piperidin-1-yl)carbonyl)oxy-18,19-epoxytricosa-8,12,14-trien-11-olide compound 42), (8E,12E,14E)-7-((4-ethylhomopiperazin-1-yl)carbonyl)oxy-3,16,21-trihydroxy-6,10,12,16,20-pentamethyl-18,19-epoxytricosa-8,12,14-trien-11-olide (compound 43), (8E,12E,14E)-3,16,21-trihydroxy-7-((4-isopropylpiperazin-1-yl)carbonyl)oxy-6,10,12,16,20-pentamethyl-18,19-epoxytricosa-8,12,14-trien-11-olide (compound 44), (8E,12E,14E)-3,16,21-trihydroxy-7-(((1S,4S)-5-isopropyl-2,5-diazabicyclo[2.2.1]heptan-2-yl)carbonyl)oxy-6,10,12,16,20-pentamethyl-18,19-epoxytricosa-8,12,14-trien-11-olide (compound 49), (8E,12E,14E)-7-(N-(2-(N',N'-dimethylamino)ethyl)-N-methylcarbamoyloxy)-3,16,21-trihydroxy-6,10,12,16,20-pentamethyl-18,19-epoxytricosa-8,12,14-trien-11-olide (compound 50), (8E,12E,14E)-7-(N-(2-(N',N'-dimethylamino)ethyl)carbamoyloxy)-3,16,21-trihydroxy-6,10,12,16,20-pentamethyl-18,19-epoxytricosa-8,12,14-trien-11-olide (compound 51) or (8E,12E,14E)-3,16,21-trihydroxy-6,10,12,16,20-pentamethyl-7-(((1S,4S)-5-methyl-2,5-diazabicyclo[2.2.1]heptan-2-yl)carbonyl)oxy-18,19-epoxytricosa-8,12,14-trien-11-olide (compound 55). Of these, for example, compound 29, compound 39, compound 43, compound 44 and compound 55 are more preferable.

Next, a method for producing the compound of the formula (I) of the present invention will be described.

The compound of the formula (I) can be produced by chemical modification of, a key compound such as a 6-deoxy 11107 compound or a 6-deoxy compound using a conventional method as follows. The 6-deoxy 11107 compound is obtained by culturing, under aerobic conditions, a strain belonging to the genus *Streptomyces*, which is capable of producing a 6-deoxy 11107 compound as a physiologically active substance of the formula (I), wherein [1] W is

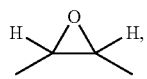

$R^3$ and $R^{21}$ are a hydroxyl group, $R^7$ is an acetoxy group, and $R^{16}$, $R^{17}$, $R^{20}$ and $R^{21'}$ are a hydrogen atom (6-deoxy 11107B)

[3] W is

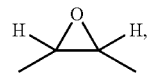

$R^3$, $R^{16}$ and $R^{21}$ are a hydroxyl group, $R^7$ is an acetoxy group, and $R^{17}$, $R^{20}$ and $R^{21'}$ are a hydrogen atom (6-deoxy 11107D),

[7] W is

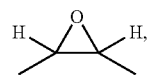

$R^3$, $R^{17}$, $R^{16}$ and $R^{21}$ are a hydroxyl group, $R^7$ is an acetoxy group, and $R^{20}$ and $R^{21'}$ are a hydrogen atom, and collecting the compound from the cells and culture solution; and the 6-deoxy compound is obtained by biologically converting a compound of the formula (I), wherein

[1] W is

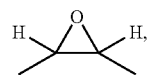

$R^3$ and $R^{21}$ are a hydroxyl group, $R^7$ is an acetoxy group, and $R^{16}$, $R^{17}$, $R^{20}$ and $R^{21'}$ are a hydrogen atom (hereinafter referred to as "6-deoxy 11107B") to a compound of the formula (I), wherein

[2] W is

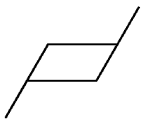

$R^3$ and $R^{21}$ are a hydroxyl group, $R^7$ is an acetoxy group, and $R^{16}$, $R^{17}$, $R^{20}$ and $R^{21}$ are a hydrogen atom,

[4] W is

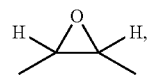

$R^{21}$ and $R^{21'}$ form an oxo group together with carbon to which $R^{21}$ and $R^{21'}$ are bonded, $R^3$, $R^{16}$ and $R^{20}$ are a hydroxyl group, $R^7$ is an acetoxy group, and $R^{17}$ is a hydrogen atom,

[5] W is

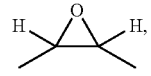

$R^3$, $R^{16}$, $R^{20}$ and $R^{21}$ are a hydroxyl group, $R^7$ is an acetoxy group, and $R^{17}$ and $R^{21'}$ are a hydrogen atom,

[6] W is

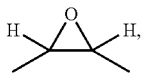

$R^3$, $R^7$, $R^{16}$ and $R^{21}$ are a hydroxyl group, and $R^{11}$, $R^{20}$ and $R^{21'}$ are a hydrogen atom or

[8] W is

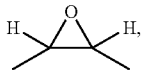

$R^{21}$ and $R^{21'}$ form an oxo group together with carbon to which $R^{21}$ and $R^{21'}$ are bonded, $R^3$ and $R^{16}$ are a hydroxyl group, $R^7$ is an acetoxy group, and $R^{17}$ and $R^{20}$ are a hydrogen atom; and by chemically modifying the key compound using a conventional method in an appropriate manner.

The present invention will be described in detail below with respect to the production of the 6-deoxy 11107 compound by fermentation, the production of the 6-deoxy compound by bioconversion reaction, and the modification of the active substance by organic synthesis.

First, a method for producing the 6-deoxy 11107 compound will be described.

The 6-deoxy 11107 compound (in particular, 6-deoxy 11107B) that can be converted into the 6-deoxy 11107D compound, a biologically active substance, of the present invention can be produced by microorganism fermentation.

As a microorganism used for producing the 6-deoxy 11107 compound, any microorganism can be used insofar as the microorganism is a strain which is capable of producing the 6-deoxy 11107 compound. For example, a strain for producing 6-deoxy 11107B can be obtained from a strain isolated from soil or a known strain which is capable of producing a 11107B analogue, by typical mutation treatment using ultraviolet rays or a mutagenic agent such as N-methyl-N'-nitro-N-nitrosoguanidine (NTG) as a mutagen, for example, or by a method such as gene disruption by homologous recombination.

As a microorganism used for producing the 6-deoxy 11107 compound, the following deposited strain can be exemplified. The above-described strain is internationally deposited with International Patent Organism Depositary (IPOD), National Institute of Advanced Industrial Science and Technology in Central 6, 1-1-1 Higashi, Tsukuba-shi, Ibaraki 305-8566, Japan. Specifically, *Streptomyces* sp. Mer-11107 was deposited with National Institute of Bioscience and Human-Technology, Agency of Industrial Science and Technology in 1-1-3 Higashi, Tsukuba-shi, Ibaraki 305-8566, Japan as FERM P-18144 on Dec. 19, 2000, and was transferred to International Patent Organism Depositary (IPOD), National Institute of Advanced-Industrial Science and Technology in Central 6, 1-1-1 Higashi, Tsukuba-shi, Ibaraki 305-8566, Japan under the international depositary number FERM BP-7812 on Nov. 27, 2001.

There are no specific limitations to the strains for producing the 6-deoxy 11107 compound, including mutants of these strains, insofar as they belong to the genus *Streptomyces*, and are capable of producing the 6-deoxy 11107 compound. In addition to the above-described strain, *Streptomyces* sp. A-1543 can be exemplified, for example. This strain was deposited with International Patent Organism Depositary, National Institute of Advanced Industrial Science and Technology in Central 6, 1-1-1 Higashi, Tsukuba-shi, Ibaraki 305-8566, Japan as FERM P-18942 on Jul. 23, 2002, and was transferred to International Patent Organism Depositary (IPOD), National Institute of Advanced Industrial Science and Technology in Central 6, 1-1-1 Higashi, Tsukuba-shi, Ibaraki 305-8566, Japan under the international depositary number FERM BP-8442 on Jul. 28, 2003.

Next, the production of the 6-deoxy 11107 compound will be described in detail with respect to 1. characteristics of the isolated production strain, 2. a method for culturing the production strain, and 3. a method for purifying the active substance.

1. Characteristics of the Isolated Production Strain

It is expected that, as a strain used in the present invention, any strain belonging to the genus *Streptomyces* which is capable of producing the 6-deoxy 11107 compound can be used. As representative strains, a strain numbered as Mer-11107 by the present inventors and A-1543 as a mutant of this strain can be given. Microbiological characteristics of these strains are as follows.

(1). Morphology

In the strain, spiral aerial hyphae are elongated from substrate hyphae. At the end of the matured aerial hyphae, a spore chain composed of about 10 to 20 cylindrical spores is formed. Each spore has a size of about 0.7 μm×1.0 μm, and has a smooth surface. No atypical organs such as sporangia, sclerotia, and flagella are observed.

(2). Growth Conditions in Various Culture Media

Culture characteristics of the strain after culturing on various culture media at 28° C. for two weeks are shown as follows. Color tones are described according to the Tresner's color wheels, and indicated as a color name and a symbol shown in parentheses.

1) Yeast-Extract Malt Extract Agar

The strain grows well. On the surface, aerial hyphae of the cultured strain are branched, become divided and form gray spores (light gray; d). The reverse side color is light melon yellow (3ea). No soluble pigment is observed.

2) Oatmeal Agar

The strain grows moderately. On the surface, the aerial hyphae of the cultured strain are slightly branched, become divided to form gray spores (gray; g). The reverse side color is Nude tan (4 gc) or putty (1½ ec). No soluble pigment is observed.

3) Inorganic Salts-Starch Agar

The strain grows well. On the surface, aerial hyphae adhere of the cultured strain are branched, become divided and form gray spores (gray; e). The reverse side color is fawn (4ig) or gray (g). No soluble pigment production is observed.

4) Glycerol-Asparagine Agar

The strain grows well. On the surface, aerial hyphae of the cultured strain are branched, become divided and form white spores (white; a). The reverse side color is pearl pink (3ca). No soluble pigment is observed.

5) Peptone-Yeast Extract-Iron Agar

The strain grows poorly. On the surface, no aerial hyphae of the cultured strain are branched. The reverse side color is light melon yellow (3ea). No soluble pigment is observed.

6) Tyrosine Agar

The strain grows well. On the surface, aerial hyphae adhere of the cultured strain are branched, become divided and form white spores (white; a). The reverse side color is pearl pink (3ca). No soluble pigment is observed.

(3). Various Carbon Sources Utilization

Growth conditions of the strain after culturing in a medium, in which various carbon sources are added to a Pridham-Godlieb agar culture medium, at 28° C. for two weeks are shown as follows.
1) L-arabinose ±
2) D-xylose ±
3) D-glucose +
4) D-fructose +
5) Sucrose +
6) Inositol +
7) L-rhamnose –
8) D-mannitol +
9) Raffinose +

(The symbol "+" means "positive", the symbol "±" means "weakly positive", and the symbol "–" means "negative").

(4). Physiological Properties

Physiological properties of the strain are as follows.

(a) Temperature range for growth (yeast-malt extract agar, cultured for two weeks): 12° C. to 37° C.

(b) Optimal temperature range for growth (yeast extract-malt extract agar, cultured for two weeks): 21° C. to 33° C.

(c) Gelatin liquefaction (glucose-peptone-gelatin medium): negative (d) Milk coagulation (skim milk medium): negative (e) Milk peptonization (skim milk medium): negative (f) Starch hydrolysis (Inorganic salt-starch): positive (g) Formation of melanoid pigment (peptone-yeast extract-iron agar): negative (tyrosine agar): negative (h) Hydrogen sulfide production (peptone-yeast extract-iron agar): negative (i) Nitrate reduction (0.1% potassium nitrate-containing broth): negative (j) NaCl tolerance (yeast extract-malt extract agar, cultured for two weeks):

Growing at NaCl concentration of 4% or less (5). Cell Component

LL-diaminopimelic acid was detected from the cell walls of the strain.

2. A Method for Culturing the Production Strain

The 6-deoxy 11107 compound of the present invention can be produced by inoculating the above-described strain into a nutrient culture medium, and aerobically culturing the strain. As a strain for producing the 6-deoxy 11107 compound, any strain belonging to the genus *Streptomyces* which is capable of producing the 6-deoxy 11107 compound can be used in the present invention without limitations to the above-described strain.

Although the method for culturing the above-described microorganism is, in principle, in accordance with a method for culturing a common microorganism, it is usually preferable that the method be conducted under aerobic conditions as shaking flask culture, tank culture, or the like by liquid culture. Any culture medium may be used for the culture, insofar as the medium contains a nutrient source that can be utilized by a microorganism belonging to the genus *Streptomyces*. Any of various synthetic culture media semi-synthetic culture media and natural culture media can be used. In the culture medium composition, as carbon sources, glucose, sucrose, fructose, glycerol, dextrin, starch, molasses and soybean oil, for example, can be used singly or in a combination of two or more. As nitrogen sources, organic nitrogen sources such as pharmamedia, peptone, meat extract, soybean meal, casein, amino acid, yeast extract and urea, for example, and inorganic nitrogen sources such as sodium nitrate and ammonium sulfate, for example, can be used singly or in a combination of two or more. In addition, for example, salts such as sodium chloride, potassium chloride, calcium carbonate, magnesium sulfate, sodium phosphate, potassium phosphate, and cobalt chloride, heavy metal salts, and vitamins such as vitamin B and biotin can be added for use as required. In the case where a culture medium is foamed when culturing, various antifoaming agents can be appropriately added to the culture medium. When the antifoaming agent is added, the concentration must be adjusted so that production of the target substance is not adversely affected. For example, the concentration used is preferably 0.05% or less.

The culture conditions can be appropriately selected, insofar as the above-described strain is grown well so that the above-described substance can be produced. It is preferable that the pH of a culture medium be adjusted to about 5 to 9, for example, and typically near neutral. It is appropriate that the culture temperature be maintained at typically 20 to 40° C., and preferably 23 to 35° C. The culture period is about two to eight days, and typically about three to five days. As a matter of course, various culture conditions as described above can be changed according to the species and properties of the microorganism used, external conditions, and the like, and optimal conditions can be selected. The 6-deoxy 11107 compound of the present invention accumulated in a culture solution can be collected by a typical separation methods utilizing its characteristics, for example, solvent extraction or resin adsorption.

3. A Method for Purifying the Active Substance

After termination of the culture, in order to collect the 6-deoxy 11107 compound from a culture solution, separation and purification methods used for isolating a microbial metabolite from the culture solution can be generally used. For example, all known methods such as organic solvent extraction using methanol, ethanol, butanol, ethyl acetate, chloroform, or the like, various types of ion exchange chromatography, gel filtration chromatography using Sephadex LH-20 or the like, active carbon, adsorption-desorption treatment by adsorption chromatography or thin-layer chromatography using silica gel or the like, and high-performance liquid chromatography using a reverse phase column are applicable to this method. The purification method is not specifically limited to the methods listed here.

By using these methods singly, in a combination of two or more in an arbitrary order, or repetitively, the 6-deoxy 11107 compound can be isolated and purified.

Second, a method for producing the 6-deoxy 11107 compound will be described.

1. A Microorganism Which Produces the 6-deoxy Compound by Bioconversion

The 6-deoxy compound of the present invention can be obtained by hydroxylation of the hydrogen atom at the 16-position of the 6-deoxy 11107 compound obtained in the above-described method (in particular, 6-deoxy 11107B) by bioconversion.

As a microorganism used for producing the 6-deoxy 11107 compound, any microorganism can be used insofar as the microorganism is a strain capable of hydroxylating the hydrogen atom at the 16-position of the 6-deoxy 11107 compound (in particular, 6-deoxy 11107B) to convert the compound into the 6-deoxy 11107D compound of the present invention. As representative examples of such a microorganism, strain A-1544 and strain A-1545 separated from the soil by the present inventors can be given. These strains were deposited with International Patent Organism Depositary, National Institute of Advanced Industrial Science and Technology in Central 6, 1-1-1 Higashi, Tsukuba-shi, Ibaraki 305-8566, Japan as FERM P-18943 and FERM P-18944, respectively, on Jul. 23, 2002, and were transferred to International Patent Organism Depositary (IPOD), National Institute of Advanced Industrial Science and Technology in Central 6, 1-1-1 Higashi, Tsukuba-shi, Ibaraki 305-8566, Japan under the international depositary numbers FERM BP-8446 and FERM BP-8447, respectively, on Jul. 30, 2003.

2. Production of the 6-deoxy Compound by Bioconversion Reaction

The 6-deoxy compound is produced by causing the 6-deoxy 11107 compound (in particular, 6-deoxy 11107B) to come in contact with cells or a cell preparation of the above-described strain or its mutant. Typically, the 6-deoxy compound is produced by adding the 6-deoxy 11107 compound (in particular, 6-deoxy 11107B) as a precursor compound to a culture solution obtained by inoculating the above-described strain into a nutrient source-containing culture medium and aerobically culturing the strain, or to a suspension of washed cells of the above-described strain in an appropriate buffer solution. When the compound is produced in a culture solution, the 6-deoxy 11107 compound (in particular, 6-deoxy 11107B) may be added to the culture solution in any time before the culture or in a prescribed period of time after initiation of the culture. Although such a strain for preparing a culture solution or washed cells can be cultured, or such a strain with the precursor compound added can be cultured, typically according to a method for culturing a common microorganism, it is usually preferable that the culture be conducted under aerobic conditions as shaking flask culture or tank culture by liquid culture, or the like.

Any culture medium may be used for the culture, insofar as the medium contains a nutrient source that can be utilized by a microorganism. Any of various synthetic culture media, semi-synthetic culture media and natural culture media can be used.

In the culture medium composition, as carbon sources, glucose, galactose, sucrose, maltose, fructose, glycerin, dextrin, starch, molasses and soybean oil, for example, can be used singly or in a combination of two or more. As nitrogen sources, organic nitrogen sources such as pharmamedia, peptone, meat extract, soybean meal, fish meal, gluten meal, casein, dry yeast, amino acid, yeast extract and urea, for example, and inorganic nitrogen sources such as sodium nitrate and ammonium sulfate, for example, can be used singly or in a combination of two or more. In addition, for example, salts such as sodium chloride, potassium chloride, calcium carbonate, magnesium sulfate, sodium phosphate, potassium phosphate, copper sulfate, iron sulfate, manganese chloride, and cobalt chloride, heavy metal salts, vitamins such as vitamin B and biotin, and clathrating agent such as cyclodextrins can be added for use as required. In the case where a culture medium is foamed when culturing, various antifoaming agents can be appropriately added to the culture medium. When the antifoaming agent is added, the concentration must be adjusted so that production of the target substance is not adversely affected.

The culture conditions can be appropriately selected, insofar as the above-described strain is grown well so that the 6-deoxy 11107 compound (in particular, 6-deoxy 11107B) can.be converted to produce the 6-deoxy compound. It is preferable that the pH of a culture medium be adjusted to 5 to 9, for example, and typically near the neutrality. It is appropriate that the culture temperature be maintained at typically 20 to 40° C., and preferably 24 to 30° C. The culture days are one to eight days, and typically two to five days.

As a matter of course, various culture conditions as described above can be adjusted according to the species and properties of the microorganism used, external conditions, and the like, and optimal conditions can be selected. The 6-deoxy compound accumulated in a culture solution can be recovered by a typical separation methods utilizing its characteristics, for example, solvent extraction or resin adsorption.

3. A Method for Purifying the 6-deoxy Compound

After termination of the culture, in order to collect the 6-deoxy compound from a culture solution, separation and purification methods used for isolating a microbial metabolite from the culture solution can be generally employed, according to the method of purifying the 6-deoxy 11107 compound (in particular, 6-deoxy 11107B) as described above. By using these methods singly, in a combination of two or more in an arbitrary order, or repetitively, the 6-deoxy compound can be isolated and purified.

Next, a method for preparing the compound of the formula (I) other than the 6-deoxy 11107 compound and the 6-deoxy compound will be described.

Various compounds of the formula (I) can be synthesized by converting a hydroxyl group and/or an acetoxy group on the isolated and purified 6-deoxy 11107 or 6-deoxy compound as a starting compound using a general organic synthetic procedures. Typical examples of the synthetic method include A. a method for preparing an urethane derivative, B. a method for preparing a thiourethane derivative, C. a method for preparing an ether derivative, D. a method for preparing an ester derivative, E. a method for preparing a phosphoric ester derivative or amidophosphoric ester derivative, F. a method for preparing a sulfuric ester derivative or amidosulfuric ester derivative, G. a method for preparing a halogen derivative, H. a method for preparing a sulfonic ester derivative, I. a method for preparing an amine derivative and J. a method for preparing an oxo derivative by oxidation of a hydroxyl group. Introduction and removal of a protective group for a hydroxyl group, while depending on the type of the productive group and the stability of the compound used for the preparation, can be conducted according to beed by the method described in document (see T. W. Green, Protective Groups in Organic Synthesis, John Wiley & Sons Inc., 3rd Edition) or a method similar to this method. The compound of the formula (I) can be prepared by using the introduction or removal reactions of the protective group for a hydroxyl group and the above-described preparation in a suitable combination. Specifically, the compound of the formula (I), wherein $R^3$, $R^7$, $R^{16}$, $R^{17}$, $R^{20}$ and $R^{21}$ are substituents as listed in the above-described category 10), can be prepared using the preparation for an urethane derivative, a thiourethane derivative, an amidosulfuric ester derivative and an amine derivative, or the like; the compound of the formula (I), wherein $R^3$, $R^7$, $R^{16}$, $R^{17}$, $R^{20}$ and $R^{21}$ are substituents as listed in the above-described categories 3) to 6), can be prepared using the perparation for an ether derivative; the compound of the formula (I), wherein $R^3$, $R^7$, $R^6$, $R^{17}$, $R^{20}$ and $R^{21}$ are substituents as listed in the above-described category 7), can be prepared using the preparation for an ester derivative; the compound of the formula (I), wherein $R^3$, $R^7$, $R^{16}$, $R^{17}$, $R^{20}$ and $R^{21}$ are substituents as listed in the above-described category 12) or 13), can be prepared using the preparation for a phosphoric ester derivative or the preparation for an amidophosphoric ester derivative; the compound of the formula (I), wherein $R^3$, $R^7$, $R^{16}$, $R^{17}$, $R^{20}$ and $R^{21}$ are substituents as listed in the above-described category 11), can be prepared using the preparation for a sulfuric ester derivative or the preparation for a sulfonic ester derivative; the compound of the formula (I), wherein $R^3$, $R^7$, $R^{16}$, $R^{17}$, $R^{20}$ and $R^{21}$ are substituents as listed in the above-described category 9), can be prepared using the preparation for a halogen derivative; the compound of the formula (I), wherein $R^3$, $R^7$, $R^{16}$, $R^{17}$, $R^{20}$ and $R^{21}$ are substituents as listed in the above-described category 8), can be prepared using an introduction and removal reactions of a protective group for a hydroxyl group; and an oxo derivative of the compound of the formula (I) in the above-described category 1) can be prepared by using the preparation for an oxo derivative by oxidation of a hydroxyl group.

Next, various synthetic methods used for preparing the compounds of the formula (I) will be described.

A. A Method for Preparing an Urethane Derivative

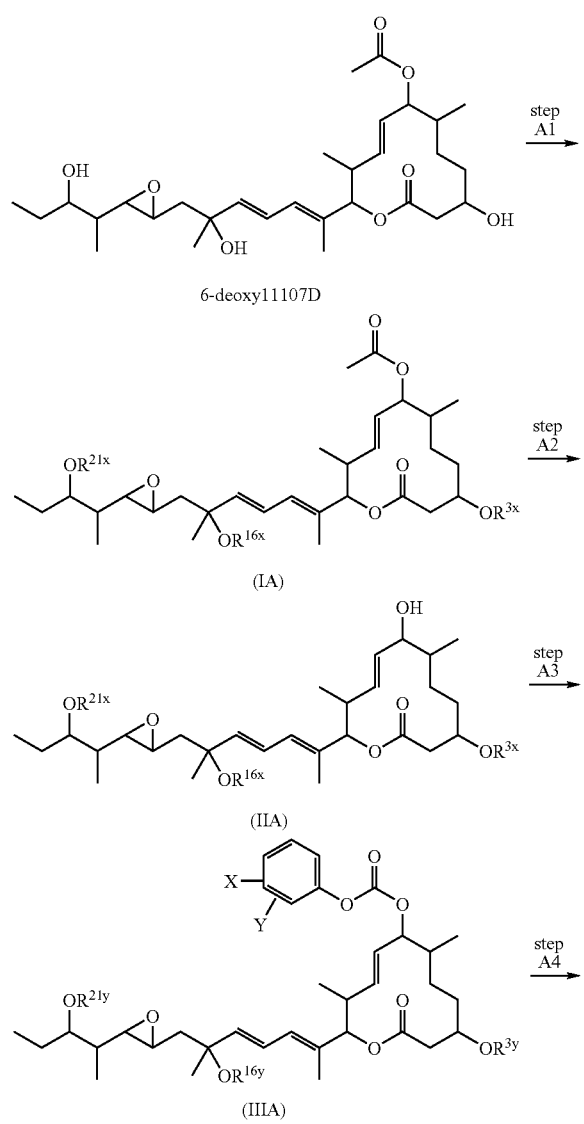

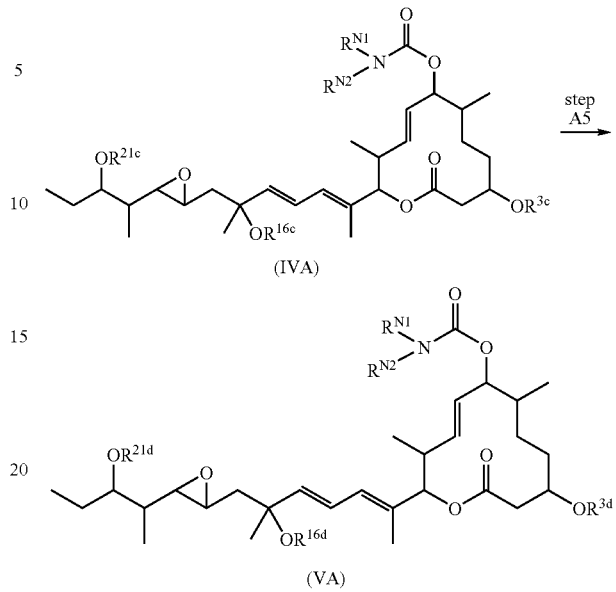

In the formulas, $R^{3x}$, $R^{16x}$ and $R^{21x}$ independently represent a hydrogen atom or a protective group, provided that $R^{3x}$, $R^{16x}$ and $R^{21x}$ do not concurrently represent a hydrogen atom; $R^{3y}$, $R^{16y}$ and $R^{21y}$ independently represent a hydrogen atom, a protective group or a group represented by the formula $R^fO$—CO—, wherein $R^f$ represents a $C_6$ to $C_{14}$ aryl group which may have (a) substituent(s), provided that $R^{3y}$, $R^{16y}$ and $R^{21y}$ do not concurrently represent a hydrogen atom; and $R^{3c}$, $R^{16c}$ and $R^{21c}$ independently represent a hydrogen atom, a protective group or a group represented by the formula $R^{N1}R^{N2}N$—CO—, wherein $R^{N1}$ and $R^{N2}$ are the same as defined above, provided that $R^{3c}$, $R^{16c}$ and $R^{21c}$ do not concurrently represent a hydrogen atom.

The step A1 is a step of preparing the compound of the formula (IA). This step is carried out by protecting the hydroxyl group(s) of 6-deoxy 11107D (the above-described compound as defined in [3]).

The reaction for protecting the hydroxyl group(s), which varies depending on the type of the protective group, is carried out by a procedure well known in the synthetic organic chemistry.

Examples of the protective group include 1-ethoxyethyl, tetrahydropyranyl, 1-methyl-1-methoxyethyl, 1-(2-chloroethoxy)ethyl, 1-methoxycyclohexyl, 4-methoxytetrahydropyranyl, 4-methoxytetrahydrothiopyranyl, 4-methoxytetrahydrothiopyranyl-S,S-dioxide, methoxymethyl, methylthiomethyl, methoxyethoxymethyl, trichloroethoxymethyl, trimethylsilylethyl, trimethylsilylethoxymethyl, tert-butyldimethylsilyl, triethylsilyl, diethylisopropylsilyl, trimethylsilyl, triisopropylsilyl, methyl-di-tert-butylsilyl, diphenylmethylsilyl, benzyl, p-methoxybenzyl, p-methylbenzyl, p-nitrobenzyl, p-chlorobenzyl and triphenylmethyl. All or part of hydroxyl groups can be appropriately protected by these protective groups.

For example, each derivative in which a hydroxyl group is protected by 1-ethoxyethyl, tetrahydropyranyl, 1-methoxycyclohexyl, 4-methoxytetrahydropyranyl 4-methoxytetrahydrothiopyranyl or 4-methoxytetrahydrothiopyranyl-S,S-dioxide can be synthesized by treating 6-deoxy 11107D with a corresponding vinyl ether such as ethyl vinyl ether or dihydropyran in the presence of an acid. As the acid, general organic acids such as pyridinium p-toluenesulfonate (PPTS), p-toluenesulfonic acid, camphorsulfonic acid, acetic acid, trifluoroacetic acid or methanesulfonic acid, for example, and general inorganic acids such as hydrogen chloride, nitric acid, hydrochloric acid and sulfuric acid, for example are used. Preferably, for example, pyridinium p-toluenesulfonate (PPTS), p-toluenesulfonic acid and camphorsulfonic acid are used. Although there are no specific limitations to the solvent used for the reaction, an inert solvent which can not easily react with a starting material is desirable. Examples of such solvents include ethers such as tetrahydrofuran, diethyl ether, diiso-propyl ether, dioxane and dimethoxyethane; halogenated hydrocarbons such as dichloromethane, chloroform, carbon tetrachloride and 1,2-dichloroethane; hydrocarbons such as hexane, benzene and toluene; ketones such as acetone and methyl ethyl ketone; nitriles such as acetonitrile; amides such as N,N-dimethylformamide, N,N-dimethylacetamide, N-methyl-2-pyridone and hexamethylphosphoramide; and sulfoxides such as dimethyl sulfoxide. Preferably, for example, dichloromethane, chloroform and tetrahydrofuran are used. The reaction time is 10 minutes to five days, and preferably one to two days. The reaction temperature is −78° C. to a reflux temperature, and preferably room temperature. The amounts of vinyl ether and the acid used for the reaction are 1 to 200 equivalents and 0.05 to 2 equivalents, respectively, and preferably 30 to 50 equivalents and 0.1 to 0.3 equivalent, respectively, to 6-deoxy 11107D.

Examples of other protective groups include methoxymethyl, methylthiomethyl, methoxyethoxymethyl, trichloroethoxymethyl, trimethylsilylethyl, trimethylsilylethoxymethyl, tert-butyldimethylsilyl, triethylsilyl, trimethylsilyl, diethylisopropylsilyl, triisopropylsilyl, tert-butyldimethylsilyl, diphenylmethylsilyl, benzyl, p-methoxybenzyl, p-methylbenzyl, p-nitrobenzyl, p-chlorobenzyl and triphenyl methyl. A derivative in which the hydroxyl group is protected by these protective groups can be synthesized by reacting a starting material with a chloride, bromide or trifluoromethanesulfonate of the respective protective group in the presence of a base. As the base, a general organic base or inorganic base is used. Examples of the organic base include aromatic bases such as imidazole, 4-(N,N-dimethylamino)pyridine (which is synonymous with 4-dimethylaminopyridine, N,N-dimethylaminopyridine and dimethylaminopyridine used in this specification), pyridine, 2,6-lutidine and collidine; tertiary amines such as N-methylpiperidine, N-methylpyrrolidine, triethylamine, trimethylamine, diisopropylethylamine, cyclohexyldimethylamine, N-methylmorpholine and 1,8-bis(dimethylamino)naphthalene; secondary amines such as diisobutylamine and dicyclohexylamine; alkyl lithium such as methyl lithium and butyl lithium; and metal alkoxides such as sodium methoxide and sodium ethoxide. Examples of the inorganic base include alkali metal hydrides such as sodium hydride and potassium hydride; alkaline earth metal hydrides such as calcium hydride; alkali metal hydroxides such as sodium hydroxide and potassium hydroxide; alkali metal carbonates such as sodium carbonate, potassium carbonate and cesium carbonate; and alkali metal hydrogencarbonates such as sodium hydrogen carbonate. As examples of the preferable base used for protecting the hydroxyl group with a silyl protective group are aromatic bases such as imidazole, 4-dimethylaminopyridine and tertiary amines such as triethylamine. Although there are no specific limitations to the solvent used for the reaction, a solvent which can not easily react with the starting material is desirable. Examples of such solvents are the above-described inert solvents, of which preferred examples are tetrahydrofuran, dichloromethane and N,N-dimethylformamide. The reaction time is 10 minutes to three days, and preferably one to two days. The reaction temperature is −78° C. to a reflux temperature, and preferably −10° C. to 50° C. The amounts of the chloride, bromide or trifluoromethanesulfonate and the base used for the reaction are 1 to 20 equivalents and 0.5 to 30 equivalents, respectively, and preferably 1 to 15 equivalents and 0.5 to 20 equivalents, respectively, to 6-deoxy 11107D.

The hydroxyl group(s) of 6-deoxy 11107D can be selectively protected by selecting the reagent used for protecting the hydroxyl group(s) and the equivalence thereof. For Example, a compound in which the hydroxyl groups at the 3-position and the 21-position are selectively protected can be obtained by carrying out the reaction at room temperature using chlorotriethylsilane, triethylamine and 4-dimethylaminopyridine in dichloromethane, or tert-butylchlorodimethylsilane and imidazole in N,N-dimethylformamide. In this procedure, for example, the hydroxyl group at the 3-position can be preferentially protected by limiting the equivalence of chlorotriethylsilane or tert-butylchlorodimethylsilane. Further, after protecting two or three of the four hydroxyl groups by silyl groups, the remaining two or one hydroxyl groups can be protected by the above-described ethoxyethyl groups or the like.

The step A2 is a step of preparing the compound of the formula (IIA). This step is carried out by converting the acetoxy group of the compound of the formula (IA) into the hydroxyl group by treating a base in an inert solvent.

Examples of the base are inorganic bases including alkali metal hydrides such as sodium hydride and potassium hydride; alkaline earth metal hydrides such as calcium hydride; alkali metal hydroxides such as lithium hydroxide, sodium hydroxide and potassium hydroxide; alkali metal carbonates such as lithium carbonate, sodium carbonate and potassium carbonate; alkali metal hydrogen carbonates such as sodium hydrogen carbonate; and metal alkoxides such as lithium methoxide, sodium methoxide, sodium ethoxide and potassium tert-butoxide, as well as bases such as guanidine and ammonia. Preferable examples of the base are potassium carbonate and guanidine.

Examples of the inert solvent used herein include, in addition to the above-described inert solvents, alcoholic solvents such as methanol, ethanol, isopropanol and tert-butanol, and water. These solvents can be used in a mixture of two or more. Preferable example of the solvent is alcoholic solvent, or a mixture of an alcohol and a halogen solvent. The reaction time is 10 minutes to five days, and preferably 30 minutes to one day. The reaction temperature is −78° C. to a reflux temperature, and preferably room temperature. The amount of the base used for the reaction is 1 to 10 equivalents, and preferably 2 to 5 equivalents, to the compound of the formula (IA).

The step A3 is a step of preparing the compound of the formula (IIIA). This step is carried out by treating the hydroxyl group of the compound of the formula (IIA) with a chloroformate derivative or carbonyldiimidazole in the presence of a base. Examples of the chloroformate derivative include 4-nitrophenyl chloroformate, phenyl chloroformate, 4-chlorophenyl chloroformate, 4-bromophenyl chloroformate and 2,4-dinitrophenyl chloroformate. Examples of the base include the above-described organic bases and inorganic bases. Preferably, for example, diisopropylethylamine, 4-dimethylaminopyridine, triethylamine, pyridine, 2,6-lutidine and sodium hydride are used. Although there are no specific limitations to the solvent used for the reaction, a solvent that does not easily react with the starting material is desirable. Examples of such solvents are the above-described inert solvents, of which, for example, tetrahydrofuran, dichloromethane and N,N-dimethylformamide are preferably used. The amounts of the chloroformate derivative and the base used for the reaction are 1 to 10 equivalents and 1 to 20 equivalents, respectively, and preferably 1 to 5 equivalents and 1 to 10 equivalents, respectively, to the compound of the formula (IIA). The reaction time is 10 minutes to 30 hours, and preferably one to four hours. The reaction temperature is −78° C. to a reflux temperature, and preferably −10° C. to 50° C.

With regard to the hydroxyl compound of the formula $(IA)_{2LA}$ in which one to three of $OR^{3A}$, $OR^{6A}$, $OR^{16A}$ and $OR^{21A}$ are not protected in the step A1, the hydroxyl group can be converted into a carbonate group by the step A3. Specifically, by treating the compound with a base and a chloroformate derivative in equivalents corresponding to the number of hydroxyl groups to be converted into carbonate groups, the hydroxyl groups other than the hydroxyl group at the 7-position of the compound (IA) can be converted into carbonate groups, as in the case of the hydroxyl group at the 7-position.

The step A4 is a step of preparing the compound of the formula (IVA). This step is carried out by treating the carbonate in the compound of the formula (IIIA) with an amine ($R^{N1}R^{N2}H$) that can form a desired compound of the formula (I) in an inert solvent in the presence of a base, or with the amine alone.

Examples of the amine used herein include methylamine, ethylamine, propylamine, butylamine, octylamine, decylamine, cyclopropylamine, cyclopentylamine, cyclohexylamine, dimethylamine, diethylamine, ethylmethylamine, ethylenediamine, 1,3-propanediamine, 1,4-butanediamine, N,N-dimethylethylenediamine, N,N-dimethyl-1,3-propanediamine, N,N-dimethyl-1,4-butanediamine, N,N-diethylethylenediamine, N,N-diethyl-1,3-propanediamine, N,N-diethyl-1,4-butanediamine, N,N,N'-trimethylethylenediamine, N,N,N'-trimethyl-1,3-propanediamine, N,N,N'-trimethyl-1,4-butanediamine, N-ethyl-N',N'-dimethylethylenediamine, N-ethyl-N',N'-dimethyl-1,3-propanediamine, N-ethyl-N',N'-dimethyl-1,4-butanediamine, N,N,N'-triethylethylenediamine, N,N,N'-triethyl-1,3-propanediamine, N,N,N'-triethyl-1,4-butanediamine, N,N-diethyl-N'-methylethylenediamine, N,N-diethyl-N'-methyl-1,3-propanediamine, N,N-diethyl-N'-methyl-1,4-butanediamine, N,N-dimethyl-N-phenylethylenediamine, N,N'-dimethyl-N-phenyl-1,3-propanediamine, N-benzyl-N,N'-dimethylethylenediamine, N-benzyl-N,N'-dimethyl-1,3-propanediamine, morpholine, thiomorpholine, thiomorpholine-S-oxide, thiomorpholine-S,S-dioxide, pyrrolidine, piperidine, piperazine, homopiperazine, 4-hydroxypiperidine, 4-methoxypiperidine, 1-methylpiperazine, 1-ethylpiperazine, 1-propylpiperazine, 1-butylpiperazine, 1-isopropylpiperazine, 1-cyclobutylpiperazine, 1-cyclopentylpiperazine, 1-cyclohexylpiperazine, 1-cycloheptylpiperazine, 1-cyclooctylpiperazine, 1-(cyclopropylmethyl)piperazine, 1-benzylpiperazine, 1-methylhomopiperazine, 1-ethylhomopiperazine, 1-(2-aminoethyl)pyrrolidine, 1-(2-(N-methylamino)ethyl)pyrrolidine, 1-(3-aminopropyl)pyrrolidine, 1-(3-(N-methylamino)propyl)pyrrolidine, 1-(2-aminoethyl)piperidine, 1-(2-(N-methylamino)ethyl)piperidine, 1-(3-aminopropyl)piperidine, 1-(3-(N-methylamino)propyl)piperidine, 4-(2-aminoethyl)morpholine, 4-(2-(methylamino)ethyl)morpholine, 4-(3-aminopropyl)morpholine, 4-(3-(N-methylamino)propyl)morpholine, 1-(2-aminoethyl)-4-methylpiperazine, 1-(3-aminopropyl)-4-methylpiperazine, 1-(3-(N-methylamino)propyl)-4-methylpiperazine, 1-amino-4-methylpiperidine, 1-methylamino-4-methylpiperidine, 1-ethyl-4-(N-methylamino)piperidine, 1-methylamino-4-propylpiperidine, 1-butyl-4-(N-methylamino)piperidine, 1-(N,N-dimethylamino)piperidine, 1-(N,N-diethylamino)piperidine, 4-(pyrrolidin-1-yl)piperidine, 4-(piperidin-1-yl)piperidine, 3-aminoquinuclidine, 3-(N-methylamino)quinuclidine, aniline, N-methylaniline, N,N-dimethyl-p-phenylenediamine, N,N-dimethyl-m-phenylenediamine, N,N,N'-trimethyl-p-phenylenediamine, N,N,N'-trimethyl-m-phenylenediamine, 1-naphthylamine, 2-naphthylamine, benzylamine, N-methylbenzylamine, phenethylamine, N-methylphenethylamine, 2-picolylamine, 3-picolylamine, 4-picolylamine, N-methyl-2-picolylamine, N-methyl-3-picolylamine, N-methyl-4-picolylamine, 2,5-diazabicyclo[2.2.1]heptane, 2-methyl-2,5-diazabicyclo[2.2.1]heptane, 3,8-diazabicyclo[3.2.1]octane and 1,4-diazabicyclo[4.3.0]nonane.

Examples of the base are the above-described organic bases and inorganic bases, of which, for example, diisopropylethylamine, dimethylaminopyridine, triethylamine, pyridine, 2,6-lutidine and sodium hydride are preferably used. Although there are no specific limitations to the solvent used for the reaction, a solvent which does not easily react with the starting material is desirable. Examples of such solvents are the above-described inert solvents of which, for example, tetrahydrofuran, dichloromethane and N,N-dimethylformamide are preferably used. The amounts of the amine and the base used for the reaction are 1 to 10 equivalents and 2 to 20 equivalents, respectively, and preferably 1.5 to 5 equivalents and 2 to 10 equivalents, respectively, to the compound of the formula (IIIA). The reaction time is 10 minutes to 30 hours, and preferably one to two hours. The reaction temperature is −78° C. to a reflux temperature, and preferably −10° C. to 50° C.

The compound of the formula (IVA) can also be prepared by treating the compound of the formula (IIA) with an isocyanate in an inert solvent in the presence of a base and/or cuprous chloride. Although there are no limitations to the isocyanate, ethyl isocyanate, methyl isocyanate, or phenyl isocyanate can be illustrated by an example. Examples of the base are the above-described organic bases and inorganic bases, of which, for example, diisopropylethylamine, dimethylaminopyridine, triethylamine, pyridine, 2,6-lutidine and sodium hydride are preferably used. Although there are no specific limitations to the solvent used for the reaction, a solvent which does not easily react with the starting material is desirable. Examples of such solvents are the above-described inert solvents, of which, for example, tetrahydrofuran, dichloromethane and N,N-dimethylformamide are preferably used. The amounts of the base and the isocyanate used for the reaction are 3 to 100 equivalents and 1 to 20 equivalents, respectively, and preferably 5 to 20 equivalents and 3 to 10 equivalents, respectively, to the compound of the formula (IIIA). In the case where cuprous chloride is used, the amount thereof is 1 to 10 equivalents, and preferably 2 to 6 equivalents. The reaction time is 10 minutes to 30 hours, and preferably one to two hours. The reaction temperature is −78° C. to a reflux temperature, and preferably −10° C. to 50° C.

Further, the compound with a hydroxyl group, in which one or two of $OR^{3X}$ or $^{16X}$ and $OR^{21X}$ have not been protected in the step A1, can be converted into a derivative having a plurality of urethane structures, by converting the hydroxyl group into a carbonate group in the step A3, and then converting the carbonate group into a carbamoyloxy group in the step A4.

The step A5 is a step of preparing the compound of the formula (VA). This step is carried out by subjecting the urethane derivative of the formula (IVA) to deprotection treatment in an inert solvent in the manner as described below. The reaction for deprotecting the protective group of the hydroxyl group, which varies depending on the type of the protective group, is carried out by a method well known in the synthetic organic chemistry.

The deprotection reaction for the respective hydroxyl groups protected by, for example, 1-ethoxyethyl, tetrahydropyranyl, 1-methoxycyclohexyl, 4-methoxytetrahydropyranyl, 4-methoxytetrahydrothiopyranyl or 4-methoxytetrahydrothiopyranyl-S,S-dioxide can be easily carried out by acid-treatment in an inert solvent. As the acid, the above-described organic acids and inorganic acids, and the like are used. Preferable examples include pyridinium p-toluenesulfonate, p-toluenesulfonic acid and camphorsulfonic acid. Although there are no specific limitations to the solvent used for the reaction, a solvent which does not easily react with the precursor is desirable. For example, alcohols solvents such as methanol, ethanol, isopropanol and tert-butanol are preferable. These can be used in a mixture with the above-described inert solvents. The amount of acid used for the reaction is 0.5 to 5 equivalents, and preferably 1 to 3 equivalents, to the compound of the formula (IVA). The reaction time is 10 minutes to ten days, and preferably one to four days. The reaction temperature is −78° C. to a reflux temperature, and preferably −10° C. to 50° C.

Further, in the case where the hydroxyl group is protected by other protective group, for example, tert-butyldimethylsilyl, triethylsilyl, diethylisopropylsilyl, trimethylsilyl, triisopropylsilyl, di-tert-butylmethylsilyl or diphenylmethylsilyl, the protective group can be deprotected, for example, by a treatment of a fluorine anion or acid. As the fluorine anion, tetrabutylammonium fluoride, hydrogen fluoride, potassium fluoride and hydrogen fluoride-pyridine are used, for example. As the acid, the above-described organic acids and inorganic acids, and the like are used. Preferable examples include acetic acid, formic acid, trifluoroacetic acid, pyridinium p-toluenesulfonate and camphorsulfonic acid. Although there are no specific limitations to the solvent used for the reaction, a solvent which does not easily react with the starting material is desirable. Examples thereof are the above-described inert solvents, of which, for example, tetrahydrofuran, diethyl ether and water are preferably used. The amounts of fluorine anion and the acid used for the reaction are 1 to 5 equivalents and 0.5 to 5 equivalents, respectively, and preferably 1 to 4 equivalents and 0.5 to 3 equivalents, respectively, to the compound of the formula (IVA). The reaction time is 10 minutes to 30 hours, and preferably one to two hours. The reaction temperature is −78° C. to a reflux temperature, and preferably −10° C. to 50° C.

By combining various methods for protecting hydroxyl groups as described for the first step with various deprotection methods as described for the fifth step, each of the hydroxyl groups at the 3-position and the 21-position can be selectively subjected to the derivation to obtain the urethane derivative.

In addition, a method for selective modification of the hydroxyl group at the 3-position or 21-position, conducted by using various combination of protection and deprotection methods, can also be used for in other modification methods as described below.

B. A Method for Preparing a Thiourethane Derivative

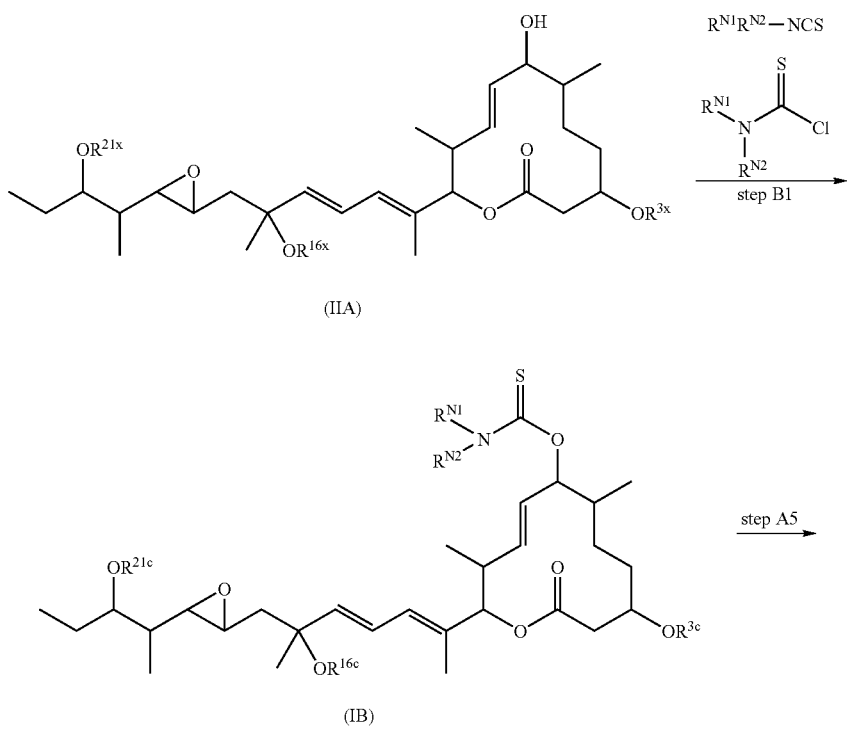

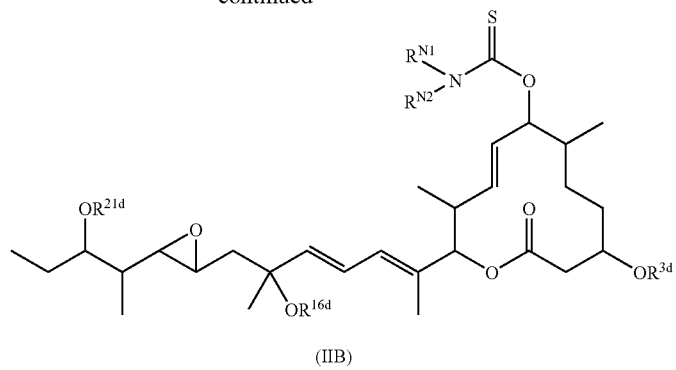

(IIB)

In the formula, $R^{3x}$, $R^{16x}$ and $R^{21x}$ represents the same as defined above; $R^{3c}$, $R^{16c}$ and $R^{21c}$ independently represents a hydrogen atom, a protective group or a group represented by the formula $R^{N1}R^{N2}N-CS-$, wherein $R^{N1}$ and $R^{N2}$ represents the same as defined above, provided that $R^{3c}$, $R^{16c}$ and $R^{21c}$ do not concurrently represent a hydrogen atom; and $R^{3d}$, $R^{16d}$ and $R^{21d}$ independently represents a hydrogen atom, or a group represented by the formula $R^{N1}R^{N2}N-CS-$, wherein $R^{N1}$ and $R^{N2}$ represents the same as defined above.

The step B1 is a step of synthesizing the compound of the formula (IB) by using an isothiocyanate or a thiocarbamoyl chloride instead of the isocyanate. This step is carried out by treating the compound of the formula (IIA) with an isothiocyanate or a thiocarbamoyl chloride in an inert solvent in the presence of a base or bis(tributyltin)oxide. Although there are no limitations to the isothiocyanate used herein, ethyl isothiocyanate, methyl isothiocyanate, phenyl isothiocyanate, benzyl isothiocyanate, allyl isothiocyanate, 2-(N,N-dimethylamino)ethyl isothiocyanate, 2-(N,N-diethylamino) ethyl isothiocyanate, 3-(N,N-dimethylamino)propyl isothiocyanate, 3-(N,N-diethylamino)propyl isothiocyanate, 2-(morpholin-4-yl)ethyl isothiocyanate, 2-(piperidin-1-yl) ethyl isothiocyanate and 2-(pyrrolidin-1-yl)ethyl isothiocyanate can be illustrated by examples. Although there are no limitations to the thiocarbamoyl chloride used herein, N,N-dimethylthiocarbamoyl chloride, N-phenyl-N-methylthiocarbamoyl chloride, (morpholin-4-yl)thio carbamoyl chloride, (4-methylpiperazin-1-yl)thio carbamoyl chloride and (4-methylhomopiperazin-1-yl)thio carbamoyl chloride can be illustrated by examples. Examples of the base are the above-described organic bases and inorganic bases, of which, for example, diisopropylethylamine, 4-dimethylaminopyridine, triethylamine, pyridine, 2,6-lutidine and sodium hydride are preferably used. Although there are no specific limitations to the solvent used for the reaction, a solvent which does not easily react with the starting material is desirable. Examples of the solvent are the above-described inert solvents, of which, for example, tetrahydrofuran, dichloromethane, N,N-dimethylformamide and toluene are preferably used. The amounts of base or bis(tributyltin) oxide and the isothiocyanate or thiocarbamoyl chloride used for the reaction are 1 to 5 equivalents and 1 to 10 equivalents, respectively, and preferably 1 to 3 equivalents and 2 to 5 equivalents, respectively, to the compound of the formula (IIA). The reaction time is 10 minutes to 72 hours, and preferably 1 to 24 hours. The reaction temperature is −78° C. to a reflux temperature, and preferably −10° C. to 70° C.

Further, by converting the hydroxyl group in the compound of the formula (IIA), in which one or two of $OR^{3x}$, $OR^{16x}$ and $OR^{21x}$ have not been protected, into a thiocarbamoyloxy group in the step B1, the compound of the formula (IB) having a plurality of thiocarbamoyl groups can be synthesized as well.

Subsequently, by removing the protective group(s) of the hydroxyl group(s) in the step A5, a thiourethane derivative of the formula (IIB) can be synthesized.

C. A Method for Preparing an Ether Derivative

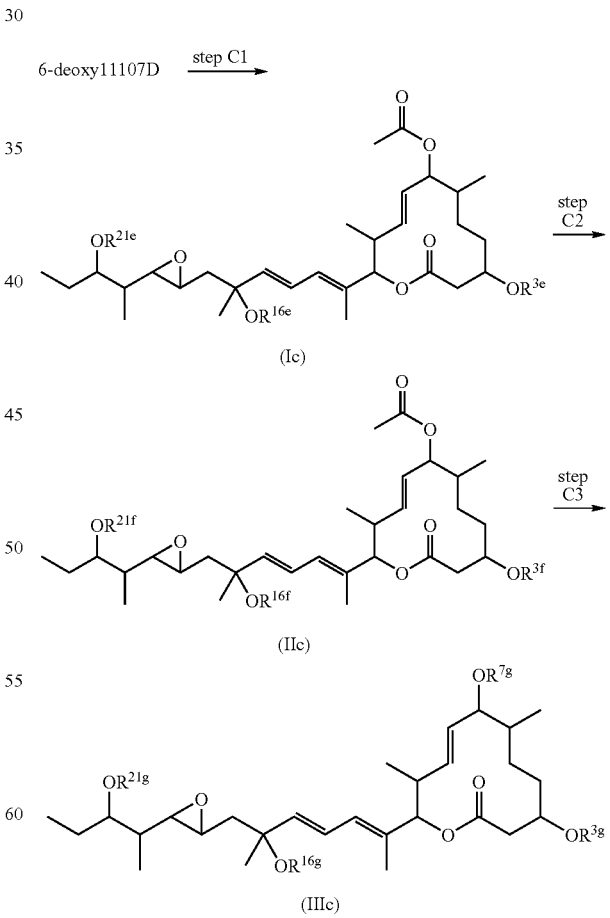

In the formula, $R^{3e}$, $R^{16e}$ and $R^{21e}$ independently represent a hydrogen atom or a protective group, provided that $R^{3e}$, $R^{16e}$ and $R^{21e}$ do not concurrently represent a hydrogen atom, and at least one of $R^{3e}$, $R^{16e}$ and $R^{21e}$ represents a hydrogen atom; $R^{3f}$, $R^{16f}$ and $R^{21f}$ independently represent a protective group or a $C_1$ to $C_{22}$ alkyl group which may have a substituent; $R^{3g}$, $R^{16g}$ and $R^{21g}$ independently represent a hydrogen atom, an alkyl group or a carbamoyl group; and $R^{7g}$ represents an acetyl group or a carbamoyl group.

The step C1 is a step of synthesizing a compound of the formula (IC). This step is carried out in a same manner as in the reaction procedure corresponding to the step A1 of the method A. The number of the protected hydroxyl groups is one or two, however.

Alternatively, by combining various methods for protecting a hydroxyl group corresponding to the step A1 of the method A with various methods for deprotecting a protected hydroxyl group corresponding to the step A5, a compound in which one of the substituents at the 3-position and 21-position is a hydroxyl group, and the other is a protected hydroxyl group can be synthesized.

above-described inert solvents, of which, for example, diethyl ether, tetrahydrofuran, dimethoxyethane and toluene are preferably used. The amounts alkylating agent and the base used for the reaction are 3 to 20 equivalents and 5 to 30 equivalents, respectively, and preferably 3 to 5 equivalents and 5 to 10 equivalents, respectively, to the compound of the formula (IC). The reaction time is 10 minutes to 48 hours, and preferably 1 to 24 hours. The reaction temperature is −78° C. to a reflux temperature, and preferably −10° C. to 70° C.

The step C3 is a step of synthesizing the compound of the formula (IIIC). In this step, by carrying out the step A2, step A3, step A4 and step A5 as required, a compound modified by both a carbamoyl group and an alkyl group can be obtained. Further, by carrying out only the step A5, a compound subjected only to alkylation can be obtained. The step C3 can be carried out by applying the reaction conditions of the step A2, step A3, step A4 and step A5.

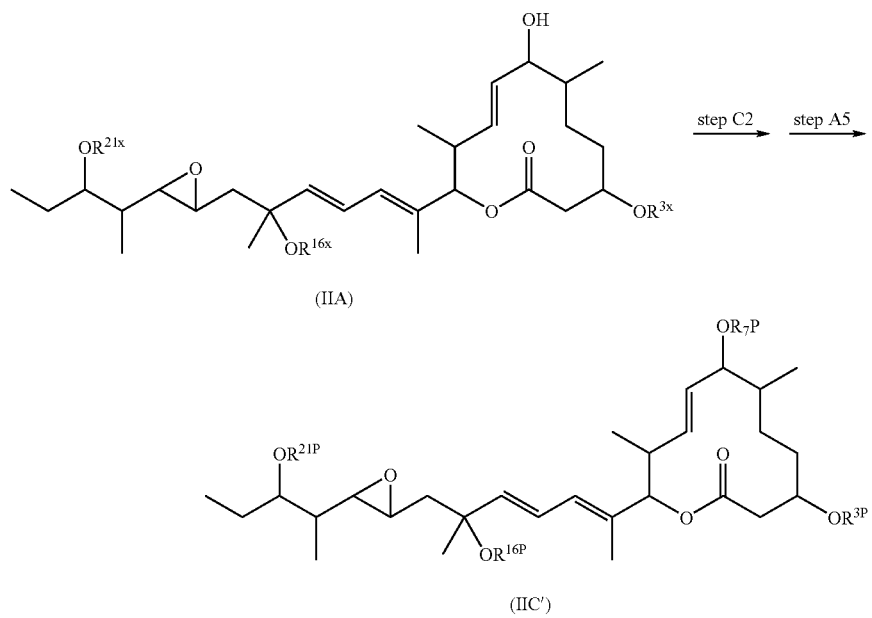

The step C2 is a step of synthesizing a compound of the. formula (IIC). This step is carried out by alkylating the unprotected hydroxyl group(s) in the compound of the formula (IC).

Alkylation can be carried out by treating the compound with an alkylating agent of the formula $R^m$—X in the presence of a base. $R^M$ represents a $C_1$ to $C_{22}$ alkyl group which may have a substituent and includes, for example, methyl group, ethyl group and benzyl group. X represents a leaving group. Examples of the leaving group include a chloro group, bromo group, iodo group and trifluoromethanesulfonyl group. Examples of the base are the above-described organic bases and inorganic bases, of which preferable examples are sodium hydride, lithium bis(trimethylsilyl)amide, lithium diisopropylamide, lithium dicyclohexylamide, potassium carbonate, cesium carbonate and 1,8-bis(N,N-dimethylamino)naphthalene. Although there are no specific limitations to the solvent used for the reaction, a solvent which does not easily react with the starting material is desirable. Examples thereof are the In the formulas, $R^{3x}$, $R^{16x}$ and $R^{21x}$ are the same as defined above; and $R^{3f'}$, $R^{7f'}$, $R^{16f'}$ and $R^{21'}$ independently represent a hydrogen atom or an alkyl group.

Also, an ether derivative represented by the formula (IIC') in which the hydroxyl group at the 7-position is alkylated can be obtained by subjecting the compound of the formula (IIA) to the step C2 followed by the step A5 in the same manner as described above.

Further, in this case, a derivative in which a thiocarbamoyl group is introduced into the hydroxyl group at the 7-position, and an alkyl group is introduced into one or two of the hydroxyl groups at the 3-position and 21-position can be obtained by subjecting the compound of the formula (IIIC) to the step B1 followed by the step A5.

Further, by using an unsaturated alkylating agent, aralkylating agent or heteroaralkylating agent that can produce the desired compound of the formula (I) instead of the above-described alkylating agent, a corresponding ether derivative can be produced.

D. A Method for Preparing an Ester Derivative

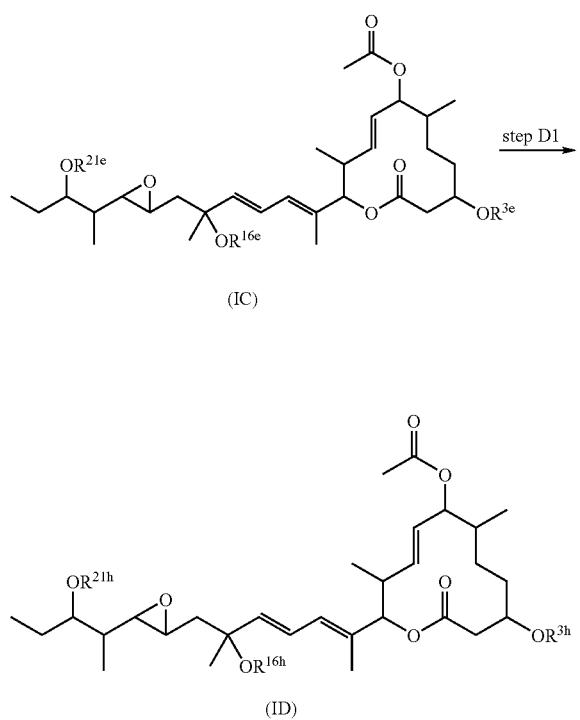

In the formulas, $R^{3e}$, $R^{16e}$ and $R^{21e}$ independently represent a hydrogen atom or a protective group, provided that $R^{3e}$, $R^{16e}$ and $R^{21e}$ do not concurrently represent a hydrogen atom, and at least one of $R^{3e}$, $R^{16e}$ and $R^{21e}$ represents a hydrogen atom; and $R^{3h}$, $R^{16h}$ and $R^{21h}$ independently represent a hydrogen atom or a group represented by the formula $R^{co}CO-$, wherein $R^{co}$ represents a hydrogen atom, a $C_1$ to $C_{22}$ alkyl group which may have a substituent, an unsaturated $C_2$ to $C_{22}$ alkyl group which may have a substituent, a $C_6$ to $C_{14}$ aryl group which may have a substituent, a 5-membered to 14-membered heteroaryl group which may have a substituent, a $C_7$ to $C_{22}$ aralkyl group which may have a substituent or a 5-membered to 14-membered heteroaralkyl group which may have a substituent, provided that $R^{3h}$, $R^{16h}$ and $R^{21h}$ do not concurrently represent a hydrogen atom.

The step D1 is a step of converting the hydroxyl group, which have not been protected, into an ester group using the compound of the formula (IC) synthesized in the step C1 as a starting material.

The esterification reaction is carried out by using an acid anhydride and a base in combination, an acid halide and a base in combination, carboxylic acid and a condensing agent in combination or Mitsunobu reaction, for example. As the acid anhydride, various carboxylic anhydrides are used. Examples include a mixed anhydrides comprising, for example, acetic acid, propionic acid, butyric acid, valeric acid or benzoic acid; a symmetrical anhydride; a cyclic anhydride such as succinic anhydride, glutaric anhydride or adipic anhydride. Acetic anhydride, propionic anhydride, butyric anhydride, benzoic anhydride and the like are preferable. As the acid halide, for example, various acid chlorides and acid bromides are used, of which a preferred examples are acetyl chloride, propionyl chloride, benzoyl chloride, and benzoyl bromide. Examples of the base are the above-described organic bases and inorganic bases, of which, preferred examples are, imidazole, 4-dimethylaminopyridine, pyridine and sodium hydride. As the carboxylic acid, various carboxylic acids are used, of which, for example, acetic acid and propionic acid are preferable. As the condensing agent, dicyclohexylcarbodiimide, trifluoroacetic anhydride, carbonyldiimidazole, N,N-diisopropylcarbodiimide and 1-ethyl-3-(3-dimethylaminopropyl)carbodiimide are preferable, for example. In the Mitsunobu reaction, the hydroxyl group can be substituted by various carboxylic acids in the presence of triphenylphosphine and diethyl azodicarboxylate or diisopropyl azodicarboxylate. Although there are no specific limitations to the solvent used for each reaction, a solvent which does not easily react with the starting material is desirable. Examples thereof are the above-described inert solvents, of which, for example, dichloromethane, chloroform and tetrahydrofuran are preferable. The amounts of the acid anhydride and the base in combination, the acid halide and the base in combination and the carboxylic acid and the condensing agent in combination, which are used for the reaction, are 1 to 10 equivalents and 3 to 20 equivalents in combination, 1 to 10 equivalents and 3 to 20 equivalents in combination, and 1 to 20 equivalents and 1 to 20 equivalents in combination, respectively, and preferably 1 to 5 equivalents and 2 to 10 equivalents in combination, 1 to 5 equivalents and 2 to 10 equivalents in combination, and 1 to 5 equivalents and 1 to 5 equivalents in combination, respectively, to the compound of the formula (IC). Further, the reaction can be accelerated by addition of 0.2 to 2 equivalents of 4-dimethylaminopyridine as required. The reaction time is 10 minutes to 30 hours, and preferably one to two hours. The reaction temperature is −78° C. to a reflux temperature, and preferably −10° C. to 50° C.

Subsequently, by removing the protective group for the hydroxyl group of the thus-synthesized ester derivative by the same reaction procedure as described for the step A5, a compound of the formula (ID) can be produced.

In addition, by carrying out the same esterification reaction as in the step D1 using 6-deoxy 11107D as a starting material, one to three hydroxyl groups can also be esterified.

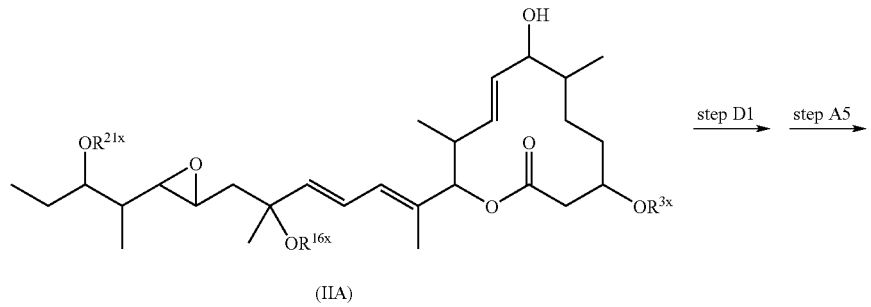

(IIA)

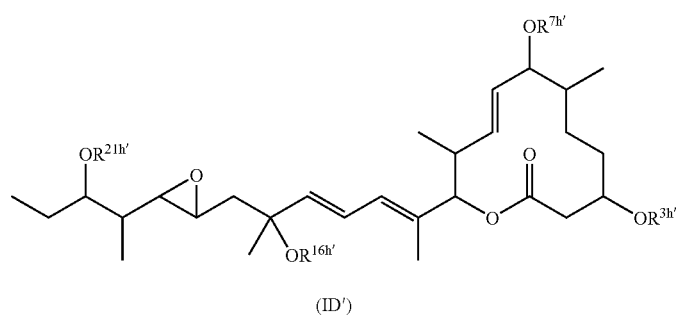

(ID')

In the formula, $R^{3x}$, $R^{6x}$ and $R^{21x}$ are the same as defined above; and $R^{3h'}$, $R^{7h'}$, $R^{16h'}$ and $R^{21h'}$ independently represent a hydrogen atom or a group represented by the formula $R^{co}CO—$, wherein $R^{co}$ represents the same group as defined above.

Further, a derivative represented by the formula (ID') in which the hydroxyl group at the 7-position is esterified can be obtained by subjecting the compound of the formula (IIA) to the step D1 in the same manner as described above, and then subjecting the product to the step A5.

E. A Method for Preparing a Phosphate Ester Derivative or Amidophosphate Ester Derivative

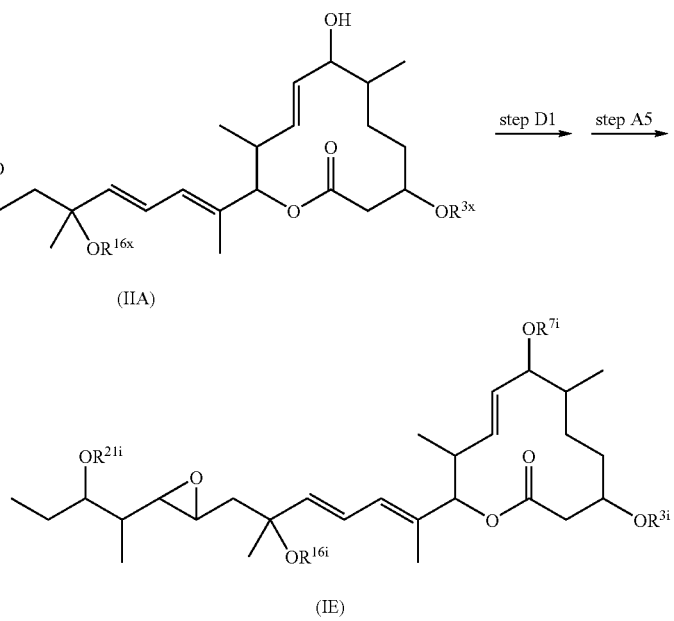

In the formula, $R^{3x}$, $R^{16x}$ and $R^{21x}$ are the same as defined above; and $R^{3i}$, $R^{7i}$, $R^{16i}$ and $R^{21i}$ independently represent a hydrogen atom, a group represented by the formula $(R^{N3}O)_2PO-$, $(R^{N1}R^{N2}N)_2PO-$, or $(R^{N1}R^{N2}N)(R^{N3}O)PO-$, wherein $R^{N1}$, $R^{N2}$ and $R^{N3}$ are the same meanings as defined above.

The step E1 is a step for converting the hydroxy group of the compound of formula (IIA) as starting material into phosphoric ester or amidophosphoric ester.

derivative by a similar reaction procedure as in the step A5, a compound of the formula (IE) can be prepared.

In addition, by carrying out the same phosphoric-esterification as in the step E1 using 6-deoxy 11107D as a starting material, one to four of the hydroxyl groups can also be phosphoric-esterified.

F. A Method for Preparing a Sulfuric Ester Derivative or Amidosulfuric Ester Derivative

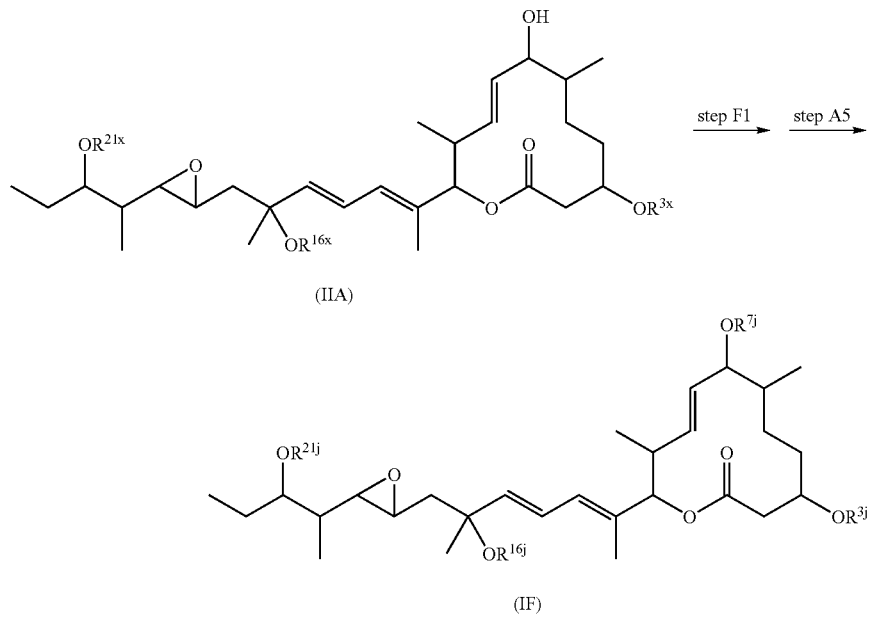

(IIA)

(IF)

The phosphoric-esterification is carried out using phosphoryl halide and a base, for example. As the phosphoryl halide, various types can be used herein, and examples thereof include a dialkoxyphosphoryl chloride, a diphenyloxyphosphoryl chloride, an alkoxy(N,N-disubstituted amino)phosphoryl chloride, an allyloxy(N,N-disubstituted amino)phosphoryl chloride, an alkoxy(N-substituted amino) phosphoryl chloride and allyloxy(N-substituted amino) phosphoryl chloride. Examples of the base are the above-described organic bases and inorganic bases, of which preferred examples are pyridine, 4-dimethylaminopyridine, triethylamine, ethyldiisopropylamine, sodium hydride, n-butyl lithium, potassium carbonate and sodium carbonate. Although there are no specific limitations to the solvent used for each reaction, a solvent which does not easily react with the starting material is desirable. Examples thereof are the above-described inert solvents, of which, for example, dichloromethane, chloroform, tetrahydrofuran and N,N-dimethylformamide are preferably used. The reaction time is 10 minutes to 72 hours, and preferably 1 to 24 hours. The amounts of the phosphorus halide and the base used for the reaction are 1 to 10 equivalents and 2 to 20 equivalents, respectively, and preferably 1 to 5 equivalents and 2 to 10 equivalents, respectively, to the compound of the formula (IIA). The reaction temperature is −78° C. to a reflux temperature, and preferably −10° C. to 50° C.

Subsequently, by removing the protective group for the hydroxyl group in the thus-synthesized phosphoric ester In the formula, $R^{3x}$, $R^{16x}$ and $R^{21x}$ are the same as defined above; and $R^{3j}$, $R^{7j}$, $R^{16j}$ and $R^{21j}$ independently represent a hydrogen atom or a group represented by the formula $R^{N1}R^{N2}N-SO_2-$ or $R^{N4}O-SO_2-$, wherein $R^{N1}$, $R^{N2}$ and $R^{N4}$ independently represent the same group as defined above.

The step F1 is a step for converting the hydroxyl group of the compound of the formula (IIA) as a starting material into sulfuric ester.

The sulfuric-esterification is carried out using sulfuric halide and a base or the like. As the sulfuric halide, various types can be used. Examples include alkoxysulfonyl chloride and N,N-disubstituted sulfamoyl chloride. As the base, the above-described organic bases and inorganic bases, and the like can be used. For example, pyridine, 4-dimethylaminopyridine, triethylamine, ethyldiisopropylamine, sodium hydride, n-butyl lithium, potassium carbonate and sodium carbonate are preferable. Although there are no specific limitations to the solvent used for each reaction, a solvent which does not easily react with the precursor is desirable. The above-described inert solvents can be used. Preferably, for example, dichloromethane, chloroform, tetrahydrofuran and N,N-dimethylformamide are used. The amounts of the sulfuric halide and the base used for the reaction are 1 to 10 equivalents and 2 to 20 equivalents, respectively and preferably 1 to 5 equivalents and 2 to 10 equivalents, respectively, to the compound of the formula (IIA). The reaction time is 10 minutes to 72 hours, and preferably 1 to 24 hours. The reaction temperature is −78° C. to a reflux temperature, and preferably −10° C. to 50° C.

Subsequently, by removing the protective group for the hydroxyl group in the thus-synthesized sulfuric ester derivative by the similar reaction manner as in the step A5, a compound of the formula (IF) can be synthesized.

In addition, by carrying out the similar sulfuric esterification as in the step F1 using 6-deoxy 11107D as a starting material, one to four of the hydroxyl groups can also be sulfuric-esterified.

G. A Method for Preparing a Halogen Derivative inorganic bases, for example, diisopropylethylamine, dimethylaminopyridine, triethylamine, pyridine, 2,6-lutidine and sodium hydride can be used. Although there are no specific limitations to the solvent used for the reaction, a solvent which does not easily react with the precursor is desirable. Examples include tetrahydrofuran, dichloromethane and N,N-dimethylformamide. In particular, fluorination reaction using diethylaminosulfur trifluoride is preferable. The amount of diethylaminosulfur trifluoride

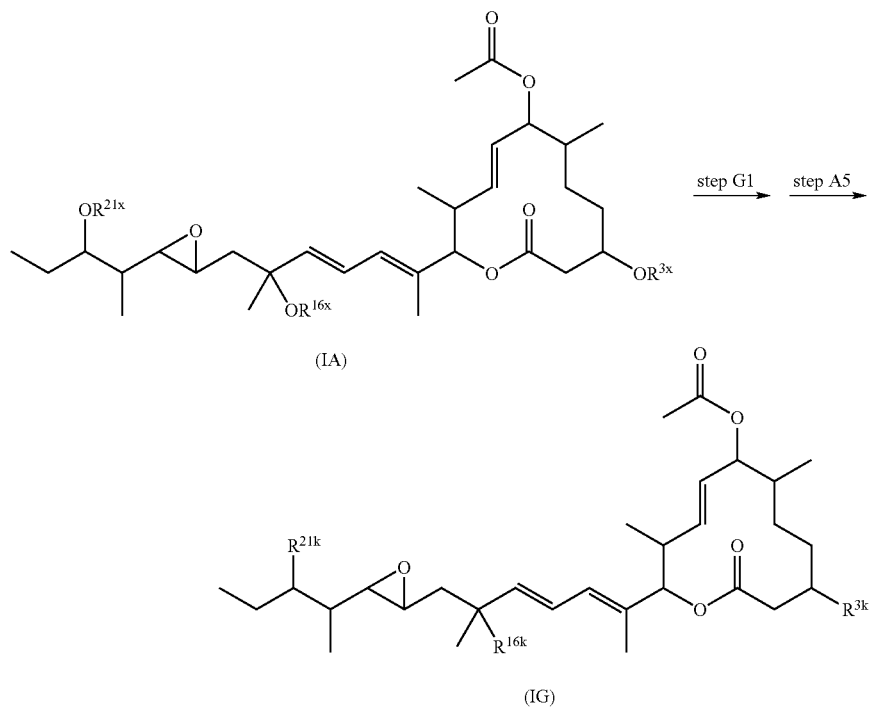

In the formulas, $R^{3x}$, $R^{16x}$ and $R^{21x}$ are the same as defined above; and $R^{3k}$, $R^{16k}$ and $R^{21k}$ independently represent a hydroxyl group or a halogen atom.

The step G1 is a step of converting a hydroxyl group into halogen using the compound of the formula (IA) as a starting material.

This halogenation reaction can be carried out by treating diethylaminosulfur trifluoride (DAST) or triphenylphosphine with carbon tetrabromide, bromine, phosphorus tribromide, iodine or carbon tetrachloride in the presence of a base, for example. As the base, common organic bases and (DAST) used for the reaction is 1 to 5 equivalents, and preferably 1 to 3 equivalents, to the compound of the formula (IA). The reaction time is 10 minutes to 10 hours. The reaction temperature is −78° C. to room temperature.

Subsequently, by removing the protective group for the hydroxyl group(s) in the thus-synthesized halogen derivative by the step A5, a compound of the formula (IG) can be synthesized.

H. A Method for Preparing a Sulfonic Ester Derivative

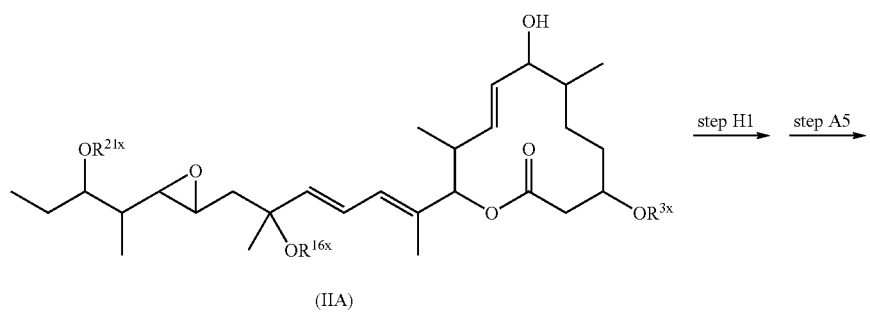

-continued

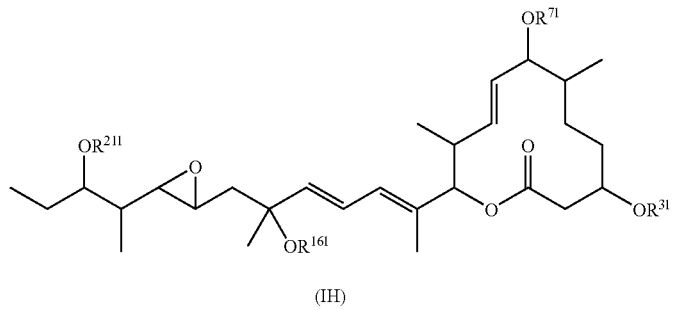

(IH)

In the formulas, $R^{3x}$, $R^{16x}$ and $R^{21x}$ are the same as defined above; and $R^{1l}$, $R^{7l}$, $R^{16l}$ and $R^{21l}$ independently represent a hydrogen atom or a group represented by the formula $R^{N5}SO_2$—, wherein $R^{N5}$ represents the same as defined above.

The step H1 is a step of sulfonylation of a hydroxyl group using the compound of the formula (IIA) as a starting material.

The sulfonylation can be carried out by treating sulfonyl chlorides such as p-toluenesulfonyl chloride, methanesulfonyl chloride and benzenesulfonyl chloride, for example, in the presence of a base. As the base, general organic bases and inorganic bases, for example, diisopropylethylamine, dimethylaminopyridine, triethylamine, pyridine, 2,6-lutidine and sodium hydride can be used. Although there are no specific limitations to the solvent used for the reaction, a solvent which does not easily react with the starting material is desirable. Examples include tetrahydrofuran, dichloromethane and N,N-dimethylformamide. The amounts of the sulfonyl chloride and the base used for the reaction are 1 to 5 equivalents and 2 to 10 equivalents, respectively, and preferably 1 to 3 equivalents and 2 to 6 equivalents, respectively, to the compound of the formula (IIA). The reaction time is 10 minutes to 30 hours. The reaction temperature is −78° C. to a reflux temperature.

Subsequently, by removing the protective group for the hydroxyl group in the thus-synthesized sulfonate derivative by the step A5, a derivative represented by the formula (IH), in which the hydroxyl group at the 7-position is sulfonylated, can be synthesized.

In addition, by carrying out the same sulfonylation as in the step H1 using 6-deoxy 11107D as a starting material, one to four of the hydroxyl groups can also be sulfonylated.

I. A Method for Preparing an Amine Derivative

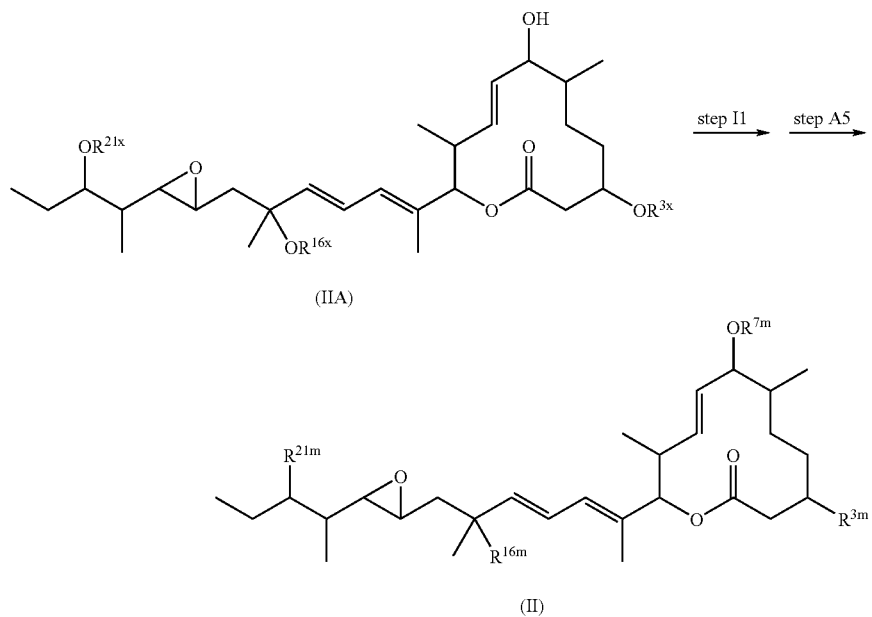

In the formulas, $R^{3x}$, $R^{16x}$ and $R^{21x}$ are the same as defined above; and $R^{3m}$, $R^{7m}$, $R^{16m}$ and $R^{21m}$ independently represent a hydroxyl group or a group of the formula $R^{N1}R^{N2}N$—, wherein $R^{N1}$ and $R^{N2}$ represent the same as defined above.

The step I1 is a step of converting a hydroxyl group directly into amine, or a step of converting a hydroxyl group into a good leaving group, then converting the leaving group into azide, and subsequently converting the azide into amine by reduction, using the compound of the formula (IIA) as a starting material.

In the case where the hydroxyl group is converted into an azide, 1) diphenylphosphoryl azide (DPPA), diethyl azodicarboxylate and triphenylphosphine, 2) DPPA and 1,8-diazabicyclo[5.4.0]undeca-7-ene (DBU), 3) hydrogen azide, diethyl azodicarboxylate and triphenylphosphine, 4) DPPA, tetramethylazodicarboxamide (TMAD) and tributylphosphine or 5) sodium azide in the presence of a base can be used, for example. As the base, the above-described organic bases and inorganic bases, and the like can be used. Preferably, for example, diisopropylethylamine, dimethylaminopyridine, triethylamine, pyridine, 2,6-lutidine and sodium hydride are used. Further, the hydroxyl group can be also converted into azide by treating with sodium azide in the presence of the palladium catalyst. Examples of the palladium catalyst include $Pd(PPh_3)_4$. Although there are no specific limitations to the solvent used for the reaction, a solvent which does not easily react with the starting material is desirable. Examples include tetrahydrofuran, dichloromethane, N,N-dimethylformamide, toluene and benzene. The reaction time is 10 minutes to 30 hours. The reaction temperature is −78° C. to a reflux temperature.

The reduction of azide into amine can be carried out by using triphenylphosphine or lithium aluminum hydride, for example. In addition, the reduction to amine can also be carried out using a catalyst such as palladium carbon or a Lindlar catalyst under hydrogen atmosphere. Although there are no specific limitations to the solvent used for the reaction, a solvent which does not easily react with the starting material is desirable. Examples include tetrahydrofuran, diethyl ether and ethanol. The reaction time is 10 minutes to 30 hours. The reaction temperature is −78° C. to a reflux temperature.

The hydroxyl group can be converted into a good leaving group according to a similar manner as described for the step G1 (halogenation) or step H1 (sulfonylation). Examples of the good leaving group include a chloro group, bromo group, iodo group, methanesulfonyl group and p-toluenesulfonyl group.

Subsequently, by treating this compound in which the hydroxyl group is converted into a leaving group with amine in an inert solvent in the presence of a base, a compound in which the hydroxyl group is converted into an amino group or an amino group having a substituent can be synthesized. Examples of the amine used include methylamine, ethyl amine, dimethylamine and diethylamine. As the base, the above-described organic bases and inorganic bases, and the like can be used. Preferably, for example, diisopropylethylamine, dimethylaminopyridine, triethylamine, pyridine, 2,6-lutidine and sodium hydride are used. Although there are no specific limitations to the solvent used for the reaction, a solvent which does not easily react with the starting material is desirable. The above-described inert solvents can be used. Preferably, for example, tetrahydrofuran, dichloromethane and N,N-dimethylformamide are used. The reaction time is 10 minutes to 30 hours, and preferably one to two hours. The reaction temperature is −78° C. to a reflux temperature, and preferably −10° C. to 50° C.

Subsequently, by removing the protective group for the hydroxyl group in the thus-synthesized amine derivative synthesized by a similar manner as in the step A5, a compound of the formula (II) can be prepared. In addition, by carrying out the same amination procedure as in the step I1 using 6-deoxy 11107D as a starting material, one or two hydroxyl groups can also be aminated.

Further, by alkylating, acylating, carbamoylating or sulfonylating the amino group respectively in the compound of the formula (II) using a method well known in the synthetic organic chemistry or the above-described method, the compound of the formula (I) can be prepared.

J. A Method for Preparing a Keto Compound (Oxidation of a Hydroxyl Group)

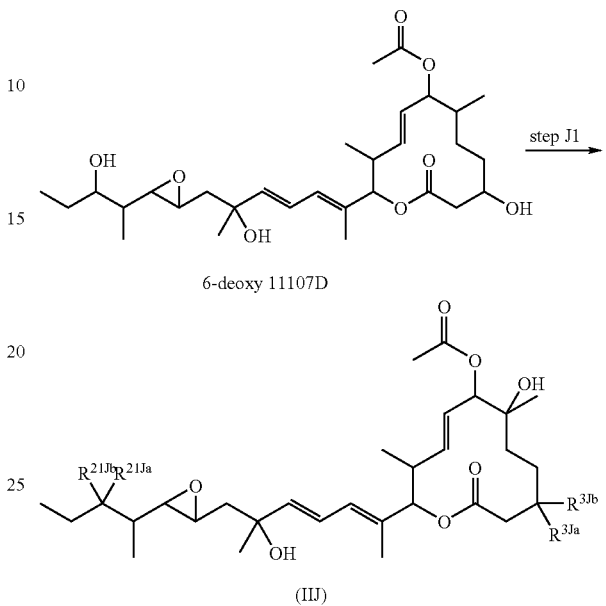

In the formula, any one of $R^{3Ja}$ and $R^{3Ja}$ represents a hydroxyl group, and the other represents a hydrogen atom, or $R^{3Ja}$ and $R^{3Ja}$, together in combination with the carbon atom to which $R^{3Ja}$ and $R^{3Ja}$ are bonded, represent an oxo group; and any one of $R^{21Ja}$ and $R^{21Ja}$ represents a hydroxyl group, and the other represents a hydrogen atom, or $R^{21Ja}$ and $R^{21Ja}$, together in combination with the carbon atom to which $R^{21Ja}$ and $R^{21Ja}$ are bonded, represent an oxo group.

The step J1 is a step of synthesizing an oxo-compound represented by the formula (IIJ) by oxidation of the hydroxyl group of 6-deoxy 11107D as a starting material.

The oxidizing agent used in this step is, for example, manganese dioxide, pyridinium chlorochromate, pyridinium dichromate, Dess-Martin reagent or reagents used in Swern oxidation. Although there are no specific limitations to the solvent used for the reaction, a solvent which does not easily react with the starting material is desirable. Examples include tetrahydrofuran, dichloromethane, chloroform and toluene. The reaction temperature is −78° C. to a reflux temperature. The reaction time is 10 minutes to 78 hours. Above all, a reaction using Dess-Martin reagent, manganese dioxide or reagents under Swern oxidation is preferable, for example. A reaction using Dess-Martin reagent is particularly preferable. As the solvent in the oxidation using Dess-Martin reagent, dichloromethane and chloroform are particularly preferable. The amount of the oxidizing agent used herein is 1 to 20 equivalents, and preferably 1 to 5 equivalents, to the compound (6-deoxy 11107D). The reaction temperature is preferably 0° C. to room temperature. The reaction time is 30 minutes to 24 hours, and preferably one to eight hours.

Further, in the step J1, by using a compound obtained by preliminary derivation by the above-described method for an urethane derivative, thiourethane derivative, ester derivative, alkyl derivative, or the like, instead of 6-deoxy 11107D, a compound in which the hydroxyl group at the 3-position or 21-position of these derivatives is converted into an oxo moiety can be synthesized. In addition, by oxidizing the hydroxyl group at the 7-position of the compound represented by the formula (IIA), a 7-oxo compound can also be obtained.

Moreover, by combining protection and deprotection procedures of the above-described steps A1 and A5 with the step JI in various manners, the hydroxyl groups at the 3-position, the 7-position and/or the 21-position can be selectively converted into an oxo moiety. Further, by conducting urethane derivation, thiourethane derivation, ester derivation or alkyl derivation of a compound respectively, of which the hydroxyl group is preliminarily converted into an oxo moiety, according to the above-described method, a compound modified by both the corresponding modification and the oxo-derivatization can be synthesized, respectively.

By an appropriate combination of the reactions A to J and the protection and deprotection procedures of the hydroxyl group as described above, the compound represented by the formula (I) can be synthesized.

After termination of the reaction, the target product of each reaction is isolated from a reaction mixture according to a conventional procedure. For example, the target product can be obtained by removing an insoluble matter by filtration and removing the solvent by evaporation in an appropriate manner, if insoluble matter is present, or by diluting the reaction mixture with an organic solvent such as ethyl acetate, washing the mixture with water, drying the organic layer with anhydrous magnesium sulfate, and then evaporation. If required, the target product can be further purified by a conventional procedure, for example, column chromatography, thinlayer chromatography or high performance liquid chromatography.

The compound of the formula (I) can be synthesized from the isolated and purified 6-deoxy 11107D and 6-deoxy 11107D compound using a common organic synthetic procedure. Representative A. urethane derivatives, B. thiourethane derivatives, C. ether derivatives, D. ester derivatives, E. phosphoric ester derivatives or monoamidosulfuric ester derivatives, F. sulfonic ester derivatives and amidosulfonic ester derivatives, G. halogen derivatives, H. sulfonate derivatives, I. amine derivatives and J. keto compounds can be produced in the above-described methods by changing the conditions of the step 1A of protecting a hydroxyl group.

Next, in order to prove the usefulness of the present invention, VEGF transcription inhibitory action, action of inhibiting proliferation of WiDr human colon cancer cells, solid cancer proliferation inhibitory action, body weight reduction (acute toxicity) and stability in an aqueous solution of compounds as representatives of the compound of the formula (I) of the present invention were measured.

Test Example 1

Construction of a Reporter System for Screening a Compound Inhibiting VEGF Transcription In order to prepare a reporter system in which transcription from a VEGF promoter is reflected, a VEGF promoter sequence was cloned and inserted into a placental alkaline phosphatase (PLAP) vector to construct a reporter vector.

In order to obtain a promoter region of human VEGF, a VEGF genome was cloned from a phage library. Based on VEGF cDNA (GenBank accession number: X62568), a PCR primer in the sequence described as SEQ ID NO: 1 or SEQ ID NO: 2 was designed to conduct PCR, thereby obtaining about a fragment of 340 bp. A human genomic phage library (human genomic library, Clontech) was screened using this fragment as a probe to obtain pUC18-VEGFA containing a VEGF5' franking region of about 5.4 kb. This pUC18-VEGFA was cut with Kpn I/Nhe I to obtain a VEGF promoter region of about 2.3 kb, and the region was inserted into the multicloning site Kpn I/Nhe I of the placental alkaline phosphatase (PLAP) reporter vector (Goto et al., Mol. Pharmacol., 49, 860-873, 1996) to construct a VEGF-PLAP vector.

The above-described VEGF-PLAP vector was introduced into U251 cells cultured in a Dulbecco's modified Eagle's medium containing 10% fetal bovine serum (DMEM, manufactured by Sigma Co.), and cultured in the presence of 1 mg/mL G418 (Merck & Co., Inc.) to establish a G418-resistant stable clone (U251/1-8 cells).

As in a report by Minchenko et al. (Cell. Mol. Biol. Res., 40, 35-39, 1994), U251/1-8 cells were confirmed to be a reporter system which secretes PLAP into a culture medium under hypoxic conditions (2% $O_2$ incubator), and in which transcription from a VEGF promoter is reflected. A compound inhibiting VEGF production induced by hypoxic stimulation was screened using this clone.

Test Example 2

VEGF Transcription Inhibitory Activity of a 6-deoxy 11107D Derivative

In order to eliminate influence of the alkali phosphatase in the serum, the U251/1-8 cells were washed with a sufficient amount of PBS (Phosphate buffered saline) twice, and treated at 65° C. for 20 minutes to inactivate the alkaline phosphatase in the serum. $4 \times 10^4$ cells/180 µL per well of the cells diluted in the DMEM culture medium containing 10% of this serum were plated in a 96-well plate.

The cells were cultured in a $CO_2$ incubator (5% $CO_2$) at 37° C. overnight, and 20 µL of the above-described culture solution containing the test compound at threefold serial dilutions was added. Subsequently, the cells were cultured in hypoxic (2% $O_2$) incubator for 18 hours. To measure the PLAP activity in the culture supernatant liquid, 10 µL of the culture supernatant liquid was added to 50 µL of a 0.28 M $Na_2CO_3$—$NaHCO_3$ buffer solution (pH 10.0, 8.0 mM $MgSO_4$), and finally 50 µL of an alkaline phosphatase substrate (Lumistain, Genome Science Laboratories Co., Ltd.) was added thereto. After the reaction for one hour, chemiluminescence was detected using a microplate reader (PerkinElmer) to measure the PLAP activity as the alkaline phosphatase activity. The PLAP activity under normoxic conditions was defined as 0%, the PLAP activity of the cells when treated under hypoxic conditions was defined as 100%, and the concentration for inhibiting 50% of the PLAP activity was defined as the $IC_{50}$ value of PLAP. The $IC_{50}$ values of the 6-deoxy 11107D derivatives shown in examples were determined (n=2 to 3). The $IC_{50}$ values of the representative compounds are shown in Table 1.

TABLE 1

| Test compound | VEGF transcription inhibitory activity ($IC_{50}$: nM) |
|---|---|
| Compound 18** | 1.0 |
| Compound 19* | 1.1 |
| Compound 20** | 1.1 |
| Compound 21** | 2.0 |
| Compound 22** | 2.5 |
| Compound 23* | 14.7 |

TABLE 1-continued

| Test compound | VEGF transcription inhibitory activity ($IC_{50}$: nM) |
| --- | --- |
| Compound 29** | 1.3 |
| Compound 39** | 1.3 |
| Compound 43* | 2.3 |
| Compound 44* | 2.4 |
| Compound 55** | 1.1 |

The compound of the formula (I) exhibited strong VEGF transcription inhibitory activity.

Test Example 3

Action of Inhibiting Proliferation of WiDr Human Colon Cancer Cells $2 \times 10^3$ cells/well of WiDr human colon cancer cells cultured in a Dulbecco's modified Eagle's medium containing 10% fetal bovine serum, penicillin (100 units/mL) and streptomycin (100 μg/mL) (DMEM, manufactured by Sigma Co.) were plated in a 96-well plate. The cells were cultured in a $CO_2$ incubator overnight, and 20 μL of the above-described culture solution containing the test compound at threefold serial dilutions was added for culturing the cells. After three days, 50 μL of a 3.3 mg/mL MTT solution was added, and the cells were further cultured for one hour. Then, formazan generated by reduction using living cells was extracted with 100 μL of DMSO to measure the absorbance (A540/A660), which was used as an index of the number of living cells.

The concentration for inhibiting 50% of proliferation of WiDr human colon cancer cells ($IC_{50}$ value) of the compound of the formula (I) was determined (n=2 to 3). The $IC_{50}$ values of the representative compounds are shown in Table 2.

TABLE 2

| Test compound | WiDr human colon cancer cell proliferation inhibitory activity ($IC_{50}$: nM) |
| --- | --- |
| Compound 18** | 0.5 |
| Compound 19* | 0.3 |
| Compound 20** | 0.2 |
| Compound 21** | 0.6 |
| Compound 22** | 1.1 |
| Compound 23* | 3.8 |
| Compound 29** | 0.3 |
| Compound 39** | 0.5 |
| Compound 43** | 0.5 |
| Compound 44* | 0.6 |
| Compound 55** | 0.6 |

The compound of the formula (I) exhibited strong WiDr human colon cancer cell proliferation inhibitory action.

Test Example 4

Solid Cancer Growth Inhibitory Action

In order to examine the solid cancer growth inhibitory activity of the compound of the formula (I) in vivo, WiDr human colon cancer cells were subcutaneously implanted into the body of each nude mouse. When the tumor volume of each mouse reached about 100 mm3, the mice were classified into groups so that both groups had an uniform average tumor volume of the mice. The control group consisted of ten mice, and the 6-deoxy 11107D derivative-administration group consisted of five mice. The derivative was intravenously injected at 0.625 mg/kg/day, 1.25 mg/kg/day, 2.5 mg/kg/day, 5 mg/kg/day, or 10 mg/kg/day to each mouse of the administration group, and a vehicle was administered to each mouse of the control group.

The tumor volumes on the 15th day were measured to determine the relative tumor weight ratio (T/C %), based on the tumor weight of each mouse of the control group as 100%. Each T/C % for the representative compounds of the formula (I) is shown in Table 3. The body weights on the day of the start of administration, 5th day, 8th day, 12th day and 15th (or 16th) day were measured to examine the relative body weight variations in the case of administering the representative compounds, based on the body weights on the day of the start of administration as 100%. The minimum relative body weight ratios, which are the relative body weight ratios on the day when the body weights were lightest, are shown in Table 3.

TABLE 3

| Test compound | Amount administered (mg/kg/day) | WiDr human colon tumor growth inhibitory activity T/C(%) | Minimum relative body weight ratio |
| --- | --- | --- | --- |
| Compound 43 | 1.25 | 9 | 0.83 |
| Compound 55 | 0.625 | 11 | 0.80 |

The compound of the formula (I) exhibited action for inhibiting growth of WiDr human colon tumors even in vivo at a dose not causing a significant reduction in the body weight.

Test Example 5

Stability in an Aqueous Solution

The compound of the formula (I) was dissolved in DMSO at a concentration of 10 to 20 mM, and the solution was diluted with a pH 7 Britton-Robinson buffer solution to about 500-fold. This solution was used as a sample solution, and was incubated at 25° C. for 24 hours.

The sample solution before and after the incubation was analyzed using high-performance liquid chromatography to obtain a chromatogram. The percentage of the compound remaining in the sample solution after the incubation was determined from the peak area of the chromatogram. The results for the representative compounds are shown in Table 4.

TABLE 4

| Test compound | Remaining percentage (%) |
| --- | --- |
| FD-895 | 83.0 |
| Compound 18 | 95.0 |
| Compound 19 | 95.5 |
| Compound 20 | 95.6 |
| Compound 21 | 94.8 |
| Compound 22 | 95.4 |
| Compound 39 | 95.9 |
| Compound 43 | 95.8 |
| Compound 44 | 95.4 |
| Compound 55 | 95.7 |

While the content of FD895 was decreased to 83% after 24 hours, the remaining percentages of the compounds 18, 19, 20, 22, 39, 43, 44 and 55 as the representatives of the compound of the formula (I) were all 95 to 96%. This data indicates that the 6-deoxy 11107D derivative as the compound of the formula (I) are stable in aqueous solutions.

As is clear from the above-described pharmacological test examples, the compound of the formula (I) of the present invention alters gene expression, and thus inhibits VEGF production, in particular. Therefore, the compound is expected to be used as a tumor treating agent, in particular, a solid cancer treating agent, cancer metastasis inhibitor, diabetic retinopathy treating agent, rheumatoid arthritis treating agent or ecchymoma treating agent. Furthermore, as can be seen in the toxicity test in Test Example 4, since the action of inhibiting growth of WiDr human colon cancer tumors is exhibited at a dose not causing a significant reduction in the body weights of the test mice, the compound of the formula (I) is a compound which is highly safe. Accordingly, the compound is effective for preventing or treating a disease for which gene expression control is effective, a disease for which VEGF production inhibitory action is effective, and a disease for which angiogenesis inhibitory action is effective. The "prevention or treatment" refers to prevention, treatment, or both. More specifically, the compound of the formula (I) of the present invention is effective as an antitumor drug, in particular, an antitumor drug or tumor metastasis inhibitor against a solid cancer. Examples of the solid cancer include a pancreatic cancer, stomach cancer, colon cancer, breast cancer, prostate cancer, lung cancer, renal cancer, brain tumor, head and neck cancer, esophagus cancer, skin cancer, hepatic cancer, uterine cancer, cancer of the uterine cervix, bladder cancer, thyroid cancer, testicular tumor, villus cancer, osteosarcoma, soft-tissue sarcomata and ovarian cancer. The compound is particularly preferably used for cancers such as a colon cancer, breast cancer, prostate cancer, lung cancer, head and neck cancer, and ovarian cancer. Further, the compound is also effective as an anticancer drug against leukemia. In addition, the compound is also effective as a hemangioma treating agent. Moreover, the compound is effective as a diabetic retinopathy treating agent, rheumatoid arthritis treating agent or hemangioma treating agent based on the VEGF production inhibitory action. Alternatively, the compound is also effective as an agent for treating inflammatory diseases consisting of osteoarthritis, psoriasis, delayed hypersensitive reaction and atherosclerosis.

When the above-described compound is to be prepared as an injectable solution, a pH adjuster, buffering agent, stabilizer, solubilizer, or the like are added to the active ingredient, as required, to prepare an injectable solution for subcutaneous, intramuscular, intra-articular or intravenous administration.

When the above-described compound is to be administered as an agent for treating or preventing various diseases, the compound may be orally administered as tablets, powder, granules, capsules, syrup, or the like, or the compound may be parenterally administered as a spray, a suppository, an injectable solution, an external use or drops. The dose significantly varies according to the degree of symptom, the age, the type of liver disease, and the like, the dose for the adult is typically about 1 mg to 100 mg per day in a single dose or in divided doses of several times.

A drug product is produced using general ingredients in a conventional method. Specifically, when an oral solid formulation is to be prepared, a vehicle and, as required, a binder, disintegrating agent, lubricant, coloring agent, flavoring or odor-masking agent, or the like are added to the active ingredient, and then the mixture is fabricated into tablets, coated tablets, granules, powder, capsules, or the like. These tablets or granules may be appropriately coated with sugar, gelatin, or other coatings, naturally.

According to the present invention, the compound of the formula (I) of the present invention inhibits VEGF production and angiogenesis, in particular, by altering gene expression, exhibits an excellent antitumor effect in a in vivo solid cancer model, and also has stability in an aqueous solution. Therefore, the present invention can provide a cancer treating agent, in particular, a solid cancer treating agent, cancer metastasis inhibitor, diabetic retinopathy treating agent, rheumatoid arthritis treating agent or ecchymoma treating agent, for example.

EXAMPLES

The present invention will be described in more detail below with reference to examples consisting of methods for producing 6-deoxy 11107B (Examples 1 to 4), bioconversion reactions from 6-deoxy 1107B to 6-deoxy 11107D (Examples 5 to 11), 6-deoxy 11107D analogues (Examples 12 to 17) and 6-deoxy 11107D derivatives (Examples 18 to 60), as well as reference examples. However, the present invention should not be limited to these examples.

The abbreviations used in the chemical formulas of the examples are shown below.

DEIPS: Diethylisopropylsilyl group
EE: 1-Ethoxyethyl group
TES: Triethylsilyl group Example 1

Acquisition of a Mutant of Mer-11107

In the present invention, *Streptomyces* sp. Mer-11107 (depositary number: FERM BP-7812) was mutated with N-methyl-N'-nitroso-N-nitrosoguanidine in a Tris-maleate buffer solution (pH 6.0) (100 µg/mL, 28° C., one hour), and the strain was smeared on an yeast-malt agar culture medium to form spores. The resulting spores were collected, and a part of the spores were diluted and smeared on an yeast-malt agar culture solution to form colonies. Each cell as sampled from colonies, inoculated into a 15 mL-volume test tube containing 2 mL of a seed culture medium (glucose: 2%, soybean meal (Esusan meat, manufactured by Ajinomoto Co., Inc.): 1%, yeast extract (manufactured by Oriental Yeast Co., Ltd.): 0.5%, sodium chloride: 0.25% and calcium carbonate: 0.32%, pH 6.8), and cultured on a shaking culture apparatus at 25° C. for two days. Further, 0.5 mL of the seed culture solution (of which the remainder was frozen) was inoculated into a 15 mL-volume test tube containing 2 mL of a production culture medium (soluble starch: 7%, gluten meal: 0.8%, pharmamedia: 0.8% and calcium carbonate: 0.1%; pH 7.5), and the cells were cultured on a shaking culture apparatus at 25° C. for four days. The culture solution was extracted with ethyl acetate, and analyzed by TLC (Merck 5715, acetone:toluene=1:1, colored with phosphomolybdic acid) to select the strain A-1543, a strain in which a spot other than 11107B (Rf: about 0.5) appeared. This strain was deposited with International Patent Organism Depositary, National Institute of Advanced Industrial Science and Technology in Central 6, 1-1-1 Higashi, Tsukuba-shi, Ibaraki 305-8566, Japan as FERM P-18942 on Jul. 23, 2002, and was transferred to International Patent Organism Depositary (IPOD), National Institute of Advanced Industrial Science and Technology in Central 6, 1-1-1 Higashi, Tsukuba-shi, Ibaraki 305-8566, Japan under the international depositary number FERM BP-8442 on Jul. 28, 2003.

Example 2

Culture of A-1543

A frozen seed culture of A-1543 in advance was melted. 0.2 mL of the melt was inoculated into a 250 mL-volume conical flask containing 20 mL of a seed culture medium (glucose: 2%, soybean meal (Esusan meat, manufactured by Ajinomoto Co., Inc.): 1%, yeast extract (manufactured by Oriental Yeast Co., Ltd.): 0.5%, sodium chloride: 0.25% and calcium carbonate: 0.32%; pH 6.8), and the cells were cultured on a shaking culture apparatus at 25° C. for three days. Further, 0.6 mL of the seed culture solution was inoculated into a 60 mL of a production culture medium (soluble starch: 5%, gluten meal: 1%, pharmamedia: 2% and calcium carbonate: 0.1%; pH 7.5), and the seed mash was cultured on a shaking culture apparatus at 25° C. for five days.

Example 3

Purification of 6-deoxy 11107B and 6-deoxy 11107BI

The culture solution prepared by the method of Example 2 (1.2 L) was separated into a filtrate and cells using a centrifuge. The supernatant liquid was extracted with ethyl acetate (1.2 L). The cells were extracted with acetone (500 mL), and the extract was filtrated to obtain an acetone extract. Acetone of the acetone extract was removed by distillation under reduced pressure, and then the distilled product was extracted with ethyl acetate (1 L). The respective ethyl acetate layer was washed with water, and dried by dehydration with anhydrous sodium sulfate. Then, these layers were concentrated together under reduced pressure to obtain 531 mg of a crude active fraction. This crude active fraction was subjected to silica gel column chromatography (Kiesel gel 60, 25 g), washed with toluene (50 mL), and eluted with a mixed solution of toluene with ethyl acetate (3:1; v/v)(300 mL) to obtain 161 mg of a crude active fraction containing 6-deoxy 11107B and 34 mg of a crude active fraction containing 6-deoxy 11107B1. The resulting crude active fraction containing 6-deoxy 11107B was subjected to preparative high-performance liquid chromatography (HPLC) under the preparative conditions (A1) described below to obtain a 6-deoxy 11107B fraction eluted. Then, the solvent was removed by distillation to obtain 118.8 mg of 6-deoxy 11107B. Similarly, the crude active fraction containing 6-deoxy 11107BI was fractionated using HPLC under the preparative conditions (A2) described below, and then the solvent was removed by distillation to obtain 11.0 mg of 6-deoxy 11107BI.

Preparative HPLC Conditions (A1)
Column: CAPCELL PAK C18 UG120, diameter: 30 mm, length:
250 mm (manufactured by Shiseido Co., Ltd.)
Flow rate: 20 mL/min
Detection: 240 nm
Eluate: Acetonitrile/water (60:40, v/v), isocratic Preparative HPLC Conditions (A2)
Column: CAPCELL PAK C18 UG120, diameter: 30 mm, length:
250 mm (manufactured by Shiseido Co., Ltd.)
Flow rate: 20 mL/min
Detection: 240 nm
Eluate: Acetonitrile/water (65:35, v/v), isocratic The retention time of the above-described compounds when analyzed under the following analytical HPLC conditions is shown below. Analytical HPLC conditions (a)
Column: CAPCELL PAK C18 SG120, diameter: 4.6 mm, length: 250 mm (manufactured by Shiseido Co., Ltd.)
Temperature: 40° C.
Flow rate: 1 mL/min
Detection: 240 nm
Eluate: Acetonitrile/water (60:40, v/v), isocratic
Retention time:
6-deoxy 11107B: 12.0 minutes
6-deoxy 11107BI: 26.4 minutes

Example 4

Physicochemical Properties of 6-deoxy 11107B

Physicochemical properties of 6-deoxy 11107B are shown below. 6-deoxy 11107B was determined to have a structure represented by the formula (XVI″).
1. Characteristics: Colorless powder
2. Molecular weight: 520, ESI-MS 543 (M+Na)$^+$, ESI-MS 519 (M−H)$^−$
3. Solubility: soluble in dimethyl sulfoxide, pyridine, methanol, and acetone, poorly soluble in water
4. Color reaction: Positive for iodine, sulfuric acid, and phosphomolybdic acid
5. Ultraviolet spectrum (methanol, maximum value) nm: 240 (ε33500)
6. Infrared absorption spectrum (KBr)cm$^{-1}$: 3449, 2965, 1734, 1456, 1372, 1242, 1170
7.
$^1$H-NMR spectrum (CD$_3$OD, 400 MHz): δ ppm (integration, multiplicity, coupling constant J (Hz)): 0.87 (3H, d, J=7.0 Hz), 0.90 (3H, d, J=7.0 Hz), 0.94 (3H, d, J=7.3 Hz), 0.97 (3H, d, J=7.0 Hz), 1.08 (3H, d, J=7.0 Hz), 1.17-1.21 (1H, m), 1.24-1.36 (2H, m), 1.42-1.52 (3H, m), 1.61-1.66 (3H, m), 1.74 (3H, d, J=1.1 Hz), 1.89-1.96 (1H, m), 2.00 (3H, s), 2.41-2.47 (1H, m), 2.43 (1H, dd, J=5.5, 13.9 Hz), 2.51-2.58 (1H, m), 2.56 (1H, dd, J=3.7, 13.9 Hz), 2.65 (1H, dd, J=2.2, 8.1 Hz), 2.72 (1H, dt, J=2.2, 5.9 Hz), 3.51 (1H, dt, J=4.4, 8.4 Hz), 3.75-3.80 (1H, m), 4.91 (1H, dd, J=8.8, 10.6 Hz), 5.00 (1H, d, J=10.6 Hz), 5.42 (1H, dd, J=9.2, 15.0 Hz), 5.49 (1H, dd, J=9.2, 15.0 Hz), 5.65 (1H, dd, J=8.4, 15.0 Hz), 6.08 (1H, d, J=10.6 Hz), 6.32 (1H, dd, J=10.6, 15.0 Hz)

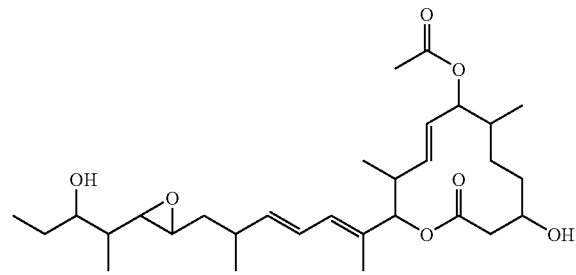

(XVI″)

Example 5

Physicochemical Properties of 6-deoxy 11107BI

Physicochemical properties of 6-deoxy 11107BI are shown below. 6-deoxy 11107BI was determined to have a structure represented by the following formula.

1. Molecular weight: 504, ESI-MS 527 (M+Na)$^+$, ESI-MS 503 (M−H)$^−$
2. $^1$H-NMR spectrum (CD$_3$OD, 400 MHz): δ ppm (integration, multiplicity, coupling constant J (Hz)): 0.86 (3H, d, J=6.6 Hz), 0.92 (3H, t, J=7.3 Hz), 0.97 (3H, d, J=6.6 Hz), 0.98 (3H, d, J=6.6 Hz), 1.01 (3H, d, J=7.0 Hz), 1.25-1.35 (3H, m), 1.53-1.61 (3H, m), 1.72 (3H, d, J=0.7 Hz), 1.89-1.95 (1H, m), 2.00 (3H, s), 2.02-2.05 (2H, m), 2.10 (1H, dd, J=7.0, 14.3 Hz), 2.27-2.31 (1H, m), 2.43 (1H, dd, J=5.1, 13.9 Hz), 2.50-2.56 (1H, m), 2.56 (1H, dd, J=3.3, 13.9 Hz), 3.18 (1H, dt, J=3.3, 8.8 Hz), 3.75-3.80 (1H, m), 4.91 (1H, covered with H$_2$O), 5.00 (1H, d, J=10.6 Hz), 5.32 (1H, dd, J=7.3, 15.4 Hz), 5.38 (1H, dd, J=6.2, 15.4 Hz), 5.41 (1H, dd, J=9.2, 15.0 Hz), 5.49 (1H, dd, J=9.2, 15.4 Hz), 5.64 (1H, dd, J=7.7, 15.0 Hz), 6.06 (1H, d, J=11.0 Hz), 6.21 (1H, dd, J=9.9, 15.0 Hz)

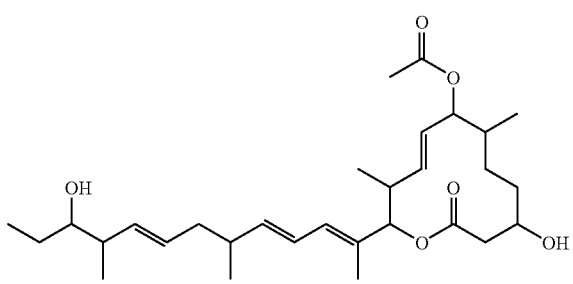

Example 6

Acquisition of a Strain for Converting 6-deoxy 11107B Into 6-deoxy 11107D

A part of a slant culture medium (yeast-malt agar culture medium) of a strain separated from the soil was inoculated into a 250 mL-volume conical flask containing 20 mL of a seed culture medium (soluble starch: 2.4%, glucose: 0.1%, soybean meal (Esusan meat, manufactured by Ajinomoto Co., Inc.): 0.5%, beef extract (manufactured by Diffco Co.): 0.3%, yeast extract (manufactured by Diffco Co.): 0.5%, tryptone peptone (manufactured by Diffco Co.): 0.5%, and calcium carbonate: 0.4%), and the cells were cultured on a shaking culture apparatus at 28° C. for three days to obtain a seed culture solution. Further, 0.6 mL of the seed culture solution was inoculated into a 500 mL-volume conical flask containing 60 mL of a production culture medium (potato starch: 2%, glucose: 2%, soybean meal (Esusan meat, manufactured by Ajinomoto Co., Inc.): 2%, yeast extract: 0.5%, sodium chloride: 0.25%, calcium carbonate: 0.32%, copper sulfate: 0.0005%, manganese chloride: 0.0005% and zinc sulfate: 0.0005%; pH 7.4), and the cells were cultured on a shaking culture apparatus at 28° C. for four days. 2 mL each of the resulting culture solution was dispensed to a 15 mL-volume test tube, and centrifuged at 3,000 rpm for five minutes to harvest the cells. The cells were suspended in 2 mL of a 50 mM phosphate buffer solution (pH 6.0). Next, 6-deoxy 11107B as a substrate was prepared as a 5 mg/mL solution in dimethylsulfoxide, and 0.04 mL each of the solution was added to the suspension. After the addition, the mixture was shaken at 28° C. for 23 hours to conduct hydroxylation reaction. After the reaction, an HPLC analysis was conducted to select two strains in which the peak of 6-deoxy 11107D appears, strain A-1544 and strain A-1545. These strains were deposited with International Patent Organism Depositary, National Institute of Advanced Industrial Science and Technology in Central 6, 1-1-1 Higashi, Tsukuba-shi, Ibaraki 305-8566, Japan as FERM P-18943 and FERM P-18944, respectively, on Jul. 23, 2002, and were transferred to International Patent Organism Depositary (IPOD), National Institute of Advanced Industrial Science and Technology in Central 6, 1-1-1 Higashi, Tsukuba-shi, Ibaraki 305-8566, Japan under the international depositary numbers FERM BP-8446 and FERM BP-8447, respectively, on Jul. 30, 2003.

The retention time of the above-described compounds when analyzed under the following analytical HPLC conditions are shown below. Analytical HPLC conditions (b)
Column: CAPCELL PAK C18 SG120, diameter: 4.6 mm, length: 250 mm (manufactured by Shiseido Co., Ltd.)
Temperature: 40° C.
Flow rate: 1 mL/min
Detection: 240 nm
Eluate: Acetonitrile/water (50:50, v/v), isocratic
Retention time:
6-deoxy 11107B: 27.2 minutes
6-deoxy 11107D: 8.2 minutes

Example 7

Culture of A-1544

A part of a slant culture medium (yeast-malt agar culture medium) of A-1544 was inoculated into a 250 mL-volume conical flask containing 25 mL of a seed culture medium (potato starch: 2%, glucose: 2%, soybean meal (Esusan meat, manufactured by Ajinomoto Co., Inc.): 2%, yeast extract: 0.5%, sodium chloride: 0.25%, calcium carbonate: 0.32%, copper sulfate: 0.0005%, manganese chloride: 0.0005% and zinc sulfate: 0.0005%; pH 7.4), and the cells were cultured on a shaking culture apparatus at 28° C. for three days to obtain a seed culture solution. 0.75 mL each of this culture solution was dispensed to a 2 mL-volume serum tube (manufactured by Sumitomo Bakelite Co., Ltd.), and the same amount of 40% glycerol aqueous solution was added to the solution. The mixture was stirred and then frozen at −70° C. to prepare frozen seed culture. This frozen seed culture was melted. The 0.25 mL of the culture was inoculated into a 250 mL-volume conical flask containing 25 mL of a seed culture medium (potato starch: 2%, glucose: 2%, soybean meal (Esusan meat, manufactured by Ajinomoto Co., Inc.): 2%, yeast extract: 0.5%, sodium chloride: 0.25%, calcium carbonate: 0.32%, copper sulfate: 0.0005%, manganese chloride: 0.0005% and zinc sulfate: 0.0005%; pH 7.4), and the cells were cultured on a shaking culture apparatus at 28° C. for two days to obtain a seed culture solution. Further, 0.25 mL of the seed culture solution was inoculated into a 250 mL-volume conical flask containing 25 mL of a production culture medium (potato starch: 2%, glucose: 2%, soybean meal (S-San meat, manufactured by Ajinomoto Co., Inc.): 2%, yeast extract: 0.5%, sodium chloride: 0.25%, calcium carbonate: 0.32%, copper sulfate: 0.0005%, manganese chloride: 0.0005% and zinc sulfate: 0.0005%; pH 7.4), and the cells were cultured on a shaking culture apparatus at 25° C. for four days.

Example 8

Production of 6-deoxy 11107D by Bioconversion Reaction

Each of the strain A-1544 culture solutions obtained by the method of Example 7 (30 conical flasks with a volume of 25 mL/250 mL each) was centrifuged at 3,000 rpm for 10 minutes to harvest the cells. The cells were suspended in 25 mL of a 50 mM phosphate buffer solution (pH 6.0). Next, 6-deoxy 11107B as a substrate was prepared as a 50 mg/mL solution in dimethylsulfoxide, and 0.25 mL each of the solution was added to the suspension. After the addition, the mixture was shaken at 28° C. for 22 hours to conduct hydroxylation reaction. After the reaction, the reaction product was centrifuged at 5,000 rpm for 20 minutes to separate the product into a filtrate and cells. The supernatant liquid was extracted with ethyl acetate (750 mL). The cells were extracted with acetone (500 mL), and the extract was filtrated to obtain an acetone extract. Acetone of the acetone extract was removed by distillation under reduced pressure, and then the distilled product was extracted with ethyl acetate (750 mL). The respective ethyl acetate-layer was washed with water, and dried by dehydration with anhydrous sodium sulfate. Then, these layers were concentrated together under reduced pressure to obtain 365 mg of a crude active fraction. This crude active fraction was subjected to silica gel column chromatography (Kiesel gel 60, 35 g), washed with toluene (70 mL), and then eluted with a mixed solution of toluene with acetone (4:1; v/v)(500 mL) and a mixed solution of toluene with acetone (2:1; v/v)(300 mL) to obtain 139 mg of a crude active fraction containing 6-deoxy 11107D and 6-deoxy 11107BP, 78 mg of a crude active fraction containing 6-deoxy 11107AV and 78 mg of a crude active fraction containing 6-deoxy 11107D 20-OH and 6-deoxy 11107F. The resulting crude active fraction containing 6-deoxy 11107D and 6-deoxy 11107BP was subjected to preparative high-performance liquid chromatography (HPLC) under the preparative conditions (B1) described below to obtain a 6-deoxy 11107D fraction and 6-deoxy 11107BP fraction eluted. Then, the solvent was removed by distillation to obtain 6-deoxy 11107D (67.0 mg) and 6-deoxy 11107BP (8.1 mg). Similarly, the crude active fraction containing 6-deoxy 11107AV and the crude active fraction containing 6-deoxy 11107D 20-OH and 6-deoxy 11107F were fractionated using HPLC under the preparative conditions (A1) described above and the preparative conditions (B2) described below, respectively. Then, the solvents were removed by distillation to obtain 6-deoxy 11107AV (9.3 mg), 6-deoxy 11107D 20-OH (19.9 mg), and 6-deoxy 11107F (22.1 mg).

Example 9

Culture of Strain A-1545

A part of a slant culture medium (yeast-malt agar culture medium) of A-1545 was inoculated into a 250 mL-volume conical flask containing 25 mL of a seed culture medium (potato starch: 2%, glucose: 2%, soybean meal (Esusan meat, manufactured by Ajinomoto Co., Inc.): 2%, yeast extract: 0.5%, sodium chloride: 0.25%, calcium carbonate: 0.32%, copper sulfate: 0.0005%, manganese chloride: 0.0005% and zinc sulfate: 0.0005%; pH 7.4), and the cells were cultured on a shaking culture apparatus at 28° C. for three days to obtain a seed culture solution. 0.75 mL each of this culture solution was dispensed to a 2 mL-volume serum tube (manufactured by Sumitomo Bakelite Co., Ltd.), and the same amount of 40% glycerol aqueous solution was added to the solution. The mixture was stirred and then frozen at −70° C. to prepare frozen seed culture. This frozen seed culture was melted, and 0.25 mL of the culture was inoculated into a 250 mL-volume conical flask containing 25 mL of a seed culture medium (potato starch: 2%, glucose: 2%, soybean meal (Esusan meat, manufactured by Ajinomoto Co., Inc.): 2%, yeast extract: 0.5%, sodium chloride: 0.25%, calcium carbonate: 0.32%, copper sulfate: 0.0005%, manganese chloride: 0.0005% and zinc sulfate: 0.0005%; pH 7.4), and the cells were cultured on a shaking culture apparatus at 28° C. for two days to obtain a seed culture solution. Further, 0.25 mL of the seed culture solution was inoculated into a 250 mL-volume conical flask containing 25 mL of a production culture medium (potato starch: 2%, glucose: 2%, soybean meal (Esusan meat, manufactured by Ajinomoto Co., Inc.): 2%, yeast extract: 0.5%, sodium chloride: 0.25%, calcium carbonate: 0.32%, copper sulfate: 0.0005%, manganese chloride: 0.0005% and zinc sulfate: 0.0005%; pH 7.4), and the cells were cultured on a shaking culture apparatus at 25° C. for four days.

Example 10

Production of 6-deoxy 11107D by Bioconversion Reaction

Each of the strain A-1545 culture solutions obtained by the method of Example 9 (40 conical flasks with a volume of 25 mL/250 mL each) was centrifuged at 3,000 rpm for 10 minutes to harvest the cells. The cells was suspended in 25 mL of a 50 mM phosphate buffer solution (pH 6.0). Next, 6-deoxy 11107B as a substrate was prepared as a 50 mg/mL solution in dimethylsulfoxide, and 0.25 mL each of the solution was added to the suspension. After the addition, the mixture was shaken at 28° C. for 22 hours to conduct hydroxylation reaction. After the reaction, the reaction product was centrifuged at 5,000 rpm for 20 minutes to separate the product into a filtrate and cells. The supernatant liquid was extracted with ethyl acetate (1 L). The cells were extracted with acetone (500 mL), and the extract was filtrated to obtain an acetone extract. Acetone of the acetone extract was removed by distillation under reduced pressure, and then the distilled product was extracted with ethyl acetate (1 L). The respective ethyl acetate layer was washed with water, and dried by dehydration with anhydrous sodium sulfate. Then, these layers were concentrated together under reduced pressure to obtain 537 mg of a crude active fraction. This crude active fraction was subjected to silica gel column chromatography (Kiesel gel 60, 50 g), washed with toluene (100 mL), and then eluted with a mixed solution of toluene with acetone (4:1; v/v)(600 mL) and a mixed solution of toluene with acetone (2:1; v/v)(600 mL) to obtain 112 mg of a crude active fraction containing 6-deoxy 11107D and 47 mg of a crude active fraction containing 6-deoxy 11107D 20-OH, 6-deoxy 11107D 17-OH and 6-deoxy 11107D 17-OH (17-position epimer). The resulting crude active fraction containing 6-deoxy 11107D was subjected to preparative high-performance liquid chromatography (HPLC) under the preparative conditions (B1) described below to obtain a 6-deoxy 11107D fraction eluted. Then, the solvent was removed by distillation to obtain 6-deoxy 11107D (67.2 mg). Similarly, the crude active fraction containing 6-deoxy 11107AV and the crude active fraction containing 6-deoxy 11107D 20-OH, 6-deoxy 11107D 17-OH and 6-deoxy 11107D 17-OH (17-position epimer) were fractionated using HPLC under the preparative conditions (A1) described above and the preparative conditions (B2) described below, respectively. Then, the solvents were removed by distillation to obtain 6-deoxy 11107AV (5.7 mg), 6-deoxy 11107D 20-OH (9.0 mg), 6-deoxy 11107D 17-OH (5.9 mg), and 6-deoxy 11107D 17-OH (17-position epimer) (6.4 mg).

Preparative HPLC conditions (B1)
Column: CAPCELL PAK C18 UG120, diameter: 30 mm, length:
250 mm (manufactured by Shiseido Co., Ltd.)
Flow rate: 20 mL/min
Detection: 240 nm
Eluate: Acetonitrile/water (40:60, v/v), isocratic Preparative HPLC Conditions (B2)
Column: CAPCELL PAK C18 UG120, diameter: 30 mm, length:
250 mm (manufactured by Shiseido Co., Ltd.)
Flow rate: 20 mL/min
Detection: 240 nm
Eluate: Acetonitrile/water (35:65, v/v), isocratic The retention time of the above-described compounds when analyzed under the following analytical HPLC conditions is shown below. Analytical HPLC conditions (c)
Column: CAPCELL PAK C18 SG120, diameter: 4.6 mm, length: 250 mm (manufactured by Shiseido Co., Ltd.)
Temperature: 40° C.
Flow rate: 1 mL/min
Detection: 240 nm
Eluate: Acetonitrile/water (45:55, v/v), isocratic
Retention time:
6-deoxy 11107D: 12.5 minutes
Analogue 1 (6-deoxy 11107BP): 11.4 minutes
Analogue 2 (6-deoxy 11107D 20-OH): 7.3 minutes
Analogue 3 (6-deoxy 11107F): 4.6 minutes
Analogue 4 (6-deoxy 11107D 17-OH): 7.8 minutes
Analogue 5 (6-deoxy 11107D 17-OH): 8.3 minutes
Analogue 6 (6-deoxy 11107AV): 17.8 minutes Example 11

Physicochemical Properties of 6-deoxy 11107D

Physicochemical properties of 6-deoxy 11107D are shown below. 6-deoxy 11107D was determined to have a structure represented by the formula (XVII').

1. Molecular weight: 536, ESI MS 559 (M+Na)$^+$, ESI-MS 535 (M−H)$^-$

2. $^1$H-NMR spectrum (CD$_3$OD, 400 MHz): δ ppm (integration, multiplicity, coupling constant J (Hz)): 0.87 (3H, d, J=7.0 Hz), 0.90 (3H, d, J=7.0 Hz), 0.94 (3H, t, J=7.3 Hz), 0.97 (3H, d, J=6.6 Hz), 1.21-1.26 (1H, m), 1.29-1.37 (3H, m), 1.34 (3H, s), 1.44-1.52 (2H, m), 1.60-1.64 (1H, m), 1.65 (1H, dd, J=6.2, 13.9 Hz), 1.77 (3H, d, J=1.1 Hz), 1.86 (1H, dd, J=5.4, 13.9 Hz), 1.89-1.94 (1H, m), 2.00 (3H, s), 2.43 (1H, dd, J=5.5, 13.9 Hz), 2.50-2.60 (1H, m), 2.56 (1H, dd, J=3.3, 13.9 Hz), 2.66 (1H, dd, J=2.2, 7.7 Hz), 2.89 (1H, dt, J=2.2, 6.2 Hz), 3.52 (1H, dt, J=4.8, 8.4 Hz), 3.75-3.80 (1H, m), 4.90 (1H, covered with H$_2$O), 5.01 (1H, d, J=10.6 Hz), 5.42 (1H, dd, J=9.2, 15.0 Hz), 5.50 (1H, dd, J=9.2, 15.0 Hz), 5.86 (1H, d, J=15.0 Hz), 6.13 (1H, d, J=10.6 Hz), 6.52 (1H, dd, J=11.0, 15.0 Hz)

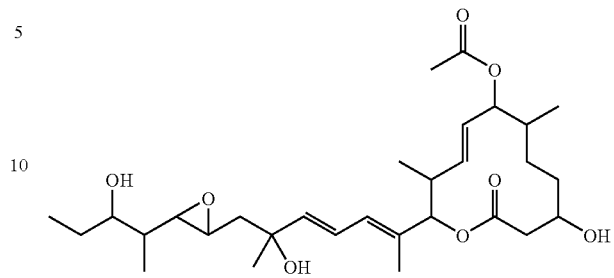

(XVII')

Example 12

Physicochemical Properties of Analogue 1 (6-deoxy 11107BP)

Physicochemical properties of an analogue 1 are shown below. The analogue 1 was determined to have a structure represented by the following formula.

1. Molecular weight: 550, ESI-MS 573 (M+Na)$^+$, ESI-MS 549 (M−H)$^-$

2. $^1$H-NMR spectrum (CD$_3$OD, 400 MHz): δ ppm (integration, multiplicity, coupling constant J (Hz)): 0.86 (3H, d, J=7.0 Hz), 0.97 (3H, d, J=6.6 Hz), 1.01 (3H, t, J=7.0 Hz), 1.25 (3H, s), 1.29-1.35 (2H, m), 1.34 (3H, s), 1.58-1.65 (2H, m), 1.68 (1H, dd, J=6.2, 13.9 Hz), 1.77 (3H, d, J=1.1 Hz), 1.86 (1H, dd, J=5.5, 13.9 Hz), 1.88-1.93 (1H, m), 2.00 (3H, s), 2.42 (1H, dd, J=5.1, 14.3 Hz), 2.52-2.58 (1H, m), 2.56 (1H, dd, J=3.3, 14.3 Hz), 2.61-2.76 (2H, m), 3.00 (1H, d, J=2.2 Hz), 3.17 (1H, dt, J=2.2, 5.9 Hz), 3.75-3.80 (1H, m), 4.91 (1H, dd, J=9.2, 10.3 Hz), 5.01 (1H, d, J=10.6 Hz), 5.42 (1H, dd, J=9.2, 15.0 Hz), 5.50 (1H, dd, J=9.2, 15.0 Hz), 5.87 (1H, d, J=15.4 Hz), 6.14 (1H, d, J=11.0 Hz), 6.53 (1H, dd, J=11.0, 15.4 Hz)

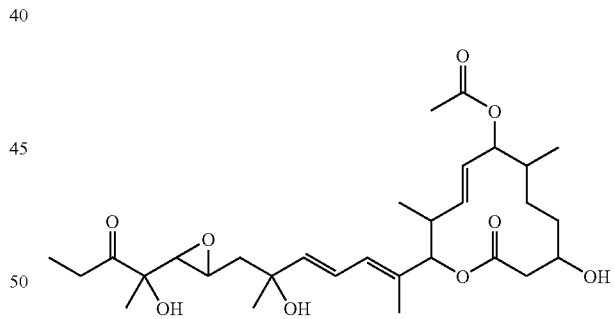

Example 13

Physicochemical Properties of Analogue 2 (6-deoxy 11107D 20-OH)

Physicochemical properties of an analogue 2 are shown below. The analogue 2 was determined to have a structure represented by the following formula.

1. Molecular weight: 552, ESI-MS 575 (M+Na)$^+$, ESI-MS 551 (M−H)$^-$

2. $^1$H-NMR spectrum (CD$_3$OD, 400 MHz): δ ppm (integration, multiplicity, coupling constant J (Hz)): 0.87 (3H, d, J=7.0 Hz), 0.97 (3H, d, J=7.0 Hz), 1.01 (3H, t, J=7.3 Hz), 1.04 (3H, s), 1.25-1.35 (3H, m), 1.35 (3H, s), 1.55-1.65 (2H, m), 1.69 (1H, dd, J=5.9, 13.9 Hz), 1.72-1.77 (1H, m), 1.77 (3H, s), 1.86 (1H, dd, J=5.9, 13.9 Hz), 1.88-1.95 (1H, m), 2.00 (3H, s), 2.43 (dd, J=5.4, 13.9 Hz), 2.50-2.60 (1H, m), 2.56 (1H, dd, J=3.3, 13.9 Hz), 2.90 (1H, d, J=2.2 Hz), 3.10 (1H, dt, J=2.2, 5.9 Hz), 3.30 (1H, dd, J=2.0, 10.7 Hz), 3.75-3.81 (1H, m), 4.71 (1H, dd, J=9.2, 10.3 Hz), 5.01 (1H, d, J=10.6 Hz), 5.42 (1H, dd, J=8.8, 15.0 Hz), 5.50 (1H, dd, J=8.9, 15.0 Hz), 5.87 (1H, d, J=15.4 Hz), 6.13 (1H, d, J=11.0 Hz), 6.52 (1H, dd, J=11.0, 15.4 Hz)

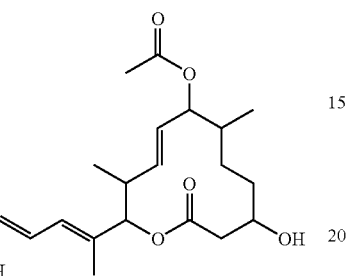

Example 14

Physicochemical Properties of Analogue 3 (6-deoxy 11107F)

Physicochemical properties of an analogue 3 are shown below. The analogue 3 was determined to have a structure represented by the following formula.

1. Molecular weight: 494, ESI-MS 517 (M+Na)$^+$, ESI-MS 493 (M−H)$^-$

2. $^1$H-NMR spectrum (CD$_3$OD, 400 MHz): δ ppm (integration, multiplicity, coupling constant J (Hz)): 0.90 (6H, d, J=7.0 Hz), 0.94 (3H, t, J=7.3 Hz), 1.07 (3H, d, J=6.6 Hz), 1.21-1.26 (2H, m), 1.27-1.30 (1H, m), 1.34 (3H, s), 1.43-1.54 (2H, m), 1.57-1.68 (3H, m), 1.78 (3H, s), 1.87 (1H, dd, J=5.1, 13.9 Hz), 2.42 (1H, dd, J=5.5, 14.3 Hz), 2.52-2.58 (1H, m), 2.57 (1H, dd, J=3.3, 14.3 Hz), 2.67 (1H, dd, J=2.2, 8.1 Hz), 2.89 (1H, dt, J=2.2, 5.9 Hz), 3.52 (1H, dt, J=4.8, 9.2 Hz), 3.57 (1H, dd, J=9.5, 9.9 Hz), 3.73-3.79 (1H, m), 5.02 (1H, d, J=10.6 Hz), 5.31 (1H, dd, J=9.5, 15.0 Hz), 5.47 (1H, dd, J=9.2, 15.0 Hz), 5.86 (1H, d, J=15.0 Hz), 6.12 (1H, d, J=11.0 Hz), 6.53 (1H, dd, J=11.0, 15.0 Hz)

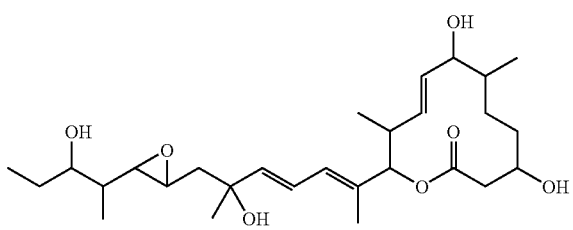

Example 15

Physicochemical Properties of Analogue 4 (6-deoxy 11107D 17-OH)

Physicochemical properties of an analogue 4 are shown below. The analogue 4 was determined to have a structure represented by the following formula.

1. Molecular weight: 552, ESI-MS 575 (M+Na)$^+$, ESI-MS 551 (M−H)$^-$

2. $^1$H-NMR spectrum (CD$_3$OD, 400 MHz): δ ppm (integration, multiplicity, coupling constant J (Hz)): 0.87 (3H, d, J=6.2 Hz), 0.88 (3H, d, J=7.0 Hz), 0.94 (3H, t, J=7.3 Hz), 0.97 (3H, d, J=7.0 Hz), 1.25-1.25 (3H, m), 1.32 (3H, s), 1.44-1.55 (2H, m), 1.57-1.67 (2H, m), 1.77 (3H, s), 1.88-1.95 (1H, m), 2.00 (3H, s), 2.43 (1H, dd, J=5.5, 13.9 Hz), 2.57 (1H, dd, J=3.3, 13.9 Hz), 2.51-2.61 (1H, m), 2.84 (1H, dd, J=2.2, 7.7 Hz), 2.92 (1H, dd, J=2.2, 6.6 Hz), 3.12 (1H, d, J=6.6 Hz), 3.54 (1H, dt, J=4.8, 7.7 Hz), 3.74-3.81 (1H, m), 4.91 (1H, dd, J=9.1, 10.3 Hz), 5.01 (1H, d, J=10.6 Hz), 5.42 (1H, dd, J=9.1, 14.7 Hz), 5.50 (1H, dd, J=8.8, 14.7 Hz), 5.92 (1H, d, J=15.0 Hz), 6.14 (1H, d, J=11.0 Hz), 6.58 (1H, dd, J=11.0, 15.0 Hz)

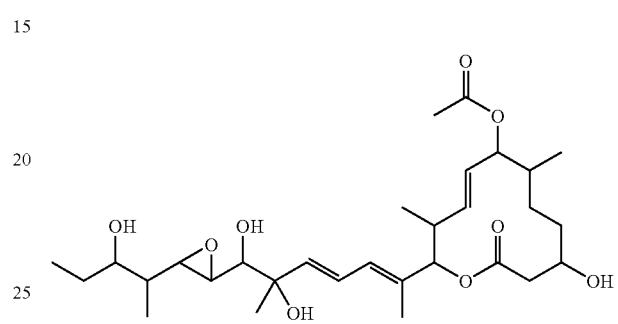

Example 16

Physicochemical Properties of Analogue 5 (6-deoxy 11107D 17-OH)

Physicochemical properties of an analogue 5 are shown below. The analogue 5 was determined to have a structure represented by the following formula. This compound is a stereoisomer of the hydroxyl group at the 17-position of the analogue 4.

1. Molecular weight: 552, ESI-MS 575 (M+Na)$^+$, ESI-MS 551 (M−)$^-$

2. $^1$H-NMR spectrum (CD$_3$OD, 400 MHz): δ ppm (integration, multiplicity, coupling constant J (Hz)): 0.87 (3H, d, J=6.6 Hz), 0.89 (3H, d, J=7.0 Hz), 0.94 (3H, t, J=7.3 Hz), 0.97 (3H, d, J=7.0 Hz), 1.20-1.40 (3H, m), 1.34 (3H, s), 1.43-1.67 (4H, m), 1.77 (3H, s), 1.87-1.96 (1H, m), 2.00 (3H, s), 2.43 (1H, dd, J=5.1, 13.9 Hz), 2.57 (1H, dd, J=3.3, 13.9 Hz), 2.54-2.55 (1H, m), 2.93-2.96 (2H, m), 3.44 (1H, d, J=3.3 Hz), 3.52 (1H, dt, J=4.4, 8.4 Hz), 3.74-3.81 (1H, m), 4.91 (1H, covered with H$_2$O), 5.01 (1H, d, J=10.6 Hz), 5.42 (1H, dd, J=8.8, 15.0 Hz), 5.50 (1H, dd, J=9.2, 15.0 Hz), 5.93 (1H, d, J=15.4 Hz), 6.13 (1H, d, J=11.0 Hz), 6.59 (1H, dd, J=11.0, 15.9 Hz)

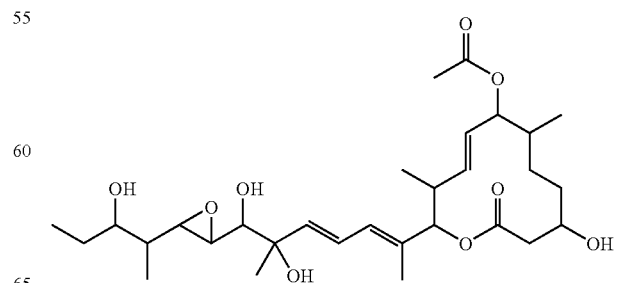

Example 17

Physicochemical Properties of Analogue 6 (6-deoxy 11107AV)

Physicochemical properties of an analogue 6 are shown below. The analogue 6 was determined to have a structure represented by the following formula.

1. Molecular weight: 534, ESI-MS 557 (M+Na)$^+$, ESI-MS 533 (M−)$^−$
2. $^1$H-NMR spectrum (CD$_3$OD, 400 MHz): δ ppm (integration, multiplicity, coupling constant J (Hz)): 0.87 (3H, d, J=6.6 Hz), 0.97 (3H, d, J=7.7 Hz), 0.98 (3H, t, J=7.3 Hz), 1.07 (3H, d, J=7.0 Hz), 1.28-1.32 (2H, m), 1.33 (3H, s), 1.58-1.64 (2H, m), 1.63 (1H, dd, J=6.6, 14.3 Hz), 1.77 (3H, d, J=1.1 Hz), 1.88-1.94 (1H, m), 1.89 (1H, dd, J=5.1, 14.3 Hz), 2.28-2.35 (1H, m), 2.42 (1H, dd, J=5.5, 14.3 Hz), 2.52-2.63 (4H, m), 2.75 (1H, dd, J=2.2, 8.4 Hz), 2.91 (1H, dt, J=2.2, 6.6 Hz), 3.75-3.80 (1H, m), 4.91 (1H, dd, J=8.8, 10.3 Hz), 5.01 (1H, d, J=10.6 Hz), 5.42 (1H, dd, J=8.8, 15.0 Hz), 5.50 (1H, dd, J=9.2, 15.0 Hz), 5.86 (1H, d, J=15.4 Hz), 6.13 (1H, d, J=11.0 Hz), 6.52 (1H, dd, J=11.0, 15.4 Hz)

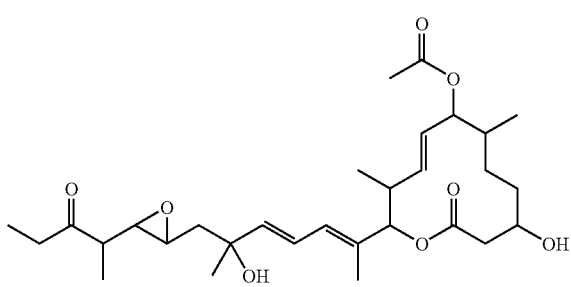

Example 18

(8E,12E,14E)-3,16,21-trihydroxy-6,10,12,16,20-pentamethyl-7-((4-methylpiperazin-1-yl)carbonyl)oxy-18,19-epoxytricosa-8,12,14-trien-11-olide (compound 18)

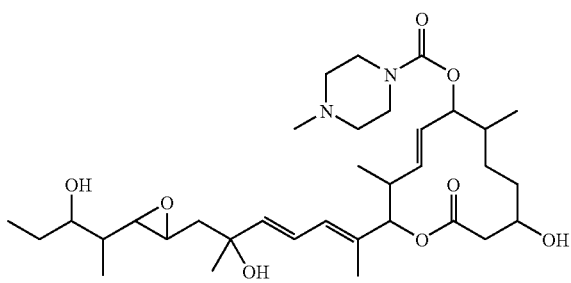

Example 18-1 Step (1) (8E,12E,14E)-7-acetoxy-3,16,21-tris(1-ethoxyethoxy)-6,10,12,16,20-pentamethyl-18,19-epoxytricosa-8,12,14-trien-11-olide

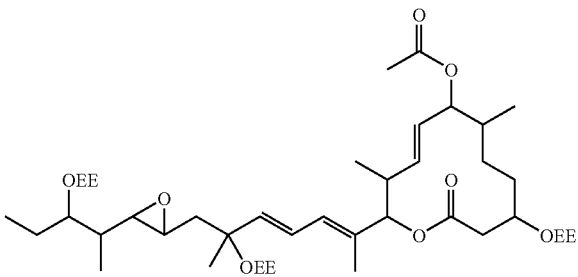

(8E,12E,14E)-7-acetoxy-3,16,21-trihydroxy-6,10,12,16,20-pentamethyl-18,19-epoxytricosa-8,12,14-trien-11-olide (6-deoxy 11107D) (129 mg, 240 μmol) was dissolved in methylene chloride (2 mL). Ethyl vinyl ether (1.4 mL, 14.4 mmol) and pyridinium p-toluenesulfonate (19.9 mg, 79.2 μmol) were added to the reaction mixture at room temperature, and the reaction mixture was stirred at the same temperature for 4.5 hours. This reaction mixture was diluted with ethyl acetate (30 mL), and the organic layer was washed with purified water (10 mL) and brine (10 mL). The resulting organic layer was dried over anhydrous sodium sulfate, and then filtered. The filtrate was concentrated under reduced pressure to obtain the title compound as a crude product (188 mg).

ESI-MS m/z 775 (M+Na)$^+$.

Example 18-2 Step (2) (8E,12E,14E)-3,16,21-tris(1-ethoxyethoxy)-7-hydroxy-6,10,12,16,20-pentamethyl-18,19-epoxytricosa-8,12,14-trien-11-olide

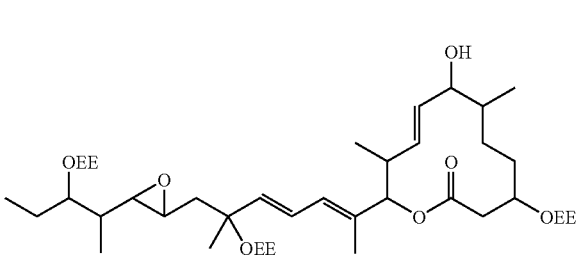

(8E,12E,14E)-7-acetoxy-3,16,21-tris(1-ethoxyethoxy)-6,10,12,16,20-pentamethyl-18,19-epoxytricosa-8,12,14-trien-11-olide (186 mg) as the crude product was dissolved in methanol (2 mL). Potassium carbonate (75.0 mg, 543 μmol) was added to the reaction mixture, and the reaction mixture was stirred at room temperature for three hours. This reaction solution was diluted with ethyl acetate (50 mL), and the organic layer was washed with brine (10 mL) twice. The organic layer was dried over anhydrous sodium sulfate, filtered and concentrated. The resulting concentrate was purified by silica gel column chromatography (Merck Silica gel 60, 63 to 200 μm; hexane:ethyl acetate=3:1->2:1) to obtain the title compound (131 mg, 185 μmol, 78.6%, 2 steps) as a colorless oil.

ESI-MS m/z 733 (M+Na)+.

Example 18-3 Step (3) (8E,12E,14E)-3,16,21-tris(1-ethoxyethoxy)-6,10,12,16,20-pentamethyl-7-(4-nitrophenoxy)carboxy-18,19-epoxytricosa-8,12,14-trien-11-olide

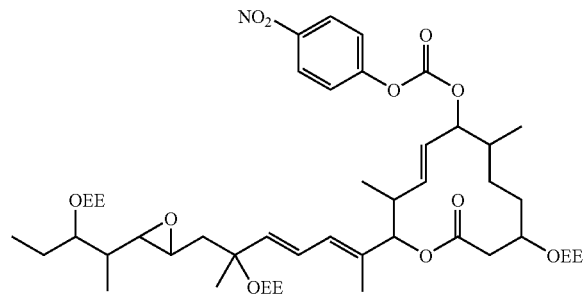

(8E,12E,14E)-3,16,21-tris(1-ethoxyethoxy)-7-hydroxy-6,10,12,16,20-pentamethyl-18,19-epoxytricosa-8,12,14-trien-11-olide (129 mg, 182 μmol) was dissolved in methylene chloride (1 mL). Triethylamine (127 μL, 911 μmol) and 4-dimethylaminopyridine (67.0 mg, 548 μmol) were added to the reaction mixture, and the reaction mixture was stirred at room temperature for 30 minutes. A solution of 4-nitrophenyl chloroformate (112 mg, 556 μmol) in methylene chloride (1 mL) was added dropwise to this reaction mixture and the reaction mixture was stirred at room temperature for 3.5 hours. The reaction mixture was diluted with ethyl acetate (30 mL), and the organic layer was washed with a saturated aqueous solution of sodium hydrogencarbonate (10 mL) and purified water (10 mL) twice, and with brine (10 mL). The resulting organic layer was dried over anhydrous sodium sulfate, filtered and concentrated. The resulting concentrate was purified by silica gel column chromatography (Merck Silica gel 60, 63 to 200 μm; hexane:ethyl acetate=5:1->4:1) to obtain the title compound (137 mg, 156 μmol, 85.8%) as a colorless oil.

ESI-MS m/z 898 (M+Na)+.

Example 18-4 Step (4) (8E,12E,14E)-3,16,21-tris-(1-ethoxyethoxy)-6,10,12,16,20-pentamethyl-7-((4-methylpiperazin-1-yl)carbonyl)oxy-18,19-epoxytricosa-8,12,14-trien-11-olide

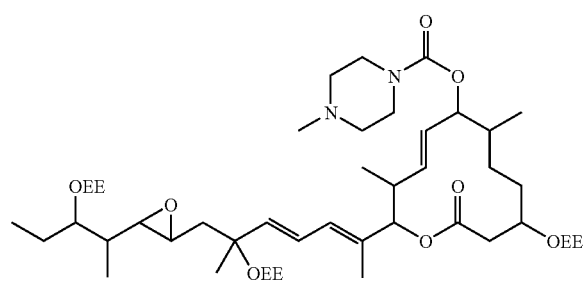

(8E,12E,14E)-3,16,21-tris(1-ethoxyethoxy)-6,10,12,16,20-pentamethyl-7-(4-nitrophenoxy)carboxy-18,19-epoxytricosa-8,12,14-trien-11-olide (26.6 mg, 30.4 μmol) was dissolved in tetrahydrofuran (0.5 mL). A solution of 1-methyl piperazine (4.4 μL, 49 μmol) in tetrahydrofuran (0.5 mL) was added to the reaction mixture and the reaction mixture was stirred at room temperature for 2.5 hours. This reaction solution was concentrated, and the concentrate was purified by silica gel column chromatography (Fuji Silysia NH Silica gel, 100 μm; hexane:ethyl acetate=1:1) to obtain the title compound (25.1 mg, 30.0 μmol, 98.7%) as a colorless oil.

ESI-MS m/z 837 (M+H)+.

Example 18-5 Step (5) (8E,12E,14E)-3,16,21-trihydroxy-6,10,12,16,20-pentamethyl-7-((4-methylpiperazin-1-yl)carbonyl)oxy-18,19-epoxytricosa-8,12,14-trien-11-olide (compound 18)

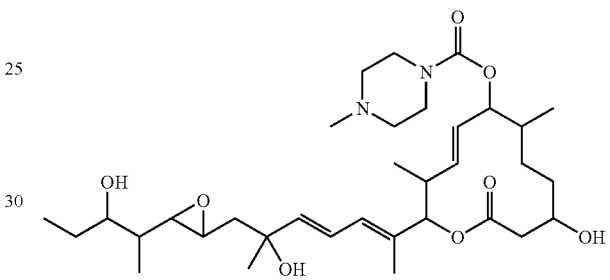

(8E,12E,14E)-3,16,21-tris-(1-ethoxyethoxy)-6,10,12,16,20-pentamethyl-7-((4-methylpiperazin-1-yl)carbonyl)oxy-18,19-epoxytricosa-8,12,14-trien-11-olide (25.1 mg, 30.0 limol) was dissolved in a 1:1 mixed solution of tetrahydrofuran and 2-methyl-1-propanol (1 mL). Pyridinium p-toluenesulfonate (23.7 mg, 94.3 μmol) was added to the reaction mixture at room temperature. The reaction mixture was stirred at the same temperature for 24.5 hours, and then pyridinium p-toluenesulfonate (8.7 mg, 34.6 μmol) was further added to the reaction mixture. The reaction mixture was stirred for 4.5 hours. The reaction mixture was diluted with ethyl acetate (30 mL), and the organic layer was washed with a saturated aqueous solution of sodium hydrogencarbonate (6 mL) and purified water (6 mL) twice, and with brine (6 mL). The resulting organic layer was dried over anhydrous sodium sulfate, filtered and concentrated. The resulting concentrate was purified by thin-layer chromatography (Fuji Silysia NH Silica gel plate; chloroform:methanol=40:1) to obtain the title compound (12.2 mg, 19.6 μmol, 65.3%) as a colorless oil.

$^1$H-NMR spectrum (CD$_3$OD, 400 MHz) δ (ppm): 0.87 (3H, d, J=7.0 Hz), 0.89 (3H, d, J=6.6 Hz), 0.93 (3H, t, J=7.3 Hz), 0.99 (3H, d, J=6.6 Hz), 1.19-1.37 (3H, m), 1.33 (3H, s), 1.40-1.65 (4H, m), 1.65 (1H, dd, J=5.5, 14.3 Hz), 1.77 (3H, d, J=0.7 Hz), 1.86 (1H, dd, J=5.5, 14.3 Hz), 1.89-1.97 (1H, m), 2.29 (3H, s), 2.35-2.45 (5H, m), 2.53-2.60 (1H, m), 2.56 (1H, dd, J=3.7, 13.9 Hz), 2.66 (1H, dd, J=2.2, 8.1 Hz), 2.88 (1H, dt, J=2.2, 5.5 Hz), 3.42-3.54 (5H, m), 3.74-3.81 (1H, m), 4.79 (1H, dd, J=9.2, 9.2 Hz), 5.01 (1H, d, J=10.6 Hz), 5.44 (1H, dd, J=8.8, 15.0 Hz), 5.50 (1H, dd, J=9.2, 15.0 Hz), 5.86 (1H, d, J=15.0 Hz), 6.12 (1H, d, J=11.0 Hz), 6.52 (1H, dd, J=11.0, 15.0 Hz); ESI-MS m/z 621 (M+H)+.

Example 19

(8E,12E,14E)-3,16,21-trihydroxy-6,10,12,16,20-pentamethyl-7-((4-methylhomopiperazin-1-yl)carbonyl)oxy-18,19-epoxytricosa-8,12,14-trien-11-olide (compound 19)

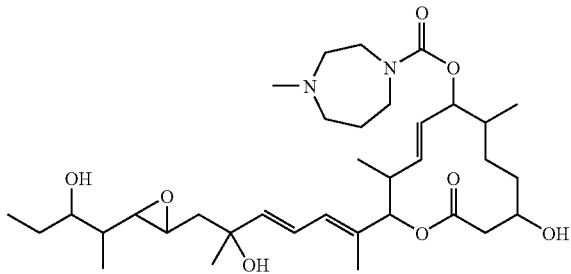

The title compound (colorless oil) was synthesized in the same manner as in Example 18.

$^1$H-NMR spectrum (CD$_3$OD, 400 MHz) δ (ppm): 0.87 (3H, d, J=7.0 Hz), 0.89 (3H, d, J=7.0 Hz), 0.93 (3H, t, J=7.3 Hz), 0.98-1.03 (3H, m), 1.20-1.68 (8H, m), 1.33 (3H, s), 1.77 (3H, s), 1.83-1.98 (4H, m), 2.34 (3H, s), 2.42 (1H, dd, J=5.5, 13.9 Hz), 2.50-2.66 (6H, m), 2.66 (1H, dd, J=2.2, 7.7 Hz), 2.89 (1H, dd, J=2.2, 6.2 Hz), 3.44-3.59 (5H, m), 3.74-3.80 (1H, m), 4.80 (1H, dd, J=9.2, 9.2 Hz), 5.02 (1H, d, J=10.6 Hz), 5.44 (1H, dd, J=9.2, 15.0 Hz), 5.50 (1H, dd, J=9.2, 15.0 Hz), 5.86 (1H, d, J=15.0 Hz), 6.12 (1H, d, J=11.0 Hz), 6.52 (1H, dd, J=11.0, 15.0 Hz); ESI-MS m/z 635 (M+H)$^+$.

Example 20

(8E,12E,14E)-7-(N-(2-(N',N'-diethylamino)ethyl-N-methyl)carbamoyloxy)-3,16,21-trihydroxy-6,10,12,16,20-pentamethyl-18,19-epoxytricosa-8,12,14-trien-11-olide (compound 20)

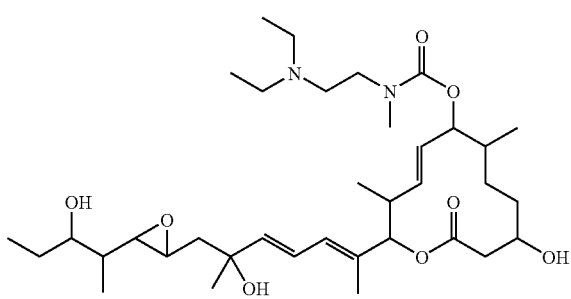

The title compound (colorless oil) was synthesized in the same manner as in Example 18.

$^1$H-NMR spectrum (CD$_3$OD, 400 MHz) δ (ppm): 0.87 (3H, d, J=8.1 Hz), 0.89 (3H, d, J=7.0 Hz), 0.93 (3H, t, J=7.3 Hz), 0.98-1.11 (9H, m), 1.19-1.68 (8H, m), 1.33 (3H, s), 1.77 (3H, s), 1.86 (1H, dd, J=5.5, 14.3 Hz), 1.88-1.98 (1H, m), 2.42 (1H, dd, J=5.5, 14.3 Hz), 2.51-2.63 (8H, m), 2.66 (1H, dd, J=2.2, 8.1 Hz), 2.87-2.95 (1H, m), 3.30-3.39 (2H, m), 3.52 (1H, dt, J=4.4, 8.8 Hz), 3.74-3.82 (1H, m), 4.80 (1H, dd, J=9.2, 9.2 Hz), 5.01 (1H, d, J=10.6 Hz), 5.44 (1H, dd, J=9.2, 15.0 Hz), 5.50 (1H, dd, J=9.2, 15.0 Hz), 5.86 (1H, d, J=15.4 Hz), 6.12 (1H, d, J=11.0 Hz), 6.52 (1H, dd, J=11.0, 15.4 Hz); ESI-MS m/z 651 (M+H)$^+$.

Example 21

(8E,12E,14E)-3,16,21-trihydroxy-6,10,12,16,20-pentamethyl-7-((4-(piperidin-1-yl)piperidin-1-yl)carbonyl)oxy-18,19-epoxytricosa-8,12,14-trien-11-olide (compound 21)

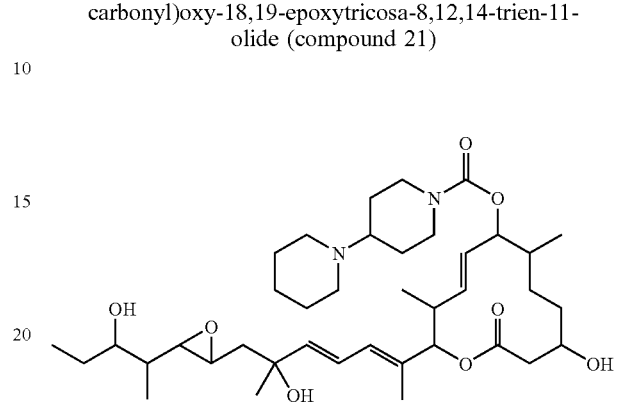

The title compound (colorless oil) was synthesized in the same manner as in Example 18.

$^1$H-NMR spectrum (CD$_3$OD, 400 MHz) δ (ppm): 0.87 (3H, d, J=7.0 Hz), 0.89 (3H, d, J=7.3 Hz), 0.93 (3H, t, J=7.3 Hz), 0.99 (3H, d, J=6.6 Hz), 1.19-1.67 (16H, m), 1.33 (3H, s), 1.77 (3H, s), 1.82-1.97 (4H, m), 2.42 (1H, dd, J=5.5, 14.3 Hz), 2.42-2.61 (7H, m), 2.66 (1H, dd, J=2.2, 8.1 Hz), 2.69-2.86 (2H, m), 2.88 (1H, dt, J=2.2, 5.9 Hz), 3.52 (1H, dt, J=4.8, 8.4 Hz), 3.73-3.81 (1H, m), 4.12-4.22 (2H, m), 4.77 (1H, dd, J=9.2, 9.2 Hz), 5.01 (1H, d, J=10.6 Hz), 5.43 (1H, dd, J=9.2, 15.0 Hz), 5.49 (1H, dd, J=9.2, 15.0 Hz), 5.86 (1H, d, J=15.0 Hz), 6.12 (1H, d, J=11.0 Hz), 6.52 (1H, dd, J=11.0, 15.0 Hz); ESI-MS m/z 689 (M+H)$^+$.

Example 22

(8E,12E,14E)-7-(N-(2-(N',N'-diethylamino)ethyl)carbamoyloxy)-3,16,21-trihydroxy-6,10,12,16,20-pentamethyl-18,19-epoxytricosa-8,12,14-trien-11-olide (compound 22)

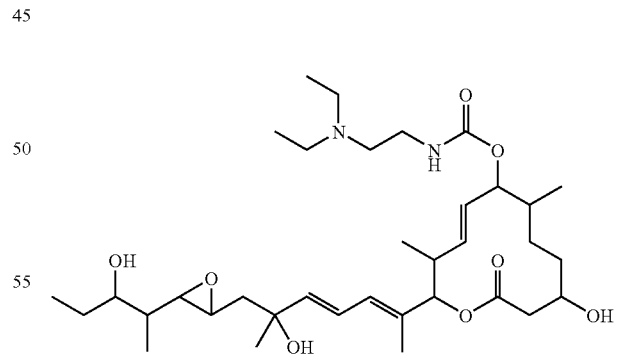

The title compound (colorless oil) was synthesized in the same manner as in Example 18.

$^1$H-NMR spectrum (CD$_3$OD, 400 MHz) δ (ppm): 0.87 (3H, d, J=7.3 Hz), 0.89 (3H, d, J=7.3 Hz), 0.93 (3H, t, J=7.3 Hz), 0.99 (3H, d, J=7.0 Hz), 1.05 (6H, t, J=7.0 Hz), 1.19-1.65 (7H, m), 1.33 (3H, s), 1.65 (1H, dd, J=5.5, 13.9 Hz), 1.76 (3H, s), 1.80-1.90 (1H, m), 1.86 (1H, dd, J=5.5, 13.9 Hz), 2.42 (1H, dd, J=5.1, 13.9 Hz), 2.51-2.59 (4H, m), 2.58 (4H, q, J=7.0 Hz), 2.66 (1H, dd, J=2.2, 7.7 Hz), 2.89 (1H, dt, J=2.2, 5.5 Hz), 3.15-3.20 (2H, m), 3.52 (1H, dt, J=4.4, 8.4 Hz), 3.72-3.80 (1H, m), 4.74 (1H, dd, J=9.5, 9.5 Hz), 5.01 (1H, d, J=10.6 Hz), 5.41 (1H, dd, J=9.2, 15.0 Hz), 5.48 (1H, dd, J=9.5, 15.0 Hz), 5.86 (1H, d, J=15.4 Hz), 6.12 (1H, d, J=11.0 Hz), 6.52 (1H, dd, J=11.0, 15.4 Hz); ESI-MS m/z 637 (M+H)$^+$.

Example 23

(8E,12E,14E)-7-((4-(2,2-dimethylpropyl)piperazin-1-yl)carbonyl)oxy-3,16,21-trihydroxy-6,10,12,16,20-pentamethyl-18,19-epoxytricosa-8,12,14-trien-11-olide (compound 23)

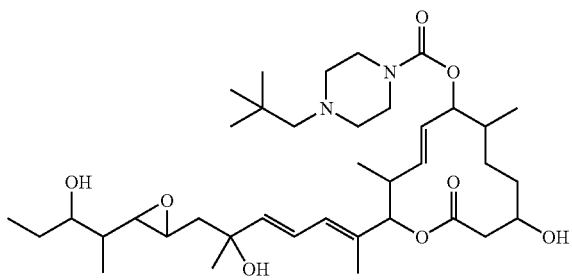

Example 23-1 Step (1) (8E,12E,14E)-7-acetoxy-6,10,12,16,20-pentamethyl-3,16,21-tris(triethylsiloxy)-18,19-epoxytricosa-8,12,14-trien-11-olide

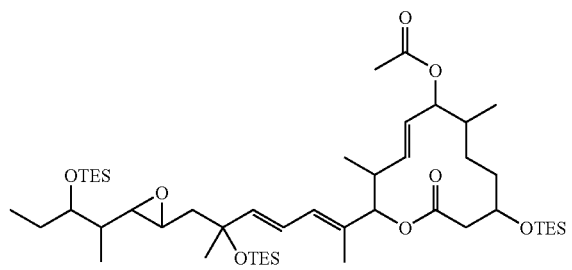

A solution of (8E,12E,14E)-7-acetoxy-3,16,21-trihydroxy-6,10,12,16,20-pentamethyl-18,19-epoxytricosa-8,12,14-trien-11-olide (54 mg, 0.1 mmol), 4-dimethylaminopyridine (124 mg, 1 mmol), and triethylamine (102 mg, 1 mmol) in methylene chloride (2.5 mL) was cooled to 5° C. A solution of triethylsilyl chloride (152 mg, 1 mmol) in methylene chloride (0.5 mL) was added dropwise to the reaction mixture, and then the reaction mixture was stirred at room temperature overnight. The reaction mixture was diluted with ethyl acetate, and then the organic layer was washed with water. The resulting organic layer was dried over anhydrous magnesium sulfate, filtered and concentrated under reduced pressure. The resulting residue was purified by silica gel column chromatography (Kanto silica gel 60N, 40 to 50 μm; ethyl acetate-hexane, 1:19->1:14) to obtain the title compound (77.1 mg, 88%) as a colorless oil.

ESI-MS m/z 901 (M+Na)$^+$.

Example 23-2 Step (2) (8E,12E,14E)-7-hydroxy-6,10,12,16,20-pentamethyl-3,16,21-tris(triethylsiloxy)-18,19-epoxytricosa-8,12,14-trien-11-olide

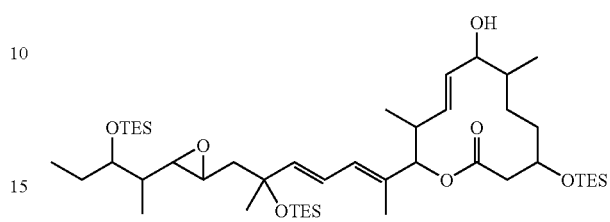

(8E,12E,14E)-7-acetoxy-6,10,12,16,20-pentamethyl-3,16,21-tris(triethylsiloxy)-18,19-epoxytricosa-8,12,14-trien-11-olide (77 mg, 0.0875 mmol) was dissolved in methanol (2 mL). Potassium carbonate (36.5 mg, 0.262 mmol) and methanol (1 mL) were added to this methanolic solution, and the reaction mixture was stirred at room temperature for four hours. The reaction mixture was diluted with ethyl acetate, and then the organic layer was washed with brine. The organic layer was dried with anhydrous magnesium sulfate, filtered and concentrated under reduced pressure. The resulting residue was purified by silica gel column chromatography (Kanto silica gel 60N, 40 to 50 μm; ethyl acetate-hexane, 1:9->1:6->1:4->1:3) to obtain the title compound (38.6 mg, 50%) as a colorless oil.

ESI-MS m/z 859 (M+Na)$^+$.

Example 23-3 Step (3) (8E,12E,14E)-6,10,12,16,20-pentamethyl-7-((4-nitrophenoxy)carboxy)-3,16,21-tris(triethylsiloxy)-18,19-epoxytricosa-8,12,14-trien-11-olide

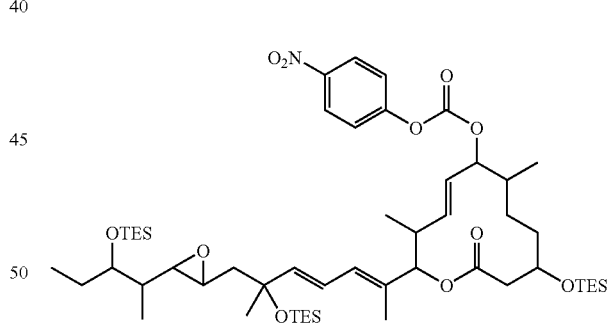

A solution of (8E,12E,14E)-7-hydroxy-6,10,12,16,20-pentamethyl-3,16,21-tris(triethylsiloxy)-18,19-epoxytricosa-8,12,14-trien-11-olide (38.6 mg, 0.046 mmol), 4-dimethylaminopyridine (26 mg, 0.207 mmol) and triethylamine (28 mg, 0.276 mmol) in methylene chloride (2 mL) was cooled to 5° C. A solution of 4-nitrophenyl chloroformate (29 mg, 0.138 mmol) in methylene chloride (1 mL) was added to the reaction mixture, and the reaction mixture was stirred at 5° C. for one hour. The reaction mixture was diluted with ethyl acetate, and then the organic layer was washed with an aqueous solution of sodium hydrogencarbonate. The organic layer was sequentially washed with an aqueous solution of ammonium chloride, an aqueous solution of sodium hydrogencarbonate and water, dried with anhydrous magnesium sulfate, and filtered. Then, the filtrate was concentrated under reduced pressure. The resulting residue was purified by silica gel column chromatography (Kanto silica gel 60N, 40 to 50 μm; ethyl acetate-hexane, 1:14) to obtain the title compound (46.1 mg, 100%) as a yellow pale oil.

ESI-MS m/z 1024 (M+Na)+.

Example 23-4 Step (4) (8E,12E,14E)-7-((4-(2,2-dimethylpropyl)piperazin-1-yl)carbonyl)oxy-6,10,12,16,20-pentamethyl-3,16,21-tris(triethylsiloxy)-18,19-epoxytricosa-8,12,14-trien-11-olide

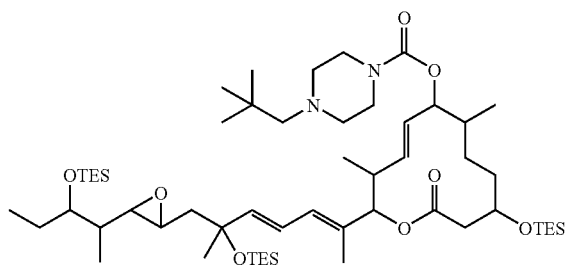

A solution of 1-(2,2-dimethylpropyl)piperazine ditrifluoroacetate (12 mg, 20 μmol) and triethylamine (10 mg, 0.1 mmol) in tetrahydrofuran (0.7 mL) was added dropwise to a solution of (8E,12E,14E)-6,10,12,16,20-pentamethyl-7-((4-nitrophenoxy)carboxy)-3,16,21-tris(triethylsiloxy)-18,19-epoxytricosa-8,12,14-trien-11-olide (10 mg, 10 μmol) in tetrahydrofuran (0.5 mL), and the reaction mixture was stirred at room temperature for three hours. The reaction mixture was diluted with ethyl acetate, and then the organic layer was washed with an aqueous solution of sodium hydrogencarbonate. The organic layer was dried over anhydrous magnesium sulfate, filtered and concentrated under reduced pressure. The resulting residue was purified by thin-layer chromatography (Merck, Art 1.05628; ethyl acetate-hexane, 1:6) to obtain the title compound (9.7 mg, 95%) as a colorless oil.

ESI-MS m/z 1019 (M+H)+.

Example 23-5 Step (5) (8E,12E,14E)-7-((4-(2,2-dimethylpropyl)piperazin-1-yl)carbonyl)oxy-3,16,21-trihydroxy-6,10,12,16,20-pentamethyl-18,19-epoxytricosa-8,12,14-trien-11-olide (compound 23)

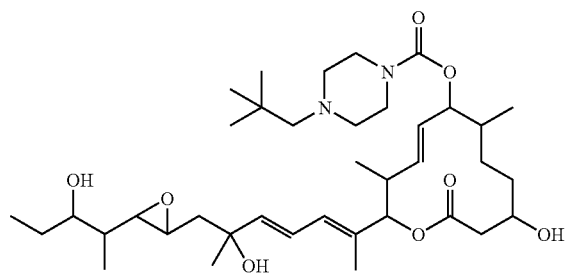

A solution of (8E,12E,14E)-7-((4-(2,2-dimethylpropyl)piperazin-1-yl)carbonyl)oxy-6,10,12,16,20-pentamethyl-3,16,21-tris(triethylsiloxy)-18,19-epoxytricosa-8,12,14-trien-11-olide (9.7 mg, 9.5 μmol) in tetrahydrofuran (1 mL) was cooled to 5° C. Tetrabutylammonium fluoride (1.0M solution in tetrahydrofuran, 31 μL, 31 μmol) was added dropwise to the reaction mixture, and the reaction mixture was stirred at room temperature for two hours. The reaction mixture was diluted with ethyl acetate, and then the organic layer was washed with an aqueous solution of sodium hydrogencarbonate. The organic layer was dried over anhydrous magnesium sulfate, filtered and concentrated under reduced pressure. The resulting residue was purified by thin-layer chromatography (Fuji Silysia NH Silica gel plate; methanol-methylene chloride, 1:49) to obtain the title compound (6.3 mg, 98%) as a colorless oil.

$^1$H-NMR spectrum (CD$_3$OD, 400 MHz) δ (ppm): 0.85-0.92 (15H, m), 0.94 (3H, t, J=7.6 Hz), 0.99 (3H, d, J=6.8 Hz), 1.19-1.69 (11H, m), 1.77 (3H, d, J=0.8 Hz), 1.86 (1H, dd, J=5.2, 14.0 Hz), 1.87-1.97 (1H, m), 2.09 (2H, s), 2.38-2.61 (7H, m), 2.67 (1H, dd, J=2.4, 8.0 Hz), 2.89 (1H, dt, J=2.0, 6.0 Hz), 3.34-3.52 (4H, m), 3.52 (1H, td, J=4.4, 7.6 Hz), 3.74-3.81 (1H, m), 4.75-4.82 (1H, m), 5.01 (1H, d, J=10.8 Hz), 5.43 (1H, dd, J=8.8, 14.8 Hz), 5.50 (1H, dd, J=9.2, 14.8 Hz), 5.86 (1H, d, J=15.2 Hz), 6.12 (1H, d, J=11.2 Hz), 6.52 (1H, dd, J=11.2, 15.2 Hz); ESI-MS m/z 677 (M+H)+.

Example 24

(8E,12E,14E)-7-((4-ethylpiperazin-1-yl)carbonyl)oxy-3,16,21-trihydroxy-6,10,12,16,20-pentamethyl-18,19-epoxytricosa-8,12,14-trien-11-olide (compound 24)

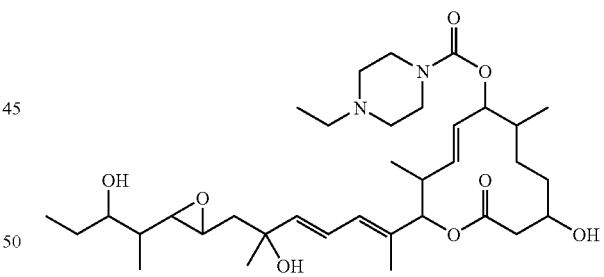

The title compound (colorless oil) was synthesized in the same manner as in Example 23.

$^1$H-NMR spectrum (CD$_3$OD, 400 MHz) δ (ppm): 0.88 (3H, d, J=6.4 Hz), 0.90 (3H, d, J=7.2 Hz), 0.94 (3H, t, J=7.6 Hz), 1.00 (3H, d, J=6.8 Hz), 1.11 (3H, t, J=7.2 Hz), 1.19-1.70 (11H, m), 1.77 (3H, d, J=0.8 Hz), 1.86 (1H, dd, J=5.6, 14.0 Hz), 1.88-1.99 (1H, m), 2.38-2.49 (7H, m), 2.51-2.61 (2H, m), 2.66 (1H, dd, J=2.4, 8.0 Hz), 2.89 (1H, dt, J=2.0, 6.0 Hz), 3.40-3.57 (5H, m), 3.74-3.82 (1H, m), 4.76-4.83 (1H, m), 5.01 (1H, d, J=10.8 Hz), 5.44 (1H, dd, J=8.8, 15.2 Hz), 5.51 (1H, dd, J=9.2, 14.8 Hz), 5.87 (1H, d, J=15.2 Hz), 6.13 (1H, d, J=10.8 Hz), 6.52 (1H, dd, J=10.8, 15.2 Hz); ESI-MS m/z 635 (M+H)+.

Example 25

(8E,12E,14E)-7-((4-(N,N-dimethylamino)piperidin-1-yl)carbonyl)oxy-3,16,21-trihydroxy-6,10,12,16,20-pentamethyl-18,19-epoxytricosa-8,12,14-trien-11-olide (compound 25)

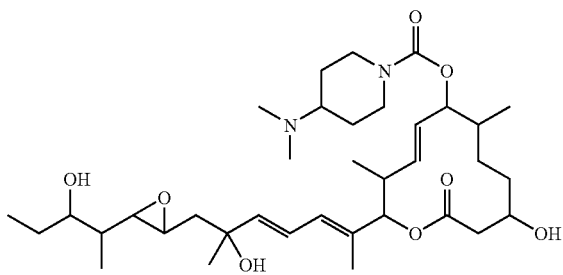

The title compound (colorless oil) was synthesized in the same manner as in Example 23.

$^1$H-NMR spectrum (CD$_3$OD, 400 MHz) δ (ppm): 0.88 (3H, d, J=6.8 Hz), 0.90 (3H, d, J=7.2 Hz), 0.94 (3H, t, J=7.6 Hz), 1.00 (3H, d, J=6.8 Hz), 1.19-1.70 (13H, m), 1.77 (3H, d, J=0.8 Hz), 1.82-1.99 (4H, m), 2.28 (6H, s), 2.32-2.46 (2H, m), 2.50-2.62 (2H, m), 2.67 (1H, dd, J=2.4, 7.6 Hz), 2.68-2.88 (2H, m), 2.89 (1H, dt, J=2.4, 6.0 Hz), 3.52 (1H, td, J=4.4, 8.0 Hz), 3.74-3.82 (1H, m), 4.11-4.21 (2H, m), 4.75-4.82 (1H, m), 5.02 (1H, d, J=10.8 Hz), 5.44 (1H, dd, J=8.8, 15.2 Hz), 5.50 (1H, dd, J=9.2, 14.8 Hz), 5.86 (1H, d, J=15.2 Hz), 6.13 (1H, d, J=10.8 Hz), 6.52 (1H, dd, J=10.8, 15.2 Hz); ESI-MS m/z 649 (M+H)$^+$.

Example 26

(8E,12E,14E)-7-(N-(3-(N',N'-dimethylamino)propyl)carbamoyloxy)-3,16,21-trihydroxy-6,10,12,16,20-pentamethyl-18,19-epoxytricosa-8,12,14-trien-11-olide (compound 26)

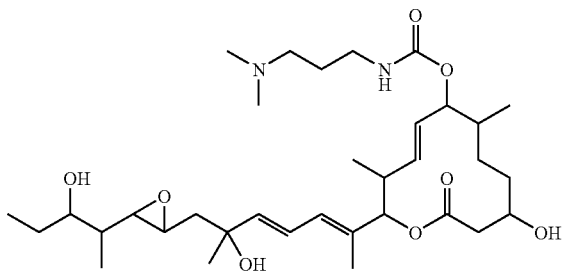

The title compound (colorless oil) was synthesized in the same manner as in Example 18.

$^1$H-NMR spectrum (CD$_3$OD, 400 MHz) δ (ppm): 0.88 (3H, d, J=6.8 Hz), 0.89 (3H, d, J=7.2 Hz), 0.94 (3H, t, J=7.4 Hz), 1.00 (3H, d, J=6.4 Hz), 1.19-1.71 (10H, m), 1.34 (3H, s), 1.77 (3H, s), 1.82-1.90 (2H, m), 2.24 (6H, s), 2.34 (2H, t, J=7.6 Hz), 2.42 (1H, dd, J=5.4, 14.2 Hz), 2.50-2.60 (2H, m), 2.66 (1H, dd, J=2.2, 7.8 Hz), 2.89 (1H, dt, J=2.2, 5.6 Hz), 3.10 (2H, t, J=6.8 Hz), 3.48-3.55 (1H, m), 3.72-3.82 (1H, m), 4.74 (1H, dd, J=9.4, 9.4 Hz), 5.02 (1H, d, J=10.8 Hz), 5.37-5.53 (2H, m), 5.86 (1H, d, J=15.2 Hz), 6.12 (1H, d, J=10.8 Hz), 6.52 (1H, dd, J=10.8, 15.2 Hz); ESI-MS m/z 623 (M+H)$^+$.

Example 27

(8E,12E,14E)-7-(N-(3-(N',N'-dimethylamino)propyl)-N-methylcarbamoyloxy)-3,16,21-trihydroxy-6,10,12,16,20-pentamethyl-18,19-epoxytricosa-8,12,14-trien-11-olide (compound 27)

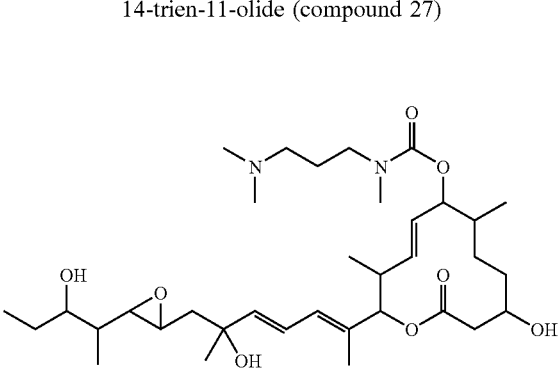

The title compound (colorless oil) was synthesized in the same manner as in Example 18.

$^1$H-NMR spectrum (CD$_3$OD, 400 MHz) δ (ppm): 0.88 (3H, d, J=7.2 Hz), 0.89 (3H, d, J=7.2 Hz), 0.94 (3H, t, J=7.4 Hz), 1.01 (3H, d, J=6.4 Hz), 1.19-1.79 (10H, m), 1.34 (3H, s), 1.77 (3H, s), 1.82-1.98 (2H, m), 2.26 (6H, s), 2.28-2.37 (2H, m), 2.42 (1H, dd, J=5.2, 14.0 Hz), 2.51-2.59 (2H, m), 2.66 (1H, dd, J=2.2, 7.8 Hz), 2.83-2.94 (4H, m), 3.22-3.37 (2H, covered with CD$_3$OD), 3.48-3.55 (1H, m), 3.74-3.82 (1H, m), 4.70-4.96 (1H, covered with H$_2$O), 5.02 (1H, d, J=10.8 Hz), 5.40-5.55 (2H, m), 5.86 (1H, d, J=15.6 Hz), 6.12 (1H, d, J=10.8 Hz), 6.52 (1H, dd, J=10.8, 15.2 Hz); ESI-MS m/z 637 (M+H)$^+$.

Example 28

(8E,12E,14E)-3,16,21-trihydroxy-6,10,12,16,20-pentamethyl-7-((piperazin-1-yl)carbonyl)oxy-18,19-epoxytricosa-8,12,14-trien-11-olide (compound 28)

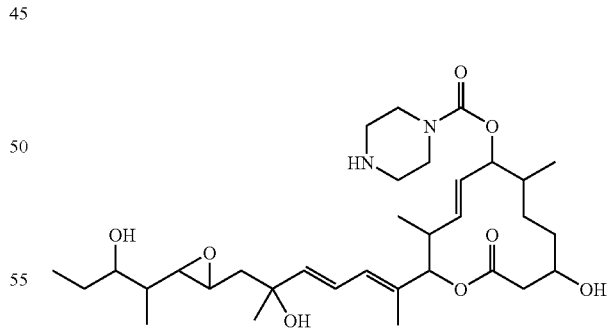

The title compound (colorless oil) was synthesized in the same manner as in Example 18.

$^1$H-NMR spectrum (CD$_3$OD, 400 MHz) δ (ppm): 0.87 (3H, d, J=7.0 Hz), 0.89 (3H, d, J=6.6 Hz), 0.93 (3H, t, J=7.3 Hz), 0.99 (3H, d, J=7.2 Hz), 1.19-1.37 (3H, m), 1.33 (3H, s), 1.40-1.54 (2H, m), 1.54-1.68 (3H, m), 1.75 (3H, s), 1.82-1.98 (2H, m), 2.35-2.46 (1H, m), 2.48-2.60 (2H, m), 2.62-2.68 (1H, m), 2.68-2.80 (4H, m), 2.82-2.92 (1H, m), 3.34-3.54 (5H, m), 3.72-3.82 (1H, m), 4.74-4.92 (1H, covered with H₂O), 5.01 (1H, d, J=10.4 Hz), 5.34-5.54 (2H, m), 5.86 (1H, d, J=15.0 Hz), 6.12 (1H, d, J=11.0 Hz), 6.52 (1H, dd, J=11.0, 15.0 Hz); ESI-MS m/z 607 (M+H)⁺.

Example 29

(8E,12E,14E)-3,16,21-trihydroxy-6,10,12,16,20-pentamethyl-7-(N-methyl-N-(1-methylpiperidin-4-yl)carbamoyloxy)-18,19-epoxytricosa-8,12,14-trien-11-olide (compound 29)

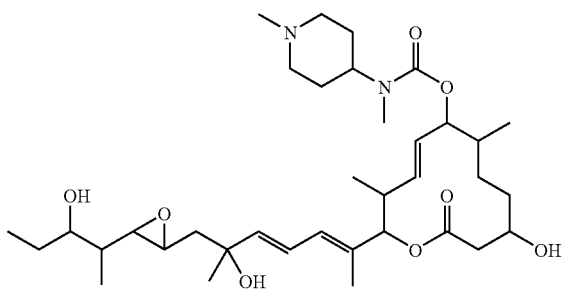

The title compound (colorless oil) was synthesized in the same manner as in Example 18.

¹H-NMR spectrum (CD₃OD, 40 MHz) δ (ppm): 0.88 (3H, d, J=6.8 Hz), 0.89 (3H, d, J=7.2 Hz), 0.93 (3H, t, J=7.6 Hz), 0.99 (3H, d, J=6.8 Hz), 1.00-1.04 (1H, m), 1.19-1.68 (11H, m), 1.33 (3H, s), 1.77 (3H, s), 1.86 (1H, dd, J=5.2, 14.0 Hz), 1.90-1.98 (1H, m), 2.04-2.16 (2H, m), 2.28 (3H, s), 2.42-2.60 (3H, m), 2.66 (1H, dd, J=2.4, 8.0 Hz), 2.79 (3H, s), 2.84-2.98 (3H, m), 3.52 (1H, dt, J=4.4, 8.4 Hz), 3.72-3.80 (1H, m), 3.82-3.98 (1H, m), 4.76-4.92 (1H, covered with H₂O), 5.01 (1H, d, J=10.4 Hz), 5.44 (1H, dd, J=9.2, 15.2 Hz), 5.50 (1H, dd, J=9.2, 15.2 Hz), 5.86 (1H, d, J=15.2 Hz), 6.12 (1H, d, J=10.8 Hz), 6.52 (1H, dd, J=10.8, 15.2 Hz); ESI-MS m/z 649.(M+H)⁺.

Example 30

(8E,12E,14E)-3,16,21-trihydroxy-6,10,12,16,20-pentamethyl-7-((4-(1-methylpiperidin-4-yl)piperazin-1-yl)carbonyl)oxy-18,19-epoxytricosa-8,12,14-trien-11-olide (compound 30)

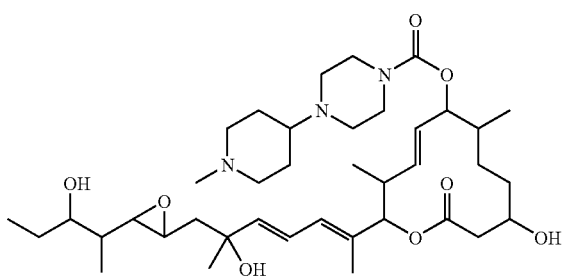

Example 30-1 Step (1) (8E,12E,14E)-7-acetoxy-3,21-bis(diethylisopropylsiloxy)-16-hydroxy-6,10,12,16,20-pentamethyl-18,19-epoxytricosa-8,12,14-trien-11-olide

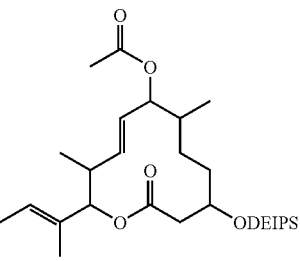

A solution of (8E,12E,14E)-7-acetoxy-3,16,21-trihydroxy-6,10,12,16,20-pentamethyl-18,19-epoxytricosa-8,12,14-trien-11-olide (177 mg, 0.33 mmol) and imidazole (450 mg, 6.61 mmol) in methylene chloride (6 mL) was cooled to 5° C. A solution of diethylisopropylsilyl chloride (272 mg, 1.65 mmol) in methylene chloride (1.5 mL) was added dropwise to the reaction mixture, and the reaction mixture was stirred at room temperature for two hours. The reaction mixture was diluted with ethyl acetate, and then the organic layer was washed with water. The resulting organic layer was washed with brine dried over anhydrous magnesium sulfate, filtered and concentrated under reduced pressure. The resulting residue was purified by silica gel column chromatography (Kanto silica gel 60N, 40 to 100 μm; ethyl acetate-hexane, 1:19->1:9->1:6->1:4) to obtain the title compound (242.9 mg, 93%) as a colorless oil.

ESI-MS m/z 815 (M+Na)⁺.

Example 30-2 Step (2) (8E,12E,14E)-3,21-bis(diethylisopropylsiloxy)-7,16-dihydroxy-6,10,12,16,20-pentamethyl-18,19-epoxytricosa-8,12,14-trien-11-olide

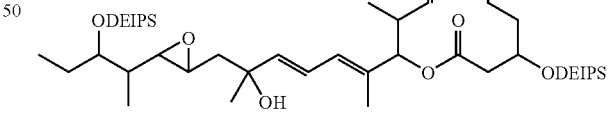

A 0.2M guanidine/guanidine nitrate solution (methanol-methylene chloride, 9:1)(3.9 mL, 0.78 mmol) was added to (8E,12E,14E)-7-acetoxy-3,21-bis(diethylisopropylsiloxy)-16-hydroxy-6,10,12,16,20-pentamethyl-18,19-epoxytricosa-8,12,14-trien-11-olide (307 mg, 0.3868 mmol), and the reaction mixture was stirred at room temperature for 13 hours. The reaction mixture was diluted with ethyl acetate, and then the organic layer was washed with an aqueous solution of ammonium chloride. The resulting organic layer was dried over anhydrous magnesium sulfate, filtered and concentrated under reduced pressure. The resulting residue was purified by silica gel column chromatography (Kanto silica gel 60N, 40 to 50 μm; ethyl acetate-hexane, 1:4) to obtain the title compound (271.5 mg, 93%) as a colorless oil. ESI-MS m/z 773 (M+Na)+.

Example 30-3 Step (3) (8E,12E,14E)-3,21-bis(diethylisopropylsiloxy)-16-hydroxy-6,10,12,16,20-pentamethyl-7-((4-nitrophenoxy)carboxy)-18,19-epoxytricosa-8,12,14-trien-11-olide

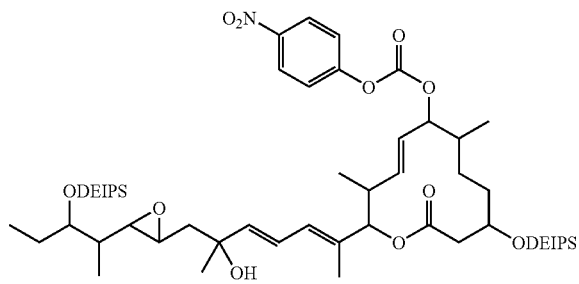

A solution of (8E,12E,14E)-3,21-bis(diethylisopropylsiloxy)-7,16-dihydroxy-6,10,12,16,20-pentamethyl-18,19-epoxytricosa-8,12,14-trien-11-olide (271 mg, 0.3605 mmol), 4-dimethylaminopyridine (22 mg, 0.18 mmol) and triethylamine (369 mg, 3.61 mmol) in methylene chloride (5 mL) was cooled to 5° C. A solution of 4-nitrophenyl chloroformate (374 mg, 1.8 mmol) in methylene chloride (3 mL) was added dropwise to the solution, and the reaction mixture was stirred at 5 to 10° C. for one hour. The reaction mixture was diluted with ethyl acetate, and then the organic layer was washed with an aqueous solution of sodium hydrogencarbonate. The resulting organic layer was washed with water, dried over anhydrous magnesium sulfate, filtered and concentrated under reduced pressure. The resulting residue was purified by silica gel column chromatography (Kanto silica gel 60N, 40 to 50 μm; ethyl acetate-hexane, 1:9->1:7->1:6) to obtain the title compound (319.6 mg, 97%) as a yellow pale oil.
ESI-MS m/z 938 (M+Na)+.

Example 30-4 Step (4) (8E,12E,14E)-3,21-bis(diethylisopropylsiloxy)-16-hydroxy-6,10,12,16,20-pentamethyl-7-((4-(1-methylpiperidin-4-yl)piperazin-1-yl)carbonyl)oxy-18,19-epoxytricosa-8,12,14-trien-11-olide

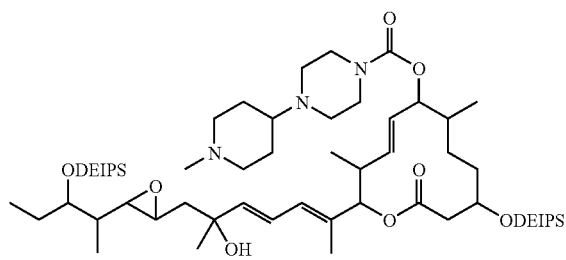

A solution of 1-(4-methylpiperidin-1-yl)-piperazine (11.7 mg, 63.3 μmol) in tetrahydrofuran (1 mL) and triethylamine (13 mg, 0.127 mmol) were added dropwise to a solution of (8E,12E,14E)-3,21-bis(diethylisopropylsiloxy)-16-hydroxy-6,10,12,16,20-pentamethyl-7-((4-nitrophenoxy)carboxy)-18,19-epoxytricosa-8,12,14-trien-11-olide (29 mg, 31.6 μmol) in tetrahydrofuran (2 mL), and the reaction mixture was stirred at room temperature for two hours. The reaction mixture was diluted with ethyl acetate, and then the organic layer was washed with an aqueous solution of sodium hydrogencarbonate. The resulting organic layer was dried over anhydrous magnesium sulfate, filtered and concentrated under reduced pressure. The resulting residue was purified by thin-layer chromatography (Fuji Silysia NH Silica gel plate; ethyl acetate-hexane, 9:1) to obtain the title compound (18.5 mg, 61%) as a colorless oil.

Example 30-5 Step (5) (8E,12E,14E)-3,16,21-trihydroxy-6,10,12,16,20-pentamethyl-7-((4-(1-methylpiperidin-4-yl)piperazin-1-yl)carbonyl)oxy-18,19-epoxytricosa-8,12,14-trien-11-olide (compound 30)

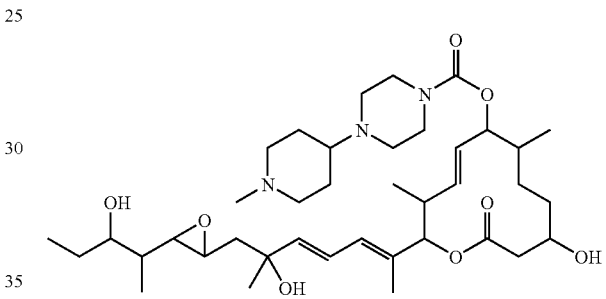

A solution of (8E,12E,14E)-3,21-bis(diethylisopropylsiloxy)-16-hydroxy-6,10,12,16,20-pentamethyl-7-((4-(1-methylpiperidin-4-yl)piperazin-1-yl)carbonyl)oxy-18,19-epoxytricosa-8,12,14-trien-11-olide (18.5 mg, 19.2 μmol) in tetrahydrofuran (2 mL) was cooled to 5° C. Tetrabutylammonium fluoride (1.0 M solution in tetrahydrofuran, 42.3 μL, 42.3 μmol) was added dropwise to the solution, and the reaction mixture was stirred at room temperature for four hours. The reaction mixture was diluted with ethyl acetate, and then the organic layer was washed with an aqueous solution of sodium hydrogencarbonate. The resulting organic layer was washed with an aqueous solution of sodium hydrogencarbonate, dried over anhydrous magnesium sulfate, filtered concentrated under reduced pressure. The resulting residue was purified by thin-layer chromatography (Fuji Silysia NH Silica gel plate; methanol-dichloromethane, 1:24) to obtain the title compound (7.6 mg, 56%) as a colorless oil.

$^1$H-NMR spectrum (CD$_3$OD, 400 MHz) δ (ppm): 0.88 (3H, d, J=6.8 Hz), 0.90 (3H, d, J=7.2 Hz), 0.94 (3H, t, J=7.6 Hz), 1.00 (3H, d, J=6.8 Hz), 1.19-1.69 (13H, m), 1.77 (3H, s), 1.82-1.97 (4H, m), 1.98-2.06 (2H, m), 2.25 (3H, s), 2.24-2.32 (1H, m), 2.42 (1H, dd, J=5.2, 14.0 Hz), 2.48-2.60 (6H, m), 2.66 (1H, dd, J=2.4, 8.0 Hz), 2.87-2.95 (3H, m), 3.38-3.55 (5H, m), 3.74-3.81 (1H, m), 4.75-4.82 (1H, m), 5.01 (1H, d, J=10.4 Hz), 5.44 (1H, dd, J=8.8, 14.8 Hz), 5.50 (1H, dd, J=9.2, 14.8 Hz), 5.86 (1H, d, J=15.2 Hz), 6.12 (1H, d, J=11.2 Hz), 6.52 (1H, dd, J=10.8, 15.2 Hz); ESI-MS m/z 704 (M+H)+.

Example 31

(8E,12E,14E)-7-((4-(2-cyanoethyl)piperazin-1-yl)carbonyl)oxy-3,16,21-trihydroxy-6,10,12,16,20-pentamethyl-18,19-epoxytricosa-8,12,14-trien-11-olide (compound 31)

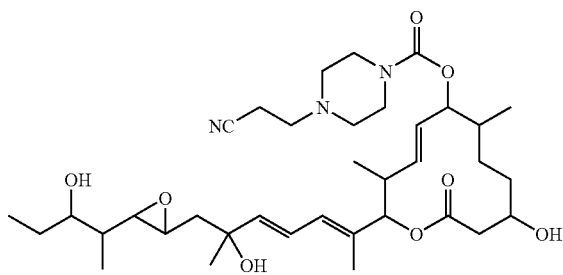

The title compound (colorless oil) was synthesized in the same manner as in Example 18.

$^1$H-NMR spectrum (CD$_3$OD, 400 MHz) δ (ppm): 0.88 (3H, d, J=6.8 Hz), 0.90 (3H, d, J=6.8 Hz), 0.94 (3H, t, J=7.6 Hz), 1.00 (3H, d, J=6.8 Hz), 1.19-1.69 (11H, m), 1.77 (3H, d, J=0.8 Hz), 1.86 (1H, dd, J=5.2, 14.0 Hz), 1.88-1.98 (1H, m), 2.38-2.51 (5H, m), 2.52-2.60 (2H, m), 2.61-2.70 (5H, m), 2.89 (1H, dt, J=2.0, 6.0 Hz), 3.40-3.56 (5H, m), 3.74-3.81 (1H, m), 4.76-4.82 (1H, m), 5.01 (1H, d, J=10.4 Hz), 5.44 (1H, dd, J=8.8, 14.8 Hz), 5.50 (1H, dd, J=9.2, 14.8 Hz), 5.86 (1H, d, J=15.2 Hz), 6.12 (1H, d, J=10.8 Hz), 6.52 (1H, dd, J=10.8, 15.2 Hz); ESI-MS m/z 660 (M+H)$^+$, 682 (M+Na)$^+$.

Example 32

(8E,12E,14E)-3,16,21-trihydroxy-6,10,12,16,20-pentamethyl-7-(((2S)-2-((pyrrolidin-1-yl)methyl)pyrrolidin-1-yl)carbonyl)oxy-18,19-epoxytricosa-8,12,14-trien-11-olide (compound 32)

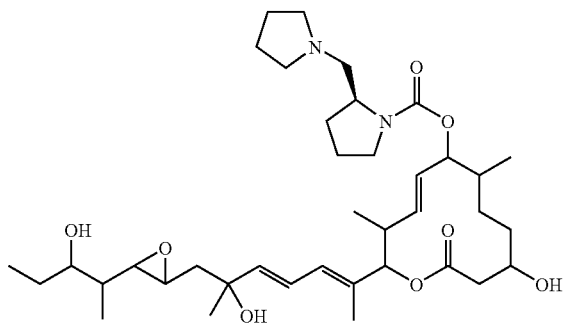

The title compound (colorless oil) was synthesized in the same manner as in Example 30.

$^1$H-NMR spectrum (CD$_3$OD, 400 MHz) δ (ppm): 0.88 (3H, d, J=6.4 Hz), 0.90 (3H, d, J=7.2 Hz), 0.94 (3H, t, J=7.6 Hz), 0.97-1.07 (3H, m), 1.19-2.03 (25H, m), 2.38-2.69 (10H, m), 2.89 (1H, dt, J=2.0, 6.0 Hz), 3.30-3.40 (1H, covered with CD$_3$OD), 3.52 (1H, td, J=4.4, 8.4 Hz), 3.73-3.81 (1H, m), 3.89-3.99 (1H, m), 4.74-4.86 (1H, covered with H$_2$O), 5.02 (1H, d, J=10.8 Hz), 5.40-5.55 (2H, m), 5.87 (1H, d, J=15.2 Hz), 6.13 (1H, d, J=11.2 Hz), 6.52 (1H, dd, J=11.2, 15.2 Hz); ESI-MS m/z 675 (M+H)$^+$.

Example 33

(8E,12E,14E)-7-((4-(2-(N,N-dimethylamino)ethyl)piperazin-1-yl)carbonyl)oxy-3,16,21-trihydroxy-6,10,12,16,20-pentamethyl-18,19-epoxytricosa-8,12,14-trien-11-olide (compound 33)

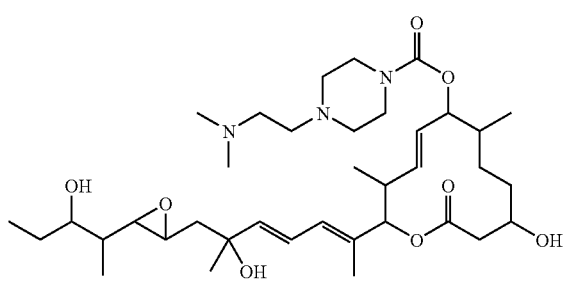

The title compound (colorless oil) was synthesized in the same manner as in Example 30.

$^1$H-NMR spectrum (CD$_3$OD, 400 MHz) δ (ppm): 0.88 (3H, d, J=6.4 Hz), 0.90 (3H, d, J=6.8 Hz), 0.94 (3H, t, J=7.6 Hz), 1.00 (3H, d, J=6.8 Hz), 1.19-1.69 (11H, m), 1.77 (3H, d, J=0.8 Hz), 1.86 (1H, dd, J=5.2, 14.0 Hz), 1.88-1.98 (1H, m), 2.28 (6H, s), 2.39-2.49 (5H, m), 2.49-2.61 (6H, m), 2.66 (1H, dd, J=2.4, 8.0 Hz), 2.89 (1H, dt, J=2.0, 6.0 Hz), 3.40-3.56 (5H, m), 3.75-3.81 (1H, m), 4.75-4.83 (1H, m), 5.02 (1H, d, J=10.8 Hz), 5.44 (1H, dd, J=8.8, 14.8 Hz), 5.50 (1H, dd, J=9.2, 14.8 Hz), 5.86 (1H, d, J=15.2 Hz), 6.13 (1H, d, J=11.2 Hz), 6.52 (1H, dd, J=10.8, 15.2 Hz); ESI-MS m/z 678 (M+H)$^+$.

Example 34

(8E,12E,14E)-7-((4-benzylpiperazin-1-yl)carbonyl)oxy-3,16,21-trihydroxy-6,10,12,16,20-pentamethyl-18,19-epoxytricosa-8,12,14-trien-11-olide (compound 34)

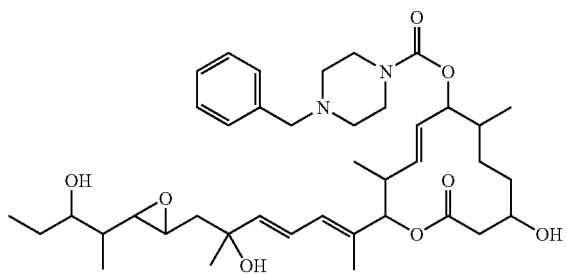

The title compound (colorless oil) was synthesized in the same manner as in Example 18.

$^1$H-NMR spectrum (CD$_3$OD, 400 MHz) δ (ppm): 0.88 (3H, d, J=6.8 Hz), 0.90 (3H, d, J=7.2 Hz), 0.94 (3H, t, J=7.2 Hz), 0.99 (3H, d, J=7.2 Hz), 1.14-1.32 (3H, m), 1.34 (3H, s), 1.36-1.70 (5H, m), 1.77 (3H, d, J=1.2 Hz), 1.78-1.96 (2H, m), 2.36-2.48 (5H, m), 2.52-2.60 (2H, m), 2.67 (1H, dd, J=2.4, 10.4 Hz), 2.89 (1H, dt, J=1.6, 5.2 Hz), 3.41-3.58 (7H, m), 3.74-3.82 (1H, m), 4.78 (1H, dd, J=9.0, 9.0 Hz), 5.01 (1H, d, J=10.4 Hz), 5.44-5.54 (2H, m), 5.87 (1H, d, J=15.2 Hz), 6.12 (1H, d, J=10.8 Hz), 6.52 (1H, dd, J=11.2, 15.2 Hz), 7.22-7.38 (5H, m); ESI-MS m/z 697 (M+H)$^+$.

Example 35

(8E,12E,14E)-3,16,21-trihydroxy-6,10,12,16,20-pentamethyl-7-(N-(1-methylpiperidin-4-yl)carbamoyloxy)-18,19-epoxytricosa-8,12,14-trien-11-olide (compound 35)

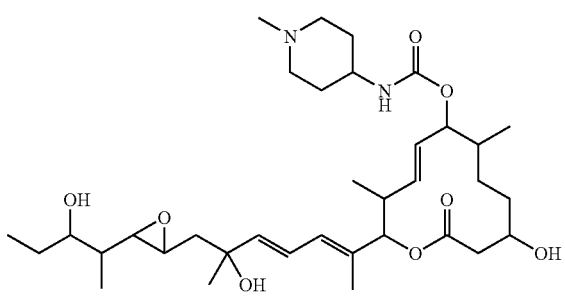

The title compound (colorless oil) was synthesized in the same manner as in Example 18.

$^1$H-NMR spectrum (CD$_3$OD, 400 MHz) δ (ppm): 0.88 (3H, d, J=7.2 Hz), 0.90 (3H, d, J=7.2 Hz), 0.94 (3H, t, J=7.6 Hz), 0.99 (3H, d, J=6.8 Hz), 1.20-1.32 (3H, m), 1.34 (3H, s), 1.36-1.72 (5H, m), 1.77 (3H, d, J=1.2 Hz), 1.80-1.90 (6H, m), 2.04-2.18 (2H, m), 2.26 (3H, s), 2.42 (1H, dd, J=5.6, 14.8 Hz), 2.51-2.59 (2H, m), 2.67 (1H, dd, J=2.4, 8.0 Hz), 2.78-2.86 (2H, m), 2.89 (1H, dt, J=2.4, 6.0 Hz), 3.35-3.40 (1H, m), 3.48-3.54 (1H, m), 3.74-3.80 (1H, m), 4.70-4.79 (1H, m), 5.01 (1H, d, J=10.8 Hz), 5.38-5.42 (2H, m), 5.86 (1H, d, J=15.6 Hz), 6.12 (1H, d, J=11.2 Hz), 6.52 (1H, dd, J=11.2, 15.2 Hz); ESI-MS m/z 635 (M+H)$^+$.

Example 36

(8E,12E,14E)-3,16,21-trihydroxy-6,10,12,16,20-pentamethyl-7-((4-(pyridin-4-yl)piperazin-1-yl)carbonyl)oxy-18,19-epoxytricosa-8,12,14-trien-11-olide (compound 36)

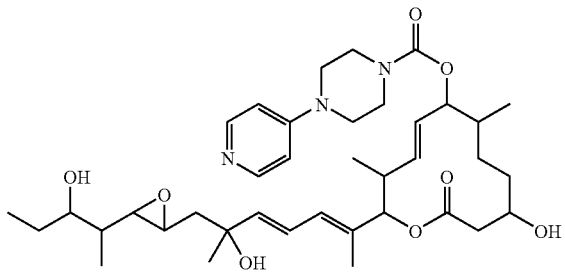

The title compound (colorless oil) was synthesized in the same manner as in Example 18.

$^1$H-NMR spectrum (CD$_3$OD, 400 MHz) δ (ppm): 0.88 (3H, d, J=6.8 Hz), 0.89 (3H, d, J=7.2 Hz), 0.93 (3H, t, J=7.2 Hz), 1.01 (3H, d, J=6.8 Hz), 1.20-1.32 (3H, m), 1.34 (3H, s), 1.35-1.70 (5H, m), 1.77 (3H, s), 1.82-2.01 (2H, m), 2.43 (1H, dd, J=5.2, 14.0 Hz), 2.51-2.62 (2H, m), 2.66 (1H, dd, J=2.0, 8.0 Hz), 2.89 (1H, dt, J=2.4, 6.0 Hz), 3.38-3.48 (4H, m), 3.49-3.55 (1H, m), 3.56-3.66 (4H, m), 3.74-3.82 (1H, m), 4.80-4.92 (1H, covered with H$_2$O), 5.02 (1H, d, J=10.8 Hz), 5.40-5.56 (2H, m), 5.87 (1H, d, J=14.8 Hz), 6.13 (1H, d, J=10.8 Hz), 6.52 (1H, dd, J=10.8, 15.2 Hz), 6.86 (2H, d, J=6.4 Hz), 8.12 (2H, d, J=6.4 Hz); ESI-MS m/z 684 (M+H)$^+$.

Example 37

(8E,12E,14E)-7-((4-cyclohexylpiperazin-1-yl)carbonyl)oxy-3,16,21-trihydroxy-6,10,12,16,20-pentamethyl-18,19-epoxytricosa-8,12,14-trien-11-olide (compound 37)

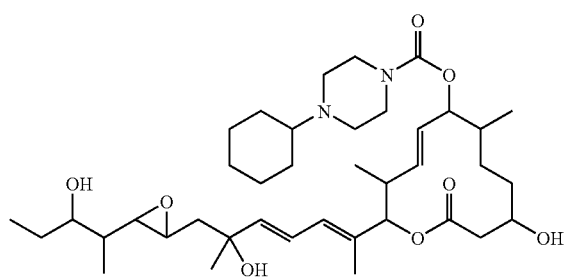

The title compound (colorless oil) was synthesized in the same manner as in Example 18.

$^1$H-NMR spectrum (CD$_3$OD, 400 MHz) δ (ppm): 0.88 (3H, d, J=6.8 Hz), 0.89 (3H, d, J=7.2 Hz), 0.94 (3H, t, J=7.4 Hz), 1.00 (3H, d, J=6.4 Hz), 1.08-1.41 (8H, m), 1.34 (3H, s), 1.41-1.70 (6H, m), 1.70-1.98 (6H, m) 1.77 (3H, s), 2.25-2.35 (1H, m), 2.42 (1H, dd, J=5.4, 14.2 Hz), 2.50-2.63 (6H, m), 2.66 (1H, dd, J=2.2, 7.8 Hz), 2.89 (1H, dt, J=2.2, 5.6 Hz), 3.37-3.55 (5H, m), 3.74-3.82 (1H, m), 4.75-4.82 (1H, m), 5.02 (1H, d, J=10.8 Hz), 5.40-5.54 (2H, m), 5.86 (1H, d, J=15.2 Hz), 6.12 (1H, d, J=10.8 Hz), 6.52 (1H, dd, J=10.8, 15.2 Hz); ESI-MS m/z 689 (M+H)$^+$.

Example 38

(8E,12E,14E)-3,16,21-trihydroxy-6,10,12,16,20-pentamethyl-7-((4-(tetrahydropyran-4-yl)piperazin-1-yl)carbonyl)oxy-18,19-epoxytricosa-8,12,14-trien-11-olide (compound 38)

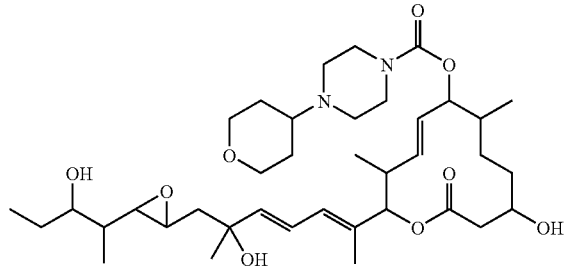

The title compound (colorless oil) was synthesized in the same manner as in Example 18.

$^1$H-NMR spectrum (CD$_3$OD, 400 MHz) δ (ppm): 0.88 (3H, d, J=6.8 Hz), 0.89 (3H, d, J=7.2 Hz), 0.94 (3H, t, J=7.4

Hz), 1.00 (3H, d, J=6.4 Hz), 1.20-1.98 (14H, m), 1.34 (3H, s), 1.77 (3H, s), 2.38-2.62 (8H, m), 2.66 (1H, dd, J=2.2, 7.8 Hz), 2.89 (1H, dt, J=2.2, 5.6 Hz), 3.37-3.56 (7H, m), 3.74-3.82 (1H, m), 3.94-4.02 (2H, m) 4.76-4.82 (1H, m), 5.02 (1H, d, J=10.4 Hz), 5.40-5.54 (2H, m), 5.86 (1H, d, J=15.2 Hz), 6.12 (1H, d, J=10.0 Hz), 6.52 (1H, dd, J=10.8, 15.2 Hz); ESI-MS m/z 691 (M+H)$^+$.

Example 39

(8E,12E,14E)-3,16,21-trihydroxy-7-((4-isopropylhomopiperazin-1-yl)carbonyl)oxy-6,10,12,16,20-pentamethyl-18,19-epoxytricosa-8,12,14-trien-11-olide (compound 39)

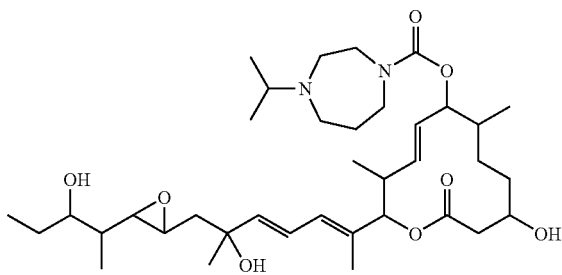

(8E,12E,14E)-3,21-bis(diethylisopropylsiloxy)-16-hydroxy-6,10,12,16,20-pentamethyl-7-((4-nitrophenoxy)carboxy)-18,19-epoxytricosa-8,12,14-trien-11-olide (31 mg, 0.034 mmol) obtained in the Example 30-3 step was dissolved in tetrahydrofuran (2 mL). Then, 1-isopropyl homopiperazine (9.7 mg, 0.068 mmol) and triethylamine (10.3 mg, 0.10 mmol) were added to the mixture, and the reaction mixture was stirred under nitrogen atmosphere at room temperature for two hours. The reaction mixture was diluted with ethyl acetate, and then the organic layer was washed with aqueous solution of sodium hydrogencarbonate and brine. The resulting organic layer was dried over anhydrous magnesium sulfate, filtered and concentrated under reduced pressure. The resulting residue was purified by silica gel column chromatography (Fuji Silysia NH Silica gel; ethyl acetate-hexane, 20:80->25:75) to give (8E,12E, 14E)-3,21-bis(diethylisopropylsiloxy)-16-hydroxy-7-((4-isopropylhomopiperazin-1-yl)carbonyl)oxy-6,10,12,16,20-pentamethyl-18,19-epoxytricosa-8,12,14-trien-11-olide (26 mg, 0.028 mmol). ESI-MS m/z 919 (M+H)$^+$.

This product (25 mg, 0.027 mmol) was dissolved in tetrahydrofuran (1 mL), and tetrabutylammonium fluoride (1.0M solution in tetrahydrofuran, 0.081 mL, 0.081 mmol) was added dropwise to the mixture. The reaction mixture was stirred under nitrogen atmosphere at room temperature for two hours. The reaction mixture was diluted with ethyl acetate, and then the organic layer was washed with aqueous solution of sodium hydrogencarbonate and brine. The resulting organic layer was dried over anhydrous magnesium sulfate, filtered and concetrated under reduced pressure. The resulting residue was purified by silica gel column chromatography (Fuji Silysia NH Silica gel; methylene chloride-methanol, 100:0.5->100:2) to give the title compound (14.6 mg) as a colorless oil.

$^1$H-NMR spectrum (CD$_3$OD, 400 MHz) δ (ppm): (CD$_3$OD, 400 MHz) δ (ppm): 0.88 (3H, d, J=6.8 Hz), 0.89 (3H, d, J=7.2 Hz), 0.94 (3H, t, J=7.4 Hz), 0.99-1.05 (9H, m), 1.16-2.00 (12H, m), 1.34 (3H, s), 1.77 (3H, s), 2.42 (1H, dd, J=5.2, 14.0 Hz), 2.48-2.76 (7H, m), 2.84-2.98 (2H, m), 3.38-3.58 (5H, m), 3.74-3.82 (1H, m), 4.76-4.91 (1H, m), 5.02 (1H, d, J=10.8 Hz), 5.40-5.56 (2H, m), 5.86 (1H, d, J=15.2 Hz), 6.12 (1H, d, J=10.0 Hz), 6.52 (1H, dd, J=10.8, 15.2 Hz); ESI-MS m/z 663 (M+H)$^+$.

Example 40

(8E,12E,14E)-3,16,21-trihydroxy-7-(1-(4-(4-hydroxypiperidin-1-yl)piperidin-1-yl)carbonyl)oxy-6,10,12,16,20-pentamethyl-18,19-epoxytricosa-8,12,14-trien-11-olide (compound 40)

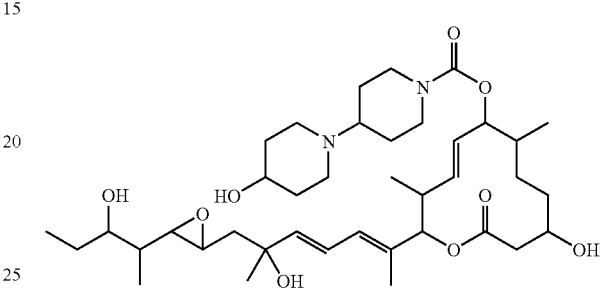

The title compound (colorless oil) was synthesized in the same manner as in Example 30.

$^1$H-NMR spectrum (CD$_3$OD, 400 MHz) δ (ppm): (CD$_3$OD, 400 MHz) δ (ppm): 0.87 (3H, d, J=6.8 Hz), 0.89 (3H, d, J=7.2 Hz), 0.94 (3H, t, J=7.4 Hz), 0.99 (3H, d, J=6.4 Hz), 1.20-1.70 (12H, m), 1.34 (3H, s), 1.77 (3H, s), 1.82-1.98 (6H, m), 2.29-2.38 (2H, m), 2.38-2.60 (4H, m), 2.66 (1H, dd, J=7.6, 2.0 Hz), 2.70-2.91 (5H, m), 3.49-3.55 (1H, m), 3.55-3.64 (1H, m), 3.74-3.81 (1H, m), 4.11-4.20 (2H, m), 4.75-4.81 (1H, m), 5.02 (1H, d, J=10.8 Hz), 5.40-5.54 (2H, m), 5.86 (1H, d, J=15.2 Hz), 6.12 (1H, d, J=10.8 Hz), 6.52 (1H, dd, J=11.2, 15.6 Hz); ESI-MS m/z 705 (M+H)$^+$.

Example 41

(8E,12E,14E)-3,16,21-trihydroxy-7-((4-(2-hydroxyethyl)piperazin-1-yl)carbonyl)oxy-6,10,12,16,20-pentamethyl-18,19-epoxytricosa-8,12,14-trien-11-olide (compound 41)

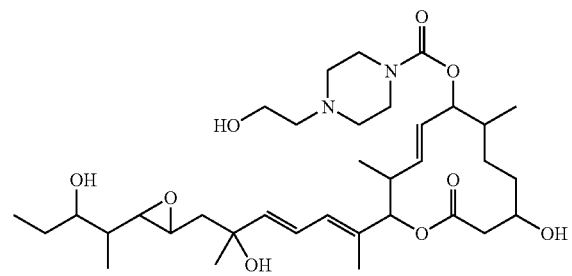

The title compound (colorless oil) was synthesized in the same manner as in Example 18.

$^1$H-NMR spectrum (CD$_3$OD, 400 MHz) δ (ppm): 0.87 (3H, d, J=6.0 Hz), 0.89 (3H, d, J=7.2 Hz), 0.94 (3H, t, J=7.3 Hz), 0.99 (3H, d, J=6.8 Hz), 1.18-1.69 (11H, m), 1.77 (3H, s), 1.86 (1H, dd, J=5.6, 14.0 Hz), 1.88-1.98 (1H, m), 2.35-2.61 (9H, m), 2.66 (1H, dd, J=2.4, 8.0 Hz), 2.82-2.92 (1H, m), 3.38-3.55 (5H, m), 3.60-3.80 (3H, m), 4.70-4.86 (1H, covered with H$_2$O), 5.01 (1H, d, J=10.8 Hz), 5.34-5.54 (2H, m), 5.86 (1H, d, J=15.2 Hz), 6.12 (1H, d, J=10.8 Hz), 6.52 (1H, dd, J=11.2, 15.2 Hz); ESI-MS m/z 651 (M+H)$^+$.

Example 42

(8E,12E,14E)-3,16,21-trihydroxy-6,10,12,16,20-pentamethyl-7-((4-(morpholin-4-yl)piperidin-1-yl)carbonyl)oxy-18,19-epoxytricosa-8,12,14-trien-11-olide (compound 42)

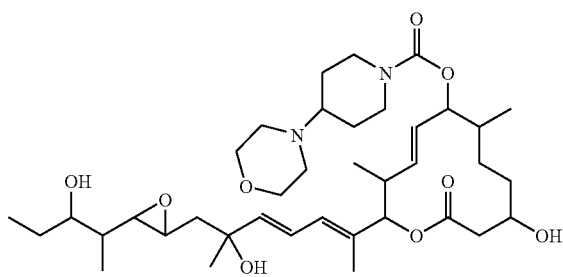

The title compound (colorless oil) was synthesized in the same manner as in Example 18.

$^1$H-NMR spectrum (CD$_3$OD, 400 MHz) δ (ppm): 0.87 (3H, d, J=7.2 Hz), 0.89 (3H, d, J=6.8 Hz), 0.94 (3H, t, J=7.6 Hz), 0.99 (3H, d, J=7.2 Hz), 1.20-1.69 (13H, m), 1.77 (3H, s), 1.82-1.98 (4H, m), 2.33-2.46 (3H, m), 2.50-2.60 (4H, m), 2.66 (1H, dd, J=2.0, 8.0 Hz), 2.72-2.86 (1H, m), 2.89 (1H, dt, J=2.0, 6.4 Hz), 3.52 (1H, dt, J=4.0, 8.0 Hz), 3.68 (4H, dd, J=4.8, 4.8 Hz), 3.73-3.82 (1H, m), 4.09-4.21 (4H, m), 4.70-4.85 (1H, m), 5.01 (1H, d, J=10.8 Hz), 5.40-5.55 (2H, m), 5.86 (1H, d, J=15.6 Hz), 6.13 (1H, d, J=11.2 Hz), 6.52 (1H, dd, J=11.2, 15.6 Hz); ESI-MS m/z 691 (M+H)$^+$.

Example 43

(8E,12E,14E)-7-((4-ethylhomopiperazin-1-yl)carbonyl)oxy-3,16,21-trihydroxy-6,10,12,16,20-pentamethyl-18,19-epoxytricosa-8,12,14-trien-11-olide (compound 43)

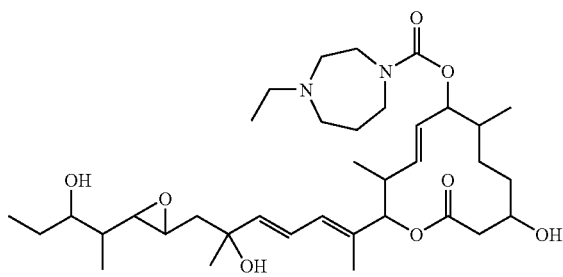

(8E,12E,14E)-3,21-bis(diethylisopropylsiloxy)-16-hydroxy-6,10,12,16,20-pentamethyl-7-((4-nitrophenoxy)carboxy)-18,19-epoxytricosa-8,12,14-trien-11-olide (40 mg, 0.044 mmol) obtained in the Example 30-3 step was dissolved in tetrahydrofuran (2 mL). Then, 1-ethyl homopiperazine (11 mg, 0.088 mmol) and triethylamine (0.061 mL, 0.44 mmol) were added to the mixture, and the reaction mixture was stirred under nitrogen atmosphere at room temperature overnight. The reaction mixture was diluted with ethyl acetate, and then the organic layer was washed with water and brine. The resulting organic layer was dried over anhydrous magnesium sulfate, filtered and concentrated under reduced pressure. The resulting residue was purified by silica gel column chromatography (Kanto Silica gel 60N, 40 to 50 µm; ethyl acetate-hexane, 1:1->methylene chloride-methanol, 1:9) to give (8E,12E,14E)-3,21-bis(diethylisopropylsiloxy)-7-((4-ethylhomopiperazin-1-yl)carbonyl)oxy-16-hydroxy-6,10,12,16,20-pentamethyl-18,19-epoxytricosa-8,12,14-trien-11-olide (34 mg, 0.038 mmol) as a colorless oil.

This product (34 mg, 0.038 mmol) was dissolved in tetrahydrofuran (1 mL), and tetrabutylammonium fluoride (1.0M solution in tetrahydrofuran, 0.187 mL, 0.187 mmol) was added dropwise to the mixture. The reaction mixture was stirred under a nitrogen atmosphere at room temperature for 17 hours. The reaction mixture was diluted with ethyl acetate, and then the organic layer was washed with aqueous solution of sodium hydrogencarbonate and brine. The resulting organic layer was dried over anhydrous magnesium sulfate, filtered and concentrated under reduced pressure. The resulting residue was purified by silica gel column chromatography (Kanto silica gel 60N, 40 to 50 µm; methylene chloride-methanol, 100:1.5->methylene chloride-methanol-28% ammonium hydroxide aqueous solution, 100:5:1) to give the title compound (23.3 mg) as a colorless oil.

$^1$H-NMR spectrum (CD$_3$OD, 400 MHz) δ (ppm): 0.88 (3H, d, J=7.2 Hz), 0.89 (3H, d, J=7.2 Hz), 0.94 (3H, t, J=7.2 Hz), 1.01 (3H, d, J=6.8 Hz), 1.09 (3H, t, J=7.2 Hz), 1.20-1.69 (11H, m), 1.77 (3H, s), 1.82-1.90 (3H, m), 1.90-1.98 (1H, m), 2.42 (1H, dd, J=5.2, 14.0 Hz), 2.52-2.72 (9H, m), 2.89 (1H, dt, J=2.4, 6.4 Hz), 3.42-3.60 (5H, m), 3.75-3.82 (1H, m), 4.70-4.90 (1H, covered with H$_2$O), 5.02 (1H, d, J=10.8 Hz), 5.40-5.55 (2H, m), 5.87 (1H, d, J=15.2 Hz), 6.13 (1H, d, J=11.2 Hz), 6.52 (1H, dd, J=11.2, 15.2 Hz); ESI-MS m/z 649 (M+H)$^+$.

Example 44

(8E,12E,14E)-3,16,21-trihydroxy-7-((4-isopropylpiperazin-1-yl)carbonyl)oxy-6,10,12,16,20-pentamethyl-18,19-epoxytricosa-8,12,14.-trien-11-olide (compound 44)

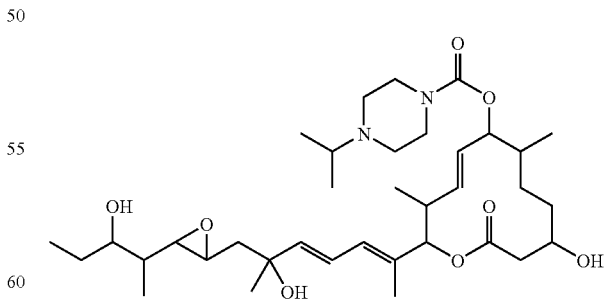

The title compound (colorless oil) was synthesized in the same manner as in Example 30.

$^1$H-NMR spectrum (CD$_3$OD, 400 MHz) δ (ppm): 0.88 (3H, d, J=6.4 Hz), 0.89 (3H, d, J=7.2 Hz), 0.94 (3H, t, J=7.6 Hz), 1.00 (3H, d, J=6.8 Hz), 1.07 (6H, d, J=6.4 Hz), 1.20-1.69 (11H, m), 1.77 (3H, brs), 1.86 (1H, dd, J=5.2, 14.0 Hz), 1.89-1.98 (1H, m), 2.42 (1H, dd, J=5.2, 14.0 Hz), 2.48-2.60 (6H, m), 2.66 (1H, dd, J=2.4, 8.0 Hz), 2.67-2.78 (1H, m), 2.89 (1H, dt, J=2.4, 6.0 Hz), 3.40-3.57 (5H, m), 3.74-3.82 (1H, m), 4.77-4.91 (1H, covered with H₂O), 5.01 (1H, d, J=10.4 Hz), 5.40-5.55 (2H, m), 5.86 (1H, d, J=15.2 Hz), 6.13 (1H, d, J=10.8 Hz), 6.52 (1H, dd, J=11.2, 15.2 Hz); ESI-MS m/z 649 (M+H)⁺.

Example 45

(8E,12E,14E)-7-((4-cyclopropylhomopiperazin-1-yl)carbonyl)oxy-3,16,21-trihydroxy-6,10,12,16,20-pentamethyl-18,19-epoxytricosa-8,12,14-trien-11-olide (compound 45)

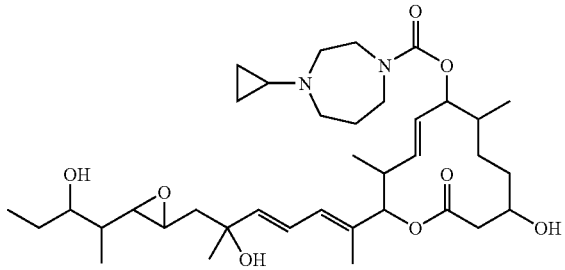

The title compound (colorless oil) was synthesized in the same manner as in Example 30.

¹H-NMR spectrum (CD₃OD, 400 MHz) δ (ppm): 0.32-0.54 (4H, m), 0.87 (3H, d, J=8.0 Hz), 0.90 (3H, d, J=7.2 Hz), 0.94 (3H, t, J=7.2 Hz), 1.00 (3H, d, J=6.0 Hz), 1.14-2.00 (19H, m), 2.42 (1H, dd, J=5.6, 14.0 Hz), 2.42-2.62 (2H, m), 2.66 (1H, dd, J=2.0, 8.0 Hz), 2.70-2.92 (5H, m), 3.37-3.58 (5H, m), 3.68-3.82 (1H, m), 4.77-4.91 (1H, covered with H₂O), 5.01 (1H, d, J=10.8 Hz), 5.44-5.55 (2H, m), 5.86 (1H, d, J=15.2 Hz), 6.13 (1H, d, J=10.8 Hz), 6.52 (1H, dd, J=11.2, 15.2 Hz); ESI-MS m/z 661 (M+H)⁺.

Example 46

(8E,12E,14E)-7-((4-cyclopropylpiperazin-1-yl)carbonyl)oxy-3,16,21-trihydroxy-6,10,12,16,20-pentamethyl-18,19-epoxytricosa-8,12,14-trien-11-olide (compound 46)

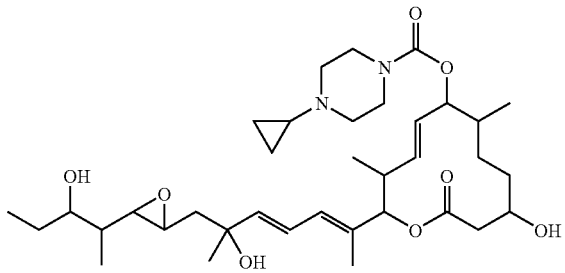

The title compound (colorless oil) was synthesized in the same manner as in Example 30.

¹H-NMR spectrum (CD₃OD, 400 MHz) δ (ppm): 0.40-0.52 (4H, m), 0.87 (3H, d, J=5.6 Hz), 0.89 (3H, d, J=7.2 Hz), 0.94 (3H, t, J=7.2 Hz), 0.98 (3H, d, J=6.0 Hz), 1.20-1.70 (12H, m), 1.77 (3H, s), 1.86 (1H, dd, J=5.2, 14.0 Hz), 1.89-1.98 (1H, m), 2.42 (1H, dd, J=5.6, 14.0 Hz), 2.50-2.63 (6H, m), 2.66 (1H, dd, J=2.0, 8.0 Hz), 2.89 (1H, dt, J=2.4, 6.0 Hz), 3.36-3.49 (4H, m), 3.52 (1H, dt, J=4.8, 7.6 Hz), 3.74-3.82 (1H, m), 4.77-4.90 (1H, covered with H₂O), 5.01 (1H, d, J=10.4 Hz), 5.44-5.55 (2H, m), 5.86 (1H, d, J=15.2 Hz), 6.13 (1H, d, J=11.2 Hz), 6.52 (1H, dd, J=11.2, 15.2 Hz); ESI-MS m/z 647 (M+H)⁺, 670 (M+Na)⁺.

Example 47

(8E,12E,14E)-3,16,21-trihydroxy-7-((N-(4-hydroxy-1-methylpiperidin-4-yl)methyl-N-methyl)carbamoyloxy)-6,10,12,16,20-pentamethyl-18,19-epoxytricosa-8,12,14-trien-11-olide (compound 47)

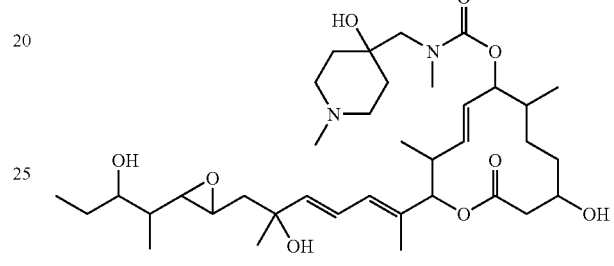

The title compound (colorless oil) was synthesized in the same manner as in Example 30.

¹H-NMR spectrum (CD₃OD, 400 MHz) δ (ppm): 0.86 (3H, d, J=6.8 Hz), 0.90 (3H, d, J=7.2 Hz), 0.94 (3H, t, J=7.2 Hz), 1.01 (3H, d, J=6.8 Hz), 1.20-1.70 (15H, m), 1.77 (3H, s), 1.86 (1H, dd, J=5.2, 14.0 Hz), 1.89-1.98 (1H, m), 2.27 (1.5H, s), 2.28 (1.5H, s), 2.34-2.46 (3H, m), 2.50-2.64 (6H, m), 2.66 (1H, dd, J=2.0, 8.0 Hz), 2.89 (1H, dt, J=2.4, 6.4 Hz), 3.01 (1.5H, s), 3.02 (1.5H, s), 3.52 (1H, dt, J=4.8, 8.0 Hz), 3.74-3.82 (1H, m), 4.74-4.92 (1H, covered with H₂O), 5.01 (1H, d, J=10.4 Hz), 5.40-5.55 (2H, m), 5.86 (1H, d, J=15.2 Hz), 6.13 (1H, d, J=10.8 Hz), 6.52 (1H, dd, J=10.8, 15.2 Hz); ESI-MS m/z 679 (M+H)⁺.

Example 48

(8E,12E,14E)-7-(((1S,4S)-5-ethyl-2,5-diazabicyclo[2.2.1]heptan-2-yl)carbonyl)oxy-3,16,21-trihydroxy-6,10,12,16,20-pentamethyl-18,19-epoxytricosa-8,12,14-trien-11-olide (compound 48)

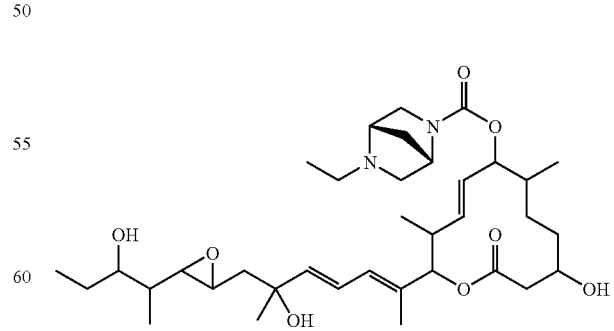

The title compound (colorless oil) was synthesized in the same manner as in Example 30.

¹H-NMR spectrum (CD₃OD, 400 MHz) δ (ppm): 0.92 (3H, d, J=6.8 Hz), 0.94 (-3H, d, J=7.2 Hz), 0.98-(3H, t, J=7.2

Hz), 1.03 (1.5H, d, J=6.8 Hz), 1.06 (1.5H, d, J=6.8 Hz), 1.10-1.22 (3H, m), 1.22-1.75 (8H, m), 1.38 (3H, s), 1.76-2.03 (4H, m), 1.82 (3H, s), 2.47 (1H, dd, J=5.6, 14.4 Hz), 2.54-2.77 (6H, m), 2.83-2.99 (2H, m), 3.22-3.33 (1H, m), 3.53-3.63 (2H, m), 3.65 (1H, brs), 3.79-3.88 (1H, m), 4.36 (0.5H, s), 4.39 (0.5H, s), 4.77-4.91 (1H, m), 5.06 (1H, d, J=10.4 Hz), 5.45-5.63 (2H, m), 5.91 (1H, d, J=15.2 Hz), 6.18 (1H, d, J=10.8 Hz), 6.57 (1H, dd, J=10.8, 15.2 Hz); ESI-MS m/z 647 (M+H)$^+$.

Example 49

(8E,12E,14E)-3,16,21-trihydroxy-7-(((1S,4S)-5-isopropyl-2,5-diazabicyclo[2.2.1]heptan-2-yl)carbonyl)oxy-6,10,12,16,20-pentamethyl-18,19-epoxytricosa-8,12,14-trien-11-olide (compound 49)

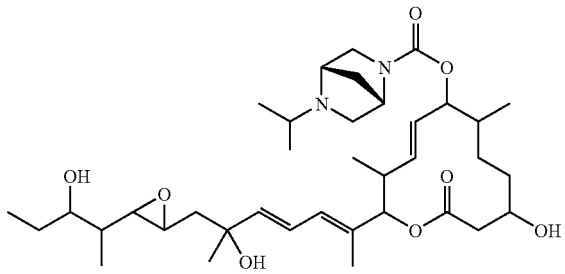

The title compound (colorless oil) was synthesized in the same manner as in Example 30.

$^1$H-NMR spectrum (CD$_3$OD, 400 MHz) δ (ppm): 0.92 (3H, d, J=7.6 Hz), 0.94 (3H, d, J=7.2 Hz), 0.98 (3H, t, J=7.6 Hz), 1.03 (1.5H, d, J=7.2 Hz), 1.06 (1.5H, d, J=7.2 Hz), 1.09-1.16 (6H, m), 1.21-1.75 (8H, m), 1.38 (3H, s), 1.77-2.03 (4H, m), 1.82 (3H, s), 2.47 (1H, dd, J=5.6, 14.4 Hz), 2.52-2.75 (5H, m), 2.94 (1H, dt, J=2.0, 6.0 Hz), 3.05-3.16 (1H, m), 3.21-3.34 (1H, m), 3.51-3.65 (2H, m), 3.77-3.89 (2H, brs), 4.35 (0.5H, s), 4.38 (0.5H, s), 4.79-4.91 (1H, m), 5.06 (1H, d, J=10.8 Hz), 5.45-5.61 (2H, m), 5.91 (1H, d, J=15.6 Hz), 6.17 (1H, d, J=10.8 Hz), 6.57 (1H, dd, J=10.8, 15.2 Hz); ESI-MS m/z 661 (M+H)$^+$.

Example 50

(8E,12E,14E)-7-(N-(2-(N',N'-dimethylamino)ethyl)-N-methylcarbamoyloxy)-3,16,21-trihydroxy-6,10,12,16,20-pentamethyl-18,19-epoxytricosa-8,12,14-trien-11-olide (compound 50)

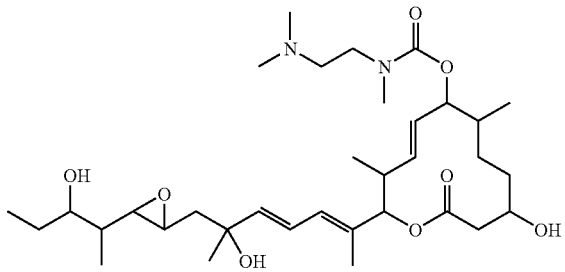

The title compound (colorless oil) was synthesized in the same manner as in Example 23.

$^1$H-NMR spectrum (CD$_3$OD, 400 MHz) δ (ppm): 0.87 (3H, d, J=7.0 Hz), 0.89 (3H, d, J=7.3 Hz), 0.93 (3H, t, J=7.3 Hz), 1.01 (3H, brd, J=6.2 Hz), 1.19-1.68 (7H, m), 1.33 (3H, s), 1.65 (1H, dd, J=6.2, 13.9 Hz), 1.77 (3H, d, J=1.1 Hz), 1.86 (1H, dd, J=6.2, 13.9 Hz), 1.89-1.98 (1H, m), 2.27 (6H, s), 2.42 (1H, dd, J=5.5, 13.9 Hz), 2.45-2.60 (4H, m), 2.66 (1H, dd, J=2.2, 7.7 Hz), 2.87-2.92 (4H, m), 3.37-3.42 (2H, m), 3.52 (1H, dt, J=4.8, 8.4 Hz), 3.74-3.81 (1H, m), 4.74-4.82 (1H, m), 5.01 (1H, d, J=10.6 Hz), 5.40-5.53 (2H, m), 5.86 (1H, d, J=15.4 Hz), 6.12 (1H, dd, J=1.1, 11.0 Hz), 6.52 (1H, d, J=11.0, 15.4 Hz); ESI-MS m/z 623 (M+H)$^+$.

Example 51

(8E,12E,14E)-7-(N-(2-(N',N'-dimethylamino)ethyl)carbamoyloxy)-3,16,21-trihydroxy-6,10,12,16,20-pentamethyl-18,19-epoxytricosa-8,12,14-trien-11-olide (compound 51)

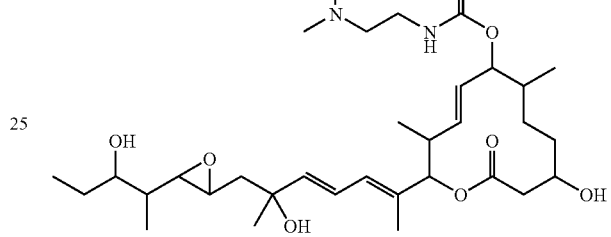

The title compound (colorless oil) was synthesized in the same manner as in Example 23.

$^1$H-NMR spectrum (CD$_3$OD, 400 MHz) δ (ppm): 0.87 (3H, d, J=7.3 Hz), 0.89 (3H, d, J=7.3 Hz), 0.93 (3H, t, J=7.3 Hz), 0.99 (3H, d, J=6.6 Hz), 1.20-1.68 (7H, m), 1.33 (3H, s), 1.65 (1H, dd, J=6.2, 13.9 Hz), 1.77 (3H, s), 1.83-1.91 (1H, m), 1.86 (1H, dd, J=6.2, 13.9 Hz), 2.25 (6H, s), 2.39-2.46 (1H, m), 2.43 (2H, t, J=7.0 Hz), 2.52-2.60 (2H, m), 2.66 (1H, dd, J=2.2, 8.1 Hz), 2.89 (1H, dt, J=2.2, 6.2 Hz), 3.21 (2H, t, J=7.0 Hz), 3.52 (1H, dt, J=4.4, 8.4 Hz), 3.73-3.81 (1H, m), 4.74 (1H, dd, J=9.5, 9.5 Hz), 5.01 (1H, d, J=10.6 Hz), 5.38-5.52 (2H, m), 5.86 (1H, d, J=15.0 Hz), 6.12 (1H, d, J=11.0 Hz), 6.52 (1H, d, J=11.0, 15.0 Hz); ESI-MS m/z 609 (M+H)$^+$.

Example 52

(8E,12E,14E)-3,16,21-trihydroxy-6,10,12,16,20-pentamethyl-7-(N-methyl-N-(2-(morpholin-4-yl)ethyl)carbamoyloxy)-18,19-epoxytricosa-8,12,14-trien-11-olide (compound 52)

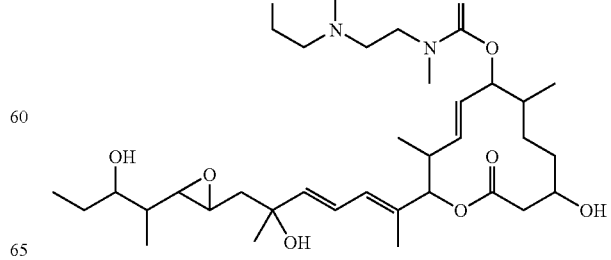

(1) (8E,12E,14E)-6,10,12,16,20-pentamethyl-7-(N-methyl-N-(2-(morpholin-4-yl)ethyl)carbamoyloxy)-3,16,21-tris(triethylsiloxy)-18,19-epoxytricosa-8,12,14-trien-11-olide (compound 52-1)

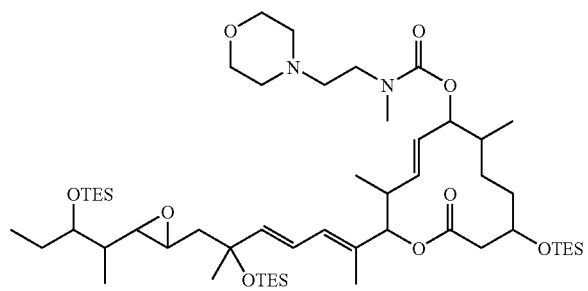

The title compound (colorless oil) was synthesized in the same manner as in Example 23.

¹H-NMR spectrum (CD₃OD, 400 MHz) δ (ppm): 0.625 (6H, q, J=8.1 Hz), 0.634 (6H, q, J=8.1 Hz), 0.65 (6H, q, J=8.1 Hz), 0.83 (3H, t, J=7.3 Hz), 0.85 (3H, d, J=7.0 Hz), 0.89 (3H, d, J=7.0 Hz), 0.93-1.01 (30H, m), 1.15-1.32 (2H, m), 1.39-1.63 (6H, m), 1.42 (3H, s), 1.75 (3H, s), 1.83-1.92 (1H, m), 1.93 (1H, dd, J=4.8, 13.9 Hz), 2.33 (1H, dd, J=6.2, 13.6 Hz), 2.44-2.60 (8H, m), 2.61 (1H, dd, J=2.2, 8.1 Hz), 2.85-2.90 (1H, m), 2.92 (3H, s), 3.38-3.49 (2H, m), 3.61-3.72 (4H, m), 3.74 (1H, dt, J=3.7, 6.6Hz), 3.90-3.98 (1H, m), 4.72-4.81 (1H, m), 4.93 (1H, d, J=10.6 Hz), 5.41-5.52 (2H, m), 5.82 (1H, d, J=15.0 Hz), 6.12 (1H, d, J=11.0 Hz), 6.50 (1H, dd, J=11.0, 15.0 Hz); ESI-MS m/z 1008 (M+H)⁺.

(2) (8E,12E,14E)-3,16,21-trihydroxy-6,10,12,16,20-pentamethyl-7-(N-methyl-N-(2-(morpholin-4-yl)ethyl)carbamoyloxy)-18,19-epoxytricosa-8,12,14-trien-11-olide (compound 52)

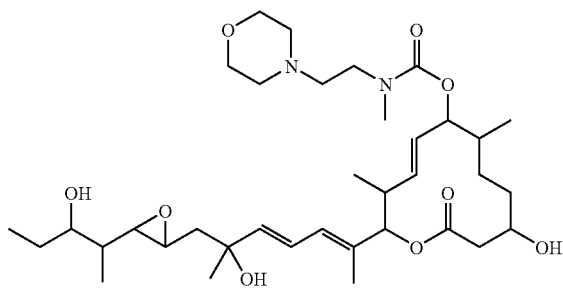

The protective groups for the hydroxyl groups in the compound 52-1 was deprotected in the same manner as in Example 23 to synthesize the title compound (colorless oil).

¹H-NMR spectrum (CD₃OD, 400 MHz) δ (ppm): 0.87 (3H, d, J=7.0 Hz), 0.89 (3H, d, J=7.0 Hz), 0.93 (3H, t, J=7.3 Hz), 1.01 (3H, d, J=7.0 Hz), 1.19-1.65 (7H, m), 1.33 (3H, s), 1.65 (1H, dd, J=5.5, 14.3 Hz), 1.77 (3H, d, J=1.1 Hz), 1.86 (1H, dd, J=5.5, 14.3 Hz), 1.89-1.98 (1H, m), 2.42 (1H, dd, J=5.5, 13.9 Hz), 2.42-2.61 (8H, m), 2.66 (1H, dd, J=2.2, 8.1 Hz), 2.86-2.94 (1H, m), 2.91 (3H, s), 3.34-3.48 (2H, m), 3.52 (1H, dt, J=4.8, 8.4 Hz), 3.63-3.71 (4H, m), 3.74-3.81 (1H, m), 4.74-4.83 (1H, m), 5.01 (1H, d, J=10.6 Hz), 5.41-5.54 (2H, m), 5.86 (1H, d, J=15.0 Hz), 6.12 (1H, d, J=11.0 Hz), 6.52 (!H, dd, J=11.0, 15.0 Hz); ESI-MS m/z 665 (M+H)⁺.

Example 53

(8E,12E,14E)-3,16,21-trihydroxy-6,10,12,16,20-pentamethyl-7-(N-methyl-N-(2-(piperidin-1-yl)ethyl)carbamoyloxy)-18,19-epoxytricosa-8,12,14-trien-11-olide (compound 53)

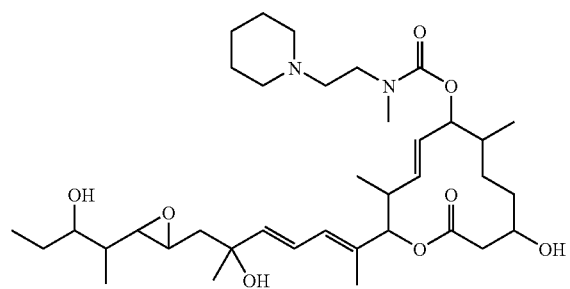

(1) (8E,12E,14E)-6,10,12,16,20-pentamethyl-7-(N-methyl-N-(2-(piperidin-1-yl)ethyl)carbamoyloxy)-3,16,21-tris(triethylsiloxy)-18,19-epoxytricosa-8,12,14-trien-11-olide (compound 53-1)

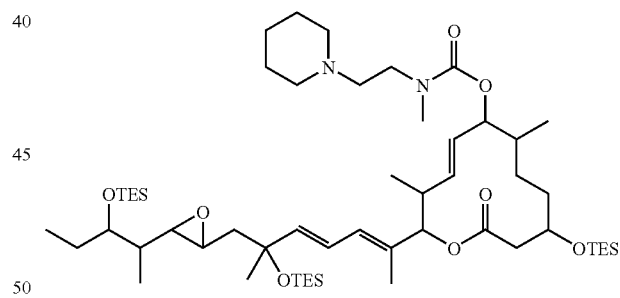

The title compound (colorless oil) was synthesized in the same manner as in Example 23.

¹H-NMR spectrum (CD₃OD, 400 MHz) δ (ppm): 0.59-0.68 (18H, m), 0.82 (3H, t, J=7.3 Hz), 0.85 (3H, d, J=7.0 Hz), 0.89 (3H, d, J=7.0 Hz), 0.95-1.02 (30H, m), 1.15-1.63 (14H, m), 1.42 (3H, s), 1.75 (3H, s), 1.83-1.92 (1H, m), 1.93 (1H, dd, J=4.8, 13.9 Hz), 2.32 (1H, dd, J=6.2, 13.6 Hz), 2.41-2.59 (8H, m), 2.61 (1H, dd, J=2.2, 8.1 Hz), 2.85-2.92 (4H, m), 3.38-3.44 (2H, m), 3.74 (1H, dt, J=3.3, 7.0 Hz), 3.91-3.98 (1H, m), 4.71-4.80 (1H, m), 4.93 (1H, d, J=10.6 Hz), 5.40-5.52 (2H, m), 5.82 (1H, d, J=15.4 Hz), 6.11 (1H, d, J=11.0 Hz), 6.50 (1H, dd, J=11.0, 15.4 Hz); ESI-MS m/z 1006 (M+H)⁺.

(2) (8E,12E,14E)-3,16,21-trihydroxy-6,10,12,16,20-pentamethyl-7-(N-methyl-N-(2-(piperidin-1-yl)ethyl)carbamoyloxy)-18,19-epoxytricosa-8,12,14-trien-11-olide (compound 53)

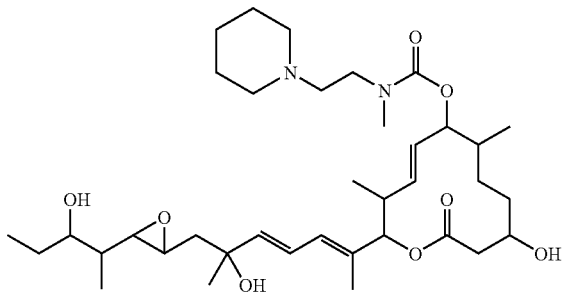

The protective groups for the hydroxyl groups in the compound 53-1 was deprotected in the same manner as in Example 23 to synthesize the title compound (colorless oil).

$^1$H-NMR spectrum (CD$_3$OD, 400 MHz) δ (ppm): 0.87 (3H, d, J=7.7 Hz), 0.89 (3H, d, J=7.3 Hz), 0.93 (3H, t, J=7.3 Hz), 1.01 (3H, brd, J=6.2 Hz), 1.19-1.68 (14H, m), 1.33 (3H, s), 1.77 (3H, d, J=1.1 Hz), 1.86 (1H, dd, J=5.5, 14.3 Hz), 1.89-1.97 (1H, m), 2.39-2.60 (9H, m), 2.66 (1H, dd, J=2.2, 8.1 Hz), 2.86-2.93 (1H, m), 2.90 (3H, s), 3.36-3.46 (2H, m), 3.52 (1H, dt, J=4.8, 8.4 Hz), 3.74-3.81 (1H, m), 4.74-4.82 (1H, m), 5.01 (1H, d, J=10.6 Hz), 5.41-5.53 (2H, m), 5.86 (1H, d, J=15.4 Hz), 6.12 (1H, d, J=11.0 Hz), 6.52 (1H, dd, J=11.0, 15.4 Hz); ESI-MS m/z 663 (M+H)$^+$.

Example 54

(8E,12E,14E)-3,16,21-trihydroxy-6,10,12,16,20-pentamethyl-7-(N-methyl-N-(2-(pyrrolidin-1-yl)ethyl)carbamoyloxy)-18,19-epoxytricosa-8,12,14-trien-11-olide (compound 54)

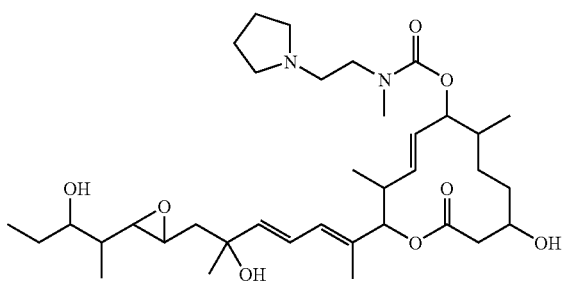

(1) (8E,12E,14E)-6,10,12,16,20-pentamethyl-7-(N-methyl-N-(2-(pyrrolidin-1-yl)ethyl)carbamoyloxy)-3,16,21-tris(triethylsilyloxy)-18,19-epoxytricosa-8,12,14-trien-11-olide (compound 54-1)

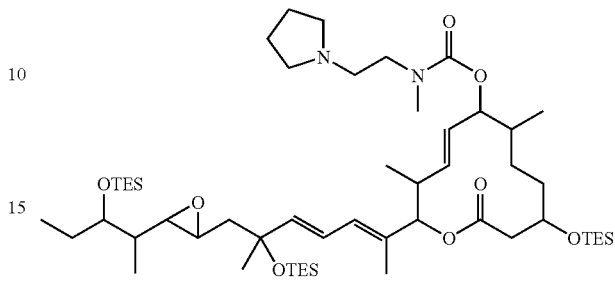

The title compound (colorless oil) was synthesized in the same manner as in Example 23.

$^1$H-NMR spectrum (CD$_3$OD, 400 MHz) δ (ppm): 0.59-0.68 (18H, m), 0.82 (3H, t, J=7.3 Hz), 0.85 (3H, d, J=7.0 Hz), 0.89 (3H, d, J=7.0 Hz), 0.95-1.02 (30H, m), 1.15-1.31 (2H, m), 1.42 (3H, s), 1.39-1.63 (6H, m), 1.75 (3H, d, J=0.7 Hz), 1.75-1.93 (5H, m), 1.93 (1H, dd, J=4.8, 13.9 Hz), 2.32 (1H, dd, J=6.2, 13.6 Hz), 2.50-2.69 (9H, m), 2.85-2.93 (4H, m), 3.39-3.46 (2H, m), 3.74 (1H, dt, J=3.3, 6.6 Hz), 3.90-3.98 (1H, m), 4.71-4.80 (1H, m), 4.93 (1H, d, J=10.6 Hz), 5.40-5.52 (2H, m), 5.82 (1H, d, J=15.0 Hz), 6.12 (1H, d, J=11.0 Hz), 6.50 (1H, dd, J=11.0, 15.0 Hz); ESI-MS m/z 992 (M+H)$^+$.

(2) (8E,12E,14E)-3,16,21-trihydroxy-6,10,12,16,20-pentamethyl-7-(N-methyl-N-(2-(pyrrolidin-1-yl)ethyl)carbamoyloxy)-18,19-epoxytricosa-8,12,14-trien-11-olide (compound 54)

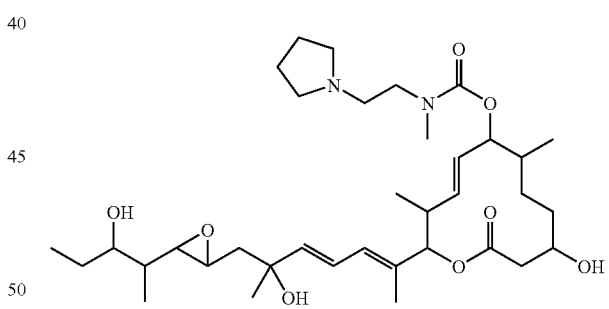

The protective groups for the hydroxyl groups in the compound 54-1 was deprotected in the same manner as in Example 23 to synthesize the title compound (colorless oil).

$^1$H-NMR spectrum (CD$_3$OD, 400 MHz) δ (ppm): 0.87 (3H, d, J=7.0 Hz), 0.89 (3H, d, J=7.3 Hz), 0.93 (3H, t, J=7.3 Hz), 1.01 (3H, brd, J=6.6 Hz), 1.19-1.65 (7H, m), 1.33 (3H, s), 1.65 (1H, dd, J=5.5, 13.9 Hz), 1.77 (3H, d, J=1.1 Hz), 1.77-1.84 (4H, m), 1.86 (1H, dd, J=5.5, 13.9 Hz), 1.89-1.98 (1H, m), 2.42 (1H, dd, J=5.1, 14.3 Hz), 2.50-2.67 (8H, m), 2.66 (1H, dd, J=2.2, 8.1 Hz), 2.86-2.93 (1H, m), 2.90 (3H, s), 3.39-3.45 (2H, m), 3.52 (1H, dt, J=4.8, 8.1 Hz), 3.74-3.82 (1H, m), 4.74-4.83 (1H, m), 5.01 (1H, d, J=10.6 Hz), 5.41-5.53 (2H, m), 5.86 (1H, d, J=15.4 Hz), 6.12 (1H, d, J=11.0 Hz), 6.52 (1H, dd, J=11.0, 15.4 Hz); ESI-MS m/z 649 (M+H)$^+$.

Example 55

(8E,12E,14E)-3,16,21-trihydroxy-6,10,12,16,20-pentamethyl-7-(((1S,4S)-5-methyl-2,5-diazabicyclo[2.2.1]heptan-2-yl)carbonyl)oxy-18,19-epoxytricosa-8,12,14-trien-11-olide (compound 55)

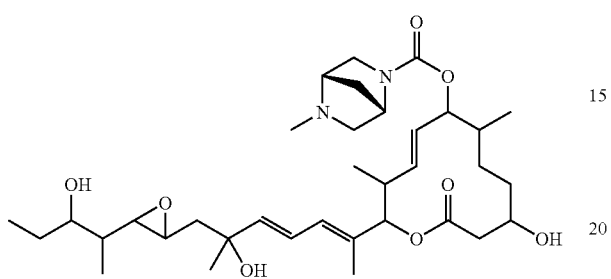

(1) (8E,12E,14E)-6,10,12,16,20-pentamethyl-7-(((1S,4S)-5-methyl-2,5-diazabicyclo[2.2.1]heptan-2-yl)carbonyl)oxy-3,16,21-tris(triethylsiloxy)-18,19-epoxytricosa-8,12,14-trien-11-olide (compound 55-1)

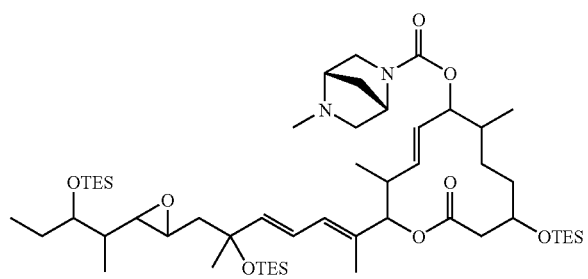

A solution of (1S,4S)-2-methyl-2,5-diazabicyclo[2.2.1]heptane (0.3M solution in N,N-dimethylformamide-chloroform (1:9), 80 μL, 24 μmol) in tetrahydrofuran (0.5 mL) was added dropwise to a solution of (8E,12E,14E)-6,10,12,16,20-pentamethyl-7-((4-nitrophenoxy)carboxy)-3,16,21-tris(triethylsiloxy)-18,19-epoxytricosa-8,12,14-trien-11-olide (12.7 mg, 12.7 μmol) obtained in the Example 23-3 step in tetrahydrofuran (0.5 mL) at room temperature. The reaction mixture was stirred at room temperature for five hours, and then the solvent was removed by evaporation. The resulting residue was purified by silica gel column chromatography (Fuji Silysia NH Silica gel; ethyl acetate:hexane=1:2) to give the title compound (12.2 mg) as a colorless oil.

$^1$H-NMR spectrum (CD$_3$OD, 400 MHz) δ (ppm): 0.59-0.68 (18H, m), 0.82 (3H, t, J=7.7 Hz), 0.85 (3H, d, J=7.0 Hz), 0.89 (3H, d, J=7.0 Hz), 0.95-1.02 (30H, m), 1.18-1.33 (2H, m), 1.39-1.63 (6H, m), 1.42 (3H, s), 1.72-1.98 (4H, m), 1.75 (3H, d, J=1.1 Hz), 2.32 (1H, dd, J=6.2, 13.6 Hz), 2.38 (1.5H, s), 2.40 (1.5H, s), 2.52-2.90 (6H, m), 3.19-3.28 (1H, m), 3.44-3.52 (2H, m), 3.74 (1H, dt, J=3.3, 6.6 Hz), 3.90-3.97 (1H, m), 4.31 (0.5H, s), 4.35 (0.5H, s), 4.71-4.79 (1H, m), 4.93 (1H, d, J=10.6 Hz), 5.41-5.52 (2H, m), 5.82 (1H, d, J=15.4 Hz), 6.11 (1H, d, J=11.0 Hz), 6.50 (1H, dd, J=11.0, 15.4 Hz); ESI-MS M/Z 976 (M+H)$^+$.

(2) (8E,12E,14E)-3,16,21-trihydroxy-6,10,12,16,20-pentamethyl-7-(((1S,4S)-5-methyl-2,5-diazabicyclo[2.2.1]heptan-2-yl)carbonyl)oxy-18,19-epoxytricosa-8,12,14-trien-1-olide (compound 55)

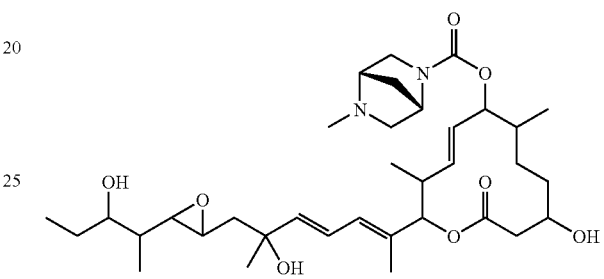

(8E,12E,14E)-6,10,12,16,20-pentamethyl-7-(((1S,4S)-5-methyl-2,5-diazabicyclo[2.2.1]heptan-2-yl)carbonyl)oxy-3,16,21-tris(triethylsiloxy)-18,19-epoxytricosa-8,12,14-trien-11-olide obtained in the Example 55-1 step (12.2 mg, 12.5 μmol) was dissolved in tetrahydrofuran (0.5 mL). Tetrabutylammonium fluoride (1.0M solution in tetrahydrofuran, 0.050 mL, 0.050 mmol) was dropwise to the mixture while stirring at room temperature. The reaction mixture was stirred at room temperature for two hours, and then tetrabutylammonium fluoride (1.0M solution in tetrahydrofuran, 0.012 mL, 0.012 mmol) was further added dropwise to the reaction mixture. The reaction mixture was further stirred for 30 minutes, and then methanol (50 μL) was added to the reaction mixture. This reaction mixture was purified by thin-layer chromatography (Fuji Silysia NH Silica gel plate; chloroform:methanol, 40:1) to give the title compound (7.3 mg) as a colorless oil.

$^1$H-NMR spectrum (CD$_3$OD, 400 MHz) δ (ppm): 0.87 (3H, d, J=6.6 Hz), 0.89 (3H, d, J=7.0 Hz), 0.93 (3H, t, J=7.3 Hz), 0.98 (1.5H, d, J=7.0 Hz), 1.01 (1.5H, d, J=7.0 Hz), 1.19-1.80 (9H, m), 1.33 (3H, s), 1.77 (3H, d, J=1.1 Hz), 1.83-1.97 (3H, m), 2.38-2.40 (1H, m), 2.38 (1.5H, s), 2.40 (1.5H, s), 2.50-2.61 (1H, m), 2.56 (1H, dd, J=3.7, 14.3 Hz), 2.62-2.71 (1H, m), 2.66 (1H, dd, J=2.2, 8.1 Hz), 2.75 (0.5H, dd, J=1.8, 10.3 Hz), 2.81 (0.5H, dd, J=1.8, 10.3 Hz), 2.89 (1H, dt, J=2.2, 5.9 Hz), 3.20 (0.5H, dd, J=1.8, 10.3 Hz), 3.25 (0.5H, dd, J=1.8, 10.3 Hz), 3.44-3.55 (3H, m), 3.74-3.81 (1H, m), 4.31 (0.5H, s), 4.34 (0.5H, s), 4.74-4.82 (1H, m), 5.01 (1H, d, J=10.6 Hz), 5.42-5.53 (2H, m), 5.86 (1H, d, J=15.4 Hz), 6.12 (1H, d, J=11.0 Hz), 6.52 (1H, dd, J=11.0, 15.4 Hz); ESI-MS m/z 633 (M+H)$^+$.

Example 56

(8E,12E,14E)-7-(N-(1-azabicyclo[2.2.2]octan-3-yl)carbamoyloxy)-3,16,21-trihydroxy-6,10,12,16,20-pentamethyl-18,19-epoxytricosa-8,12,14-trien-11-olide (compound 56)

(1) (8E,12E,14E)-7-(N-(1-azabicyclo[2.2.2]octan-3-yl)carbamoyloxy)-6,10,12,16,20-pentamethyl-3,16,21-tris(triethylsiloxy)-18,19-epoxytricosa-8,12,14-trien-11-olide (compound 56-1)

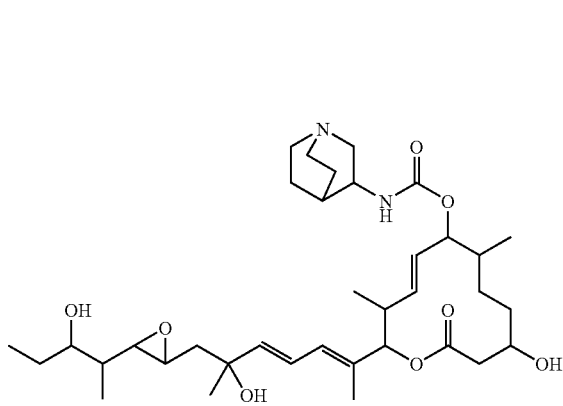

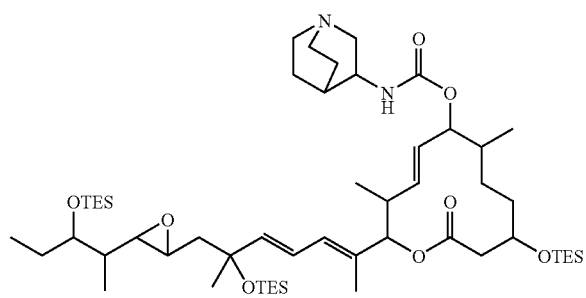

The title compound (colorless oil) was synthesized in the same manner as in Example 23.

$^1$H-NMR spectrum (CD$_3$OD, 400 MHz) δ (ppm): 0.59 (18H, m), 0.82 (3H, t, J=7.3 Hz), 0.85 (3H, d, J=7.0 Hz), 0.88 (3H, d, J=7.0 Hz), 0.95-1.01 (30H, m), 1.18-1.89 (14H, m), 1.42 (3H, s), 1.74 (3H, s), 1.93 (1H, dd, J=4.8, 13.9 Hz), 2.32 (1H, dd, J=6.2, 13.2 Hz), 2.50-2.61 (3H, m), 2.61 (1H, dd, J=2.2, 8.4 Hz), 2.72-2.91 (5H, m), 3.19-3.28 (1H, m), 3.66-3.78 (2H, m), 3.90-3.97 (1H, m), 4.68-4.75 (1H, m), 4.93 (1H, d, J=10.6 Hz), 5.38-5.50 (2H, m), 5.82 (1H, d, J=15.4 Hz), 6.11 (1H, d, J=11.0 Hz), 6.49 (1H, dd, J=11.0, 15.4 Hz); ESI-MS m/z 990 (M+H)$^+$.

(2) (8E,12E,14E)-7-(N-(1-azabicyclo[2.2.2]octan-3-yl)carbamoyloxy)-3,16,21-trihydroxy-6,10,12,16,20-pentamethyl-18,19-epoxytricosa-8,12,14-trien-11-olide (compound 56)

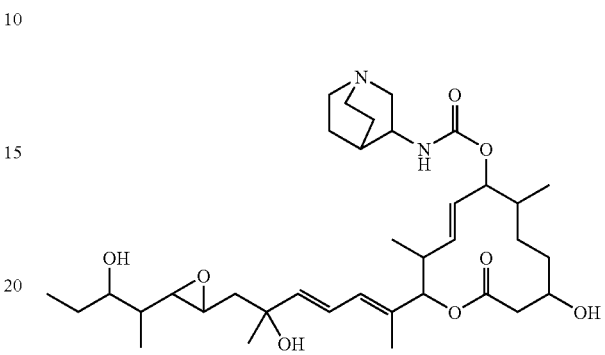

The protective groups for the hydroxyl groups in the compound 56-1 were deprotected in the same manner as in Example 23 to synthesize the title compound (colorless oil).

$^1$H-NMR spectrum (CD$_3$OD, 400 MHz) δ (ppm): 0.87 (3H, d, J=7.0 Hz), 0.89 (3H, d, J=7.3 Hz), 0.93 (3H, t, J=7.3 Hz), 1.01 (3H, d, J=6.6 Hz), 1.18-1.94 (15H, m), 1.33 (3H, s), 1.76 (3H, d, J=0.7 Hz), 2.42 (1H, dd, J=5.5, 14.3 Hz), 2.49-2.60 (3H, m), 2.66 (1H, dd, J=2.2, 8.1 Hz), 2.69-2.92 (5H, m), 3.17-3.25 (1H, m), 3.52 (1H, dt, J=4.4, 8.4 Hz), 3.64-3.70 (1H, m), 3.73-3.81 (1H, m), 4.70-4.79 (1H, m), 5.01 (1H, d, J=10.6 Hz), 5.39-5.51 (2H, m), 5.86 (1H, d, J=15.4 Hz), 6.12 (1H, d, J=11.0 Hz), 6.52 (1H, dd, J=11.0, 15.4 Hz); ESI-MS m/z 647 (M+H)$^+$.

Example 57

(8E,12E,14E)-3,16,21-trihydroxy-6,10,12,16,20-pentamethyl-7-(N-methyl-N-(2-(N'-methylamino)cyclohexyl)carbamoyloxy)-18,19-epoxytricosa-8,12,14-trien-11-olide (compound 57)

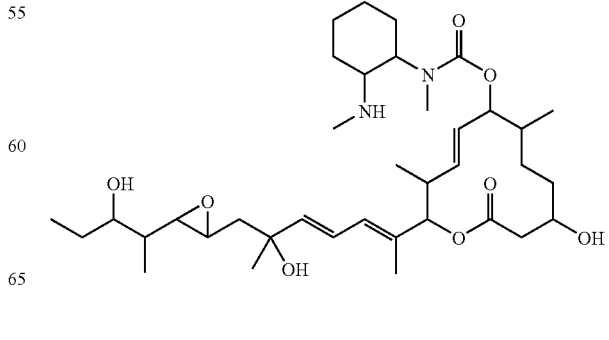

(1) (8E,12E,14E)-6,10,12,16,20-pentamethyl-7-N-methyl-N-(2-(N'-methylamino)cyclohexyl)carbamoyloxy-3,16,21-tris(triethylsiloxy)-18,19-epoxytricosa-8,12,14-trien-11-olide (compound 57-1)

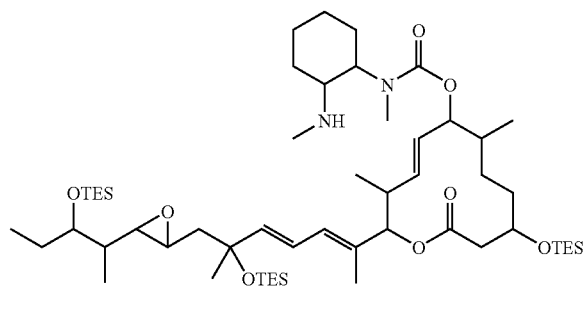

The title compound (colorless oil) was synthesized in the same manner as in Example 23.

$^1$H-NMR spectrum (CD$_3$OD, 400 MHz) δ (ppm): 0.59-0.69 (18H, m), 0.82 (3H, t, J=7.3 Hz), 0.85 (3H, d, J=7.0 Hz), 0.85-0.91 (3H, m), 0.95-1.03 (30H, m), 1.07-1.68 (13H, m), 1.42 (3H, s), 1.71-1.82 (2H, m), 1.75 (3H, s), 1.83-1.94 (1H, m), 1.94 (1H, dd, J=4.8, 13.9 Hz), 2.08-2.16 (1H, m), 2.29-2.36 (1H, m), 2.33 (3H, s), 2.47-2.61 (3H, m), 2.61 (1H, dd, J=2.2, 8.1 Hz), 2.78 (3H, s), 2.85-2.90 (1H, m), 3.72-3.86 (2H, m), 3.91-3.97 (1H, m), 4.78 (1H, dd, J=9.2, 9.2 Hz), 4.93 (1H, d, J=10.6 Hz), 5.41-5.52 (2H, m), 5.82 (1H, d, J=15.0 Hz), 6.11 (1H, d, J=11.0 Hz), 6.50 (1H, dd, J=11.0, 15.0 Hz); ESI-MS m/z 1006 (M+H)$^+$.

(2) (8E,12E,14E)-3,16,21-trihydroxy-6,10,12,16,20-pentamethyl-7-(N-methyl-N-(2-(N'-methylamino)cyclohexyl)carbamoyloxy)-18,19-epoxytricosa-8,12,14-trien-11-olide (compound 57)

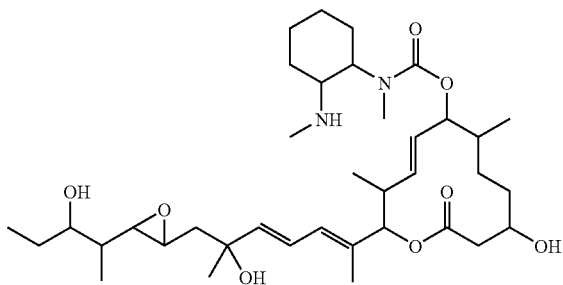

The protective groups for the hydroxyl groups in the compound 57-1 were deprotected in the same manner as in Example 23 to synthesize the title compound (colorless oil).

$^1$H-NMR spectrum (CD$_3$OD, 400 MHz) δ (ppm): 0.86 (3H, brd, J=5.9 Hz), 0.89 (3H, d, J=7.3 Hz), 0.93 (3H, t, J=7.3 Hz), 0.97-1.68 (16H, m), 1.33 (3H, s), 1.71-1.82 (2H, m), 1.76 (3H, d, J=0.7 Hz), 1.86 (1H, dd, J=5.5, 13.9 Hz), 1.90-1.99 (1H, m), 2.07-2.16 (1H, m), 2.32 (3H, s), 2.42 (1H, dd, J=5.5, 13.9 Hz), 2.47-2.63 (3H, m), 2.66 (1H, dd, J=2.2, 8.1 Hz), 2.78 (3H, s), 2.88 (1H, dt, J=2.2, 6.2 Hz), 3.52 (1H, dt, J=4.8, 8.1 Hz), 3.74-3.82 (2H, m), 4.81 (1H, dd, J=9.9, 9.9 Hz), 5.01 (1H, d, J=10.6 Hz), 5.42-5.53 (2H, m), 5.86 (1H, d, J=15.4 Hz), 6.12 (1H, d, J=11.0 Hz), 6.52 (1H, dd, J=11.0, 15.4 Hz); ESI-MS m/z 663 (M+H)$^+$.

Example 58

(8E,12E,14E)-3,16,21-trihydroxy-6,10,12,16,20-pentamethyl-7-(N-(2-(morpholin-4-yl)ethyl)carbamoyloxy)-18,19-epoxytricosa-8,12,14-trien-11-olide (compound 58)

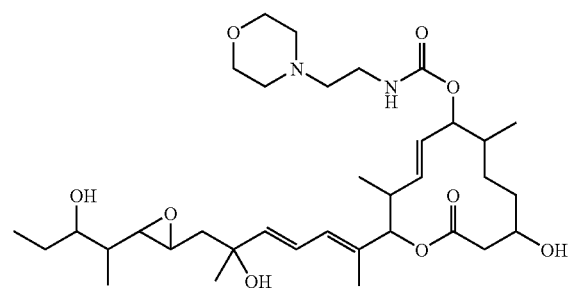

(1) (8E,12E,14E)-6,10,12,16,20-pentamethyl-7-(N-(2-(morpholin-4-yl)ethyl)carbamoyloxy)-3,16,21-tris(triethylsiloxy)-18,19-epoxytricosa-8,12,14-trien-11-olide (compound 58-1)

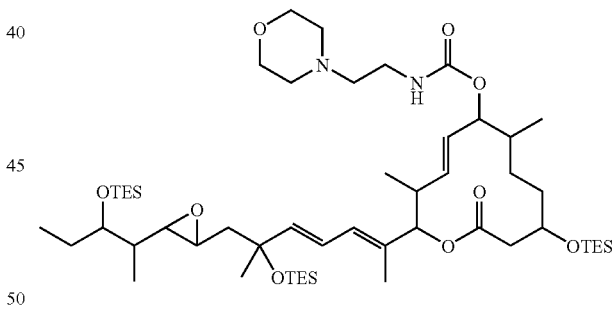

The title compound (colorless oil) was synthesized in the same manner as in Example 23.

$^1$H-NMR spectrum (CD$_3$OD, 400 MHz) δ (ppm): 0.59-0.68 (18H, m), 0.82 (3H, t, J=7.7 Hz), 0.85 (3H, d, J=6.6 Hz), 0.89 (3H, d, J=7.0 Hz), 0.95-1.02 (30H, m), 1.16-1.32 (2H, m), 1.39-1.62 (6H, m), 1.42 (3H, s), 1.75 (3H, s), 1.75-1.87 (1H, m),-1.93 (1H, dd, J=4.8, 13.9 Hz), 2.32 (1H, dd, J=6.2, 13.6 Hz), 2.42-2.61 (8H, m), 2.61 (1H, dd, J=2.2, 8.4 Hz), 2.85-2.90 (1H, m), 3.32 (2H, t, J=6.6 Hz), 3.67 (4H, t, J=4.8 Hz), 3.74 (1H, dt, J=3.3, 6.6H), 3.90-3.98 (1H, m), 4.71 (1H, dd, J=8.8, 8.8 Hz), 4.93 (1H, d, J=10.6 Hz), 5.37-5.50 (2H, m), 5.82 (1H, d, J=15.0 Hz), 6.11 (1H, d, J=11.0 Hz), 6.49 (1H, dd, J=11.0, 15.0 Hz); ESI-MS m/z 994 (M+H)$^+$.

(2) (8E,12E,14E)-3,16,21-trihydroxy-6,10,12,16,20-pentamethyl-7-(N-(2-(morpholin-4-yl)ethyl)carbamoyloxy)-18,19-epoxytricosa-8,12,14-trien-11-olide (compound 58)

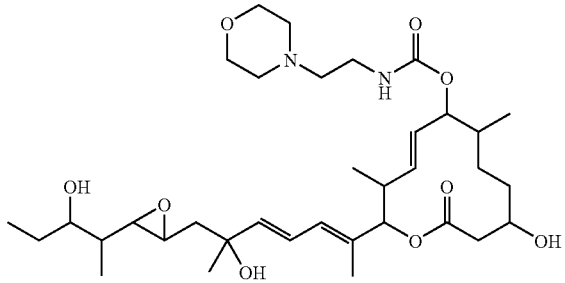

The protective groups for the hydroxyl groups in the compound 58-1 were deprotected in the same manner as in Example 23 to synthesize the title compound (colorless oil).

¹H-NMR spectrum (CD₃OD, 400 MHz) δ (ppm): 0.87 (3H, d, J=7.0 Hz), 0.89 (3H, d, J=7.0 Hz), 0.93 (3H, t, J=7.3 Hz), 1.00 (3H, d, J=7.0 Hz), 1.19-1.64 (7H, m), 1.33 (3H, s), 1.65 (1H, dd, J=5.5, 13.9 Hz), 1.76 (3H, d, J=0.7 Hz), 1.83-1.90 (1H, m), 1.86 (1H, dd, J=5.5, 13.9 Hz), 2.38-2.60 (9H, m), 2.66 (1H, dd, J=2.2, 8.1 Hz), 2.88 (1H, dt, J=2.2, 5.5 Hz), 3.23 (2H, dt, J=1.1, 7.0 Hz), 3.52 (1H, dt, J=4.8, 8.1 Hz), 3.67 (4H, t, J=4.8 Hz), 3.73-3.80 (1H, m), 4.74 (1H, dd, J=9.9, 9.9 Hz), 5.01 (1H, d, J=10.6 Hz), 5.38-5.51 (2H, m), 5.86 (1H, d, J=15.0 Hz), 6.12 (1H, d, J=11.0 Hz), 6.52 (1H, dd, J=11.0, 15.0 Hz); ESI-MS m/z 651 (M+H)⁺.

Example 59

(8E,12E,14E)-3,16,21-trihydroxy-6,10,12,16,20-pentamethyl-7-(N-(2-(piperidin-1-yl)ethyl)carbamoyloxy)-18,19-epoxytricosa-8,12,14-trien-11-olide (compound 59)

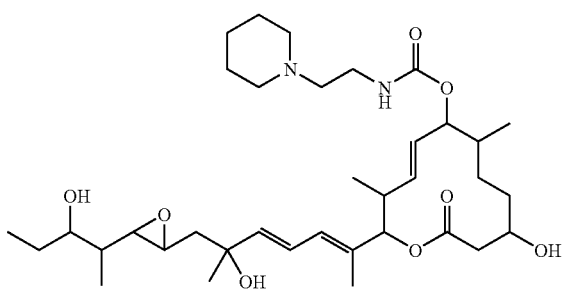

(1) (8E,12E,14E)-6,10,12,16,20-pentamethyl-7-(N-(2-(piperidin-1-yl)ethyl)carbamoyloxy)-13,16,21-tris(triethylsiloxy)-8,19-epoxytricosa-8,12,14-trien-11-olide (compound 59-1)

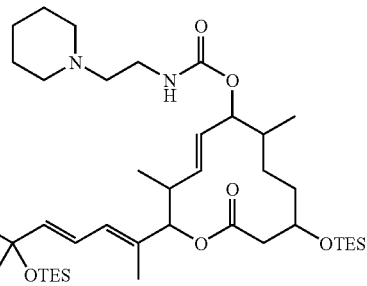

The title compound (colorless oil) was synthesized in the same manner as in Example 23.

¹H-NMR spectrum (CD₃OD, 400 MHz) δ (ppm): 0.59-0.68 (18H, m), 0.82 (3H, t, J=7.7 Hz), 0.85 (3H, d, J=7.0 Hz), 0.89 (3H, d, J=6.6 Hz), 0.95-1.02 (30H, m), 1.16-1.32 (2H, m), 1.39-1.62 (12H, m), 1.42 (3H, s), 1.74 (3H, s), 1.76-1.85 (1H, m), 1.93 (1H, dd, J=4.8, 13.9 Hz), 2.32 (1H, dd, J=6.6, 13.6 Hz), 2.41-2.61 (8H, m), 2.61 (1H, dd, J=2.2, 8.4 Hz), 2.84-2.90 (1H, m), 3.23 (2H, t, J=7.0 Hz), 3.74 (1H, dt, J=3.7, 7.0 Hz), 3.90-3.97 (1H, m), 4.70 (1H, dd, J=9.2, 9.2 Hz), 4.93 (1H, d, J=10.6 Hz), 5.37-5.50 (2H, m), 5.82 (1H, d, J=15.4 Hz), 6.11 (1H, d, J=11.0 Hz), 6.49 (1H, dd, J=11.0, 15.4 Hz); ESI-MS m/z 992 (M+H)⁺.

(2) (8E,12E,14E)-3,16,21-trihydroxy-6,10,12,16,20-pentamethyl-7-(N-(2-(piperidin-1-yl)ethyl)carbamoyloxy)-18,19-epoxytricosa-8,12,14-trien-11-olide (compound 59)

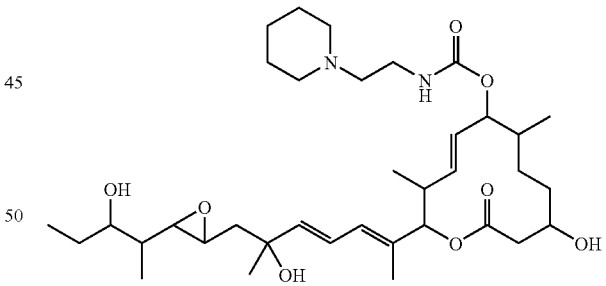

The protective groups for the hydroxyl groups in the compound 59-1 were deprotected in the same manner as in Example 23 to synthesize the title compound (colorless oil).

¹H-NMR spectrum (CD₃OD, 400 MHz) δ (ppm): 0.87 (3H, d, J=7.3 Hz), 0.89 (3H, d, J=7.3 Hz), 0.93 (3H, t, J=7.3 Hz), 0.99 (3H, d, J=7.0 Hz), 1.19-1.68 (14H, m), 1.33 (3H, s), 1.76 (3H, d, J=1.1 Hz), 1.83-1.90 (1H, m), 1.86 (1H, dd, J=5.5, 13.9 Hz), 2.38-2.60 (9H, .m), 2.66 (1H, dd, J=2.6, 8.1 Hz), 2.89 (1H, dt, J=2.6, 5.5 Hz), 3.23 (2H, dd, J=6.2, 7.7 Hz), 3.52 (1H, dt, J=4.8, 8.4 Hz), 3.73-3.80 (1H, m), 4.74 (1H, dd, J=9.9, 9.9 Hz), 5.01 (1H, d, J=10.6 Hz), 5.38-5.51 (2H, m), 5.86 (1H, d, J=15.4 Hz), 6.12 (1H, d, J=11.0 Hz), 6.52 (1H, dd, J=11.0, 15.4 Hz); ESI-MS m/z 649 (M+H)⁺.

Example 60

(8E,12E,14E)-3,16,21-trihydroxy-6,10,12,16,20-pentamethyl-7-(N-(2-(pyrrolidin-1-yl)ethyl)carbamoyloxy)-18,19-epoxytricosa-8,12,14-trien-11-olide (compound 60)

(1) (8E,12E,14E)-6,10,12,16,20-pentamethyl-7-(N-(2-(pyrrolidin-1-yl)ethyl)carbamoyloxy)-3,16,21-tris(triethylsiloxy)-18,19-epoxytricosa-8,12,14-trien-11-olide (compound 60-1)

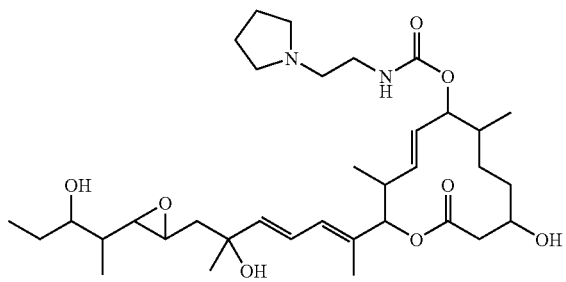

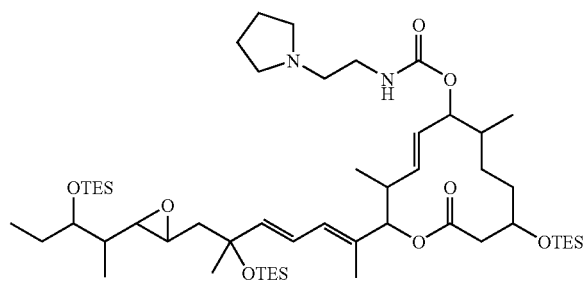

The title compound (colorless oil) was synthesized in the same manner as in Example 23.

$^1$H-NMR spectrum (CD$_3$OD, 400 MHz) δ (ppm): 0.59-0.68 (18H, m), 0.82 (3H, t, J=7.7 Hz), 0.85 (3H, d, J=7.0 Hz), 0.89 (3H, d, J=6.6 Hz), 0.95-1.02 (30H, m), 1.15-1.30 (2H, m), 1.39-1.61 (6H, m), 1.42 (3H, s), 1.75 (3H, d, J=0.7 Hz), 1.75-1.85 (5H, m), 1.93 (1H, dd, J=4.8, 13.9 Hz), 2.32 (1H, dd, J=6.6, 13.6 Hz), 2.50-2.62 (9H, m), 2.85-2.90 (1H, m), 3.24 (2H, t, J=7.0 Hz), 3.74 (1H, dt, J=3.3, 7.0 Hz), 3.90-3.97 (1H, m), 4.71 (1H, dd, J=9.5, 9.5 Hz), 4.93 (1H, d, J=10.6 Hz), 5.37-5.50 (2H, m), 5.82 (1H, d, J=15.4 Hz), 6.11 (1H, d, J=11.0 Hz), 6.49 (1H, dd, J=11.0, 15.4 Hz); ESI-MS m/z 978 (M+H)$^+$.

(2) (8E,12E,14E)-3,16,21-trihydroxy-6,10,12,16,20-pentamethyl-7-(N-(2-(pyrrolidin-1-yl)ethyl)carbamoyloxy)-18,19-epoxytricosa-8,12,14-trien-11-olide (compound 60)

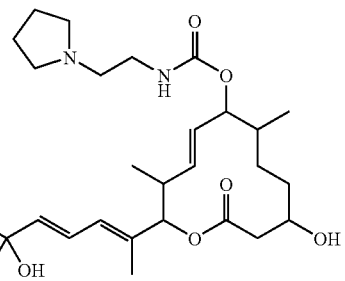

The protective groups for the hydroxyl groups in the compound 60-1 were deprotected in the same manner as in Example 23 to synthesize the title compound (colorless oil).

$^1$H-NMR spectrum (CD$_3$OD, 400 MHz) δ (ppm): 0.87 (3H, d, J=7.7 Hz), 0.89 (3H, d, J=7.3 Hz), 0.93 (3H, t, J=7.3 Hz), 1.00 (3H, d, J=6.6 Hz), 1.20-1.65 (7H, m), 1.33 (3H, s), 1.65 (1H, dd, J=5.5, 13.9 Hz), 1.76 (3H, d, J=1.1 Hz), 1.76-1.90 (5H, m), 1.86 (1H, dd, J=5.5, 13.9 Hz), 2.42 (1H, dd, J=5.1, 13.9 Hz), 2.49-2.63 (8H, m), 2.66 (1H, dd, J=2.2, 8.1 Hz), 2.89 (1H, dt, J=2.2, 5.5 Hz), 3.24 (2H, t, J=7.3 Hz), 3.52 (1H, dt, J=4.8, 8.1 Hz), 3.74-3.81 (1H, m), 4.74 (1H, dd, J=9.9, 9.9 Hz), 5.01 (1H, d, J=10.6 Hz), 5.38-5.51 (2H, m), 5.86 (1H, d, J=15.4 Hz), 6.12 (1H, d, J=11.0 Hz), 6.52 (1H, dd, J=11.0, 15.4 Hz); ESI-MS m/z 635 (M+H)$^+$.

The invention claimed is:

1. A compound represented by the formula (I):

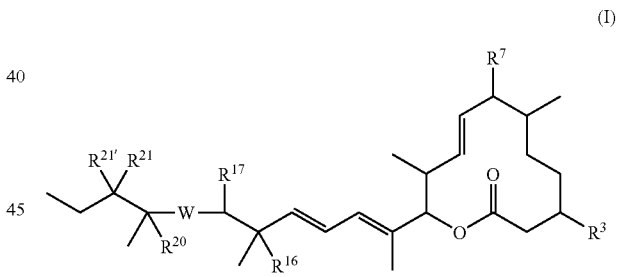

wherein W represents

and R$^3$, R$^7$, R$^{16}$, R$^{17}$, R$^{20}$, R$^{21}$ and R$^{21'}$, the same or different, independently represent
1) a hydrogen atom,
2) a hydroxyl group or oxo group, provided that the oxo group is limited to an oxo group formed by R$^3$ or R$^7$ in combination with a carbon atom to which R$^3$ or R$^7$ is bonded, and an oxo group formed by R$^{21}$ and R$^{21'}$ together in combination with the carbon atom to which R$^{21}$ and R$^{21'}$ are bonded, 3) a $C_1$ to $C_{22}$ alkoxy group which may have a substituent,
4) an unsaturated $C_2$ to $C_{22}$ alkoxy group which may have a substituent,
5) a $C_7$ to $C_{22}$ aralkyloxy group which may have a substituent,
6) a 5-membered to 14-membered heteroaralkyloxy group which may have a substituent,
7) RC(=Y)—O—, wherein Y represents an oxygen atom or sulfur atom, and R represents
   a) a hydrogen atom,
   b) a $C_1$ to $C_{22}$ alkyl group which may have a substituent,
   c) an unsaturated $C_2$ to $C_{22}$ alkyl group which may have a substituent,
   d) a $C_6$ to $C_{14}$ aryl group which may have a substituent,
   e) a 5-membered to 14-membered heteroaryl group which may have a substituent,
   f) a $C_7$ to $C_{22}$ aralkyl group which may have a substituent,
   g) a 5-membered to 14-membered heteroaralkyl group which may have a substituent,
   h) a $C_1$ to $C_{22}$ alkoxy group which may have a substituent,
   i) an unsaturated $C_2$ to $C_{22}$ alkoxy group which may have a substituent,
   j) a $C_6$ to $C_{14}$ aryloxy group which may have a substituent,
   k) a $C_3$ to $C_{14}$ cycloalkyl group which may have a substituent,
   l) a 3-membered to 14-membered non-aromatic heterocyclic group which may have a substituent or
   m) a 5-membered to 14-membered heteroaryloxy group which may have a substituent,
8) $R^{S1}R^{S2}R^{S3}SiO$—, wherein $R^{S1}$, $R^{S2}$ and $R^{S3}$, the same or different, independently represent
   a) a $C_1$ to $C_6$ alkyl group or
   b) a $C_6$ to $C_{14}$ aryl group,
9) a halogen atom,
10) $R^{N1}R^{N2}N-R^{M}$—, wherein $R^{M}$ represents
   a) a single bond,
   b) —CO—O—,
   c) —SO$_2$—O—,
   d) —CS—O— or
   e) —CO—NR$^{N3}$—, wherein $R^{N3}$ represents a hydrogen atom or a $C_1$ to $C_6$ alkyl group which may have a substituent, provided that, the leftmost bond in b) to e) is bonded to the nitrogen atom,
   $R^{N1}$ and $R^{N2}$, the same or different, independently represent
   a) a hydrogen atom,
   b) a $C_1$ to $C_{22}$ alkyl group which may have a substituent,
   c) an unsaturated $C_2$ to $C_{22}$ alkyl group which may have a substituent,
   d) an aliphatic $C_2$ to $C_{22}$ acyl group which may have a substituent,
   e) an aromatic $C_7$ to $C_{15}$ acyl group which may have a substituent,
   f) a $C_6$ to $C_{14}$ aryl group which may have a substituent,
   g) a 5-membered to 14-membered heteroaryl group which may have a substituent,
   h) a $C_7$ to $C_{22}$ aralkyl group which may have a substituent,
   i) a $C_1$ to $C_{22}$ alkylsulfonyl group which may have a substituent,
   j) a $C_6$ to $C_{14}$ arylsulfonyl group which may have a substituent,
   k) a 3-membered to 14-membered non-aromatic heterocyclic group formed by $R^{N1}$ and $R^{N2}$ together in combination with the nitrogen atom to which $R^{N1}$ and $R^{N2}$ are bonded, wherein the 3-membered to 14-membered non-aromatic heterocyclic group may have a substituent,
   l) a 5-membered to 14-membered heteroaralkyl group which may have a substituent,
   m) a $C_3$ to $C_{14}$ cycloalkyl group which may have a substituent or
   n) a 3-membered to 14-membered non-aromatic heterocyclic group which may have a substituent,
11) $R^{N4}SO_2$—O—, wherein $R^{N4}$ represents
   a) a $C_1$ to $C_{22}$ alkyl group which may have a substituent,
   b) a $C_6$ to $C_{14}$ aryl group which may have a substituent,
   c) a $C_1$ to $C_{22}$ alkoxy group which may have a substituent,
   d) an unsaturated $C_2$ to $C_{22}$ alkoxy group which may have a substituent,
   e) a $C_6$ to $C_{14}$ aryloxy group which may have a substituent,
   f) a 5-membered to 14-membered heteroaryloxy group which may have a substituent,
   g) a $C_7$ to $C_{22}$ aralkyloxy group which may have a substituent or
   h) a 5-membered to 14-membered heteroaralkyloxy group which may have a substituent,
12) $(R^{N5}O)_2PO$—O—, wherein $R^{N5}$ represents
   a) a $C_1$ to $C_{22}$ alkyl group which may have a substituent,
   b) an unsaturated $C_2$ to $C_{22}$ alkyl group which may have a substituent,
   c) a $C_6$ to $C_{14}$ aryl group which may have a substituent,
   d) a 5-membered to 14-membered heteroaryl group which may have a substituent,
   e) a $C_7$ to $C_{22}$ aralkyl group which may have a substituent or
   f) a 5-membered to 14-membered heteroaralkyl group which may have a substituent,
13) $(R^{N1}R^{N2}N)_2PO$—O—, wherein $R^{N1}$ and $R^{N2}$ are the same as defined above or
14) $(R^{N1}R^{N2}N)(R^{N5}O)PO$—O—, wherein $R^{N1}$, $R^{N2}$ and $R^{N5}$ are the same as defined above; or a pharmacologically acceptable salt thereof.

2. The compound according to claim 1 represented by the formula (I-a):

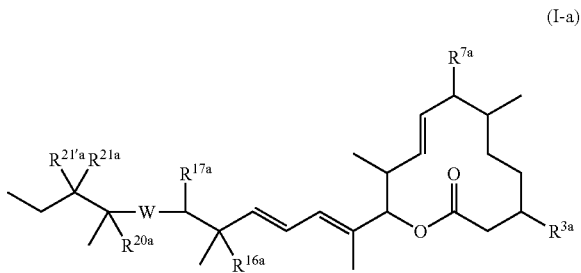

(I-a)

wherein W is the same as defined above, and $R^{3a}$, $R^{7a}$, $R^{16a}$, $R^{17a}$, $R^{20a}$, $R^{21a}$ and $R^{21a'}$, the same or different, independently represent
1) a hydrogen atom,
2) a hydroxyl group or oxo group, provided that the oxo group is limited to an oxo group formed by $R^{3a}$ or $R^{7a}$

125 in combination with the carbon atom to which $R^{3a}$ or $R^{7a}$ is bonded, and an oxo group formed by $R^{21a}$ and $R^{21a'}$ together in combination with a carbon atom to which $R^{21a}$ and $R^{21a'}$ are bonded, 3) a $C_1$ to $C_{22}$ alkoxy group which may have a substituent,
4) $R^aC(=Y^a)$—O—, wherein $Y^a$ represents an oxygen atom or sulfur atom, and $R^a$ represents
   a) a hydrogen atom,
   b) a $C_1$ to $C_{22}$ alkyl group which may have a substituent,
   c) an unsaturated $C_2$ to $C_{22}$ alkyl group which may have a substituent,
   d) a $C_6$ to $C_{14}$ aryl group which may have a substituent,
   e) a 5-membered to 14-membered heteroaryl group which may have a substituent,
   f) a $C_7$ to $C_{22}$ aralkyl group which may have a substituent,
   g) a 5-membered to 14-membered heteroaralkyl group which may have a substituent,
   h) a $C_1$ to $C_{22}$ alkoxy group which may have a substituent,
   i) an unsaturated $C_2$ to $C_{22}$ alkoxy group which may have a substituent,
   j) a $C_6$ to $C_{14}$ aryloxy group which may have a substituent,
   k) a $C_3$ to $C_{14}$ cycloalkyl group which may have a substituent,
   l) a 3-membered to 14-membered non-aromatic heterocyclic group which may have a substituent or
   m) a 5-membered to 14-membered heteroaryloxy group which may have a substituent,
5) $R^{aS1}R^{aS2}R^{aS3}SiO$—, wherein $R^{aS1}$, $R^{aS2}$ and $R^{aS3}$, the same or different, independently represent
   a) a $C_1$ to $C_6$ alkyl group or
   b) a $C_6$ to $C_{14}$ aryl group or
6) $R^{aN1}R^{aN2}N$—$R^{aM}$—, wherein $R^{aM}$ represents
   a) —CO—O— or
   b) —CS—O—, provided that, in the leftmost bond a) or b) is bonded to the nitrogen atom, and
   $R^{aN1}$ and $R^{aN2}$, the same or different, independently represent
   a) a hydrogen atom,
   b) a $C_1$ to $C_{22}$ alkyl group which may have a substituent,
   c) an unsaturated $C_2$ to $C_{22}$ alkyl group which may have a substituent,
   d) an aliphatic $C_2$ to $C_{22}$ acyl group which may have a substituent,
   e) an aromatic $C_7$ to $C_{15}$ acyl group which may have a substituent,
   f) a $C_6$ to $C_{14}$ aryl group which may have a substituent,
   g) a 5-membered to 14-membered heteroaryl group which may have a substituent,
   h) a $C_7$ to $C_{22}$ aralkyl group which may have a substituent,
   i) a $C_1$ to $C_{22}$ alkylsulfonyl group which may have a substituent,
   j) a $C_6$ to $C_{14}$ arylsulfonyl group which may have a substituent,
   k) a 3-membered to 14-membered non-aromatic heterocyclic group formed by $R^{aN1}$ and $R^{aN2}$ together in combination with the nitrogen atom to which $R^{aN1}$ and $R^{aN2}$ are bonded, wherein the 3-membered to 14-membered non-aromatic heterocyclic group may have a substituent,
   l) a 5-membered to 14-membered heteroaralkyl group which may have a substituent,

126 m) a $C_3$ to $C_{14}$ cycloalkyl group which may have a substituent or
   n) a 3-membered to 14-membered non-aromatic heterocyclic group which may have a substituent; or a pharmacologically acceptable salt thereof.

3. The compound according to claim 1 represented by the formula (I-b):

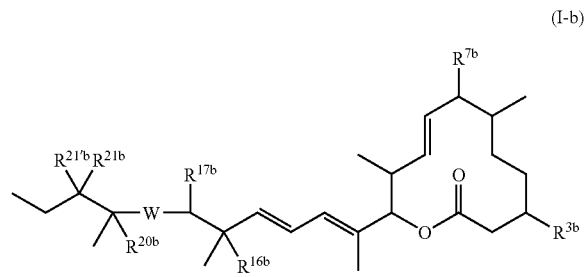

wherein W is the same as defined above, and $R^{3b}$, $R^{7b}$, $R^{16b}$, $R^{17b}$, $R^{20b}$, $R^{21b}$ and $R^{21'b}$, the same or different, independently represent
   1) a hydrogen atom,
   2) a hydroxyl group or oxo group, provided that the oxo group is limited to an oxo group formed by $R^{3b}$ or $R^{7b}$ in combination with the carbon atom to which $R^{3b}$ or $R^{7b}$ is bonded, and an oxo group formed by $R^{21b}$ and $R^{21b'}$ together in combination with the carbon atom to which $R^{21b}$ and $R^{21b'}$ are bonded,
   3) a $C_1$ to $C_{22}$ alkoxy group which may have a substituent,
   4) $R^bC(=O)$—O—, wherein $R^b$ represents
   a) a $C_1$ to $C_{22}$ alkyl group which may have a substituent,
   b) an unsaturated $C_2$ to $C_{22}$ alkyl group which may have a substituent,
   c) a $C_7$ to $C_{22}$ aralkyl group which may have a substituent,
   d) a 5-membered to 14-membered heteroaralkyl group which may have a substituent,
   e) a $C_6$ to $C_{14}$ aryloxy group which may have a substituent,
   f) a $C_3$ to $C_{14}$ cycloalkyl group which may have a substituent or
   g) a 3-membered to 14-membered non-aromatic heterocyclic group which may have a substituent,
5) $R^{bS1}R^{bS2}R^{bS3}SiO$—, wherein $R^{bS1}$, $R^{bS2}$ and $R^{bS3}$, the same or different, independently represent
   a) a $C_1$ to $C_6$ alkyl group or
   b) a $C_6$ to $C_{14}$ aryl group or
6) $R^{bN1}R^{bN2}N$—$R^{bM}$—, wherein $R^{bM}$ represents
   a) —CO—O— or
   b) —CS—O—, provided that, the leftmost bond in a) or b) is bonded to the nitrogen atom, and
   $R^{bN1}$ and $R^{bN2}$, the same or different, independently represent
   a) a hydrogen atom,
   b) a $C_1$ to $C_{22}$ alkyl group which may have a substituent,
   c) a 3-membered to 14-membered non-aromatic heterocyclic group formed by $R^{bN1}$ and $R^{bN2}$ together in combination with the nitrogen atom to which $R^{bN1}$ and $R^{bN2}$ are bonded, wherein the 3-membered to 14-membered non-aromatic heterocyclic group may have a substituent, d) a $C_3$ to $C_{14}$ cycloalkyl group which may have a substituent or e) a 3-membered to 14-membered non-aromatic heterocyclic group which may have a substituent; or a pharmacologically acceptable salt thereof.

4. The compound according to claim 1 represented by the formula (I-c):

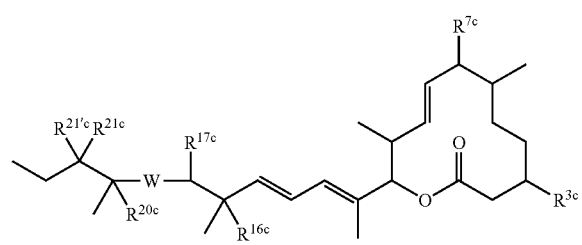

(I-c)

wherein W is the same as defined above, and $R^{3c}$, $R^{7c}$, $R^{16c}$, $R^{17c}$, $R^{20c}$, $R^{21c}$ and $R^{21'c}$, the same or different, independently represent 1) a hydrogen atom, 2) a hydroxyl group or oxo group, provided that the oxo group is limited to an oxo group formed by $R^{3c}$ or $R^{7c}$ in combination with the carbon atom to which $R^{3c}$ or $R^{7c}$ is bonded, and an oxo group formed by $R^{21c}$ and $R^{21c'}$ together in combination with the carbon atom to which $R^{21c}$ and $R^{21c'}$ are bonded, 3) $R^{c}C(=O)-O-$, wherein $R^{c}$ represents a $C_1$ to $C_{22}$ alkyl group which may have a substituent, 4) $R^{cS1}R^{cS2}R^{cS3}SiO-$, wherein $R^{cS1}$, $R^{cS2}$ and $R^{cS3}$, the same or different, independently represent a) a $C_1$ to $C_6$ alkyl group or b) a $C_6$ to $C_{14}$ aryl group or 5) $R^{cN1}R^{cN2}N-R^{cM}-$, wherein $R^{cM}$ represents $-CO-O-$, provided that the leftmost bond is bonded to the nitrogen atom, and $R^{cN1}$ and $R^{cN2}$, the same or different, independently represent a) a hydrogen atom, b) a $C_1$ to $C_{22}$ alkyl group which may have a substituent, c) a 3-membered to 14-membered non-aromatic heterocyclic group formed by $R^{cN1}$ and $R^{cN2}$ together in combination with the nitrogen atom to which $R^{cN1}$ and $R^{cN2}$ are bonded, wherein the 3-membered to 14-membered non-aromatic heterocyclic group may have a substituent, d) a $C_3$ to $C_{14}$ cycloalkyl group which may have a substituent or e) a 3-membered to 14-membered non-aromatic heterocyclic group which may have a substituent; or a pharmacologically acceptable salt thereof.

5. The compound according to claim 1 represented by the formula (I-d):

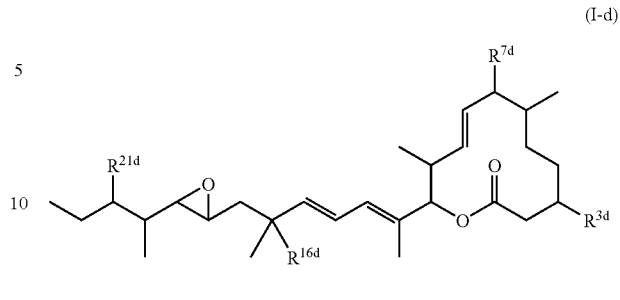

(I-d)

wherein $R^{3d}$ and $R^{16d}$, the same or different, independently represent 1) a hydroxyl group, 2) a $C_1$ to $C_{22}$ alkoxy group which may have a substituent, 3) an unsaturated $C_2$ to $C_{22}$ alkoxy group which may have a substituent, 4) a $C_7$ to $C_{22}$ aralkyloxy group which may have a substituent, 5) $R^{d}C(=O)-O-$, wherein $R^{d}$ represents a) a hydrogen atom, b) a $C_1$ to $C_{22}$ alkyl group which may have a substituent, c) an unsaturated $C_2$ to $C_{22}$ alkyl group which may have a substituent, d) a $C_6$ to $C_{14}$ aryl group which may have a substituent, e) a 5-membered to 14-membered heteroaryl group which may have a substituent, f) a $C_7$ to $C_{22}$ aralkyl group which may have a substituent, g) a 5-membered to 14-membered heteroaralkyl group which may have a substituent, h) a $C_1$ to $C_{22}$ alkoxy group which may have a substituent, i) an unsaturated $C_2$ to $C_{22}$ alkoxy group which may have a substituent, j) a $C_6$ to $C_{14}$ aryloxy group which may have a substituent or k) a 5-membered to 14-membered heteroaryloxy group which may have a substituent or 6) $R^{dN1}R^{dN2}N-CO-O-$, wherein $R^{dN1}$ and $R^{dN2}$, the same or different, independently represent a) a hydrogen atom, b) a $C_1$ to $C_{22}$ alkyl group which may have a substituent, c) an unsaturated $C_2$ to $C_{22}$ alkyl group which may have a substituent, d) a $C_6$ to $C_{14}$ aryl group which may have a substituent, e) a 5-membered to 14-membered heteroaryl group which may have a substituent, f) a $C_7$ to $C_{22}$ aralkyl group which may have a substituent, g) a 5-membered to 14-membered heteroaralkyl group which may have a substituent, h) a $C_3$ to $C_{14}$ cycloalkyl group which may have a substituent, i) a 3-membered to 14-membered non-aromatic heterocyclic group which may have a substituent or j) a 3-membered to 14-membered non-aromatic heterocyclic group formed by $R^{dN1}$ and $R^{dN2}$ together in combination with the nitrogen atom to which $R^{dN1}$ and $R^{dN2}$ are bonded, wherein the 3-membered to 14-membered non-aromatic heterocyclic group may have a substituent, and $R^{7d}$ and $R^{21d}$, the same or different, independently represent 1) a hydroxyl group,
2) a $C_1$ to $C_{22}$ alkoxy group which may have a substituent,
3) an unsaturated $C_2$ to $C_{22}$ alkoxy group which may have a substituent,
4) a $C_7$ to $C_{22}$ aralkyloxy group which may have a substituent,
5) $R^d C(=O)-O-$, wherein $R^d$ is the same as defined above,
6) $R^{dN1}R^{dN2}N-CO-O-$, wherein $R^{dN1}$ and $R^{dN2}$ are the same as defined above,
7) $R^{dN1}R^{dN2}N-SO_2-O-$, wherein $R^{dN1}$ and $R^{dN2}$ are the same as defined above,
8) $R^{dN1}R^{dN2}N-CS-O-$, wherein $R^{dN1}$ and $R^{dN2}$ are the same as defined above,
9) $R^{dN4}-SO_2-O-$, wherein $R^{dN4}$ represents
   a) a $C_1$ to $C_{22}$ alkyl group which may have a substituent,
   b) a $C_6$ to $C_{14}$ aryl group which may have a substituent,
   c) a $C_1$ to $C_{22}$ alkoxy group which may have a substituent,
   d) an unsaturated $C_2$ to $C_{22}$ alkoxy group which may have a substituent,
   e) a $C_6$ to $C_{14}$ aryloxy group which may have a substituent,
   f) a 5-membered to 14-membered heteroaryloxy group which may have a substituent,
   g) a $C_7$ to $C_{22}$ aralkyloxy group which may have a substituent or
   h) a 5-membered to 14-membered heteroaralkyloxy group which may have a substituent,
10) $(R^{dN5}O)_2PO-O-$, wherein $R^{dN5}$ represents
    a) a $C_1$ to $C_{22}$ alkyl group which may have a substituent,
    b) an unsaturated $C_2$ to $C_{22}$ alkyl group which may have a substituent,
    c) a $C_6$ to $C_{14}$ aryl group which may have a substituent,
    d) a 5-membered to 14-membered heteroaryl group which may have a substituent,
    e) a $C_7$ to $C_{22}$ aralkyl group which may have a substituent or
    f) a 5-membered to 14-membered heteroaralkyl group which may have a substituent,
11) $(R^{dN1}R^{dN2}N)_2PO-O-$, wherein $R^{dN1}$ and $R^{dN2}$ are the same as defined above or
12) $(R^{dN1}R^{dN2}N)(R^{dN5}O)PO-O-$, wherein $R^{dN1}$, $R^{dN2}$ and $R^{dN5}$ are the same as defined above; or a pharmacologically acceptable salt thereof.

6. The compound according to claim 1, wherein $R^7$ and/or $R^{21}$ are independently represented by $RC(=Y)-O-$, wherein Y and R are the same as defined above or $R^{N1}R^{N2}N-R^{M'}-$, wherein $R^{M'}$ represents
   a) $-CO-O-$ or
   b) $-CS-O-$, provided that, the leftmost bond in a) or b) is bonded to the nitrogen atom, and
   $R^{N1}$ and $R^{N2}$ are the same as defined above; or a pharmacologically acceptable salt thereof.

7. The compound according to claim 5 represented by the formula (I-e):

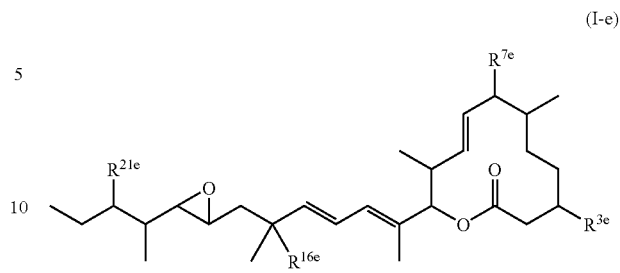

(I-e)

wherein $R^{3e}$, $R^{16e}$ and $R^{21e}$, the same or different, independently represent 1) a hydroxyl group,
2) a $C_1$ to $C_{22}$ alkoxy group which may have a substituent,
3) an unsaturated $C_2$ to $C_{22}$ alkoxy group which may have a substituent,
4) a $C_7$ to $C_{22}$ aralkyloxy group which may have a substituent,
5) an aliphatic $C_2$ to $C_6$ acyl group which may have a substituent or
6) $R^{eN1}R^{eN2}N-CO-O-$, wherein $R^{eN1}$ and $R^{eN2}$ independently represent
   a) a hydrogen atom or
   b) a $C_1$ to $C_6$ alkyl group which may have a substituent, and $R^{7e}$ represents $R^e-C(=Y^e)-O-$, wherein $Y^e$ represents an oxygen atom or sulfur atom, and $R^e$ represents
   a) a hydrogen atom,
   b) a $C_1$ to $C_{22}$ alkyl group which may have a substituent,
   c) a $C_6$ to $C_{14}$ aryl group which may have a substituent,
   d) a 5-membered to 14-membered heteroaryl group which may have a substituent,
   e) a $C_7$ to $C_{10}$ aralkyl group which may have a substituent,
   f) a 5-membered to 14-membered heteroaralkyl group which may have a substituent,
   g) a 3-membered to 14-membered non-aromatic heterocyclic group which may have a substituent
   h) a group of the formula (III):

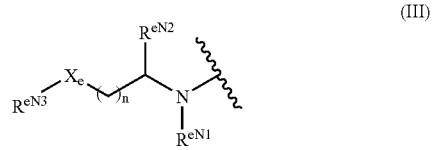

(III)

wherein A) n represents an integer of 0 to 4,
$X_e$ represents
   i) $-CHR^{eN4}-$,
   ii) $-NR^{eN5}-$,
   iii) $-O-$,
   iv) $-S-$,
   v) $-SO-$ or
   vi) $-SO_2-$,
$R^{eN1}$ represents
   i) a hydrogen atom or
   ii) a $C_1$ to $C_6$ alkyl group which may have a substituent,
$R^{eN2}$ represents
   i) a hydrogen atom or
   ii) a $C_1$ to $C_6$ alkyl group which may have a substituent, $R^{eN3}$ and $R^{eN4}$, the same or different, independently represent
  i) a hydrogen atom,
  ii) a $C_1$ to $C_6$ alkyl group which may have a substituent,
  iii) an unsaturated $C_2$ to $C_{10}$ alkyl group which may have a substituent,
  iv) a $C_6$ to $C_{14}$ aryl group which may have a substituent,
  v) a 5-membered to 14-membered heteroaryl group which may have a substituent,
  vi) a $C_7$ to $C_{10}$ aralkyl group which may have a substituent,
  vii) a $C_3$ to $C_8$ cycloalkyl group which may have a substituent,
  viii) a $C_4$ to $C_9$ cycloalkylalkyl group which may have a substituent,
  ix) a 5-membered to 14-membered heteroaralkyl group which may have a substituent,
  x) a 5-membered to 14-membered non-aromatic heterocyclic group which may have a substituent,
  xi) —$NR^{eN6}R^{eN7}$, wherein $R^{eN6}$ and $R^{eN7}$, the same or different, independently represent a hydrogen atom or a $C_1$ to $C_6$ alkyl group which may have a substituent or
  xii) a 5-membered to 14-membered non-aromatic heterocyclic group formed by $R^{eN3}$ and $R^{eN4}$ together in combination with the carbon atom to which $R^{eN3}$ and $R^{eN4}$ are bonded, wherein the 5-membered to 14-membered non-aromatic heterocyclic group may have a substituent, and
$R^{eN5}$ represents
  i) a hydrogen atom,
  ii) a $C_1$ to $C_6$ alkyl group which may have a substituent,
  iii) an unsaturated $C_2$ to $C_{10}$ alkyl group which may have a substituent,
  iv) a $C_6$ to $C_{14}$ aryl group which may have a substituent,
  v) a 5-membered to 14-membered heteroaryl group which may have a substituent,
  vi) a $C_7$ to $C_{10}$ aralkyl group which may have a substituent,
  vii) a $C_3$ to $C_8$ cycloalkyl group which may have a substituent,
  viii) a $C_4$ to $C_9$ cycloalkylalkyl group which may have a substituent,
  ix) a 5-membered to 14-membered heteroaralkyl group which may have a substituent,
  x) a 5-membered to 14-membered non-aromatic heterocyclic group which may have a substituent or
  xi) a 5-membered to 14-membered non-aromatic heterocyclic group formed by $R^{eN3}$ and $R^{eN5}$ together in combination with the nitrogen atom to which $R^{eN3}$ and $R^{eN5}$ are bonded, wherein the 5-membered to 14-membered non-aromatic heterocyclic group may have a substituent,
B)
  $X_e$, n, $R^{eN3}$, $R^{eN4}$ and $R^{eN5}$ independently represent the same group as defined above, and $R^{eN1}$ and $R^{eN2}$ independently represent a 5-membered to 14-membered non-aromatic heterocyclic group formed by $R^{eN1}$ and $R^{eN2}$ together, wherein the 5-membered to 14-membered non-aromatic heterocyclic group may have a substituent,
C)
  $X_e$, n, $R^{eN2}$, $R^{eN4}$ and $R^{eN5}$ independently represent the same group as defined above, and $R^{eN1}$ and $R^{eN3}$ independently represent a 5-membered to 14-membered non-aromatic heterocyclic group formed by $R^{eN1}$ and $R^{eN3}$ together, wherein the 5-membered to 14-membered non-aromatic heterocyclic group may have a substituent or
D)
  $X_e$, n, $R^{eN1}$, $R^{eN4}$ and $R^{eN5}$ independently represent the same group as defined above, and $R^{eN2}$ and $R^{eN3}$ independently represent a 5-membered to 14-membered non-aromatic heterocyclic group formed by $R^{eN2}$ and $R^{eN3}$ together, wherein the 5-membered to 14-membered non-aromatic heterocyclic group may have a substituent or
  i) a group of the formula (IV):

(IV)

wherein $R^{eN8}$ and $R^{eN9}$, the same or different, independently represent
  i) a hydrogen atom,
  ii) a $C_1$ to $C_6$ alkyl group which may have a substituent,
  iii) a $C_6$ to $C_{14}$ aryl group which may have a substituent,
  iv) a 5-membered to 14-membered heteroaryl group which may have a substituent,
  v) a $C_7$ to $C_{10}$ aralkyl group which may have a substituent or
  vi) a 5-membered to 14-membered heteroaralkyl group which may have a substituent; or a pharmacologically acceptable salt thereof.

8. The compound according to claim 5, wherein $R^{7e}$ and/or $R^{21e}$ are independently represented by $R^{e1}C(=Y^{e1})$—O—, wherein $Y^{e1}$ represents an oxygen atom or sulfur atom, and $R^{e1}$ represents
  1) a hydrogen atom,
  2) a $C_1$ to $C_6$ alkyl group which may have a substituent,
  3) a $C_6$ to $C_{10}$ aryl group which may have a substituent,
  4) a 5-membered to 14-membered heteroaryl group which may have a substituent,
  5) a $C_7$ to $C_{10}$ aralkyl group which may have a substituent or
  6) a 5-membered to 14-membered heteroaralkyl group which may have a substituent; or a pharmacologically acceptable salt thereof.

9. The compound according to claim 5, wherein $R^{7e}$ and/or $R^{21e}$ are independently represented by $R^{e2}C(=Y^{e2})$—O—, wherein $Y^{e2}$ represents an oxygen atom or sulfur atom, and $R^{e2}$ represents a group of the formula (III'):

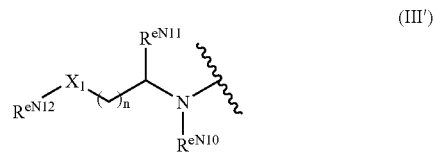

(III')

wherein A) n represents an integer of 0 to 4,
  $X_1$ represents
    1) —$CHR^{eN13}$—,
    2) —$NR^{eN14}$—,
    3) —O—,
    4) —S—, 5) —SO— or
6) —SO$_2$—, R$^{eN10}$ and R$^{eN11}$, the same or different, independently represent
1) a hydrogen atom or
2) a C$_1$ to C$_6$ alkyl group which may have a substituent, R$^{eN12}$ and R$^{eN13}$, the same or different, independently represent
1) a hydrogen atom,
2) a C$_1$ to C$_6$ alkyl group which may have a substituent,
3) an unsaturated C$_2$ to C$_{10}$ alkyl group which may have a substituent,
4) a C$_6$ to C$_{14}$ aryl group which may have a substituent,
5) a 5-membered to 14-membered heteroaryl group which may have a substituent,
6) a C$_7$ to C$_{10}$ aralkyl group which may have a substituent,
7) a C$_3$ to C$_8$ cycloalkyl group which may have a substituent,
8) a C$_4$ to C$_9$ cycloalkylalkyl group which may have a substituent,
9) a 5-membered to 14-membered heteroaralkyl group which may have a substituent,
10) a 5-membered to 14-membered non-aromatic heterocyclic group which may have a substituent,
11) —NR$^{eN15}$R$^{eN16}$, wherein R$^{eN15}$ and R$^{eN16}$, the same or different, independently represent a hydrogen atom or a C$_1$ to C$_6$ alkyl group which may have a substituent, or
12) a 5-membered to 14-membered non-aromatic heterocyclic group formed by R$^{eN12}$ and R$^{eN13}$ together, wherein the 5-membered to 14-membered non-aromatic heterocyclic group may have a substituent, and R$^{eN14}$ represents
1) a hydrogen atom,
2) a C$_1$ to C$_6$ alkyl group which may have a substituent,
3) an unsaturated C$_2$ to C$_{10}$ alkyl group which may have a substituent,
4) a C$_6$ to C$_{14}$ aryl group which may have a substituent,
5) a 5-membered to 14-membered heteroaryl group which may have a substituent,
6) a C$_7$ to C$_{10}$ aralkyl group which may have a substituent,
7) a C$_3$ to C$_8$ cycloalkyl group which may have a substituent,
8) a C$_4$ to C$_9$ cycloalkylalkyl group which may have a substituent,
9) a 5-membered to 14-membered heteroaralkyl group which may have a substituent,
10) a 5-membered to 14-membered non-aromatic heterocyclic group which may have a substituent,
11) a 5-membered to 14-membered non-aromatic heterocyclic group formed together by the nitrogen atom to which R$^{eN14}$ is bonded, and one substituent selected from the group consisting of R$^{eN10}$, R$^{eN11}$ and R$^{eN12}$, wherein the 5-membered to 14-membered non-aromatic heterocyclic group may have a substituent or
12) a 5-membered to 14-membered non-aromatic heterocyclic group formed together by the nitrogen atom to which R$^{eN14}$ is bonded, and two substituents selected from the group consisting of R$^{eN10}$, R$^{eN11}$ and R$^{eN12}$, wherein the 5-membered to 14-membered non-aromatic heterocyclic group may have a substituent or B)
n, X$_1$, R$^{eN11}$, R$^{eN13}$ and R$^{eN14}$ are the same as defined above, and R$^{eN10}$ and R$^{eN12}$ together form a 5-membered to 14-membered non-aromatic heterocyclic group, wherein the 5-membered to 14-membered non-aromatic heterocyclic group may have a substituent; or a pharmacologically acceptable salt thereof.

10. The compound according to claim 5, wherein X$_1$ represents —NR$^{eN14}$—, wherein NR$^{eN14}$ is the same as defined above; or a pharmacologically acceptable salt thereof.

11. The compound according to claim 5, wherein R$^{7e}$ and/or R$^{21e}$ independently represent R$^{e3}$C(=Y$^{e3}$)—O—, wherein Y$^{e3}$ represents an oxygen atom or sulfur atom, and R$^{e3}$ represents a group of the formula (V):

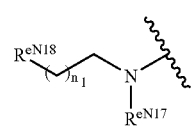

(V)

wherein n$_1$ represents an integer of 0 to 6,
R$^{eN17}$ represents
1) a hydrogen atom or
2) a C$_1$ to C$_6$ alkyl group which may have a substituent, and R$^{eN18}$ represents
1) a hydrogen atom,
2) an amino group which may have a substituent,
3) a pyridyl group which may have a substituent,
4) a pyrrolidin-1-yl group which may have a substituent,
5) a piperidin-1-yl group which may have a substituent,
6) a morpholin-4-yl group which may have a substituent or
7) a piperazin-1-yl group which may have a substituent; or a pharmacologically acceptable salt thereof.

12. The compound according to claim 5, wherein R$^{7e}$ and/or R$^{21e}$ independently represent R$^{e4}$CO—O—, wherein R$^{e4}$ represents a group of the formula (VI):

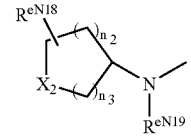

(VI)

wherein n$_2$ and n$_3$, the same or different, independently represent an integer of 0 to 4,
X$_2$ represents
1) —CHR$^{eN21}$—,
2) —NR$^{eN22}$—,
3) —O—,
4) —S—,
5) —SO— or
6) —SO$_2$—, R$^{eN19}$ represents
1) a hydrogen atom or
2) a C$_1$ to C$_6$ alkyl group which may have a substituent, $R^{eN20}$ represents
1) a hydrogen atom,
2) a $C_1$ to $C_6$ alkyl group which may have a substituent,
3) a $C_6$ to $C_{14}$ aryl group which may have a substituent or
4) a $C_7$ to $C_{10}$ aralkyl group which may have a substituent, $R^{eN21}$ represents
1) a hydrogen atom,
2) a $C_1$ to $C_6$ alkyl group which may have a substituent,
3) an unsaturated $C_2$ to $C_{10}$ alkyl group which may have a substituent,
4) a $C_6$ to $C_{14}$ aryl group which may have a substituent,
5) a 5-membered to 14-membered heteroaryl group which may have a substituent,
6) a $C_7$ to $C_{10}$ aralkyl group which may have a substituent,
7) a $C_3$ to $C_8$ cycloalkyl group which may have a substituent,
8) a $C_4$ to $C_9$ cycloalkylalkyl group which may have a substituent,
9) a 5-membered to 14-membered heteroaralkyl group which may have a substituent,
10) —$NR^{eN23}R^{eN24}$, wherein $R^{eN23}$ and $R^{eN24}$, the same or different, independently represent a hydrogen atom or a $C_1$ to $C_6$ alkyl group which may have a substituent or
11) a 5-membered to 14-membered non-aromatic heterocyclic group which may have a substituent, and $R^{eN22}$ represents
1) a hydrogen atom,
2) a $C_1$ to $C_6$ alkyl group which may have a substituent,
3) an unsaturated $C_2$ to $C_{10}$ alkyl group which may have a substituent,
4) a $C_6$ to $C_{14}$ aryl group which may have a substituent,
5) a 5-membered to 14-membered heteroaryl group which may have a substituent,
6) a $C_7$ to $C_{10}$ aralkyl group which may have a substituent,
7) a $C_3$ to $C_8$ cycloalkyl group which may have a substituent,
8) a $C_4$ to $C_9$ cycloalkylalkyl group which may have a substituent,
9) a 5-membered to 14-membered heteroaralkyl group which may have a substituent or
10) a 5-membered to 14-membered non-aromatic heterocyclic group which may have a substituent; or a pharmacologically acceptable salt thereof.

13. The compound according to claim 5, wherein $R^{7e}$ and/or $R^{21e}$ independently represent $R^{e5}CO$—O—, wherein $R^{e5}$ represents a group of the formula (VII):

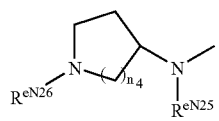

(VII)

wherein $n_4$ represents 1 or 2,
$R^{eN25}$ represents
1) a hydrogen atom or
2) a $C_1$ to $C_6$ alkyl group which may have a substituent, and $R^{eN26}$ represents
1) a hydrogen atom or
2) a $C_1$ to $C_6$ alkyl group which may have a substituent; or a pharmacologically acceptable salt thereof.

14. The compound according to claim 5, wherein $R^{7e}$ and/or $R^{21e}$ independently represent $R^{e6}CO$—O—, wherein $R^{e6}$ represents a group of the formula (VIII):

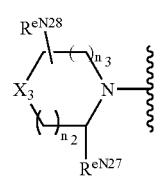

(VIII)

wherein $n_2$ and $n_3$, the same or different, independently represent an integer of 0 to 4,
$X_3$ represents
1) —$CHR^{eN29}$—,
2) —$NR^{eN30}$—,
3) —O—,
4) —S—,
5) —SO— or
6) —$SO_2$—, $R^{eN27}$ represents
1) a hydrogen atom or
2) a $C_1$ to $C_6$ alkyl group which may have a substituent, $R^{eN28}$ represents
1) a hydrogen atom,
2) a $C_1$ to $C_6$ alkyl group which may have a substituent,
3) a $C_6$ to $C_{14}$ aryl group which may have a substituent or
4) a $C_7$ to $C_{10}$ aralkyl group which may have a substituent, $R^{eN29}$ represents
1) a hydrogen atom,
2) a $C_1$ to $C_6$ alkyl group which may have a substituent,
3) an unsaturated $C_2$ to $C_{10}$ alkyl group which may have a substituent,
4) a $C_1$ to $C_6$ alkoxy group which may have a substituent,
5) a $C_6$ to $C_{14}$ aryl group which may have a substituent,
6) a 5-membered to 14-membered heteroaryl group which may have a substituent,
7) a $C_7$ to $C_{10}$ aralkyl group which may have a substituent,
8) a $C_3$ to $C_8$ cycloalkyl group which may have a substituent,
9) a $C_4$ to $C_9$ cycloalkylalkyl group which may have a substituent,
10) a 5-membered to 14-membered heteroaralkyl group which may have a substituent,
11) —$NR^{eN31}R^{eN32}$, wherein $R^{eN31}$ and $R^{eN32}$, the same or different, independently represent a hydrogen atom or a $C_1$ to $C_6$ alkyl group which may have a substituent, or form a 5-membered to 14-membered non-aromatic heterocyclic group together with the nitrogen atom to which $R^{eN31}$ and $R^{eN32}$ are bonded or
12) a 5-membered to 14-membered non-aromatic heterocyclic group which may have a substituent, and $R^{eN30}$ represents
1) a hydrogen atom,
2) a $C_1$ to $C_6$ alkyl group which may have a substituent, 3) an unsaturated $C_2$ to $C_{10}$ alkyl group which may have a substituent,
4) a $C_6$ to $C_{14}$ aryl group which may have a substituent,
5) a 5-membered to 14-membered heteroaryl group which may have a substituent,
6) a $C_7$ to $C_{10}$ aralkyl group which may have a substituent,
7) a $C_3$ to $C_8$ cycloalkyl group which may have a substituent,
8) a $C_4$ to $C_9$ cycloalkylalkyl group which may have a substituent,
9) a 5-membered to 14-membered heteroaralkyl group which may have a substituent or
10) a 5-membered to 14-membered non-aromatic heterocyclic group which may have a substituent; or a pharmacologically acceptable salt thereof.

15. The compound according to claim 5, wherein $R^{7e}$ and/or $R^{21e}$ independently represent $R^{e7}CO-O-$, wherein $R^{e7}$ represents a group of the formula (IX):

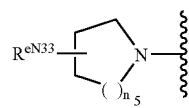

(IX)

wherein $n_5$ represents an integer of 1 to 3, and
$R^{eN33}$ represents
1) an amino group,
2) an amino group which may have a substituent,
3) a pyrrolidin-1-yl group which may have a substituent,
4) a piperidin-1-yl group which may have a substituent or
5) a morpholin-4-yl group which may have a substituent; or a pharmacologically acceptable salt thereof.

16. The compound according to claim 5, wherein $R^{7e}$ and/or $R^{21e}$ independently represent $R^{e8}CO-O-$, wherein $R^{e8}$ represents a group of the formula (X):

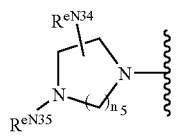

(X)

wherein $n_5$ represents an integer of 1 to 3,
$R^{eN34}$ represents
1) a hydrogen atom,
2) a $C_1$ to $C_6$ alkyl group which may have a substituent,
3) a $C_6$ to $C_{14}$ aryl group which may have a substituent or
4) a $C_7$ to $C_{10}$ aralkyl group which may have a substituent, and
$R^{eN35}$ represents
1) a hydrogen atom,
2) a $C_1$ to $C_6$ alkyl group which may have a substituent,
3) a $C_3$ to $C_8$ cycloalkyl group which may have a substituent,
4) a 3-membered to 8-membered non-aromatic heterocyclic group which may have a substituent,
5) a $C_6$ to $C_{14}$ aryl group which may have a substituent,
6) a 5-membered to 14-membered heteroaryl group which may have a substituent,
7) a $C_7$ to $C_{10}$ aralkyl group which may have a substituent,
8) a 5-membered to 14-membered heteroaralkyl group which may have a substituent or
9) a $C_4$ to $C_9$ cycloalkylalkyl group which may have a substituent; or a pharmacologically acceptable salt thereof.

17. The compound according to claim 5, wherein $R^{7e}$ and/or $R^{21e}$ independently represent $R^{e9}CO-O-$, wherein $R^{e9}$ represents a group of the formula (XI):

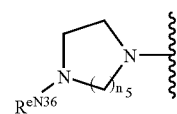

(XI)

wherein $n_5$ represents an integer of 1 to 3, and
$R^{eN36}$ represents
1) a hydrogen atom,
2) a $C_1$ to $C_6$ alkyl group which may have a substituent,
3) a $C_3$ to $C_8$ cycloalkyl group which may have a substituent,
4) a $C_4$ to $C_9$ cycloalkylalkyl group which may have a substituent,
5) a $C_7$ to $C_{10}$ aralkyl group which may have a substituent,
6) a pyridyl group which may have a substituent or
7) a tetrahydropyranyl group which may have a substituent; or a pharmacologically acceptable salt thereof.

18. The compound according to claim 5, wherein $R^{7e}$ and/or $R^{21e}$ independently represent $R^{e10}C-O-$, wherein $R^{e10}$ represents a group of the formula (XII):

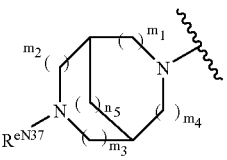

(XII)

wherein $m_1$, $m_2$, $m_3$, and $m_4$, the same or different, independently represent 0 or 1,
$n_5$ represents an integer of 1 to 3, and
$R^{eN37}$ represents
1) a hydrogen atom,
2) a $C_1$ to $C_6$ alkyl group which may have a substituent,
3) an unsaturated $C_2$ to $C_{10}$ alkyl group which may have a substituent,
4) a $C_6$ to $C_{14}$ aryl group which may have a substituent,
5) a 5-membered to 14-membered heteroaryl group which may have a substituent,
6) a $C_7$ to $C_{10}$ aralkyl group which may have a substituent,
7) a $C_3$ to $C_8$ cycloalkyl group which may have a substituent,
8) a $C_4$ to $C_9$ cycloalkylalkyl group which may have a substituent,
9) a 5-membered to 14-membered heteroaralkyl group which may have a substituent or 10) a 5-membered to 14-membered non-aromatic heterocyclic group which may have a substituent; or a pharmacologically acceptable salt thereof.

19. The compound according to claim 5, wherein $R^{7e}$ and/or $R^{21e}$ independently represent $R^{e11}CO-O-$, wherein $R^{e11}$ represents a group of the formula (XIII):

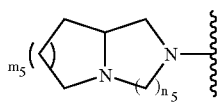
(XIII)

wherein $m_5$ represents an integer of 1 to 3, and $n_5$ represents 2 or 3; or a pharmacologically acceptable salt thereof.

20. The compound according to claim 5, wherein $R^{7e}$ and/or $R^{21e}$ independently represent $R^{e12}CO-O-$, wherein $R^{e12}$ represents a group selected from a group consisting of:

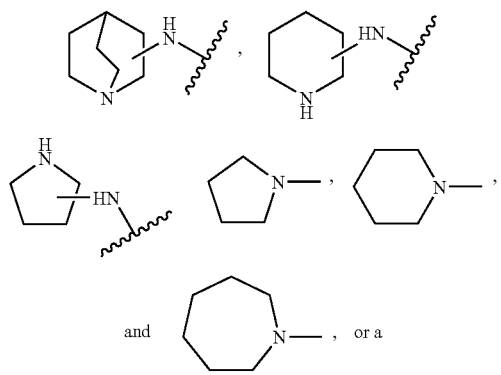

group selected from a group consisting of

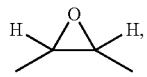

both of which may have a substituent on the ring; or a pharmacologically acceptable salt thereof.

21. The compound according to claim 1, wherein $R^{16}$ is a hydroxyl group; or a pharmacologically acceptable salt thereof.

22. The compound according to claim 1, wherein
[1] W is

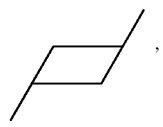

$R^3$ and $R^{21}$ are a hydroxyl group, $R^7$ is an acetoxy group, and $R^{16}$, $R^{17}$, $R^{20}$ and $R^{21'}$ are a hydrogen atom,

[2] W is

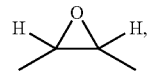

$R^3$ and $R^{21}$ are a hydroxyl group, $R^7$ is an acetoxy group, and $R^{16}$, $R^{17}$, $R^{20}$ and $R^{21'}$ are a hydrogen atom,

[3] W is

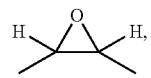

$R^3$, $R^{16}$ and $R^{21}$ are a hydroxyl group, $R^7$ is an acetoxy group, and $R^{17}$, $R^{20}$ and $R^{21'}$ are a hydrogen atom,

[4] W is

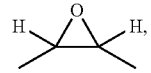

$R^{21}$ and $R^{21'}$ form an oxo group together with the carbon atom to which $R^{21}$ and $R^{21'}$ are bonded, $R^3$, $R^{16}$ and $R^{20}$ are a hydroxyl group, $R^7$ is an acetoxy group, and $R^{17}$ is a hydrogen atom,

[5] W is

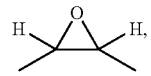

$R^3$, $R^{16}$, $R^{20}$ and $R^{21}$ are a hydroxyl group, $R^7$ is an acetoxy group, and $R^{17}$ and $R^{21'}$ are a hydrogen atom,

[6] W is

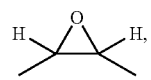

$R^3$, $R^7$, $R^{16}$ and $R^{21}$ are a hydroxyl group, and $R^{17}$, $R^{20}$ and $R^{21'}$ are a hydrogen atom,

[7] W is

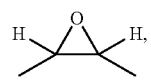

$R^3$, $R^{17}$, $R^{16}$ and $R^{21}$ are a hydroxyl group, $R^7$ is an acetoxy group, and $R^{20}$ and $R^{21'}$ are a hydrogen atom or

[8] W is $R^{21}$ and $R^{21'}$ form an oxo group together with the carbon atom to which $R^{21}$ and $R^{21'}$ are bonded, $R^3$ and $R^{16}$ are a hydroxyl group, $R^7$ is an acetoxy group, and $R^{17}$ and $R^{20}$ are a hydrogen atom; or a pharmacologically acceptable salt thereof.

23. The compound according to claim 1, which is (8E,12E,14E)-3,16,21-trihydroxy-6,10,12,16,20-pentamethyl-7-((4-methylpiperazin-1-yl)carbonyl)oxy-18,19 epoxytricosa-8,12,14-trien-11-olide, (8E,12E,14E)-3,16,21-trihydroxy-6,10,12,16,20-pentamethyl-7-((4-methylhomopiperazin-1-yl)carbonyl)oxy-18,19-epoxytricosa-8,12,14-trien-11-olide,
- (8E,12E,14E)-3,16,21-trihydroxy-6,10,12,16,20-pentamethyl-7-((4-(piperidin-1-yl)piperidin-1-yl)carbonyl)oxy-18,19-epoxytricosa-8,12,14-trien-11-olide,
- (8E,12E,14E)-7-((4-ethylpiperazin-1-yl)carbonyl)oxy-3,16,21-trihydroxy-6,10,12,16,20-pentamethyl-18,19-epoxytricosa-8,12,14-trien-11-olide, (8E,12E,14E)-7-(N-(3-(N',N'-dimethylamino)propyl)-N-methylcarbamoyloxy)-3,16,21-trihydroxy-6,10,12,16,20-pentamethyl-18,19-epoxytricosa-8,12,14-trien-11-olide, (8E,12E,14E)-3,16,21-trihydroxy-6,10,12,16,20-pentamethyl-7-((piperazin-1-yl)carbonyl)oxy-18,19-epoxytricosa-8,12,14-trien-11-olide,
- (8E,12E,14E)-3,16,21-trihydroxy-6,10,12,16,20-pentamethyl-7-(N-methyl-N-(1-methylpiperidin-4-yl)carbamoyloxy)-18,19-epoxytricosa-8,12,14-trien-11-olide,
- (8E,12E,14E)-3,16,21-trihydroxy-7-((4-isopropylhomopiperazin-1-yl)carbonyl)oxy-6,10,12,16,20-pentamethyl-18,19-epoxytricosa-8,12,14-trien-11-olide,
- (8E,12E,14E)-3,16,21-trihydroxy-7-((4-(4-hydroxypiperidin-1-yl)piperidin-1-yl)carbonyl)oxy-6,10,12,16,20-pentamethyl-18,19-epoxytricosa-8,12,14-trien-11-olide, (8E,12E,14E)-3,16,21-trihydroxy-6,10,12,16,20-pentamethyl-7-((4-(morpholin-4-yl)piperidin-1-yl)carbonyl)oxy-18,19-epoxytricosa-8,12,14-trien-11-olide,
- (8E,12E,14E)-7-((4-ethylhomopiperazin-1-yl)carbonyl)oxy-3,16,21-trihydroxy-6,10,12,16,20-pentamethyl-18,19-epoxytricosa-8,12,14-trien-11-olide, (8E,12E,14E)-3,16,21-trihydroxy-7-((4-isopropylpiperazin-1-yl)carbonyl)oxy-6,10,12,16,20-pentamethyl-18,19-epoxytricosa-8,12,14-trien-11-olide, (8E,12E,14E)-3,16,21-trihydroxy-7-(((1S,4S)-5-isopropyl-2,5-diazabicyclo[2.2.1]heptan-2-yl)carbonyl)oxy-6,10,12,16,20-pentamethyl-18,19-epoxytricosa-8,12,14-trien-11-olide,
- (8E,12E,14E)-7-(N-(2-(N',N'-dimethylamino)ethyl)-N-methylcarbamoyloxy)-3,16,21-trihydroxy-6,10,12,16,20-pentamethyl-18,19-epoxytricosa-8,12,14-trien-11-olide,
- (8E,12E,14E)-7-(N-(2-(N',N'-dimethylamino)ethyl)carbamoyloxy)-3,16,21-trihydroxy-6,10,12,16,20-pentamethyl-18,19-epoxytricosa-8,12,14-trien-11-olide or
- (8E,12E,14E)-3,16,21-trihydroxy-6,10,12,16,20-pentamethyl-7-(((1S,4S)-5-methyl-2,5-diazabicyclo[2.2.1]heptan-2-yl)carbonyl)oxy-18,19-epoxytricosa-8,12,14-trien-11-olide.

24. The compound according to claim 1, which is (8E,12E,14E)-3,16,21-trihydroxy-6,10,12,16,20-pentamethyl-7-(N-methyl-N-(1-methylpiperidin-4-yl)carbamoyloxy)-18,19-epoxytricosa-8,12,14-trien-11-olide,
- (8E,12E,14E)-3,16,21-trihydroxy-7-((4-isopropylhomopiperazin-1-yl)carbonyl)oxy-6,10,12,16,20-pentamethyl-18,19-epoxytricosa-8,12,14-trien-11-olide,
- (8E,12E,14E)-7-((4-ethylhomopiperazin-1-yl)carbonyl)oxy-3,16,21-trihydroxy-6,10,12,16,20-pentamethyl-18,19-epoxytricosa-8,12,14-trien-11-olide, (8E,12E,14E)-3,16,21-trihydroxy-7-((4-isopropylpiperazin-1-yl)carbonyl)oxy-6,10,12,16,20-pentamethyl-18,19-epoxytricosa-8,12,14-trien-11-olide or (8E,12E,14E)-3,16,21-trihydroxy-6,10,12,16,20-pentamethyl-7-(((1S,4S)-5-methyl-2,5-diazabicyclo[2.2.1]heptan-2-yl)carbonyl)oxy-18,19-epoxytricosa-8,12,14-trien-11-olide.

25. A pharmaceutical composition comprising the compound according to claim 1, in a therapeutically effective amount, or a pharmacologically acceptable salt thereof, as an active ingredient.

26. The pharmaceutical composition according to claim 25 as an angiogenesis inhibitor.

27. The pharmaceutical composition according to claim 25 as an antitumor agent.

28. The pharmaceutical composition according to claim 25 as a therapeutic agent for treating hemangioma.

29. The pharmaceutical composition according to claim 25 as a cancer metastasis inhibitor.

30. The pharmaceutical composition according to claim 25 as a therapeutic agent for inflammatory diseases consisting of deformant arthritis, rheumatoid arthritis, psoriasis, and delayed hypersensitive reaction.

31. The pharmaceutical composition according to claim 25 as a therapeutic agent for treating atherosclerosis.

32. The pharmaceutical composition according to claim 25 as a therapeutic agent for treating a solid cancer.

33. The pharmaceutical composition according to claim 32, wherein the solid tumor is lung cancer, brain tumor, breast cancer, prostate cancer, ovarian cancer, colon cancer or melanoma.

34. The pharmaceutical composition according to claim 25 as a therapeutic agent for treating leukemia.

35. A method for producing a chemical compound, comprising: culturing a microorganism belonging to the genus Streptomyces, which is capable of producing a compound of the following chemical formula (I):

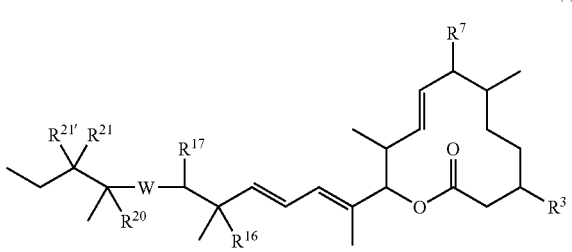

(I)

wherein [1] W is

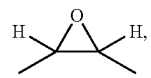

$R^3$ and $R^2$ are a hydroxyl group, $R^7$ is an acetoxy group, and $R^{16}$, $R^{17}$, $R^{20}$ and $R^{21'}$ are a hydrogen atom or

[2] W is

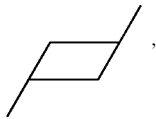

$R^3$ and $R^{21}$ are a hydroxyl group, $R^7$ is an acetoxy group, and $R^{16}$, $R^{17}$, $R^{20}$ and $R^{21'}$ are a hydrogen atom; and collecting the compound as defined in [1] or [2] from the culture.

36. *Streptomyces* sp. strain A-1543 (FERM BP-8442).

37. A method for producing a chemical compound by bioconversion with a microorganism of a compound of the following chemical formula (I):

(I)

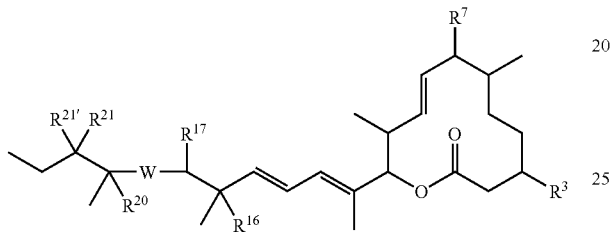

wherein [1] W is

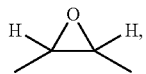

$R^3$ and $R^{21}$ are a hydroxyl group, $R^7$ is an acetoxy group, and $R^{16}$, $R^{17}$, $R^{20}$ and $R^{21'}$ are a hydrogen atom into a compound of the above formula (I), wherein
[3] W is

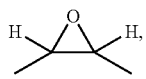

$R^3$, $R^{16}$ and $R^{21}$ are a hydroxyl group, $R^7$ is an acetoxy group, and $R^{17}$, $R^{20}$ and $R^{21'}$ are a hydrogen atom,
[4] W is

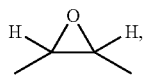

$R^{21}$ and $R^{21'}$ form an oxo group together with the carbon atom to which $R^{21}$ and $R^{21'}$ are bonded, $R^3$, $R^{16}$ and $R^{20}$ are a hydroxyl group, $R^7$ is an acetoxy group, and $R^{17}$ is a hydrogen atom,
[5] W is

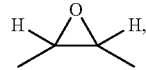

$R^3$, $R^{16}$, $R^{20}$ and $R^{12}$ are a hydroxyl group, $R^7$ is an acetoxy group, and $R^{17}$ and $R^{21'}$ are a hydrogen atom,
[6] W is

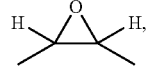

$R^3$, $R^7$, $R^{16}$ and $R^{21}$ are a hydroxyl group, and $R^{17}$, $R^{20}$ and $R^{21'}$ are a hydrogen atom,
[7] W is

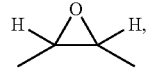

$R^3$, $R^{17}$, $R^{16}$ and $R^{21}$ are a hydroxyl group, $R^7$ is an acetoxy group, and $R^{20}$ and $R^{21'}$ are a hydrogen atom or
[8] W is

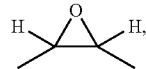

$R^{21}$ and $R^{21'}$ form an oxo group together with the carbon atom to which $R^{21}$ and $R^{21'}$ are bonded, $R^3$ and $R^{16}$ are a hydroxyl group, $R^7$ is an acetoxy group, and $R^{17}$ and $R^{20}$ are a hydrogen atom comprising:

1) a step of incubating a compound of the above formula (I) in the presence of a culture solution of a strain selected from microorganisms belonging to bacteria or a product prepared from culture cells of the strain, and
2) collecting the resulting compound from the incubated solution.

38. The method according to claim 37, wherein the microorganism belonging to bacteria is strain A-1544 (FERM BP-8446) or strain A-1545 (FERM BP-8447).

39. Strain A-1544 (FERM BP-8446) or strain A-1545 (FERM BP-8447).

* * * * *